United States Patent
Erlander et al.

(10) Patent No.: US 9,856,533 B2
(45) Date of Patent: Jan. 2, 2018

(54) PREDICTING BREAST CANCER TREATMENT OUTCOME

(75) Inventors: Mark G. Erlander, Camino del Prado, CA (US); Xiao-Jun Ma, San Diego, CA (US); Dennis C. Sgroi, Winchester, MA (US)

(73) Assignees: Biotheranostics, Inc., San Diego, CA (US); The General Hospital Corporation, Boston, MA (US)

(*) Notice: Subject to any disclaimer, the term of this patent is extended or adjusted under 35 U.S.C. 154(b) by 1660 days.

(21) Appl. No.: 10/773,761

(22) Filed: Feb. 6, 2004

(65) Prior Publication Data

US 2005/0239083 A1    Oct. 27, 2005

Related U.S. Application Data

(63) Continuation-in-part of application No. 10/727,100, filed on Dec. 2, 2003, now Pat. No. 7,504,214.

(60) Provisional application No. 60/504,087, filed on Sep. 19, 2003.

(51) Int. Cl.
    *C12Q 1/68* (2006.01)

(52) U.S. Cl.
    CPC ..... *C12Q 1/6886* (2013.01); *C12Q 2600/106* (2013.01); *C12Q 2600/154* (2013.01); *C12Q 2600/158* (2013.01)

(58) Field of Classification Search
    None
    See application file for complete search history.

(56) References Cited

U.S. PATENT DOCUMENTS

| | | |
|---|---|---|
| 4,981,783 A | 1/1991 | Augenlicht |
| 6,291,170 B1 | 9/2001 | Van Gelder et al. |
| 6,328,709 B1 | 12/2001 | Hung et al. |
| 6,482,600 B1 | 11/2002 | Burmer et al. |
| 6,642,009 B2 | 11/2003 | Hung |
| 6,673,024 B2 | 1/2004 | Soito et al. |
| 6,794,141 B2 | 9/2004 | Erlander et al. |
| 7,504,214 B2 | 3/2009 | Erlander et al. |
| 7,514,209 B2 | 4/2009 | Dai et al. |
| 7,930,105 B2 | 4/2011 | Erlander et al. |
| 9,447,470 B2 | 9/2016 | Erlander et al. |
| 2001/0039015 A1 | 11/2001 | Sauter |
| 2002/0044941 A1 | 4/2002 | Rosen et al. |
| 2002/0102265 A1 | 8/2002 | Hong et al. |
| 2003/0049701 A1 | 3/2003 | Muraca |
| 2003/0087270 A1 | 5/2003 | Schlegel et al. |
| 2003/0124128 A1 | 7/2003 | Lillie et al. |
| 2003/0138833 A1* | 7/2003 | Polyak ............. G01N 33/57488 435/6.14 |
| 2003/0219760 A1 | 11/2003 | Gordon et al. |
| 2005/0079518 A1 | 4/2005 | Baker et al. |
| 2005/0239079 A1 | 10/2005 | Erlander et al. |
| 2005/0239083 A1 | 10/2005 | Erlander et al. |
| 2006/0154267 A1 | 7/2006 | Ma et al. |
| 2011/0136680 A1 | 6/2011 | Erlander et al. |
| 2013/0281502 A1 | 10/2013 | Sgroi et al. |

FOREIGN PATENT DOCUMENTS

| | | |
|---|---|---|
| EP | 2333119 A1 | 6/2011 |
| WO | WO02/103320 | 12/2002 |
| WO | WO 03/060470 A2 | 7/2003 |
| WO | WO 2005/008213 A2 | 1/2005 |
| WO | WO 2006/004600 A1 | 1/2006 |
| WO | WO 2006/119593 A1 | 11/2006 |
| WO | WO 2006/132971 A2 | 12/2006 |
| WO | WO 2009/108215 A1 | 9/2009 |
| WO | WO 2012/079059 A2 | 6/2012 |
| WO | WO 2012/079059 A3 | 6/2012 |
| WO | WO 2013/070521 A1 | 5/2013 |
| WO | WO 2015/038682 A1 | 3/2015 |
| WO | WO 2015/184182 A1 | 12/2015 |

OTHER PUBLICATIONS

Wu, T.D. Analysing gene expression data from DNA microarrays to identify candidate genes Journal of Pathology 195(1):53-65, 2001.*
Lucentini,.J. Gene association studies typically wrong The Scientist 18(24):20, 2004.*
Chen, G. et al. Discordant protein and mRNA expression in lung adenocarcinomas Molecular & Cellular Proteomics 1:304-313, 2002.*
Okuda, H. et al. Epigenetic inactivation of the candidate tumor suppressor gene HOXB13 in human renal cell carcinoma Oncogene 25(.12):1733-1742, 2006.*
Yamamoto, H. et al. Differential involvement of the hypermethylator phenotype in hereditary and sporadic colorectal cancers with high-frequency microsatellite instability Genes, Chromosomes & Cancer 33(3):322-325, 2002.*
Van Rijnsoever, M. et al. Characterisation of colorectal cancers showing hypermethylation at multiple CpG islands Gut 51(6):797-802, 2002.*
Srinivas et al. Trends in biomarker detection for cancer detection. The Lancet (2001) 2: 698-704.*

(Continued)

*Primary Examiner* — Angela M Bertagna
(74) *Attorney, Agent, or Firm* — Jones Day

(57) ABSTRACT

Methods and compositions are provided for the identification of expression signatures in ER+ breast cancer cases, where the signatures correlate with responsiveness, or lack thereof, to treatment with tamoxifen or another antiestrogen agent against breast cancer The signature profiles are identified based upon sampling of reference breast tissue samples from independent cases of breast cancer and provide a reliable set of molecular criteria for predicting the efficacy of treating a subject with breast cancer with tamoxifen or another antiestrogen agent against breast cancer. Additional methods and compositions are provided for predicting responsiveness to tamoxifen or another antiestrogen agent against breast cancer in cases of breast cancer by use of three biomarkers. Two biomarkers display increased expression correlated with tamoxifen response while the third biomarker displays decreased expression correlated with tamoxifen response.

9 Claims, 2 Drawing Sheets

(56) References Cited

OTHER PUBLICATIONS

Feng et al. Molecular biomarkers for cancer detection in blood and bodily fluids. Critical Reviews in Clinical Laboratory Sciences. (2006) 43(5-6): 497-560.*
Bruggemeier et al. Aromatase Inhibitors in the Treatment of Breast Cancer. Endocrine Reviews (2005) 26(3): 331-345.*
Mello-Grand et al. Gene expression profiling and prediction of response to hormonal neoadjuvant treatment with anastrozole in surgically resectable breast cancer. Breast Cancer Research and Treatment (2010) 121: 399-411.*
Miller et al. Gene Expression Profiles Differentiating Between Breast Cancers Clinically Responsive or Resistant to Letrozole. Journal of Clinical Oncology (2009) 27: 1382-1387.*
Gibson et al. Genome Research (1996) 6: 995-1001.*
Gruvberger et al. Cancer Research 61: 5979-5984 (2001).*
Shi et al. Journal of Biological Chemistry 2000; 275: 19167-19176.*
Bonner et al. Science 1997; 278: 1481-1483.*
O'Driscoll et al. European Journal of Cancer 1996; 32A: 128-133.*
Herschkowitz et al. Genome Biology 2007; 8: R76.*
Salonga et al. Clinical Cancer Research 2000; 6: 1322-1327.*
Sotiriou et al. Breast Cancer Research 2002; 4: R3.*
Dabholkar et al. Journal of Clinical Investigation 1994; 94: 703-708.*
Kato et al. International Journal of Cancer (Predictive Oncology) 2001; 95: 92-95.*
Ginzinger, D.G. Experimental Hematology 2002; 30: 503-512.*
Howell et al. Journal of Steroid Biochemistry and Molecular Biology 2001; 79: 227-237.*
Clarke, R. et al. "Antiestrogen resistance in breast cancer and the role of estrogen receptor signaling", *Oncogene* 22 (2003) 22:7316-39.
Jordan, C. "Historical perspective on hormonal therapy of advanced breast cancer", *Clin. Ther.* (2002) 24 Suppl. A: A3-16.
Osborne, C.K., et al. "Growth factor receptor cross-talk with estrogen receptor as a mechanism for tamoxifen resistance in breast cancer", *The Breast* (2003) 12:362-7.
Ellis, M.J. et al. "Letrozole is more effective neoadjuvant endocrine therapy than tamoxifen for ErbB-1-and/or ERB-2-positive, estrogen receptor-positive primary breast cancer: evidence from a phase III randomized trial.", *J. Clin Oncol* (2001) 19(18):3808-16.
Buzdar, A.U., "Anastrozole: a new addition to the armamentarium against advanced breast cancer.", *Am. J. Clin Oncol* (1998) 21(2), 161-6.
Fabian, et al., "Short-Term Breast Cancer Prediction by Random Periareolar Fine-Needle Aspiration Cytology and the Gail Risk Model", *J. Natl Cancer Inst.* (2000) 92(15):1217-27.
Tan-Chiu et al., "Effects of Tamoxifen on Benign Breast Disease in Women at High Risk for Breast Cancer", *J. Natl Cancer Inst.* (2003) 95(4):302-307.
Wickerham, D.L., "Tamoxifen,—an update on current data and where it can now be used", *Breast Cancer Res. and Treatment*, (2000) 75 Suppl 1:S7-12, Discussion S33-5.
Fitzgibbons, P.L. et al. "Prognostic factors in breast cancer. College of American Pathologists Consensus Statement 1999", *Arch Pathol Lab Med* (2000) 124:966-78.
Ma, X.J. et al., "Gene expression profiles of human breast cancer progression", *Proc Natl Acad Sci USA* (2003) 100(10):5974-9.
Nicholson, R.I. et al., "Epidermal growth factor receptor expression in breast cancer: association with response to endocrine therapy", *Breast Cancer Res Treat* (1994) 29:117-25.
Daidone, M.G., et al. "Biomarkers and outcome after tamoxifen treatment in node-positive breast cancers from elderly women", *British Journal of Cancer* (2000) 82(2):270-277.
Van Der Flier, Silvia, et al. "Bcar 1/p130Cas Protein and Primary Breast Cancer: Prognosis and Response to Tamoxifen Treatment", *Journal of the National Cancer Institute*, (2000) vol. 92(2):120-127.
Luo, L-Y, et al. "Higher expression of human kallikrein 10 in breast cancer tissue predicts tamoxifen resistance", *British Journal of Cancer* (2002) 86:1790-1796.
Ellis, Matthew J., et al. "Neoadjuvant comparisons of aromatase inhibitors and tamoxifen: pretreatment determinants of response and on-treatment effect", *Journal of Steroid Biochemistry & Molecular Biology* (2003) 86:301-307.
Hilsenbeck, Susan G., et al. "Statistical Analysis of Array Expression Data as Applied to the Problem of Tamoxifen Resistance", *Journal of the National Cancer Institute* (1999) 91(5):453-459.
Vant Veer, Laura, et al. "Gone expression profiling predicts clinical outcome of breast cancer", *Nature* (2002) 415:530-536.
Ma, Xiao-Jun, et al. A two-gene expression ratio predicts clinical outcome in breast cancer patients treated with tamoxifen, *Cancer Cell* (2004) 5:607-615.
Becker, Michael, et al. "Distinct gene expression patterns in a tamoxifen-sensitive human mammary carcinoma xenograft and its tamoxifen-resistant subline MaCa 3366/TAM", *Molecular Cancer Therapeutics* (2005) 4(1):151-168.
Bardou, V.J., et al. "Progesterone receptor status significantly improves outcome prediction over estrogen receptor status alone for adjuvant endocrine therapy in two large breast cancer databases", *J. Clin Oncol* (2003) 21:1973-9.
Huang, E. et al. "Gene expression predictors of breast cancer outcomes", *Lancet* (2003) 361:1590-6.
Sørlie, T., et al. "Gene expression patterns of breast carcinomas distinguish tumor subclasses with clinical implications", *Proc Natl Acad Sci USA* (2001) 98:10869-74.
Sørlie, T, et al. "Repeated observation of breast tumor subtypes in independent gene expression data sets", *Proc Natl Acad Sci USA* (2003) 100:8418-23.
Sotiriou, C., et al. "Breast cancer classification and prognosis based on gene expression profiles from a population-based study", *Proc Natl Acad Sci USA* (2003) 100:10393-8.
Van de Vijver, M.J., et al. "A gene-expression signature as a predictor of survival in breast cancer", *N. Engl. J Med* (2002) 347:1999-2009.
Fernandez M. D., et al. "Quantitative oestrogen and progesterone receptor values in primary breast cancer and predictability of response to endocrine therapy", *Clin Oncol* (1983) 9:245-50.
Fernö, M., et al. "Results of two or five years of adjuvant tamoxifen correlated to steroid receptor and S-phase levels", *Breast Cancer Res Treat* (2000) 59:69-76.
Nardelli, G.B., et al. "Estrogen and progesterone receptors status in the prediction of response of breast cancer to endocrine therapy (preliminary report)", *Eur J Gynaecol Oncol* (1986) 7:151-8.
Osborne, C.K., et al. "The value of estrogen and progesterone receptors in the treatment of breast cancer", *Cancer* (1980) 46:2884-8.
Howell, Sacha J., et al. "The use of selective estrogen receptor modulators and selective estrogen receptor down-regulators in breast cancer", *Best Practice & Research Clinical Endocrinology & Metabolism* (2004) 18(1):47-66.
Hall, Julie M., et al. "The Multifaceted Mechanisms of Estradiol and Estrogen Receptor Signaling", *The Journal of Biological Chemistry* (2001) 276(40):36869-36872.
Levenson, Anait S., et al. "Gene Expression Profiles with Activation of the Estrogen Receptor α-selective Estrogen Receptor Modulator Complex in Breast Cancer Cells Expressing Wild-Type Estrogen Receptor", *Cancer Research* (2002) 62:4419-4426.
Jordan, V. Craig, et al. "Introducing a new section to *Breast Cancer Research*: Endocrinology and hormone therapy", *Breast Cancer Research* (2003) 5:281-283.
Dauvois, Sophie, et al. "Antiestrogen ICI 164,384 reduces cellular estrogen receptor content by increasing its turnover", *Proc. Natl. Acad. Sci.* (1992) 89:4037-4041.
Willson, T.M., et al. "Dissection of the Molecular Mechanism of Action of GW5638, a Novel Estrogen Receptor Ligand, Provides Insights into the Role of Estrogen Receptor in Bone", *Endocrinology* (1997) 138(9):3901-3911.
Wijayaratne, Ashini L., et al. "Comparative Analyses of Mechanistic Differences Among Antiestrogens", *Endocrinology* (1999) 140(12):5828-5840.

(56) References Cited

OTHER PUBLICATIONS

Dutertre, Martin, et al "Molecular Mechanisms of Selective Estrogen Receptor Modulator (SERM) Action", *The Journal of Pharmacology and Experimental Therapeutics* (2000) 295(2):431-437.
Golpon et al., "HOX Genes in Human Lung, Altered Expression in Primary Pulmonary Hypertension and Emphysema," Am. J. Patho. 158:(3) Mar. 2001, pp. 955-966.
Abramovitz et al., "A systems approach to clinical oncology: focus on breast cancer," *Proteome Sci.*, 4:5 (2006).
Alizadeh et al., "Distinct types of diffuse large B-cell lymphoma identified by gene expression profiling," *Nature*, 403(6769):503-511 (2000).
Ansfield et al., "A ten-year study of 5-flurouracil in disseminated breast cancer with clinical results and survival times," *Cancer Res.*, 29(5):1062-1066 (1969).
Benner et al., "Evolution, language and analogy in functional genomics," *Trends Genetics*, 17(7):414-418 (2001).
Bepler et al., "RRM1 and PTEN as prognostic parameters for overall and disease-free survival in patients with non-small-cell lung cancer," *J. Clin. Oncol.*, 22(10):1878-1885 (2004).
Betsil et al., "Intraductal carcinoma. Long-term follow-up after treatment by biopsy alone," *JAMA*, 239(18):1863-1867 (1978).
BIG 1-98 Collaborative Group et al., "Letrozole therapy alone or in sequence with tamoxifen in women with breast cancer," *N. Engl. J. Med.*, 361(8):766-776 (2009).
Bissett et al., "Human papillomavirus genotype detection and viral load in paired genital and urine samples from both females and males," *J. Med. Virol.*, 83:1744-1751 (2011).
Bittner et al., "Molecular classification of cutaneous malignant melanoma by gene expression profiling," *Nature*, 406(6795):536-540 (2000).
Brown et al., "Knowledge base analysis of microarray gene expression data by using support vector machines," *Proc. Natl. Acad. Sci. USA*,97(1):262-267 (2000).
Chen et al., "BRCA1, BRCA2, and Rad51 operate in a common DNA damage response pathway," *Cancer Res.*, 59(7 Suppl): 1752s-1756s (1999).
Chen et al., "Inhibition of human cancer cell growth by inducible expression of human ribonucleotide reductase antisense cDNA," *Antisense Nucleic Acid Drug Dev.*, 10(2):111-116 (2000).
Chng et al., "A gene expression based centrosome index is a powerful prognostic factor in myeloma," *Blood*, 108: Abstract 3388 (2006).
Cianfrocca et al., "Prognostic and predictive factors in early-stage breast cancer," *Oncologist*, 9(6):606-616 (2004).
Collins et al., "The application of genomic and proteomic technologies in predictive, preventive and personalized medicine," *Vascul. Pharmacol.*, 45(5):258-267 (2006).
Cornfield et al., "The prognostic significance of multiple morphologic features and biologic markers in ductal carcinoma in situ of the breast: a study of a large cohort of patients treated with surgery alone," *Cancer*, 100(11):2317-2327 (2004).
Cronin et al., "Measurement of gene expression in archival paraffin-embedded tissues: development and performance of a 92-gene reverse transcriptase-polymerase chain reaction assay," *Am. J. Pathol.*,164(1):35-42 (2004).
Cuzick et al., "Effect of anastrozole and tamoxifen as adjuvant treatment for early-stage breast cancer; 10-year analysis of the ATAC trial," *Lancet Oncol.*, 11:1135-1142 (2010).
Cuzick et al., "Prognostic value of a cominded estrogen receptor, progestrone receptor, Ki-67, and human epidermal growth factor receptor 2 immunohistochemcial score and comparison with the genomic health recurrence score in early breast cancer," *J. Clin. Oncol.*, 29(32):4273-4278 (2011).
Dalgin et al., "Portraits of breast cancer progression," *BMC Bioinformatics*,8(291):1-16 (2007).
Dalton et al., "Histologic grading of breast cancer: linkage of patient outcome with level of pathologist agreement," *Mod. Pathol.*, 13(7):730-735 (2000).
De Vos et al., "Gene expression profile of serial samples of transformed B-cell lymphomas," *Lab. Invest.*, 83(2):271-285 (2003).
Derisi et al., "Use of a cDNA microarray to analyse gene expression patterns in human cancer," *Nat. Genet.*,14(4):457-460 (1996).
Desmedt et al., "Proliferation: the most prominent predictor of clinical outcome in breast cancer," *Cell Cycle*, 5(19):2198-2202 (2006).
Desmedt et al., "Strong time dependence of the 76-gene prognostic signature for node-negative breast cancer patients in the TRANSBIG multicenter independent validation series," *Clin. Cancer Res.*, 13(11):3207-3214 (2007).
Dowsett et al., "Prediction of risk of distant recurrence using the 21-gene recurrence score in node-negative and node-ositive post-menopausal patients with breast cancer treated with anastrozole or tamoxifen; a transATAC study," *J. Clin. Oncol.*, 28(11):1829-1834 (2010).
Dowsett, "Overexpression of HER-2 as a resistance mechanism to hormonal therapy for breast cancer," *Endocr. Relat. Cancer*, 8(3):191-195 (2001).
Draghici et al., "A systems biology approach for pathway level analysis," *Genome Res.*,17:1537-1545 (2007).
Dupont et al., "Risk factors for breast cancer in women with proliferative breast disease," *N. Engl. J. Med.*,312(3):146-151 (1985).
Elston et al., "Pathological prognostic factors in breast cancer. I. The value of histological grade in breast cancer: experience from a large study with long-term follow-up," *Histopathology*, 19(5):403-410 (1991).
Ester et al., "Imparied BUB1B mRNA expression is associated with osteogenic sarcoma," *Proc. Am. Assoc. Cancer Res.*, 46:1052, abstract 4448 (2005).
Fitzgibbons et al., "Prognostic factors in breast cancer. College of American Pathologists Consensus Statement 1999," *Arch. Pathol. Lab. Med.*, 124(7):966-978 (2000).
Fraser et al., "Columnar alteration with prominent apical snouts and secretions: a spectrum of changes frequently present in breast biopsies performed for microcalcifications," *Am. J. Surg. Pathol.*, 22(12):1521-1527 (1998).
Furey et al., "Support vector machine classification and validation of cancer tissue samples using microarray expression data," *Bioinformatics*, 16(10):906-914 (2000).
Galaktionov et al., "CDC25 phosphatases as potential human oncogenes," *Science*, 269(5230):1575-1577 (1995).
Garber et al., "Diversity of gene expression in adenocarcinoma of the lung," *Proc. Natl. Acad. Sci. USA*, 98(24):13784-13789 (2001).
Gelmini et al., "Quantitative polymerase chain reaction-based homogeneous assay with fluorogenic probes to measure c-erbB-2 oncogene amplification," *Clin. Chem.*, 43(5):752-758 (1997).
GENBANK Accession No. AA454563.1, Jun. 6, 1997.B58.
Gianni et al., "Feasibility and tolerability of sequential doxorubicin/paclitaxel followed by cyclophosphamide, methotrexate, and fluorouracil and its effects on tumor response as preoperative therapy," *Clin. Cancer Res.*, 11(24 Pt 1):8715-8721 (2005).
Goetz et al., "A two-gene expression ratio of homeobox 13 and interleukin-17B receptor for prediction of recurrence and survival in women receiving adjuvant tamoxifen," *Clin. Cancer Res.*, 12(7 Pt 1):2080-2087 (2006).
Goldhirsch et al., "Meeting highlights: international expert consensus on the primary therapy of early breast cancer 2005," *Ann. Oncol.*, 16(10):1569-1583 (2005).
Golub et al., "Molecular classification of cancer: class discovery and class prediction by gene expression monitoring," *Science*, 286(5439):531-537 (1999).
Gonzalez-Angulo et al."Future of personalized medicine in oncology: a systems biology approach," *J. Clin. Oncol.*, 28(16):2777-2783 (2010).
Goss et al., "A randomized trial of letrozole in postmenopausal women after five years of tamoxifen therapy for early-stage breast cancer," *N. Engl. J. Med.*, 349(19):1793-1802 (2003).

(56) References Cited

OTHER PUBLICATIONS

Goss et al., "Randomized Trial of Letrozole Following Tamoxifen as Extended Adjuvant Therapy in Receptor-Positive Breast Cancer: Updated Findings from NCIC CTG MA.17," *J. Natl. Cancer Inst.*, 97(17):1262-1271 (2005).
Gruvberger et al., "Estrogen receptor status in breast cancer is associated with remarkably distinct gene expression patterns," *Cancer Res.*, 61(16):5979-5984 (2001).
Habel et al., "HOXB13:IL17BR and molecular grade index and risk of breast cancer death among patients with lymph node-negative invasive disease," *Breast Cancer Res.*, 15:R24 (2013).
Hartmann et al., "Benign breast disease and the risk of breast cancer," *N. Engl. J. Med.*, 353(3):229-237 (2005).
Hedenfalk et al., "Gene-expression profiles in hereditary breast cancer," *N. Engl. J. Med.*, 344(8):539-548 (2001).
Hirose et al., "MgcRacGAP is involved in cytokinesis through associating with mitotic spindle and midbody," *J. Biol. Chem.*, 276(8):5821-5828 (2001).
Holland et al., "Ductal carcinoma in situ: a proposal for a new classification," *Semin. Diang. Pathol.*, 11(3):167-180 (1994).
Ivshina et al., "Genetic reclassification of histologic grade delineates new clinical subtypes of breast cancer," *Cancer Res.*, 66(21):10292-10301 (2006).
Jansen et al., "HOXB13-to-IL17BR expression ratio is related with tumor aggressiveness and response to tamoxifen of recurrent breast cancer: a retrospective study," *J. Clin. Oncol.*, 25(6):662-668 (2007).
Jerevall et al., "Predictive relevance of HOXB13 protein expression for tamoxifen benefit in breast cancer," *Breast Cancer Res.*, 12(4):R53 (2010).
Korkaya et al., "Regulation of mammary stem/progenitor cells by PTEN/Akt/β-catenin signaling," *PLoS Biology*, 7(6):e100121 (2009).
Lennon et al., "The I.M.A.G.E. Consortium: an integrated molecular analysis of genomes and their expression," *Genomics*, 33(1):151-152 (1996).
Lewis et al., "Molecular classification of melanoma using real-time quantitative reverse transcriptase-polymerase chain reaction," *Cancer*, 104(8):1678-1686 (2005).
Lingle et al., "Centrosome amplification drives chromosomal instability in breast tumor development," *Proc. Natl. Acad. Sci. USA*, 99(4):1978-1983 (2002).
Loi et al., "Definition of clinically distinct molecular subtypes in estrogen receptor-positive breast carcinomas through genomic grade," *J. Clin. Oncol.*, 25(10):1239-1246 (2007).
Lu et al., "SSelection of potential markers for epithelial ovarian cancer with gene expression arrays and recursive descent partition analysis.," *Clin. Cancer Res.*, 10:3291-3300 (2004).
Luo et al., "Gene expression profiles of laser-captured adjacent neuronal subtypes," *Nat. Med.*, 5(1):117-122 (1999).
Ma et al., "A five-gene molecular grade index and HOXB13:IL17BR are complementary prognostic factors in early stage breast cancer," *Clin. Cancer Res.*, 14(9):2601-2608 (2008).
Ma et al., "A two-gene expression ratio predicts clinical outcome in breast cancer patients treated with tamoxifen," *Cancer Cell.*, 5(6):607-616 (2004).
Ma et al., "Gene expression profiles of human breast cancer progression," *Proc. Natl. Acad Sci. USA*, 100(10):5974-5979 (2003).
Ma et al., "HOXB13 may predict response to neoadjuvant letrozole in patients with estrogen receptor-positive breast cancer," Novartis poster, retrieved from the Internet: URL:http://www.biotheranostics.com/wp-content/uploads/Novartis-BTX_SABCS_2009.pdf, retrieved on Dec. 17, 2014, Abstract only.
Ma et al., "The HOXB13:IL17BR expression index is a prognostic factor in early-stage breast cancer," *J. Clin. Oncol.*, 24(28):4611-4619 (2006).
Maacke et al., "Over-expression of wild-type Rad51 correlates with histological grading of invasive ductal breast cancer," *Int. J. Cancer*, 88(6):907-913 (2000).
Mark et al., "HER-2/neu gene amplification in stages I-IV breast cancer detected by fluorescent in situ hybridization," *Genet. Med.*, 1(3):98-103 (1999).
Marshall et al., "Risk of breast cancer associated with tatypical hyperplasia of lobular and ductal types," *Cancer Epidemiol Biomarkers Prev.*, 6(5):297-301 (1997).
May, "How many species are there on earth?," *Science*, 241:1441-1449 (1988).
Miller et al., "An expression signature for p53 status in human breast cancer predicts mutation status, transcriptional effects, and patient survival," *Proc. Natl. Acad. Sci. USA*, 102(38):13550-13555 (2005).
Oyama et al., "Atypical cystic lobules: an early stage in the formation of low-grade ductal carcinoma in situ," *Virchows Arch.*, 435(4):413-421 (1999).
Page et al., "Combined histologic and cytologic criteria for the diagnosis of mammary atypical ductal hyperplasia," *Hum. Pathol.*, 23(10):1095-1097 (1992).
Page et al., "Intraductal carcinoma of the breast: follow-up after biopsy only," *Cancer*, 49(4):751-758 (1982).
Page et al., "Prediction of node-negative breast cancer outcome by histologic grading and S-phase analysis by flow cytometry: an Eastern Cooperative Oncology Group Study (2192)," *Am. J. Clin. Oncol.*, 24(1):10-18 (2001).
Paik et al., "A multigene assay to predict recurrence of tamoxifen-treated, node-negative breast cancer," *N. Engl. J. Med.*, 351(27):2817-2826 (2004).
Paik, "Molecular profiling of breast cancer," *Breast Cancer*, 18:59-63 (2006).
Pawitan et al., "Gene expression profiling spares early breast cancer patients from adjuvant therapy: derived and validated in two population-based cohorts," *Breast Cancer Res.*, 7(6):R953-R964 (2005).
Pepe et al., "An interpretation for the ROC curve and inference using GLM procedures," *Biometrics*, 56(2):352-359 (2000).
Perou et al., "Distinctive gene expression patterns in human mammary epithelial cells and breast cancers," *Proc. Natl. Acad. Sci. USA*, 96(16):9212-9217 (1999).
Perou et al., "Molecular portraits of human breast tumours," *Nature*, 406(6797):747-752 (2000).
Romond et al., "Trastuzumab plus adjuvant chemotherapy for operable HER2-positive breast cancer," *N. Engl. J. Med.*, 353(16):1673-1684 (2005).
Rundle et al., "Design options for molecular epidemiology research within cohort studies," *Cancer Epidemiol Biomarkers Prev.*, 14(8)1899-1907 (2005).
Scintu et al., "Genomic instability and increased expression of BUB1B and MAD2L1 genes in ductal breast carcinoma," *Cancer Letters*, 254:298-307 (2007).
Sengar et al., "The EH and SH3 domain Ese proteins regulate endocytosis by linking to dynamin and Eps15," *EMBO J.*, 18(4):1159-1171 (1999).
Sgroi et al., "In vivo gene expression profile analysis of human breast cancer progression," *Cancer Res.*, 59(22):5656-5661 (1999).
Sgroi et al., "Prediction of late disease recurrence and extended adjuvant letrozole benefit by the HOXB13/IL17BR biomarker," *JNCI*, 105(14): 1036-1042 (2013).
Shah et al., "HOXB13 mediates tamoxifen resistance and invasiveness in human breast cancer by suppressing ERα and inducing IL-6 expression," *Cancer Res.*, 73(17):5449-5458 (2013).
Sheridan et al., "Control of TRAIL-induced apoptosis by a family of signaling and decoy receptors," *Science*, 277(5327):818-821 (1997).
Shou et al., "Mechanisms of tamoxifen resistance: increased estrogen receptor-HER2/neu cross-talk in ER/HER2-positive breast cancer," *J. Natl. Cancer Inst.*, 96(12):926-935 (2004).
Singletary et al., "Revision of the American joint committee on cancer staging system for breast cancer," *J. Clin. Oncol.*, 20(17):3628-3636 (2002).
Sørlie et al., "Gene expression patterns of breast carcinomas distinguish tumor subclasses with clinical implications," *Proc. Natl. Acad. Sci. USA*, 98(19):10869-10874 (2001).

(56) References Cited

OTHER PUBLICATIONS

Sotiriou et al., "Gene expression profiling in breast cancer: understanding the molecular basis of histologic grade to improve prognosis," *J. Nat. Cancer Inst.*, 98(4):262-272 (2006).

Sotiriou et al., "Gene expression profiling in breast cancer: understanding the molecular basis of histologic grade to improve prognosis," *J. Nat. Cancer Inst.*,98(4) Supplemental Data (2006).

Sotiriou et al., "Taking gene-expression profiling to the clinic: when will molecular signatures become relevant to patient care?," *Nat. Rev. Cancer*, 7(7):545-553 (2007).

Strauss et al., "Detection and typing of human papillomavirus DNA in paired urine and cervical scrapes," *Eur. J. Epidermiol*, 15(6):537-543 (1999).

Tarca et al., "A novel signaling pathway impact analysis," *Bioinformatics*, 25:75-82 (2009).

Thomas et al., "The Elf group of Ets-related transcription factors ELF3 and ELF5," *Adv. Exper. Med. Biol.*,480:123-128 (2000).

Turner et al., "Adjuvant chemotherapy: Which patient? What regigmen?," ASCO University, 2013 ASCO Educational Book, [Retrieved on Aug. 17, 2015]. Online ebook. Retrieved from the Internet: <URL:http://meetinglibrary.asco.org/contenU145-132> 5 pages (2013).

Unger et al., "Characterization of adjacent breast tumors using oligonucleotide microarrays," *Breast Cancer Res.*, 3(5):336-341 (2001).

Van Slooten et al., "Expression of Bcl-2 in node-negative breast cancer is associated with various prognostic factors, but does not predict response to one course of perioperative chemotherapy," *Br. J. Cancer*, 74(1):78-85 (1996).

Van 'T Veer et al., "Gene expression profiling predicts clinical outcome of breast cancer," *Nature*, 415(6871):530-536 (2002).

Wang et al., "Gene-expression profiles to predict distant metastasis of lymph-node-negative primary breast cancer," *Lancet*, 365(9460):671-679 (2005).

West et al., "Predicting the clinical status of human breast cancer by using gene expression profiles," *Proc. Natl. Acad. Sci. USA*, 98(20):11462-11467 (2001).

Whitfield et al., "Identification of genes periodically expressed in the human cell cycle and their expression in tumors," *Mol. Biol. Cell.*, 13(6):1977-2000 (2002).

Xiong et al., "Biomarker identification by feature wrappers," *Genome Res.*, 11:1878-1887 (2001).

Yamamoto et al., "Overexpression of BUBR1 is associated with chromosomal instability in bladder cancer," *Cancer Genet. Cytogenet.*, 174(1):42-47 (2007).

Yang et al., "Normalization for cDNA microarray data: a robust composite method addressing single and multiple slide systematic variation," *Nucleic Acids Res.*, 30(4):e15 (2002).

Yeang et al., "Molecular classification of mulitple tumor types," *Bioinformatics*,17(Suppl. 1):S316-S322 (2001).

Yuan et al., "Increase expression of mitotic checkpoint genes in breast cancer cells with chromosomal instability," *Clin. Cancer Res.*, 12(2):405-410 (2006).

Zhou et al., "A novel transcription factor, ELF5, belongs to the ELF subfamily of ETS genes and maps to human chromosome 11p13-15, a region subject to LOH and rearrangement in human carcinoma cell lines," *Oncogene*, 17(21):2719-2732 (1998).

Zhou et al., "Overexpression of transfected human ribonucleotide reductase M2 subunit in human cancer cells enhances their invasive potential," *Clin. Exp. Metastasis*, 16(1):43-49 (1998).

Zhou et al., "Tumour amplified kinase STK15/BTAK induces centrosome amplification, aneuploidy and transformation," *Nat. Genet.*,20(2):189-193 (1998).

Arama et al., "Murine NIMA-related kinases are expressed in patterns suggesting distinct functions in gametogenesis and a role in the nervous system," Oncogene, 16:1813-1823 (1998).

Saito-Hisaminato et al., "Genome-wide profiling of gene expression in 29 normal human tissues with a cDNA microarray," DNA Res., 9:35-45 (2002).

\* cited by examiner

```
                              SEQUENCE LISTING

<160> NUMBER OF SEQ ID NOS: 412

<210> SEQ ID NO 1
<211> LENGTH: 2077
<212> TYPE: DNA
<213> ORGANISM: Homo sapiens

<400> SEQUENCE: 1
agcgcagcgt gcgggtggcc tggatcccgc gcagtggccc ggcgatgtcg ctcgtgctgc      60
taagcctggc cgcgctgtgc aggagcgccg taccccgaga gccgaccgtt caatgtggct     120
ctgaaactgg gccatctcca gagtggatgc tacaacatga tctaatcccc ggagacttga     180
gggacctccg agtagaacct gttacaacta gtgttgcaac aggggactat tcaattttga     240
tgaatgtaag ctgggtactc cgggcagatg ccagcatccg cttgttgaag gccaccaaga     300
tttgtgtgac gggcaaaagc aacttccagt cctacagctg tgtgaggtgc aattacacag     360
aggccttcca gactcagacc agaccctctg gtggtaaatg acatttttcc tacatcggct     420
tccctgtaga gctgaacaca gtctatttca ttggggccca taatattcct aatgcaaata     480
tgaatgaaga tggcccttcc atgtctgtga atttcacctc accaggctgc ctagaccaca     540
taatgaaata taaaaaaaag tgtgtcaagg ccggaagcct gtgggatccg aacatcactg     600
cttgtaagaa gaatgaggag acagtagaag tgaacttcac aaccactccc ctgggaaaca     660
gatacatggc tcttatccaa cacagcacta tcatcggggtt ttctcaggtg tttgagccac     720
accagaagaa acaaacgcga gcttcagtgg tgattccagt gactggggat agtgaaggtg     780
ctacggtgca gctgactcca tattttccta cttgtggcag cgactgcatc cgacataaag     840
gaacagttgt gctctgccca caaacaggcg tccctttccc tctggataac aacaaaagca     900
agccgggagg ctggctgcct ctcctcctgc tgtctctgct ggtggccaca tgggtgctgg     960
tggcagggat ctatctaatg tggaggcacg aaaggatcaa gaagacttcc ttttctacca    1020
ccacactact gccccccatt aaggttcttg tggtttaccc atctgaaata tgtttccatc    1080
acacaatttg ttacttcact gaatttcttc aaaaccattg cagaagtgag gtcatccttg    1140
aaaagtggca gaaaaagaaa atagcagaga tgggtccagt gcagtggctt gccactcaaa    1200
agaaggcagc agacaaagtc gtcttccttc tttccaatga cgtcaacagt gtgtgcgatg    1260
gtacctgtgg caagagcgag ggcagtccca gtgagaactc tcaagacctc ttccccttg    1320 cctttaacct tttctgcagt gatctaagaa gccagattca tctgcacaaa tacgtggtgg    1380
tctactttag agagattgat acaaaagacg attacaatgc tctcagtgtc tgccccaagt    1440
accacctcat gaaggatgcc actgctttct gtgcagaact tctccatgtc aagcagcagg    1500
tgtcagcagg aaaaagatca caagcctgcc acgatggctg ctgctccttg tagcccaccc    1560
atgagaagca agagaccttg aaggcttcct atcccaccaa ttacagggaa aaaacgtgtg    1620
atgatcctga agcttactat gcagcctaca acagcctta gtaattaaaa cattttatac    1680
caataaaatt ttcaaatatt gctaactaat gtagcattaa ctaacgattg gaaactacat    1740
ttacaacttc aaagctgttt tatacataga aatcaattac agttttaatt gaaaactata    1800
accattttga taatgcaaca ataaagcatc ttcagccaaa catctagtct tccatagacc    1860
atgcattgca gtgtacccag aactgtttag ctaatattct atgtttaatt aatgaatact    1920
aactctaaga acccctcact gattcactca atagcatctt aagtgaaaaa ccttctatta    1980
```

| | |
|---|---|
| catgcaaaaa atcattgttt ttaagataac aaaagtaggg aataaacaag ctgaacccac | 2040 |
| tttttaaaaaa aaaaaaaaaa aaaaaaaaaa aaaaaaa | 2077 |

<210> SEQ ID NO 2
<211> LENGTH: 3105
<212> TYPE: DNA
<213> ORGANISM: Homo sapiens

<400> SEQUENCE: 2

| | |
|---|---|
| agcgcagcgt gcgggtggcc tggatcccgc gcagtggccc ggcgatgtcg ctcgtgctgc | 60 |
| taagcctggc cgcgctgtgc aggagcgccg taccccgaga gccgaccgtt caatgtggct | 120 |
| ctgaaactgg gccatctcca gagtggatgc tacaacatga tctaatcccc ggagacttga | 180 |
| gggacctccg agtagaacct gttacaacta gtgttgcaac aggggactat tcaattttga | 240 |
| tgaatgtaag ctgggtactc cgggcagatg ccagcatccg cttgttgaag gccaccaaga | 300 |
| tttgtgtgac gggcaaaagc aacttccagt cctacagctg tgtgaggtgc aattacacag | 360 |
| aggccttcca gactcagacc agaccctctg gtggtaaatg gacatttttcc tacatcggct | 420 |
| tccctgtaga gctgaacaca gtctatttca ttggggccca taatattcct aatgcaaata | 480 |
| tgaatgaaga tggccctttcc atgtctgtga atttcacctc accaggctgc ctagaccaca | 540 |
| taatgaaata taaaaaaaag tgtgtcaagg ccggaagcct gtgggatccg aacatcactg | 600 |
| cttgtaagaa gaatgaggag acagtagaag tgaacttcac aaccactccc ctgggaaaca | 660 |
| gatacatggc tcttatccaa cacagcacta tcatcgggtt ttctcaggtg tttgagccac | 720 |
| accagaagaa acaaacgcga gcttcagtgg tgattccagt gactgggggat agtgaaggtg | 780 |
| ctacggtgca ggtaaagttc agtgagctgc tctggggagg aagggacat agaagactgt | 840 |
| tccatcattc attgctttta aggatgagtt ctctcttgtc aaatgcactt ctgccagcag | 900 |
| acaccagtta agtggcgttc atgggggctc tttcgctgca gcctccaccg tgctgaggtc | 960 |
| aggaggccga cgtggcagtt gtggtccctt ttgcttgtat taatggctgc tgaccttcca | 1020 |
| aagcactttt tattttcatt ttctgtcaca gacactcagg gatagcagta ccatttttact | 1080 |
| tccgcaagcc tttaactgca agatgaagct gcaaagggtt tgaaatggga aggtttgagt | 1140 |
| tccaggcagc gtatgaactc tggagagggg ctgccagtcc tctctgggcc gcagcggacc | 1200 |
| cagctggaac acaggaagtt ggagcagtag gtgctccttc acctctcagt atgtctcttt | 1260 |
| caactctagt ttttgaggtg gggacacagg aggtccagtg ggacacagcc actccccaaa | 1320 |
| gagtaaggag cttccatgct tcattccctg gcataaaaag tgctcaaaca caccagaggg | 1380 |
| ggcaggcacc agccagggta tgatggctac tacccttttc tggagaacca tagacttccc | 1440 |
| ttactacagg gacttgcatg tcctaaagca ctggctgaag gaagccaaga ggatcactgc | 1500 |
| tgctcctttt ttctagagga aatgtttgtc tacgtggtaa gatatgaccct agccctttta | 1560 |
| ggtaagcgaa ctggtatgtt agtaacgtgt acaaagttta ggttcagacc ccggagtct | 1620 |
| tgggcacgtg ggtctcgggt cactggtttt gactttaggg ctttgttaca gatgtgtgac | 1680 |
| caagggaaa atgtgcatga caacactaga ggtatgggcg aagccagaaa gaagggaagt | 1740 |
| tttggctgaa gtaggagtct tggtgagatt ttgctctgat gcatggtgtg aactttctga | 1800 |
| gcctcttgtt tttcctcagc tgactccata ttttcctact tgtggcagcg actgcatccg | 1860 |
| acataaagga acagttgtgc tctgcccaca aacaggcgtc cctttccctc tggataacaa | 1920 |
| caaaagcaag ccgggaggct ggctgcctct cctcctgctg tctctgctgg tggccacatg | 1980 |
| ggtgctggtg gcagggatct atctaatgtg gaggcacgaa aggatcaaga agacttcctt | 2040 |

```
ttctaccacc acactactgc cccccattaa ggttcttgtg gtttacccat ctgaaatatg    2100
tttccatcac acaatttgtt acttcactga atttcttcaa aaccattgca gaagtgaggt    2160
catccttgaa aagtggcaga aaaagaaaat agcagagatg gtccagtgc  agtggcttgc    2220 cactcaaaag aaggcagcag acaaagtcgt cttccttctt tccaatgacg tcaacagtgt    2280
gtgcgatggt acctgtggca agagcgaggg cagtcccagt gagaactctc aagacctctt    2340 ccccttgcc  tttaacctt  tctgcagtga tctaagaagc cagattcatc tgcacaaata    2400
cgtggtggtc tactttagag agattgatac aaaagacgat tacaatgctc tcagtgtctg    2460
ccccaagtac cacctcatga aggatgccac tgctttctgt gcagaacttc tccatgtcaa    2520
gcagcaggtg tcagcaggaa aaagatcaca agcctgccac gatggctgct gctccttgta    2580
gcccacccat gagaagcaag agaccttaaa ggcttcctat cccaccaatt acagggaaaa    2640
aacgtgtgat gatcctgaag cttactatgc agcctacaaa cagccttagt aattaaaaca    2700
ttttatacca ataaaatttt caaatattgc taactaatgt agcattaact aacgattgga    2760
aactacattt acaacttcaa agctgtttta tacatagaaa tcaattacag ttttaattga    2820
aaactataac cattttgata atgcaacaat aaagcatctt cagccaaaca tctagtcttc    2880
catagaccat gcattgcagt gtacccagaa ctgtttagct aatattctat gtttaattaa    2940
tgaatactaa ctctaagaac ccctcactga ttcactcaat agcatcttaa gtgaaaaacc    3000
ttctattaca tgcaaaaaat cattgttttt aagataacaa aagtagggaa taaacaagct    3060
gaacccactt ttaaaaaaaa aaaaaaaaaa aaaaaaaaaa aaaaa                    3105
```

<210> SEQ ID NO 3
<211> LENGTH: 2856
<212> TYPE: DNA
<213> ORGANISM: Homo sapiens
<220> FEATURE:
<221> NAME/KEY: misc_feature
<222> LOCATION: (1325)..(1325)
<223> OTHER INFORMATION: a or g or c or t/u

<400> SEQUENCE: 3

```
cggcgatgtc gctcgtgctg ataagcctgg ccgcgctgtg caggagcgcc gtaccccgag      60
agccgaccgt tcaatgtggc tctgaaactg ggccatctcc agagtggatg ctacaacatg     120
atctaatccc cggagacttg agggacctcc gagtagaacc tgttacaact agtgttgcaa     180
caggggacta ttcaattttg atgaatgtaa gctgggtact ccgggcagat gccagcatcc     240
gcttgttgaa ggccaccaag atttgtgtga cgggcaaaag caacttccag tcctacagct     300
gtgtgaggtg caattacaca gaggccttcc agactcagac cagaccctct ggtggtaaat     360
ggacattttc ctatatcggc ttccctgtag agctgaacac agtctatttc attggggccc     420
ataatattcc taatgcaaat atgaatgaag atggcccttc catgtctgtg aatttcaccct    480 caccaggctg cctagaccac ataatgaaat ataaaaaaaa gtgtgtcaag gccggaagcc     540
tgtgggatcc gaacatcact gcttgtaaga agaatgagga gacagtagaa gtgaacttca     600
caaccactcc cctgggaaac agatacatgg ctcttatcca acacagcact atcatcgggt     660
tttctcaggt gtttgagcca caccagaaga acaaacgcg  agcttcagtg gtgattccag     720
tgactgggga tagtgaaggt gctacggtgc aggtaaagtt cagtgagctg ctctggggag     780
ggaagggaca tagaagactg ttccatcatt cattgctttt aaggatgagt tctctccttgt     840 caaatgcact tctgccagca gacaccagtt aagtggcgtt catgggggtt ctttcgctgc     900
```

| | | | | | |
|---|---|---|---|---|---|
| agcctccacc | gtgctgaggt | caggaggccg | acgtggcagt | tgtggtccct | tttgcttgta | 960 |
| ttaatggctg | ctgaccttcc | aaagcacttt | ttatttttcat | tttctgtcac | agacactcag | 1020 |
| ggatagcagt | accattttac | ttccgcaagc | ctttaactgc | aagatgaagc | tgcaaagggt | 1080 |
| ttgaaatggg | aaggtttgag | ttccaggcag | cgtatgaact | ctggagaggg | gctgccagtc | 1140 |
| ctctctgggc | cgcagcggac | ccagctggaa | cacaggaagt | tggagcagta | ggtgctcctt | 1200 |
| cacctctcag | tatgtctctt | tcaactctag | ttttttgaagt | ggggacacag | gaagtccagt | 1260 |
| ggggacacag | ccactcccca | aagaataagg | aacttccatg | cttcattccc | tggcataaaa | 1320 |
| agtgntcaaa | cacaccagag | ggggcaggca | ccagccaggg | tatgatgggt | actacccttt | 1380 |
| tctggagaac | catagacttc | ccttactaca | gggacttgca | tgtcctaaag | cactggctga | 1440 |
| aggaagccaa | gaggatcact | gctgctcctt | ttttgtagag | gaaatgtttg | tgtacgtggt | 1500 |
| aagatatgac | ctagccettt | taggtaagcg | aactggtatg | ttagtaacgt | gtacaaagtt | 1560 |
| taggttcaga | ccccgggagt | cttgggcatg | tgggtctcgg | gtcactggtt | ttgactttag | 1620 |
| ggctttgtta | cagatgtgtg | accaagggga | aaatgtgcat | gacaacacta | gaggtagggg | 1680 |
| cgaagccaga | aagaagggaa | gttttggctg | aagtaggagt | cttggtgaga | ttttgctgtg | 1740 |
| atgcatggtg | tgaactttct | gagcctcttg | ttttcctca | gctgactcca | tattttccta | 1800 |
| cttgtggcag | cgactgcatc | cgacataaag | gaacagttgt | gctctgccca | caaacaggcg | 1860 |
| tcccttttccc | tctggataac | aacaaaagca | agccgggagg | ctggctgcct | ctcctcctgc | 1920 |
| tgtctctgct | ggtggccaca | tgggtgctgg | tggcagggat | ctatctaatg | tggaggcacg | 1980 |
| aaaggatcaa | gaagacttcc | ttttctacca | ccacactact | gccccccatt | aaggttcttg | 2040 |
| tggtttaccc | atctgaaata | tgtttccatc | acacaatttg | ttacttcact | gaatttcttc | 2100 |
| aaaaccattg | cagaagtgag | gtcatccttg | aaaagtggca | gaaaaagaaa | atagcagaga | 2160 |
| tgggtccagt | gcagtggctt | gccactcaaa | agaaggcagc | agacaaagtc | gtcttccttc | 2220 |
| tttccaatga | cgtcaacagt | gtgtgcgatg | gtacctgtgg | caagagcgag | ggcagtccca | 2280 |
| gtgagaactc | tcaagacctc | ttccccctg | cctttaacct | tttctgcagt | gatctaagaa | 2340 |
| gccagattca | tctgcacaaa | tacgtggtgg | tctactttag | agagattgat | acaaaagacg | 2400 |
| attacaatgc | tctcagtgtc | tgccccaagt | accacttcat | gaaggatgcc | actgctttct | 2460 |
| gtgcagaact | tctccatgtc | aagcagcagg | tgtcagcagg | aaaaagatca | caagcctgcc | 2520 |
| acgatggctg | ctgctccttg | tagcccaccc | atgagaagca | agagaccttta | aaggcttcct | 2580 |
| atcccaccaa | ttacagggaa | aaaacgtgtg | atgatcctga | agcttactat | gcagcctaca | 2640 |
| aacagcctta | gtaattaaaa | cattttatac | caataaaatt | ttcaaatatt | actaactaat | 2700 |
| gtagcattaa | ctaacgattg | gaaactacat | ttacaacttc | aaagctgttt | tatacataga | 2760 |
| aatcaattac | agctttaatt | gaaaactgta | accattttga | taatgcaaca | ataaagcatc | 2820 |
| ttccaaaaaa | aaaaaaaaa | aaaaaaaaaa | aaaaaa | | | 2856 |

```
<210> SEQ ID NO 4
<211> LENGTH: 7193
<212> TYPE: DNA
<213> ORGANISM: Homo sapiens

<400> SEQUENCE: 4
```

| | | | | | |
|---|---|---|---|---|---|
| agaataaggg | cagggaccgc | ggctcctatc | tcttggtgat | ccccttcccc | attccgcccc | 60 |
| cgcctcaacg | cccagcacag | tgccctgcac | acagtagtcg | ctcaataaat | gttcgtggat | 120 |
| gatgatgatg | atgatgatga | aaaaaatgca | gcatcaacgg | cagcagcaag | cggaccacgc | 180 |

```
gaacgaggca aactatgcaa gaggcaccag acttcctctt tctggtgaag gaccaacttc    240
tcagccgaat agctccaagc aaactgtcct gtcttggcaa gctgcaatcg atgctgctag    300
acaggccaag gctgcccaaa ctatgagcac ctctgcaccc ccacctgtag gatctctctc    360
ccaaagaaaa cgtcagcaat acgccaagag caaaaaacag ggtaactcgt ccaacagccg    420
acctgcccgc gccctttttct gtttatcact caataacccc atccgaagag cctgcattag    480
tatagtggaa tggaaaccat ttgacatatt tatattattg ctattttttg ccaattgtgt    540
ggccttagct atttacatcc cattccctga agatgattct aattcaacaa atcataactt    600
ggaaaaagta gaatatgcct tcctgattat ttttacagtc gagacatttt tgaagattat    660
agcgtatgga ttattgctac atcctaatgc ttatgttagg aatggatgga atttactgga    720
ttttgttata gtaatagtag gattgtttag tgtaattttg gaacaattaa ccaaagaaac    780
agaaggcggg aaccactcaa gcggcaaatc tggaggcttt gatgtcaaag ccctccgtgc    840 cttcgagtg ttgcgaccac ttcgactagt gtcaggggtg cccagtttac aagttgtcct    900
gaactccatt ataaaagcca tggttcccct ccttcacata gccctttttgg tattatttgt    960 aatcataatc tatgctatta taggattgga acttttatt ggaaaaatgc acaaaacatg    1020
tttttttgct gactcagata tcgtagctga agaggaccca gctccatgtg cgttctcagg    1080
gaatggacgc cagtgtactg ccaatggcac ggaatgtagg agtggctggg ttggcccgaa    1140
cggaggcatc accaactttg ataactttgc ctttgccatg cttactgtgt tcagtgcat    1200 caccatggag ggctggacag acgtgctcta ctgggtaaat gatgcgatag gatgggaatg    1260
gccatgggtg tattttgtta gtctgatcat ccttggctca tttttcgtcc ttaacctggt    1320
tcttggtgtc cttagtggag aattctcaaa ggaaagagag aaggcaaaag cacggggaga    1380
tttccagaag ctccgggaga agcagcagct ggaggaggat ctaaagggct acttggattg    1440
gatcacccaa gctgaggaca tcgatccgga gaatgaggaa gaaggaggag aggaaggcaa    1500
acgaaatact agcatgccca ccagcgagac tgagtctgtg aacacagaga acgtcagcgg    1560
tgaaggcgag aaccgaggct gctgtggaag tctctggtgc tggtggagac ggagaggcgc    1620
ggccaaggcg gggccctctg ggtgtcggcg gtggggtcaa gccatctcaa aatccaaact    1680
cagccgacgc tggcgtcgct ggaaccgatt caatcgcaga agatgtaggg ccgccgtgaa    1740
gtctgtcacg ttttactggc tggttatcgt cctggtgttt ctgaacaccct taaccatttc    1800 ctctgagcac tacaatcagc cagattggtt gacacagatt caagatattg ccaacaaagt    1860
cctcttggct ctgttcacct gcgagatgct ggtaaaaatg tacagcttgg gcctccaagc    1920
atatttcgtc tctcttttca accggtttga ttgcttcgtg gtgtgtggtg gaatcactga    1980
gacgatcctg tgtgaactgg aaatcatgtc tccctgggg atctctgtgt ttcggtgtgt    2040
gcgcctctta agaatcttca aagtgaccag gcactggact tccctgagca acttagtggc    2100
atccttatta aactccatga agtccatcgc ttcgctgttg cttctgcttt ttctcttcat    2160 tatcatctttt tccttgcttg ggatgcagct gtttggcggc aagtttaatt ttgatgaaac    2220
gcaaaccaag cggagcacct ttgacaattt ccctcaagca cttctcacag tgttccagat    2280
cctgacaggc gaagactgga atgctgtgat gtacgatggc atcatggctt acggggggccc    2340 atcctcttca ggaatgatcg tctgcatcta cttcatcatc ctcttcattt gtggtaacta    2400
tattctactg aatgtcttct ggccatcgc tgtagacaat ttggctgatg ctgaaagtct    2460
gaacactgct cagaaagaag aagcggaaga aaaggagagg aaaagattg ccagaaaaga    2520
```

```
gagcctagaa aataaaaaga acaacaaacc agaagtcaac cagatagcca acagtgacaa   2580
caaggttaca attgatgact atagagaaga ggatgaagac aaggacccct atccgccttg   2640
cgatgtgcca gtaggggaag aggaagagga agaggaggag gatgaacctg aggttcctgc   2700 cggacccgt cctcgaagga tctcggagtt gaacatgaag gaaaaaattg cccccatccc    2760
tgaagggagc gctttcttca ttcttagcaa gaccaacccg atccgcgtag gctgccacaa   2820
gctcatcaac caccacatct tcaccaacct catccttgtc ttcatcatgc tgagcagcgc   2880
tgccctggcc gcagaggacc ccatccgcag ccactccttc cggaacacga tactgggtta   2940
ctttgactat gccttcacag ccatctttac tgttgagatc ctgttgaaga tgacaacttt   3000
tggagctttc ctccacaaag gggccttctg caggaactac ttcaatttgc tggatatgct   3060
ggtggttggg gtgtctctgg tgtcatttgg gattcaatcc agtgccatct ccgttgtgaa   3120
gattctgagg gtcttaaggg tcctgcgtcc cctcagggcc atcaacagag caaaaggact   3180
taagcacgtg gtccagtgcg tcttcgtggc catcccggac atcggcaaca tcatgatcgt   3240 cactacccctc ctgcagttca tgtttgcctg tatcggggtc cagttgttca aggggaagtt   3300
ctatcgctgt acggatgaag ccaaaagtaa ccctgaagaa tgcaggggac ttttcatcct   3360
ctacaaggat ggggatgttg acagtcctgt ggtccgtgaa cggatctggc aaaacagtga   3420
tttcaacttc gacaacgtcc tctctgctat gatggcgctc ttcacagtct ccacgtttga   3480
gggctggcct gcgttgctgt ataaagccat cgactcgaat ggagagaaca tcggcccaat   3540
ctacaaccac cgcgtggaga tctccatctt cttcatcatc tacatcatca ttgtagcttt   3600
cttcatgatg aacatctttg tgggcttttgt catcgttaca tttcaggaac aaggagaaaa   3660
agagtataag aactgtgagc tggacaaaaa tcagcgtcag tgtgttgaat acgccttgaa   3720
agcacgtccc ttgcggagat acatccccaa aaaccctac cagtacaagt tctggtacgt   3780
ggtgaactct tcgcctttcg aatacatgat gtttgtcctc atcatgctca acacactctg   3840
cttggccatg cagcactacg agcagtccaa gatgttcaat gatgccatgg acattctgaa   3900
catggtcttc accggggtgt tcaccgtcga gatggttttg aaagtcatcg catttaagcc   3960
taaggggtat tttagtgacg cctggaacac gtttgactcc ctcatcgtaa tcggcagcat   4020
tatagacgtg gccctcagcg aagcggaccc aactgaaagt gaaaatgtcc ctgtcccaac   4080
tgctacacct gggaactctg aagagagcaa tagaatctcc atcaccttt tccgtctttt    4140 ccgagtgatg cgattggtga agcttctcag cagggggggaa ggcatccgga cattgctgtg   4200
gacttttatt aagtcctttc aggcgctccc gtatgtggcc ctcctcatag ccatgctgtt   4260
cttcatctat gcggtcattg gcatgcagat gtttgggaaa gttgccatga gagataacaa   4320
ccagatcaat aggaacaata acttccagac gtttcccag gcggtgctgc tgctcttcag    4380
gtgtgcaaca ggtgaggcct ggcaggagat catgctggcc tgtctcccag ggaagctctg   4440
tgaccctgag tcagattaca accccgggga ggagtataca tgtgggagca actttgccat   4500
tgtctatttc atcagttttt acatgctctg tgcatttctg atcatcaatc tgtttgtggc   4560
tgtcatcatg gataatttcg actatctgac ccgggactgg tctattttgg ggcctcacca   4620
tttagatgaa ttcaaaagaa tatggtcaga atatgaccct gaggcaaagg gaaggataaa   4680
acaccttgat gtggtcactc tgcttcgacg catccagcct cccctgggt ttgggaagtt    4740 atgtccacac agggtagcgt gcaagagatt agttgccatg aacatgcctc tcaacagtga   4800
cgggacagtc atgtttaatg caaccctgtt tgctttggtt cgaacggctc ttaagatcaa   4860
gaccgaaggg aacctggagc aagctaatga agaacttcgg gctgtgataa agaaaattg    4920
```

```
gaagaaaacc agcatgaaat tacttgacca agttgtccct ccagctggtg atgatgaggt    4980
aaccgtgggg aagttctatg ccactttcct gatacaggac tactttagga aattcaagaa    5040
acggaaagaa caaggactgg tgggaaagta ccctgcgaag aacaccacaa ttgccctaca    5100
ggcgggatta aggacactgc atgacattgg gccagaaatc cggcgtgcta tatcgtgtga    5160
tttgcaagat gacgagcctg aggaaacaaa acgagaagaa gaagatgatg tgttcaaaag    5220
aaatggtgcc ctgcttggaa accatgtcaa tcatgttaat agtgatagga gagattccct    5280
tcagcagacc aataccaccc accgtcccct gcatgtccaa aggccttcaa ttccacctgc    5340
aagtgatact gagaaaccgc tgtttcctcc agcaggaaat tcggtgtgtc ataaccatca    5400
taaccataat tccataggaa agcaagttcc cacctcaaca aatgccaatc tcaataatgc    5460
caatatgtcc aaagctgccc atggaaagcg gcccagcatt gggaaccttg agcatgtgtc    5520
tgaaaatggg catcattctt cccacaagca tgaccgggag cctcagagaa ggtccagtgt    5580
gaaaagaacc cgctattatg aaacttacat taggtccgac tcaggagatg aacagctccc    5640
aactatttgc cgggaagacc cagagataca tggctatttc agggaccccc actgcttggg    5700
ggagcaggag tatttcagta gtgaggaatg ctacgaggat gacagctcgc ccacctggag    5760
caggcaaaac tatggctact acagcagata cccaggcaga aacatcgact ctgagaggcc    5820
ccgaggctac catcatcccc aaggattctt ggaggacgat gactcgcccg tttgctatga    5880
ttcacggaga tctccaagga gacgcctact acctcccacc ccagcatccc accggagatc    5940
ctccttcaac tttgagtgcc tgcgccggca gagcagccag gaagaggtcc cgtcgtctcc    6000
catcttcccc catcgcacgg ccctgcctct gcatctaatg cagcaacaga tcatggcagt    6060
tgccggccta gattcaagta aagcccagaa gtactcaccg agtcactcga cccggtcgtg    6120
ggccacccct ccagcaaccc ctccctaccg ggactggaca ccgtgctaca ccccctgat    6180
ccaagtggag cagtcagagg ccctggacca ggtgaacggc agcctgccgt ccctgcaccg    6240
cagctcctgg tacacagacg agcccgacat ctcctaccgg actttcacac cagccagcct    6300
gactgtcccc agcagcttcc ggaacaaaaa cagcgacaag cagaggagtg cggacagctt    6360
ggtggaggca gtcctgatat ccgaaggctt gggacgctat gcaagggacc caaaatttgt    6420
gtcagcaaca aaaacgaaa tcgctgatgc ctgtgacctc accatcgacg agatggagag    6480
tgcagccagc accctgctta tgggaacgt gcgtccccga gccaacgggg atgtgggccc    6540
cctctcacac cggcaggact atgagctaca ggactttggt cctggctaca gcgacgaaga    6600
gccagaccct gggagggatg aggaggacct ggcggatgaa atgatatgca tcaccacctt    6660
gtagccccca gcgaggggca gactggctct ggcctcaggt ggggcgcagg agagccaggg    6720
gaaaagtgcc tcatagttag gaaagtttag gcactagttg ggagtaatat tcaattaatt    6780
agacttttgt ataagagatg tcatgcctca agaaagccat aaacctggta ggaacaggtc    6840
ccaagcggtt gagcctggca gagtaccatg cgctcggccc cagctgcagg aaacagcagg    6900
ccccgccctc tcacagagga tgggtgagga ggccagacct gccctgcccc attgtccaga    6960
tgggcactgc tgtggagtct gcttctccca tgtaccaggg caccaggccc acccaactga    7020
aggcatggcg gcggggtgca ggggaaagtt aaaggtgatg acgatcatca cacctcgtgt    7080
cgttacctca gccatcggtc tagcatatca gtcactgggc ccaacatatc cattttaaa    7140
ccctttcccc caaatacact gcgtcctggt tcctgtttag ctgttctgaa ata          7193
```

<210> SEQ ID NO 5

```
<211> LENGTH: 675
<212> TYPE: DNA
<213> ORGANISM: Homo sapiens

<400> SEQUENCE: 5 ttttttttt  tttttttttt  tcttacaaag  aaaaatttaa  tattcgatga  gaggttgaac    60
caggcttaaa  gcagacatac  taggaaatgg  tgcagcctgt  aagaatgcca  gtttgtaagt   120
actgactttg  gaaaagatca  tcgcctctat  cagacactta  gggtcctggt  ctggcaattt   180
tggcctgatg  tgatgccaca  agacccaaca  gagagagaca  cagagtccag  gataatgttg   240
acagtggtgt  agcccttag   gagaaatggc  gctccctgcg  gctggtatta  ggttaccatt   300
ggcaccgaag  gaaccaggag  gataagaata  tccataattt  cagagctgcc  ctggcacagt   360
acctgccccg  tcggaggctc  tcactggcaa  atgacagctc  tgtgcaagga  gcactcccaa   420
gtataaaaat  tattacacag  ttttattctg  aagaacattt  tgcattttaa  taaaaaagga   480
tttatgtcag  gaaagagtca  tttacaaacc  ttgaagtgtt  tttgcctgga  tcagagtaag   540
aatgtcttaa  gaagaggttt  gtaaggtctt  cataacaaag  tggtgtttgt  tatttacaaa   600
aaaaaaaaaa  aaaaaaatta  acaggttgtc  tgtatactat  taaaaatttt  ggaccaaaaa   660
aaaaaaaaaa  aaaaa                                                       675

<210> SEQ ID NO 6
<211> LENGTH: 1270
<212> TYPE: DNA
<213> ORGANISM: Homo sapiens

<400> SEQUENCE: 6
cgaatgcagg  cgacttgcga  gctgggagcg  atttaaaacg  ctttggattc  ccccggcctg    60
ggtggggaga  gcgagctggg  tgcccccctag  attccccgcc  cccgcacctc  atgagccgac   120
cctcggctcc  atggagcccg  gcaattatgc  caccttggat  ggagccaagg  atatcgaagg   180
cttgctggga  gcgggagggg  ggcggaatct  ggtcgcccac  tcccctctga  ccagccaccc   240
agcggcgcct  acgctgatgc  ctgctgtcaa  ctatgccccc  ttggatctgc  caggctcggc   300
ggagccgcca  aagcaatgcc  acccatgccc  tggggtgccc  caggggacgt  ccccagctcc   360
cgtgccttat  ggttactttg  gaggcgggta  ctactcctgc  cgagtgtccc  ggagctcgct   420
gaaaccctgt  gcccaggcag  ccaccctggc  cgcgtacccc  gcggagactc  ccacggccgg   480
ggaagagtac  cccagtcgcc  ccactgagtt  tgccttctat  ccgggatatc  cgggaaccta   540
ccacgctatg  gccagttacc  tggacgtgtc  tgtggtgcag  actctgggtg  ctcctggaga   600
accgcgacat  gactccctgt  tgcctgtgga  cagttaccag  tcttgggctc  tcgctggtgg   660
ctggaacagc  cagatgtgtt  gccagggaga  acagaaccca  ccaggtccct  tttggaaggc   720
agcatttgca  gactccagcg  ggcagcaccc  tcctgacgcc  tgcgcctttc  gtcgcggccg   780
caagaaacgc  attccgtaca  gcaaggggca  gttgcgggag  ctggagcggg  agtatgcggc   840
taacaagttc  atcaccaagg  acaagaggcg  caagatctcg  gcagccacca  gcctctcgga   900
gcgccagatt  accatctggt  ttcagaaccg  ccgggtcaaa  gagaagaagg  ttctcgccaa   960
ggtgaagaac  agcgctaccc  cttaagagat  ctccttgcct  gggtgggagg  agcgaaagtg  1020
ggggtgtcct  ggggagacca  gaaacctgcc  aagcccaggc  tggggccaag  gactctgctg  1080
agagggccct  agagacaaca  cccttcccag  gccactggct  gctggactgt  tcctcaggag  1140
cggcctgggt  acccagtatg  tgcagggaga  cggaaccccca  tgtgacaggc  ccactccacc  1200
agggttccca  aagaacctgg  cccagtcata  atcattcatc  ctcacagtgg  caataatcac  1260
```

```
                                                         gataaccagt                                          1270

<210> SEQ ID NO 7
<211> LENGTH: 1356
<212> TYPE: DNA
<213> ORGANISM: Homo sapiens

<400> SEQUENCE: 7
ggattccccc ggcctgggtg gggagagcga gctgggtgcc ccctagattc cccgcccccg      60
cacctcatga gccgaccctc ggctccatgg agcccggcaa ttatgccacc ttggatggag     120
ccaaggatat cgaaggcttg ctgggagcgg agggggggcg gaatctggtc gcccactccc     180
ctctgaccag ccacccagcg gcgcctacgc tgatgcctgc tgtcaactat gccccttgg     240 atctgccagg ctcggcggag ccgccaaagc aatgccaccc atgccctggg gtgccccagg     300
ggacgtcccc agctcccgtg ccttatggtt actttggagg cgggtactac tcctgccgag     360
tgtcccggag ctcgctgaaa ccctgtgccc aggcagccac cctggccgcg taccccgcgg     420
agactcccac ggccggggaa gagtacccca gccgcccac tgagtttgcc ttctatccgg     480
gatatccggg aacctaccag cctatggcca gttacctgga cgtgtctgtg gtgcagactc     540
tgggtgctcc tggagaaccg cgacatgact ccctgttgcc tgtggacagt taccagtctt     600
gggctctcgc tggtggctgg aacagccaga tgtgttgcca gggagaacag aacccaccag     660 gtccctttt gaaggcagca tttgcagact ccagcgggca gcaccctcct gacgcctgcg     720
cctttcgtcg cggccgcaag aaacgcattc cgtacagcaa ggggcagttg cgggagctgg     780
agcgggagta tgcggctaac aagttcatca ccaaggacaa gaggcgcaag atctcggcag     840
ccaccagcct ctcggagcgc cagattacca tctggtttca gaaccgccgg gtcaaagaga     900
agaaggttct cgccaaggtg aagaacagcg ctaccccta agagatctcc ttgcctgggt     960
gggaggagcg aaagtggggg tgtcctgggg agaccaggaa cctgccaagc ccaggctggg    1020
gccaaggact ctgctgagag gcccctagag acaacaccct tcccaggcca ctggctgctg    1080
gactgttcct caggagcggc ctgggtaccc agtatgtgca gggagacgga accccatgtg    1140
acagcccact ccaccagggt tcccaaagaa cctggcccag tcataatcat tcatcctgac    1200
agtggcaata atcacgataa ccagtactag ctgccatgat cgttagcctc atattttcta    1260
tctagagctc tgtagagcac tttagaaacc gctttcatga attgagctaa ttatgaataa    1320
atttggaaaa aaaaaaaaaa aaaaaaaaaa aaaaaa                              1356

<210> SEQ ID NO 8
<211> LENGTH: 60
<212> TYPE: DNA
<213> ORGANISM: Homo sapiens

<400> SEQUENCE: 8
caattacagg gaaaaaacgt gtgatgatcc tgaagcttac tatgcagcct acaaacagcc      60

<210> SEQ ID NO 9
<211> LENGTH: 60
<212> TYPE: DNA
<213> ORGANISM: Homo sapiens

<400> SEQUENCE: 9
gctctcactg gcaaatgaca gctctgtgca aggagcactc ccaagtataa aaattattac      60

<210> SEQ ID NO 10
```

```
<211> LENGTH: 60
<212> TYPE: DNA
<213> ORGANISM: Homo sapiens

<400> SEQUENCE: 10
gatcgttagc ctcatatttt ctatctagag ctctgtagag cactttagaa accgctttca        60

<210> SEQ ID NO 11
<211> LENGTH: 60
<212> TYPE: DNA
<213> ORGANISM: Homo sapiens

<400> SEQUENCE: 11
tgcctaattt cactctcaga gtgaggcagg taactggggc tccactgggt cactctgaga        60

<210> SEQ ID NO 12
<211> LENGTH: 60
<212> TYPE: DNA
<213> ORGANISM: Homo sapiens

<400> SEQUENCE: 12
ttggaagcag agtccctcta aaggtaactc ttgtggtcac tcaatattgt attggcattt        60

<210> SEQ ID NO 13
<211> LENGTH: 60
<212> TYPE: DNA
<213> ORGANISM: Homo sapiens

<400> SEQUENCE: 13
acgttagact tttgctggca ttcaagtcat ggctagtctg tgtatttaat aaatgtgtgt        60

<210> SEQ ID NO 14
<211> LENGTH: 60
<212> TYPE: DNA
<213> ORGANISM: Homo sapiens

<400> SEQUENCE: 14
ctggtcagcc actctgactt ttctaccaca ttaaattctc cattacatct cactattggt        60

<210> SEQ ID NO 15
<211> LENGTH: 60
<212> TYPE: DNA
<213> ORGANISM: Homo sapiens

<400> SEQUENCE: 15
tacaacttct gaatgctgca cattcttcca aaatgatcct tagcacaatc tattgtatga        60

<210> SEQ ID NO 16
<211> LENGTH: 60
<212> TYPE: DNA
<213> ORGANISM: Homo sapiens

<400> SEQUENCE: 16
gggatggcct ttaggccaca gtagtgtctg tgttaagttc actaaatgtg tatttaatga        60

<210> SEQ ID NO 17
<211> LENGTH: 60
<212> TYPE: DNA
<213> ORGANISM: Homo sapiens

<400> SEQUENCE: 17
ctcaaagtgc taaagctatg gttgactgct ctggtgtttt tatattcatt cgtgctttag        60
```

```
<210> SEQ ID NO 18
<211> LENGTH: 60
<212> TYPE: DNA
<213> ORGANISM: Homo sapiens

<400> SEQUENCE: 18
ctatggggat ggtccactgt cactgtttct ctgctgttgc aaatacatgg ataacacatt      60

<210> SEQ ID NO 19
<211> LENGTH: 60
<212> TYPE: DNA
<213> ORGANISM: Homo sapiens

<400> SEQUENCE: 19
actggaaaag cagatggtct gactgtgcta tggcctcatc atcaagactt tcaatcctat      60

<210> SEQ ID NO 20
<211> LENGTH: 60
<212> TYPE: DNA
<213> ORGANISM: Homo sapiens

<400> SEQUENCE: 20
acgccaagct cttcagtgaa gacacgatgt tattaaaagc ctgttttagg gactgcaaaa      60

<210> SEQ ID NO 21
<211> LENGTH: 60
<212> TYPE: DNA
<213> ORGANISM: Homo sapiens

<400> SEQUENCE: 21
tttttgtaaa atctttaacc ttcccttttgt tcttcatgta cacgctgaac tgcaattctt      60

<210> SEQ ID NO 22
<211> LENGTH: 60
<212> TYPE: DNA
<213> ORGANISM: Homo sapiens

<400> SEQUENCE: 22
aacctggggc atttagggca gaggacaaaa ggatgtcagc aattgcttgg gctgcttggc      60

<210> SEQ ID NO 23
<211> LENGTH: 60
<212> TYPE: DNA
<213> ORGANISM: Homo sapiens

<400> SEQUENCE: 23
ctggaacctc tggactcccc atgctctaac tcccacactc tgctatcaga aacttaaact      60

<210> SEQ ID NO 24
<211> LENGTH: 60
<212> TYPE: DNA
<213> ORGANISM: Homo sapiens

<400> SEQUENCE: 24
aaccccagaa ccatctaaga catgggattc agtgatcatg tggttctcct tttaacttac      60

<210> SEQ ID NO 25
<211> LENGTH: 60
<212> TYPE: DNA
<213> ORGANISM: Homo sapiens

<400> SEQUENCE: 25
ggccatgtgc catggtattt gggtcctggg agggtgggtg aaataaaggc atactgtctt      60
```

```
<210> SEQ ID NO 26
<211> LENGTH: 60
<212> TYPE: DNA
<213> ORGANISM: Homo sapiens

<400> SEQUENCE: 26
gtgtaggcag tcatggcacc aaagccacca gactgacaaa tgtgtatcag atgcttttgt    60

<210> SEQ ID NO 27
<211> LENGTH: 60
<212> TYPE: DNA
<213> ORGANISM: Homo sapiens

<400> SEQUENCE: 27
gaaaacctct tcaaaagaca aaaagctggc actgcattct ctctctgtag caggacagaa    60

<210> SEQ ID NO 28
<211> LENGTH: 60
<212> TYPE: DNA
<213> ORGANISM: Homo sapiens

<400> SEQUENCE: 28
cacatcttta gggtcagtga acaatggggc acatttggca ctagcttgag cccaactctg    60

<210> SEQ ID NO 29
<211> LENGTH: 60
<212> TYPE: DNA
<213> ORGANISM: Homo sapiens

<400> SEQUENCE: 29
gccttaattt cctcatctga aaactggaag gcctgacttg acttgttgag cttaagatcc    60

<210> SEQ ID NO 30
<211> LENGTH: 60
<212> TYPE: DNA
<213> ORGANISM: Homo sapiens

<400> SEQUENCE: 30
cttcagggga ggatcaagct ttgaaccaaa gccaatcact ggcttgattt gtgttttta    60

<210> SEQ ID NO 31
<211> LENGTH: 60
<212> TYPE: DNA
<213> ORGANISM: Homo sapiens

<400> SEQUENCE: 31
acaagttttc actgaatgag catggcagtg ccactcaaga aaatgaatct ccaaagtatc    60

<210> SEQ ID NO 32
<211> LENGTH: 25
<212> TYPE: DNA
<213> ORGANISM: Homo sapiens

<400> SEQUENCE: 32
ctgaagctta ctatgcagcc tacaa    25

<210> SEQ ID NO 33
<211> LENGTH: 29
<212> TYPE: DNA
<213> ORGANISM: Homo sapiens

<400> SEQUENCE: 33
tccaatcgtt agttaatgct acattagtt    29
```

```
<210> SEQ ID NO 34
<211> LENGTH: 19
<212> TYPE: DNA
<213> ORGANISM: Homo sapiens

<400> SEQUENCE: 34
cagccttagt aattaaaac                                              19

<210> SEQ ID NO 35
<211> LENGTH: 23
<212> TYPE: DNA
<213> ORGANISM: Homo sapiens

<400> SEQUENCE: 35
gccatgatcg ttagcctcat att                                         23

<210> SEQ ID NO 36
<211> LENGTH: 25
<212> TYPE: DNA
<213> ORGANISM: Homo sapiens

<400> SEQUENCE: 36
caattcatga aagcggtttc taaag                                       25

<210> SEQ ID NO 37
<211> LENGTH: 22
<212> TYPE: DNA
<213> ORGANISM: Homo sapiens

<400> SEQUENCE: 37
tctatctaga gctctgtaga gc                                          22

<210> SEQ ID NO 38
<211> LENGTH: 24
<212> TYPE: DNA
<213> ORGANISM: Artificial Sequence
<220> FEATURE:
<223> OTHER INFORMATION: PCR primer

<400> SEQUENCE: 38
ttcatcctga cagtggcaat aatc                                        24

<210> SEQ ID NO 39
<211> LENGTH: 30
<212> TYPE: DNA
<213> ORGANISM: Artificial Sequence
<220> FEATURE:
<223> OTHER INFORMATION: PCR primer

<400> SEQUENCE: 39
ctagatagaa aatatgaggc taacgatcat                                  30

<210> SEQ ID NO 40
<211> LENGTH: 19
<212> TYPE: DNA
<213> ORGANISM: Artificial Sequence
<220> FEATURE:
<223> OTHER INFORMATION: Flurogenic MGB probe

<400> SEQUENCE: 40
cgataaccag tactagctg                                              19

<210> SEQ ID NO 41
```

```
<211> LENGTH: 28
<212> TYPE: DNA
<213> ORGANISM: Artificial Sequence
<220> FEATURE:
<223> OTHER INFORMATION: PCR primer

<400> SEQUENCE: 41
gcattaacta acgattggaa actacatt                                            28

<210> SEQ ID NO 42
<211> LENGTH: 26
<212> TYPE: DNA
<213> ORGANISM: Artificial Sequence
<220> FEATURE:
<223> OTHER INFORMATION: PCR Primer

<400> SEQUENCE: 42
ggaagatgct ttattgttgc attatc                                              26

<210> SEQ ID NO 43
<211> LENGTH: 20
<212> TYPE: DNA
<213> ORGANISM: Artificial Sequence
<220> FEATURE:
<223> OTHER INFORMATION: Flurogenic MGB probe

<400> SEQUENCE: 43
acaacttcaa agctgtttta                                                     20

<210> SEQ ID NO 44
<211> LENGTH: 561
<212> TYPE: DNA
<213> ORGANISM: Homo sapiens
<220> FEATURE:
<221> NAME/KEY: misc_feature
<222> LOCATION: (475)..(475)
<223> OTHER INFORMATION: a or g or c or t/u

<400> SEQUENCE: 44
ccggcgatgt cgctcgtgct gctaagcctg gccgcgctgt gcaggagcgc cgtaccccga         60
gagccgaccg ttcaatgtgg ctctgaaact gggccatctc cagagtggat gctacaacat        120
gatctaatcc cgggagactt gagggacctc cgagtagaac ctgttacaac tagtgttgca        180 acagggggact attcaattttt gatgaatgta agctgggtac tccgggcaga tgccagcatc      240
cgcttgttga aggccaccaa gatttgtgtg acgggcaaaa gcaacttcca gtcctacagc        300
tgtgtgaggt gcaattacac agaggccttc cagactcaga ccagaccctc tggtggtaaa        360
tggacatttt cctacatcgg cttccctgta gagctgaaca cagtctattt cattggggcc        420
cataatattc ctaatgcaaa tatgaatgaa gatggccctt ccatgtctgt gaatntcacc        480
tcaccaggct gcctagacca cataatgaaa tataaaaaaa agtgtgtcaa ggccggaagc        540
ctgtgggatc cgaacatcac t                                                  561

<210> SEQ ID NO 45
<211> LENGTH: 467
<212> TYPE: DNA
<213> ORGANISM: Homo sapiens

<400> SEQUENCE: 45
tttttttttt tttttttttta aaagtgggtt cagcttgttt attccctact tttgttatct       60 taaaacaat gatttttgc atgtaataga aggttttca cttaagatgc tattgagtga          120
atcagtgagg ggttcttaga gttagtattc attaattaaa catagaatat tagctaaaca        180
```

| | |
|---|---|
| gttctgggta cactgcaatg catggtctat ggaagactag atgtttggct gaagatgctt | 240 |
| tattgttgca ttatcaaaat ggttatagtt ttcaattaaa actgtaattg atttctatgt | 300 |
| ataaaacagc tttgaagttg taaatgtagt ttccaatcgt tagttaatgc tacattagtt | 360 |
| agcaatattt gaaaatttta ttggtataaa atgttttaat tactaaggct gtttgtaggc | 420 |
| tgcatagtaa gcttcaggat catcacacgt ttttccctg taattgg | 467 |

<210> SEQ ID NO 46
<211> LENGTH: 2042
<212> TYPE: DNA
<213> ORGANISM: Homo sapiens

<400> SEQUENCE: 46

| | |
|---|---|
| ggcccggcga tgtcgctcgt gctgctaagc ctggccgcgc tgtgcaggag cgccgtaccc | 60 |
| cgagagccga ccgttcaatg tggctctgaa actgggccat ctccagagtg gatgctacaa | 120 |
| catgatctaa tcccgggaga cttgagggac ctccgagtag aacctgttac aactagtgtt | 180 |
| gcaacagggg actattcaat tttgatgaat gtaagctggg tactccgggc agatgccagc | 240 |
| atccgcttgt tgaaggccac caagatttgt gtgacgggca aaagcaactt ccagtcctac | 300 |
| agctgtgtga ggtgcaatta cacagaggcc ttccagactc agaccagacc ctctggtggt | 360 |
| aaatggacat tttcctacat cggcttccct gtagagctga acacagtcta tttcattggg | 420 |
| gcccataata ttcctaatgc aaatatgaat gaagatggcc cttccatgtc tgtgaatttc | 480 |
| acctcaccag gctgcctaga ccacataatg aaatataaaa aaaagtgtgt caaggccgga | 540 |
| agcctgtggg atccgaacat cactgcttgt aagaagaatg aggagacagt agaagtgaac | 600 |
| ttcacaacca ctcccctggg aaacagatac atggctctta ccaacacag cactatcatc | 660 |
| gggttttctc aggtgtttga ccacaccag aagaaacaaa cgcgagcttc agtggtgatt | 720 |
| ccagtgactg gggatagtga aggtgctacg gtgcagctga ctccatattt tcctacttgt | 780 |
| ggcagcgact gcatccgaca taaggaaca gttgtgctct gcccacaaac aggcgtccct | 840 |
| ttccctctgg ataacaacaa agcaagccg ggaggctggc tgcctctcct cctgctgtct | 900 |
| ctgctggtgg ccacatgggt gctggtggca gggatctatc taatgtggag gcacgaaagg | 960 |
| atcaagaaga cttccttttc taccaccaca ctactgcccc ccattaaggt tcttgtggtt | 1020 |
| tacccatctg aaatatgttt ccatcacaca atttgttact tcactgaatt tcttcaaaac | 1080 |
| cattgcagaa gtgaggtcat ccttgaaaag tggcagaaaa agaaaatagc agagatgggt | 1140 |
| ccagtgcagt ggcttgccac tcaaaagaag gcagcagaca aagtcgtctt ccttctttcc | 1200 |
| aatgacgtca acagtgtgtg cgatggtacc tgtggcaaga gcgagggcag tcccagtgag | 1260 |
| aactctcaag acctcttccc ccttgccttt aacctttct gcagtgatct aagaagccag | 1320 |
| attcatctgc acaaatacgt ggtggtctac tttagagaga ttgatacaaa agacgattac | 1380 |
| aatgctctca gtgtctgccc caagtaccac ctcatgaagg atgccactgc tttctgtgca | 1440 |
| gaacttctcc atgtcaagca gcaggtgtca gcaggaaaaa gatcacaagc ctgccacgat | 1500 |
| ggctgctgct ccttgtagcc cacccatgag aagcaagaga ccttaaaggc ttcctatccc | 1560 |
| accaattaca gggaaaaaac gtgtgatgat cctgaagctt actatgcagc ctacaaacag | 1620 |
| ccttagtaat taaaacattt tataccaata aaattttcaa atattgctaa ctaatgtagc | 1680 |
| attaactaac gattggaaac tacatttaca acttcaaagc tgttttatac atagaaatca | 1740 |
| attacagttt taattgaaaa ctataaccat tttgataatg caacaataaa gcatcttcag | 1800 |

| | |
|---|---|
| ccaaacatct agtcttccat agaccatgca ttgcagtgta cccagaactg tttagctaat | 1860 |
| attctatgtt taattaatga atactaactc taagaacccc tcactgattc actcaatagc | 1920 |
| atcttaagtg aaaaacctcc tattacatgc aaaaaatcat tgttttttaag ataacaaaag | 1980 |
| tagggaataa acaagctgaa cccactttta aaaaaaaaaa aaaaaaaaaa aaaaaaaaaa | 2040 |
| aa | 2042 |

```
<210> SEQ ID NO 47
<211> LENGTH: 842
<212> TYPE: DNA
<213> ORGANISM: Homo sapiens

<400> SEQUENCE: 47
```

| | |
|---|---|
| agcggagctg cgggtggcct ggatcccgcg cagtggcccg gcgatgtcgc tcgtgctgct | 60 |
| aagcctggcc acgctgtgca ggagcgccgt accccgagag ccgaccgttc aatgtggctc | 120 |
| tgaaactgtg gacattttcc tatatcggct tccctgtaga gctgaaaaca gtctatttca | 180 |
| ttggggccca taatattcct aatgcaaata tgaatgaaga tggcccttcc atgtctgtga | 240 |
| atttcacctc accaggctgc ctagaccaca taatgaaata taaaaaagt gtgtcaaggc | 300 |
| cggaagcctg tgggatccga acatcactgc ttgtaagaag aatgaggaga cagtagaagt | 360 |
| gaacttcaca accactcccc tgggaaacag atacatggct catccaacac agcactatca | 420 |
| tcgggttttc tcaggtgttt gagccacacc agaagaaaca aacgcgagct tcagtggtga | 480 |
| ttccagtgac tggggatagt gaaggtgcta cggtgcagct gactccatat tttcctactt | 540 |
| gtggcagcga ctgcatccga cataaaggaa cagttgtgct ctgcccacaa acaggcgtcc | 600 |
| ctttcccctc tggataacaa caaaagcaag ccgggaggct ggctgcctct cctcctgctg | 660 |
| tctctgctgg ttggccacat tgggtgctgg tgcagggat ctatctaatg tggaggcacg | 720 |
| aaaggatcca gaagacttcc ttttctacca caaactactg cccccattaa ggtcctgtgg | 780 |
| ttacccatct tgaaatatgt tcctcacaca atttgttact tcactgaatt cttcaaaacc | 840 |
| tg | 842 |

```
<210> SEQ ID NO 48
<211> LENGTH: 788
<212> TYPE: DNA
<213> ORGANISM: Homo sapiens
<220> FEATURE:
<221> NAME/KEY: misc_feature
<222> LOCATION: (675)..(675)
<223> OTHER INFORMATION: a or g or c or t/u

<400> SEQUENCE: 48
```

| | |
|---|---|
| agcggagcgt gcgggtggcc tggatcccgc gcagtggccc ggcgatgtcg ctcgtgctgc | 60 |
| taagcctggc cacgctgtgc aggagcgccg taccccgaga gccgaccgtt caatgtggct | 120 |
| ctgaaactgt ggacattttc ctatatcggc ttccctgtag agctgaaaac agtctatttc | 180 |
| attggggccc ataatattcc taatgcaaat atgaatgaag atggcccttc catgtctgtg | 240 |
| aatttcacct caccaggctg cctagaccac ataatgaaat ataaaaaaa gtgtgtcaag | 300 |
| gccggaagcc tgtgggatcc gaacatcact gcttgtaaga agaatgagga cagtagaa | 360 |
| gtgaacttca caaccactcc cctgggaaac agatacatgg ctcatccaac acagcactat | 420 |
| catcgggttt tctcaggtgt ttgagccaca ccagaagaaa caaacgcgag cttcagtggt | 480 |
| gattccagtg actggggata gtgaaggtgc tacggtgcag ctgactccat attttcctac | 540 |
| ttgtggcagc gactgcatcc gacataaagg aacagttgtg ctctgcccac aaacaggcgt | 600 |

```
ccctttccct ctggataaca acaaaagcaa gccgggaggc tggctgcctc tcctcctgct    660
gtctctgctg gtggncacat tgggtgctgg tggcagggat ctatctaatg tggaggcacg    720
aaaggatcag aagacttcct tttctaccac cacatactgc cccccattaa ggttcttgtg    780
gtttaccc                                                              788
```

<210> SEQ ID NO 49
<211> LENGTH: 946
<212> TYPE: DNA
<213> ORGANISM: Homo sapiens

<400> SEQUENCE: 49

```
ggcgatgtcg ctcgtgctgc taagcctggc cgcgctgtgc aggagcgccg taccccgaga     60
gccgaccgtt caatgtggct ctgaaactgg gccatctcca gagtggatgc tacaacatga    120
tctaatcccg ggagacttga gggacctccg agtagaacct gttacaacta gtgttgcaac    180 agggactat tcaattttga tgaatgtaag ctgggtactc cggcagatg ccagcatccg      240 cttgttgaag gccaccaaga tttgtgtgac gggcaaaagc aacttccagt cctacagctg    300
tgtgaggtgc aattacacag aggccttcca gactcagacc agaccctctg gtggtaaatg    360 gacatttttcc tatatcggct tccctgtaga gctgaacaca gtctatttca ttggggccca   420
taatattcct aatgcaaata tgaatgaaga tggcccttcc atgtctgtga atttcacctc    480
accaggaagc ctgtgggatc cgaacatcac tgcttgtaag aaagaatgag gagacagtag    540
aagtgaactt cacaaccact cccctgggaa acagatacat ggctcttatc caacacagca    600
ctatcatcgg gtttctcagg tgtttgagcc acaccagaag aaacaaacgc gagcttcagt    660
ggtgattcca gtgactgggg atagtgaagg tgctacggtg cagctgactc catattttcc    720
tacttgtggc agcgactgca atccgacata aggaacagt tgtgctctgc ccacaaacag     780
gcgtcccttt ccctcttgga tagcaacaga agcaagccgg gaggctggtg cctcttcttc    840
tggtgtctct gctggtggca cattgagtgc tggtggcagg atccatctaa gtggaggcc     900 ccaaaggacc aggaaagact tcctttatta gcaccaagta ttgccc                   946
```

<210> SEQ ID NO 50
<211> LENGTH: 488
<212> TYPE: DNA
<213> ORGANISM: Homo sapiens

<400> SEQUENCE: 50

```
tggctgaaga tgctttattg ttgcattatc aaaatggtta tagttttcaa ttaaaactgt     60
aattgatttc tatgtataaa acagctttga agttgtaaat gtagtttcca atcgttagtt    120
aatgctacat tagttagcaa tatttgaaaa ttttattggt ataaaatgtt ttaattacta    180
aggctgtttg taggctgcat agtaagcttc aggatcatca cacgtttttt ccctgtaatt    240
ggtgggatag gaagccttta aggtctcttg cttctcatgg gtgggctaca aggagcagca    300
gccatcgtgg caggcttgtg atcttttttcc tgctgacacc tgctacttga catggagaag    360
ttctgcacag aaagcagtgg catccttcat gaggtggtac ttggggcaga cactgagagc    420
attgtaatcg tcttttgtat caatctctct aaagtagacc accacgtatt tgtgcagatg    480
aatctggc                                                              488
```

<210> SEQ ID NO 51
<211> LENGTH: 509
<212> TYPE: DNA

<210> SEQ ID NO 51
<211> LENGTH: 509
<212> TYPE: DNA
<213> ORGANISM: Homo sapiens

<400> SEQUENCE: 51

```
tttgtttggc tgaagatgct ttattgttgc attatcaaaa tggttatagt tttcaattaa    60
aactgtaatt gatttctatg tataaaacag ctttgaagtt gtaaatgtag tttccaatcg   120
ttagttaatg ctacattagt tagcaatatt tgaaaatttt attggtataa aatgttttaa   180
ttactaaggc tgtttgtagg ctgcatagta agcttcagga tcatcacacg ttttttccct   240
gtaattggtg ggataggaag cctttaaggt ctcttgcttt tcatgggtgg gctacaagga   300
gcagcagcca tcgtggcagg cttgtgatct ttttcctgct gacacctgct gcttgacatg   360
gagaagttct gcacagaaag cagtggcatc cttcatgagg tggtacttgg ggcagacact   420
gagagcattg taatcgtctt ttgtatcaat ctctctaaag tagaccacca cgtatttgtg   480
cagatgaatc tggcttctta gatcactgc                                     509
```

<210> SEQ ID NO 52
<211> LENGTH: 502
<212> TYPE: DNA
<213> ORGANISM: Homo sapiens

<400> SEQUENCE: 52

```
tggcatgaga tgctatattg ttgcattatc aaaatgggtt tagtcttcaa ttaacactgt    60
aattgatttc tatgtataaa acagctttga agttgtaaat gtggtttcca atcgtcagtt   120
aatgctacat tagttagcaa tatttgaaaa ttttattggt ataaaatgtt ttaattacta   180
aggctgtttg taggctgcat agtaagcttc aggatcatca cacgtttttt ccctgtaatt   240
ggtgggatag gaagccttta aggtctcttg cttctcatgg gtgggctaca aggagcagca   300
gccatcgtgg caggcttgtg atcttttcc tgctgacacc tgctgcttga catggagaag   360
ttctgcacag aaagcagtgg catccttcat gaggtggtac ttggggcaga cactgagagc   420
attgtaatcg tcttttgtat caatctctct aaagtagacc accacgtatt tgtgcagatg   480
aatctggctt cttagatcac tg                                            502
```

<210> SEQ ID NO 53
<211> LENGTH: 460
<212> TYPE: DNA
<213> ORGANISM: Homo sapiens

<400> SEQUENCE: 53

```
gtttggctga agatgcttta ttgttgcatt atcaaaatgg ttatagtttt caattaaaac    60
tgtaattgat ttctatgtat aaaacacgct ttgaagttgt aaatgtagtt tccaatcgtt   120
agttaatgct acattagtta gcaatatttg aaaattttat tggtataaaa tgttttaatt   180
actaaggctg tttgtaggct gcatagtaag cttcaggatc atcacgtt ttttccctgt    240
aattggtggg ataggaagcc tttaaggtct cttgcttctc atgggtgggc tacaaggagc   300
agcagccatc gtggcaggct tgtgatcttt ttcctgctga cacctgctgc ttgacatgga   360
gaagttctgc acagaaagca gtggcatcct tcatgaggtg gtacttgggg cagacactga   420
gagcattgta atcgtctttt gtatcaatct ctctaaagta                         460
```

<210> SEQ ID NO 54
<211> LENGTH: 510
<212> TYPE: DNA
<213> ORGANISM: Homo sapiens

<400> SEQUENCE: 54

```
tggctgaaga tgctttattg ttgcattatc aaaatggtta tagttttcaa ttaaaactgt    60
aattgatttc tatgtataaa acagcgttga agttgtaaat gtagtttcca atcgttagtt   120
aatgctacat tagttagcaa tatttgaaaa ttttattggt ataaaatgtt ttaattacta   180
aggctgtttg taggctgcat agtaagcttc aggatcatca cacgttttt  ccctgtaatt   240 ggtgggatag gaagccttta aggtctcttg cttctcatgg gtgggctaca aggagcagca   300
gccatcgtgg caggcttgtg atcttttttcc tgctgacacc tgctgcttga catggagaag   360
ttctgcacag aaagcagtgg catccttcat gaggtggtac ttggggcaga cactgagagc   420
attgtaatcg tcttttgtat caatctctct aaagtagacc accacgtatt tgtgcagatg   480
aatctggctt cttagatcac tgcagaaaag                                    510
```

<210> SEQ ID NO 55
<211> LENGTH: 465
<212> TYPE: DNA
<213> ORGANISM: Homo sapiens

<400> SEQUENCE: 55

```
tttttttttt acaacttcaa agctgtttta tacatagaaa tcaattacag ttttaattga    60
aaactataac cattttgata atgcaacaat aaagcatctt cagccaaaca tctagtcttc   120
catagaccat gcattgcagt gtacccagaa ctgtttagct aatattctat gtttaattaa   180
tgaatactaa ctctaagaac ccctcactga ttcactcaat agcatcttaa gtgaaaaacc   240
ttctattaca tgcaaaaaat cattgttttt aagataacaa aagtagggaa taaacaagct   300
gaacccactt ttactggacc aaatgatcta ttatatgtgt accacttgta tgatttggta   360
tttgcataag accttccctc tacaaactag attcatatct tgattcttgt acaggtgcct   420
tttaacatga acaacaaaat acccacaaac ttgtctactt ttgcc                   465
```

<210> SEQ ID NO 56
<211> LENGTH: 506
<212> TYPE: DNA
<213> ORGANISM: Homo sapiens

<400> SEQUENCE: 56

```
tagtaattaa aacattttat accaataaaa ttttcaaata ttgctaacta atgtagcatt    60
aactaacgat tggaaactac atttacaact tcaaagctgt tttatacata gaaatcaatt   120
acagttttaa ttgaaaacta taaccatttt gataatgcaa caataaagca tcttcagcca   180
aacatctagt cttccataga ccatgcattg cagtgtaccc agaactgttt agctaatatt   240
ctatgtttaa ttaatgaata ctaactctaa gaacccctca ctgattcact caatagcatc   300
ttaagtgaaa aaccttctat tacatgcaaa aaatcattgt ttttaagata acaaaagtag   360
ggaataaaca agctgaaccc acttttactg gaccaaatga tctattatat gtgtaaccac   420
ttgtatgatt tggtatttgc ataagaccttt ccctctacaa actagattca tatcttgatt   480
cttgtacagg tgccttttaa catgaa                                        506
```

<210> SEQ ID NO 57
<211> LENGTH: 427
<212> TYPE: DNA
<213> ORGANISM: Homo sapiens

<400> SEQUENCE: 57

```
tttttttttt ttttttagca atatttgaaa attttattgg tataaaatgt tttaattact    60
```

```
aaggctgttt gtaggctgca tagtaagctt caggatcatc acacgttttt tccctgtaat    120
tggtgggata ggaagccttt aaggtctctt gcttctcatg ggtgggctac aaggagcagc    180
agccatcgtg gcaggcttgt gatctttttc ctgctgacac ctgctacttg acatggagaa    240
gttctgcaca gaaagcagtg gcatccttca tgaggtggta cttggggcag acactgagag    300
cattgtaatc gtcttttgta tcaatctctc taaagtagac caccacgtat tgtgcagat     360 gaatctggct tcttagatca ctgcagaaaa ggttaaaggc aaggggggaag aggtcttgag   420 agttctc                                                              427
```

<210> SEQ ID NO 58
<211> LENGTH: 467
<212> TYPE: DNA
<213> ORGANISM: Homo sapiens
<220> FEATURE:
<221> NAME/KEY: misc_feature
<222> LOCATION: (434)..(434)
<223> OTHER INFORMATION: a or g or c or t/u

<400> SEQUENCE: 58

```
ttaaagtggg ttcagcttgt ttattcccta cttttgttat cttaaaaaca atgattttt     60 gcatgtaata gaaggttttt cacttaagat gctattgagt gaatcagtga ggggttctta   120
gagttagtat tcattaatta aacatagaat attagctaaa cagttctggg tacactgcaa   180
tgcatggtct atggaagact agatgtttgg ctgaagatgc tttattgttg cattatcaaa   240
atggttacag ttttcaatta aagctgtaat tgatttctat gtataaaaca gctttgaagt   300
tgtaaatgta gtttccaatc gttagttaat gctacattag ttagcaatat ttgaaaattt   360
tattggtata aaatgttta  attactaagg ctgtttgtag gctgcatagt aagcttcagg   420
atcatcacac gttnttttccc tgtaattggt gggataggaa gcccttta               467
```

<210> SEQ ID NO 59
<211> LENGTH: 420
<212> TYPE: DNA
<213> ORGANISM: Homo sapiens

<400> SEQUENCE: 59

```
agttagcaat atttgaaaat tttattggta taaaatgttt taattactaa ggctgtttgt    60
aggctgcata gtaagcttca ggatcatcac acgttttttc cctgtaattg gtgggatagg   120
aagcctttaa ggtctcttgc ttctcatggg tgggctacaa ggagcagcag ccatcgtggc   180
aggcttgtga tctttttcct gctgacacct gctacttgac atggagaagt tctgcacaga   240
aagcagtggc atccttcatg aggtggtact tggggcagac actgagagca ttgtaatcgt   300
cttttgtatc aatctctcta aagtagacca ccacgtattt gtgcagatga atctggcttc   360
ttagatcact gcagaaaagg ttaaaggcaa ggggaagag gtcttgagag ttctcactgg    420
```

<210> SEQ ID NO 60
<211> LENGTH: 434
<212> TYPE: DNA
<213> ORGANISM: Homo sapiens

<400> SEQUENCE: 60

```
ttggctgaag atgctttatt gttgcattat caaaatggtt atagttttca attaaaactg    60
taattgattt ctatgtataa aacagctttg aagttgtaaa tgtagtttcc aatcgttagt   120
taatgctaca ttagttagca atatttgaaa atttattgg tataaaatgt tttaattact    180
aaggctgttt gtaggcttgc atagaagctt caggatcatc acacgttttt tccctgtaat   240
```

```
tggtgggata ggaagccttt aaggtctctt gcttctcatg ggtgggctac aaggagcagc    300
agccatcgtg gcaggcttgt gatcttttc ctgctgacac ctgctgcttg acatggagaa    360
gttctgcaca gaaagcagtg gcatccttca tgaggtggta cttggggcag acactgagag    420
cattgtaatc gtct                                                     434
```

<210> SEQ ID NO 61
<211> LENGTH: 416
<212> TYPE: DNA
<213> ORGANISM: Homo sapiens

<400> SEQUENCE: 61

```
tttttttttt agcaatattt gaaaatttta ttggtataaa atgttttaat tactaaggct    60
gtttgtaggc tgcatagtaa gcttcaggat catcacacgt tttttccctg taattggtgg   120
gataggaagc ctttaaggtc tcttgcttct catgggtggg ctacaaggag cagcagccat   180
cgtggcaggc ttgtgatctt tttcctgctg acacctgcta cttgacatgg agaagttctg   240
cacagaaagc agtggcatcc ttcatgaggt ggtacttggg gcagacactg agagcattgt   300
aatcgtcttt tgtatcaatc tctctaaagt agaccaccac gtatttgtgc agatgaatct   360
ggcttcttag atcactgcag aaaaggttaa aggcaagggg gaagaggtct tgagag       416
```

<210> SEQ ID NO 62
<211> LENGTH: 414
<212> TYPE: DNA
<213> ORGANISM: Homo sapiens

<400> SEQUENCE: 62

```
tttggctgaa gatgctttat tgttgcatta tcaaaatggt tacagttttc aattaaagct    60
gtaattgatt tctatgtata aaacagcttt gaagttgtaa atgtagtttc caatcgttag   120
ttaatgctac attagttagc aatatttgaa aattttattg gtataaaatg ttttaattac   180
taaggctgtt tgtaggctgc atagtaagct tcaggatcat cacacgtttt ttccctgtaa   240
ttggtgggat aggaagcctt taaggtctct tgcttctcat gggtgggcta caaggagcag   300
cagccatcgt ggcaggcttg tgatcttttt cctgctgaca cctgctgctt gacatggaga   360
agttctgcac agaaagcagt ggcatccttc atgaggtggt acttggggca gaca         414
```

<210> SEQ ID NO 63
<211> LENGTH: 409
<212> TYPE: DNA
<213> ORGANISM: Homo sapiens

<400> SEQUENCE: 63

```
ttctctggct gaagatgctt tattgttgca ttatcaaaat ggttacagtt ttcaattaaa    60
gctgtaattg atttctatgt ataaaacagc tttgaagttg taaatgtagt ttccaatcgt   120
tagttaatgc tacattagtt agcaatattt gaaaatttta ttggtataaa atgttttaat   180
tactaaggct gtttgtaggc tgcatagtaa gcttcaggat catcacacgt tttttccctg   240
taattggtgg gataggaagc ctttaaggtc tcttgcttct catgggtggg ctacaaggag   300
cagcagccat cgtggcaggc ttgtgatctt tttcctgctg acacctgctg cttgacatgg   360
agaagttctg cacagaaagc agtggcatcc ttcatgaggt ggtacttgg               409
```

<210> SEQ ID NO 64
<211> LENGTH: 414
<212> TYPE: DNA

<213> ORGANISM: Homo sapiens

<400> SEQUENCE: 64

| | | | | | |
|---|---|---|---|---|---|
| tttttttttt | ttttttacaa | ccttgaaagc | tgttttatac | atagaaatca | attacagttt | 60 |
| taattgaaaa | ctataaccat | tttgataatg | caacaataaa | gcatcttcag | ccaaacatct | 120 |
| agtcttccat | agaccatgca | ttgcagtgta | cccagaactg | tttagctaat | attctatgtt | 180 |
| taattaatga | atactaactc | taagaacccc | tcactgattc | actcaatagc | atcttaagtg | 240 |
| aaaaccttc | tattacatgc | aaaaaatcat | tgttttttaag | ataacaaaag | tagggaataa | 300 |
| acaagctgaa | cccactttta | ctggaccaaa | tgatctatta | tatgtgtaac | cacttgtatg | 360 |
| atttggattt | gcataagacc | ttccctctac | aaactagatt | catatcttga | ttct | 414 |

<210> SEQ ID NO 65
<211> LENGTH: 414
<212> TYPE: DNA
<213> ORGANISM: Homo sapiens

<400> SEQUENCE: 65

| | | | | | |
|---|---|---|---|---|---|
| tttttttttt | ttttttacaa | ctgcaaagct | gttttataca | tagaaatcaa | ttacagtttt | 60 |
| aattgaaaac | tataaccatt | ttgataatgc | aacaataaag | catcttcagc | caaacatcta | 120 |
| gtcttccata | gaccatgcat | tgcagtgtac | ccagaactgt | ttagctaata | ttctatgttt | 180 |
| aattaatgaa | tactaactct | aagaacccct | cactgattca | ctcaatagca | tcttaagtga | 240 |
| aaaccttct | attacatgca | aaaaatcatt | gttttttaaga | taacaaagt | agggaataaa | 300 |
| caagctgaac | ccacttttac | tggaccaaat | gatctattat | atgtgtaacc | acttgtatga | 360 |
| tttggtattt | gcataagacc | ttccctctac | aaactagatt | catatcttga | ttct | 414 |

<210> SEQ ID NO 66
<211> LENGTH: 484
<212> TYPE: DNA
<213> ORGANISM: Homo sapiens

<400> SEQUENCE: 66

| | | | | | |
|---|---|---|---|---|---|
| tttttttagtt | agcaatatt | gaaaatttta | ttggtataaa | atgttttaat | tactaaggct | 60 |
| gtttgtaggc | tgcatagtaa | gcttcaggat | catcacacgt | ttttttccctg | taattggtgg | 120 |
| gataggaagc | ctttaaggtc | tcttgcttct | catgggtggg | ctacaaggag | cagcagccat | 180 |
| cgtggcaggc | ttgtgatctt | tttcctgctg | acacctgcta | cttgacatgg | agaagttctg | 240 |
| cacagaaagc | agtggcatcc | ttcatgaggt | ggtacttggg | gcagacactg | agagcattgt | 300 |
| aatcgtcttt | tgtatcaatc | tctctaaagt | agaccaccac | gtatttgtgc | agatgaatct | 360 |
| ggcttcttag | atcactgcag | aaaaggttaa | aggcaagggg | gaagaggtct | tgagagttct | 420 |
| cactgggact | gccctcgctc | ttgccacagg | taccatcgca | cacactgttg | acgtcattgg | 480 |
| aaag | | | | | | 484 |

<210> SEQ ID NO 67
<211> LENGTH: 398
<212> TYPE: DNA
<213> ORGANISM: Homo sapiens

<400> SEQUENCE: 67

| | | | | | |
|---|---|---|---|---|---|
| ggctgaagat | gctttattgt | tgcattatca | aaatggttat | agttttcaat | taaaactgta | 60 |
| attgatttct | atgtataaaa | cagctttgaa | gttgtaaatg | tagtttccaa | tcgttagtta | 120 |
| atgctacatt | agttagcaat | atttgaaaat | tttattggta | taaaatgttt | taattactaa | 180 |

```
ggctgtttgt aggctgcata gtaagcttca ggatcatcac acgttttttc cctgtaattg    240
gtgggatagg aagcctttaa ggtctcttgc ttctcatggg tgggctacaa ggagcagcag    300
ccatcgtggc aggcttgtga tcttttcct gctgacacct gctgcttgac atggagaagt    360
tctgcacaga aagcagtggc atccttcatg aggtggta                            398
```

<210> SEQ ID NO 68
<211> LENGTH: 401
<212> TYPE: DNA
<213> ORGANISM: Homo sapiens

<400> SEQUENCE: 68

```
ttggctgaag atgctttatt gttgcattat caaaatggtt acagttttca attaaagctg    60
taattgattt ctatgtataa aacagctttg aagttgtaaa tgtagtttcc aatcgttagt    120
taatgctaca ttagttagca atatttgaaa attttattgg tataaaatgt tttaattact    180
aaggctgttt gtaggctgca tagtaagctt caggatcatc acgttttt tccctgtaat     240 tggtgggata ggaagccttt aaggtctctt gcttctcatg ggtgggctac aaggagcagc    300
agccatcgtg gcaggcttgt gatcttttc ctgctgacac ctgctgcttg acatggagaa    360
gttctgcaca gaaagcagtg gcatccttca tgaggtggta c                        401
```

<210> SEQ ID NO 69
<211> LENGTH: 392
<212> TYPE: DNA
<213> ORGANISM: Homo sapiens
<220> FEATURE:
<221> NAME/KEY: misc_feature
<222> LOCATION: (228)..(228)
<223> OTHER INFORMATION: a or g or c or t/u

<400> SEQUENCE: 69

```
ttggctgaag atgctttatt gttgcattat caaaatggtt atagttttca attaaaactg    60
taattgattt ctatgtataa aacagctttg aagttgtaaa tgtagtttcc aatcgttagt    120
taatgctaca ttagttagca atatttgaaa attttattgg tataaaatgt tttaattact    180
aaggctgttt gtaggctgca tagtaagctt caggatcatc acgttntt tccctgtaat     240 tggtgggata ggaagccttt aaggtctctt gcttctcatg ggtgggctac aaggagcagc    300
agccatcgtg gcaggcttgt gatcttttc ctgctgacac ctgctgcttg acatggagaa    360
gttctgcaca gaaagcagtg gcatccttca tg                                  392
```

<210> SEQ ID NO 70
<211> LENGTH: 386
<212> TYPE: DNA
<213> ORGANISM: Homo sapiens

<400> SEQUENCE: 70

```
gtttggctga agatgcttta ttgttgcatt atcaaaatgg ttatagtttt caattaaaac    60
tgtaattgat ttctatgtat aaaacagctt tgaagttgta aatgtagttt ccaatcgtta    120
gttaatgcta cattagttag caatatttga aaattttatt ggtataaaat gttttaatta    180
ctaaggctgt ttgtaggctg catagtaagc ttcaggatca tcacacgttt tttccctgta    240
attggtggga taggaagcct ttaaggtctc ttgcttctca gggtgggct acaaggagca    300 gcagccatcg tggcagcttg gtgatctttt cctgctgac acctgctgct tgacatgaag    360
aagttctgca cagaaagcag tggcat                                         386
```

<210> SEQ ID NO 71
<211> LENGTH: 386
<212> TYPE: DNA
<213> ORGANISM: Homo sapiens

<400> SEQUENCE: 71

```
gtttggctga agatgcttta ttgttgcatt atcaaaatgg ttatagtttt caattaaaac    60
tgtaattgat ttctatgtat aaaacagctt tgaagttgta aatgtagttt ccaatcgtta   120
gttaatgcta cattagttag caatatttga aaattttatt ggtataaaat gttttaatta   180
ctaaggctgt ttgtaggctg catagtaagc ttcaggatca tcacacgttt tttcccctgta  240
attggtggga taggaagcct ttaaggtctc ttgcttctca tgggtgggct acaaggagca   300
gcagccatcg tggcaggctt ggatcttttt cctgctgaca cctgctgctt gacattggaa   360
agttctgcac agaaagcagt ggcatc                                        386
```

<210> SEQ ID NO 72
<211> LENGTH: 386
<212> TYPE: DNA
<213> ORGANISM: Homo sapiens

<400> SEQUENCE: 72

```
ttttggctga tgatgcttta ttgttgcatt atcaaaatgg ttacagtttt caattaaagc    60
tgtaattgat ttctatgtat aaaacagctt tgaagttgta aatgtagttt ccaatcgtta   120
gttaatgcta cattagttag caatatttga aaattttatt ggtataaaat gttttaatta   180
ctaaggctgt ttgtaggctg catagtaagc ttcaggatca tcacacgttt tttcccctgta  240
attggtggga taggaagcct ttaaggtctc ttgcttctca tgggtgggct acaaggagca   300
gcagccatcg tggcaggctt gtgatctttt tcctgctgac acctgctgct tgacatggag   360
aagttctgca cagaaagcag tggcat                                        386
```

<210> SEQ ID NO 73
<211> LENGTH: 373
<212> TYPE: DNA
<213> ORGANISM: Homo sapiens

<400> SEQUENCE: 73

```
ggctgaagat gctttattgt tgcattatca aaatggttac agttttcaat taaagctgta    60
attgatttct atgtataaaa cagctttgaa gttgtaaatg tagtttccaa tcgttagtta   120
atgctacatt agttagcaat atttgaaaat tttattggta taaaatgttt taattactaa   180
ggctgtttgt aggctgcata gtaagcttca ggatcatcac acgttttttc cctgtaattg   240
gtgggatagg aagcctttaa ggtctcttgc ttctcatggg tggctacaa ggagcagcag    300
ccatcgtggc aggcttgtga tcttttttcct gctgacacct gctgcttgac atggagaagt  360
tctgcacaga aag                                                      373
```

<210> SEQ ID NO 74
<211> LENGTH: 403
<212> TYPE: DNA
<213> ORGANISM: Homo sapiens

<400> SEQUENCE: 74

```
gattggctgt tttatgcttt attgttgcat tatcaaaatg gttatagttt tcaattaaaa    60
ctgtaattga tttctatgta taaaacagct ttgaagttgt aaatgtagtt tccaatcgtt   120
agttaatgct acattagtta gcaatatttg aaaattttat tggtataaaa tgttttaatt   180
```

```
actaaggctg tttgtaggct gcatagtaag cttcaggatc atcacacgtt ttttccctgt    240
tattggtggg ataggaagcc tttaaggtct cttgcttctc atgggtgggc tacaaggagc    300
agcagccatc gtggcaggct tgtgatcttt ttcctgctga cacctgctgc ttgacatgga    360
gaagttctgc acaaaaagca gtggcatcct tcatgaggtg gta                      403

<210> SEQ ID NO 75
<211> LENGTH: 457
<212> TYPE: DNA
<213> ORGANISM: Homo sapiens

<400> SEQUENCE: 75
gcaatatttt aaaatttat tggtataaaa tgttttaatt actaaggctg tttgtaggct     60
gcatagtaag cttcaggatc atcacacgtt ttttccctgt aattggtggc ataggaagcc    120
tttaaggtct cttgcttctc atggtgtggg ctacaaggag cagcagccat cgtggcaggc    180
ttgtgatctt tttcctgctg acacctgctg cttgacatgg agaagttctg cacagaaagc    240
agtggcatcc ttcatgaggt ggtacttggg gcagacactg agagcattgt aatcgtcttt    300
tgtatcaatc tctctaaagt agaccaccac gtatttgtgc agatgaatct ggcttcttag    360
atcactgcag aaaaggttaa aggcaagggg gaagaggtct tgagagttct cactgggact    420
gccctcgctc ttgccacagg taccatcgca cacactg                             457

<210> SEQ ID NO 76
<211> LENGTH: 365
<212> TYPE: DNA
<213> ORGANISM: Homo sapiens

<400> SEQUENCE: 76
tttttttttt acaacttcaa agctgtttta tacatagaaa tcaattacag ttttaattga    60
aaactataac cattttgata atgcaacaat aaagcatctt cagccaaaca tctagtcttc    120
catagaccat gcattgcagt gtacccagaa ctgtttagct aatattctat gtttaattaa    180
tgaatactaa ctctaagaac ccctcactga ttcactcaat agcatcttaa gtgaaaaacc    240
ttctattaca tgcaaaaaat cattgttttt aagataacaa agtagggaa taaacaagct     300 gaacccactt ttactggacc aaatgatcta ttatatgtgt aaccacttgt atgatttggt    360
atttg                                                                365

<210> SEQ ID NO 77
<211> LENGTH: 356
<212> TYPE: DNA
<213> ORGANISM: Homo sapiens
<220> FEATURE:
<221> NAME/KEY: misc_feature
<222> LOCATION: (277)..(277)
<223> OTHER INFORMATION: a or g or c or t/u
<220> FEATURE:
<221> NAME/KEY: misc_feature
<222> LOCATION: (322)..(322)
<223> OTHER INFORMATION: a or g or c or t/u

<400> SEQUENCE: 77
gtttcgctga agatgcttta ttgttgcatt atcaaaatgg ttatagtttt caattaaaac    60
tgtaattgat ttctatgtat aaaacagctt tgaagttgta aatgtagttt ccaatcgtta    120
gttaatgcta cattagttag caatatttga aaatttatt ggtataaaat gttttaatta     180
ctaaggctgt ttgtaggctg catagtaagc ttaaggccca tcacacgttt tttccctgta    240
```

```
attggtggga taggaagcct ttaaggtctc ttgcttntca tgggtgggct acaaggagca    300
gcagccatcg tggcaggctt gngatctttt tcctgctggc ccctgctgct tgacat        356
```

<210> SEQ ID NO 78
<211> LENGTH: 413
<212> TYPE: DNA
<213> ORGANISM: Homo sapiens
<220> FEATURE:
<221> NAME/KEY: misc_feature
<222> LOCATION: (1)..(1)
<223> OTHER INFORMATION: a or g or c or t/u
<220> FEATURE:
<221> NAME/KEY: misc_feature
<222> LOCATION: (264)..(264)
<223> OTHER INFORMATION: a or g or c or t/u

<400> SEQUENCE: 78

```
naaagcactg gctgaaggaa gccaagagga tcactgctgc tcctttttc tagaggaaat     60 gtttgtctac gtggtaagat atgacctagc cctttaggt aagcgaactg gtatgttagt    120
aacgtgtaca aagtttaggt tcagaccccg ggagtcttgg gcacgtgggt ctcgggtcac   180
tggttttgac tttagggctt tgttacagat gtgtgaccaa ggggaaaatg tgcatgacaa   240
cactagaggt atgggcgaca cganaacgaa cgggaagttt tggctgaagt aggagtcttg   300
gtgagatttt gctctgatgc atggtgtgaa cttctgagc ctcttgtttt tcctcaagct    360
gactccatat tttcctactt gtggcagcga ctgcatccga cataaaggaa cag          413
```

<210> SEQ ID NO 79
<211> LENGTH: 394
<212> TYPE: DNA
<213> ORGANISM: Homo sapiens

<400> SEQUENCE: 79

```
tagcaatatt tgaaatttt attggtataa atgtttaa ttactaaggc tgtttgtagg       60
ctgcatagta agcttcagga tcatcacacg ttttttccct gtaattggtg ggataggaag   120
cctttaaggt ctcttgcttc tcatgggtgg gctacaagga gcagcagcca tcgtggcagg   180
cttgtgatct ttttcctgct gacacctgct gcttgacatg gagaagttct gcacagaaag   240
cagtggcatc cttcatgagg tggtacttgg ggcagacact gagagcattg taatcgtctt   300
ttgtatcaat ctctctaaag tagaccacca cgtatttgtg cagatgaatc tggcttctta   360
gatcactgca gaaaaggtta aaggcaaggg ggga                                394
```

<210> SEQ ID NO 80
<211> LENGTH: 437
<212> TYPE: DNA
<213> ORGANISM: Homo sapiens

<400> SEQUENCE: 80

```
agcaatattt gaaaatttta ttggtataaa atgttttaat tactaaggct gtttgtaggc    60
tgcatagtaa gcttcaggat catcacacgt tttttccctg taattggtgg cataggaagc   120
ctttaaggtc tcttgcttct catgggtggg ctacaaggag cagcagccat cgtggcaggc   180
ttgtgatctt tttcctgctg acacctgctg cttgacatgg agaagttctg cacagaaagc   240
agtggcatcc ttcatgaggt ggtacttggg gcagacactg agagcattgt aatcgtcttt   300
tgtatcaatc tctctaaagt agaccaccac gtatttgtgc agatgaatct ggcttcttag   360
atcactgcag aaaaggttaa aggcaagggg gaagaggtct tgagagttct cactgggact   420
gccctcgctc ttgccac                                                   437
```

<210> SEQ ID NO 81
<211> LENGTH: 321
<212> TYPE: DNA
<213> ORGANISM: Homo sapiens

<400> SEQUENCE: 81

| | | | | | |
|---|---|---|---|---|---|
| ttttttttt | tagcaatatt | tgaaaatttt | attggtataa | aatgttttaa | ttactaaggc | 60 |
| tgtttgtagg | ctgcatagta | agcttcagga | tcatcacacg | ttttttccct | gtaattggtg | 120 |
| ggataggaag | cctttaaggt | ctcttgcttc | tcatgggtgg | gctacaagga | gcagcagcca | 180 |
| tcgtggcagg | cttgtgatct | ttttcctgct | gacacctgct | gcttgacatg | gagaagttct | 240 |
| gcacaaaaag | cagtggcatc | cttcatgagg | tggtacttgg | ggcagacact | gagagcattg | 300 |
| taatcgtctt | ttgtatcaat | c | | | | 321 |

<210> SEQ ID NO 82
<211> LENGTH: 321
<212> TYPE: DNA
<213> ORGANISM: Homo sapiens

<400> SEQUENCE: 82

| | | | | | |
|---|---|---|---|---|---|
| ttttttttt | tagcaatatt | tgaaaatttt | attggtataa | aatgttttaa | ttactaaggc | 60 |
| tgtttgtagg | ctgcatagta | agcttcagga | tcatcacacg | ttttttccct | gtaattggtg | 120 |
| ggataggaag | cctttaaggt | ctcttgcttc | tcatgggtgg | gctacaagga | gcagcagcca | 180 |
| tcgtggcagg | cttgtgatct | ttttcctgct | gacacctgct | gcttgacatg | gagaagttct | 240 |
| gcacaaaaag | cagtggcatc | cttcatgagg | tggtacttgg | ggcagacact | gagagcattg | 300 |
| taatcgtctt | ttgtatcaat | c | | | | 321 |

<210> SEQ ID NO 83
<211> LENGTH: 314
<212> TYPE: DNA
<213> ORGANISM: Homo sapiens

<400> SEQUENCE: 83

| | | | | | |
|---|---|---|---|---|---|
| ttttatacat | agaaatcaat | tacagcttta | attgaaaact | ataaccatttt | tgataatgca | 60 |
| acaataaagc | atcttcagcc | aaacatctag | tcttccatag | accatgcatt | gcagtgtacc | 120 |
| cagaactgtt | tagctaatat | tctatgttta | attaatgaat | actaactcta | agaacccctc | 180 |
| actgattcac | tcaatagcat | cttaagtgaa | aaaccttcta | ttacatgcaa | aaaatcattg | 240 |
| tttttaagat | aacaaaagta | gggaataaac | aagctgaacc | cacttttact | ggaccaaatg | 300 |
| atctattata | tgtg | | | | | 314 |

<210> SEQ ID NO 84
<211> LENGTH: 286
<212> TYPE: DNA
<213> ORGANISM: Homo sapiens

<400> SEQUENCE: 84

| | | | | | |
|---|---|---|---|---|---|
| ggctgaagat | gctttattgt | tgcattatca | aaatggttat | agttttcaat | taaaactgta | 60 |
| attgatttct | atgtataaaa | cagctttgaa | gttgtaaatg | tagttccaa | tcgttagtta | 120 |
| atgctacatt | agttagcaat | atttgaaaat | tttattggta | taaaatgttt | taattactaa | 180 |
| ggctgtttgt | aggctgcata | gtaagcttca | ggatcatcac | acgttttttc | ccctgtatgg | 240 |
| gtgggatagg | aagcctttaa | ggtctcttgc | ttctcatggg | tgggct | | 286 |

```
<210> SEQ ID NO 85
<211> LENGTH: 333
<212> TYPE: DNA
<213> ORGANISM: Homo sapiens
<220> FEATURE:
<221> NAME/KEY: misc_feature
<222> LOCATION: (2)..(2)
<223> OTHER INFORMATION: a or g or c or t/u
<220> FEATURE:
<221> NAME/KEY: misc_feature
<222> LOCATION: (8)..(8)
<223> OTHER INFORMATION: a or g or c or t/u
<220> FEATURE:
<221> NAME/KEY: misc_feature
<222> LOCATION: (24)..(25)
<223> OTHER INFORMATION: a or g or c or t/u
<220> FEATURE:
<221> NAME/KEY: misc_feature
<222> LOCATION: (27)..(28)
<223> OTHER INFORMATION: a or g or c or t/u
<220> FEATURE:
<221> NAME/KEY: misc_feature
<222> LOCATION: (30)..(31)
<223> OTHER INFORMATION: a or g or c or t/u
<220> FEATURE:
<221> NAME/KEY: misc_feature
<222> LOCATION: (39)..(39)
<223> OTHER INFORMATION: a or g or c or t/u
<220> FEATURE:
<221> NAME/KEY: misc_feature
<222> LOCATION: (48)..(48)
<223> OTHER INFORMATION: a or g or c or t/u
<220> FEATURE:
<221> NAME/KEY: misc_feature
<222> LOCATION: (51)..(51)
<223> OTHER INFORMATION: a or g or c or t/u
<220> FEATURE:
<221> NAME/KEY: misc_feature
<222> LOCATION: (67)..(67)
<223> OTHER INFORMATION: a or g or c or t/u
<220> FEATURE:
<221> NAME/KEY: misc_feature
<222> LOCATION: (75)..(75)
<223> OTHER INFORMATION: a or g or c or t/u
<220> FEATURE:
<221> NAME/KEY: misc_feature
<222> LOCATION: (80)..(80)
<223> OTHER INFORMATION: a or g or c or t/u
<220> FEATURE:
<221> NAME/KEY: misc_feature
<222> LOCATION: (85)..(87)
<223> OTHER INFORMATION: a or g or c or t/u
<220> FEATURE:
<221> NAME/KEY: misc_feature
<222> LOCATION: (95)..(95)
<223> OTHER INFORMATION: a or g or c or t/u
<220> FEATURE:
<221> NAME/KEY: misc_feature
<222> LOCATION: (98)..(98)
<223> OTHER INFORMATION: a or g or c or t/u
<220> FEATURE:
<221> NAME/KEY: misc_feature
<222> LOCATION: (106)..(106)
<223> OTHER INFORMATION: a or g or c or t/u
<220> FEATURE:
<221> NAME/KEY: misc_feature
<222> LOCATION: (109)..(109)
<223> OTHER INFORMATION: a or g or c or t/u
<220> FEATURE:
<221> NAME/KEY: misc_feature
<222> LOCATION: (123)..(123)
<223> OTHER INFORMATION: a or g or c or t/u
<220> FEATURE:
<221> NAME/KEY: misc_feature
<222> LOCATION: (128)..(128)
<223> OTHER INFORMATION: a or g or c or t/u
<220> FEATURE:
<221> NAME/KEY: misc_feature
```

```
<222> LOCATION: (144)..(146)
<223> OTHER INFORMATION: a or g or c or t/u
<220> FEATURE:
<221> NAME/KEY: misc_feature
<222> LOCATION: (180)..(180)
<223> OTHER INFORMATION: a or g or c or t/u
<220> FEATURE:
<221> NAME/KEY: misc_feature
<222> LOCATION: (191)..(191)
<223> OTHER INFORMATION: a or g or c or t/u
<220> FEATURE:
<221> NAME/KEY: misc_feature
<222> LOCATION: (217)..(217)
<223> OTHER INFORMATION: a or g or c or t/u
<220> FEATURE:
<221> NAME/KEY: misc_feature
<222> LOCATION: (234)..(234)
<223> OTHER INFORMATION: a or g or c or t/u
<220> FEATURE:
<221> NAME/KEY: misc_feature
<222> LOCATION: (307)..(307)
<223> OTHER INFORMATION: a or g or c or t/u
<220> FEATURE:
<221> NAME/KEY: misc_feature
<222> LOCATION: (327)..(327)
<223> OTHER INFORMATION: a or g or c or t/u

<400> SEQUENCE: 85
tnaggaanga gaagaagcga gatnnanntn nagaaatang tggtggcnta ntttagagag      60
attgatncaa aagcngattn caatnnnctc agtgnctncc caagtnccnc ctcatgaagg     120
atncactnct ttctgtgcag actnnncatg tcaagcagca ggtgtcagca ggaaaaagan    180
cacaagctcc ncgatggctg ctgctccttg tagcccncca tgagaagcaa gagncttaaa   240
ggcttcctat cccaccaatt acagggaaaa acgtgtgatg acctgagctt actatgcagc   300
ctacaancag ccttagtaat taaaccnttt att                                333

<210> SEQ ID NO 86
<211> LENGTH: 522
<212> TYPE: DNA
<213> ORGANISM: Homo sapiens
<220> FEATURE:
<221> NAME/KEY: misc_feature
<222> LOCATION: (1)..(1)
<223> OTHER INFORMATION: a or g or c or t/u
<220> FEATURE:
<221> NAME/KEY: misc_feature
<222> LOCATION: (3)..(4)
<223> OTHER INFORMATION: a or g or c or t/u
<220> FEATURE:
<221> NAME/KEY: misc_feature
<222> LOCATION: (161)..(161)
<223> OTHER INFORMATION: a or g or c or t/u
<220> FEATURE:
<221> NAME/KEY: misc_feature
<222> LOCATION: (231)..(231)
<223> OTHER INFORMATION: a or g or c or t/u
<220> FEATURE:
<221> NAME/KEY: misc_feature
<222> LOCATION: (299)..(299)
<223> OTHER INFORMATION: a or g or c or t/u
<220> FEATURE:
<221> NAME/KEY: misc_feature
<222> LOCATION: (339)..(339)
<223> OTHER INFORMATION: a or g or c or t/u
<220> FEATURE:
<221> NAME/KEY: misc_feature
<222> LOCATION: (445)..(445)
<223> OTHER INFORMATION: a or g or c or t/u
<220> FEATURE:
<221> NAME/KEY: misc_feature
<222> LOCATION: (467)..(467)
<223> OTHER INFORMATION: a or g or c or t/u
<220> FEATURE:
```

```
<221> NAME/KEY: misc_feature
<222> LOCATION: (490)..(490)
<223> OTHER INFORMATION: a or g or c or t/u
<220> FEATURE:
<221> NAME/KEY: misc_feature
<222> LOCATION: (516)..(516)
<223> OTHER INFORMATION: a or g or c or t/u

<400> SEQUENCE: 86
nannatgaag atgctttatt gttgcattat caaaatggtt acagttttca attaaagctg      60
taattgattt ctatgtataa aacagctttg aagttgtaaa tgtagtttcc aatcgttagt     120
taatgctaca ttagttagca atatttgaaa attttattgg nataaaatgt tttaattact     180
aaggctgttt gtaggctgca tagtaagctt caggatcatc acacgttttt nccctgtaat     240
tgggtgggga tagggaagcc ctttaagggt ctccttgcttc tcatggggtg ggcctacna     300 agggagcagc cagcccatcg tggccagggc cttgtgganc cttttccct gcctggacac      360 cctgcctgcc ttggaccatg gggaggaagg ttctggcacc aggaaagcca ggtggcccat     420
cccttccatg agggtggggt acttngggg gccaggacca ctgaggngcc attggtaatc      480
cgtccttttn gtatccaatc ccctcctaag gtaggncccc cc                        522

<210> SEQ ID NO 87
<211> LENGTH: 277
<212> TYPE: DNA
<213> ORGANISM: Homo sapiens
<220> FEATURE:
<221> NAME/KEY: misc_feature
<222> LOCATION: (240)..(240)
<223> OTHER INFORMATION: a or g or c or t/u

<400> SEQUENCE: 87
ttttgtgggt tcagcttgtt tattccctac ttttgttatc ttaaaaacaa tgattttttg      60
catgtaatag aaggtttttc acttaagatg ctattgagtg aatcagtgag gggttcttag     120
agttagtatt cattaattaa acatagaata ttagctaaac agttctgggt acactgcaat     180
gcatggtcta tggaagacta gatgtttggc tgaagatgct tttattgttg cattatcaan     240
atggtttata gttttcaatt aaaactgtaa ttgattt                             277

<210> SEQ ID NO 88
<211> LENGTH: 265
<212> TYPE: DNA
<213> ORGANISM: Homo sapiens
<220> FEATURE:
<221> NAME/KEY: misc_feature
<222> LOCATION: (211)..(211)
<223> OTHER INFORMATION: a or g or c or t/u
<220> FEATURE:
<221> NAME/KEY: misc_feature
<222> LOCATION: (220)..(220)
<223> OTHER INFORMATION: a or g or c or t/u
<220> FEATURE:
<221> NAME/KEY: misc_feature
<222> LOCATION: (250)..(250)
<223> OTHER INFORMATION: a or g or c or t/u

<400> SEQUENCE: 88
ggctgaagat gctttattgt tgcattatca aaatggttat agttttcaat taaaactgta      60
attgatttct atgtataaaa cagctttgaa gttgtaaatg tagtttccaa tcgttagtta     120
atgctacatt agttagcaat atttgaaaat tttattggta taaatgtttt taattactaa     180
ggctgtttgt aggctgcata gtaagcttaa ngatcatacn cacgttttc cctgaatttg      240 gtgggataan gaagccttta aaggt                                          265
```

<210> SEQ ID NO 89
<211> LENGTH: 350
<212> TYPE: DNA
<213> ORGANISM: Homo sapiens
<220> FEATURE:
<221> NAME/KEY: misc_feature
<222> LOCATION: (17)..(17)
<223> OTHER INFORMATION: a or g or c or t/u
<220> FEATURE:
<221> NAME/KEY: misc_feature
<222> LOCATION: (72)..(72)
<223> OTHER INFORMATION: a or g or c or t/u
<220> FEATURE:
<221> NAME/KEY: misc_feature
<222> LOCATION: (326)..(326)
<223> OTHER INFORMATION: a or g or c or t/u
<220> FEATURE:
<221> NAME/KEY: misc_feature
<222> LOCATION: (341)..(341)
<223> OTHER INFORMATION: a or g or c or t/u

<400> SEQUENCE: 89
ttgaaaattt tattggnata aaatgtttta attactaagg ctgtttgtag gctgcatagt      60
aagcttcagg ancatcacac gttttttccc tgtaattggt ggcataggaa gcctttaagg    120
tctcttgctt ctcatgggtg ggctacaagg agcagcagcc atcgtggcag gcttgtgatc    180
tttttcctgc tgacacctgc tgcttgacat ggagaagttc tgcacagaaa gcagtggcat    240
ccttcatgag gtggtacttg gggcagacac tgagagcatt gtaatcgtct tttgtatcaa    300
tctctctaaa gtagaccacc accgtntttg tgcagatgga ntctggcttc                350

<210> SEQ ID NO 90
<211> LENGTH: 452
<212> TYPE: DNA
<213> ORGANISM: Homo sapiens
<220> FEATURE:
<221> NAME/KEY: misc_feature
<222> LOCATION: (227)..(227)
<223> OTHER INFORMATION: a or g or c or t/u
<220> FEATURE:
<221> NAME/KEY: misc_feature
<222> LOCATION: (230)..(230)
<223> OTHER INFORMATION: a or g or c or t/u
<220> FEATURE:
<221> NAME/KEY: misc_feature
<222> LOCATION: (234)..(234)
<223> OTHER INFORMATION: a or g or c or t/u
<220> FEATURE:
<221> NAME/KEY: misc_feature
<222> LOCATION: (429)..(429)
<223> OTHER INFORMATION: a or g or c or t/u

<400> SEQUENCE: 90
aggcactatc atcgggtttt ctcaggtgtt tgagccacac cagaagaaac aaacgcgagc     60
ttcagtggtg attccagtga ctggggatag tgaaggtgct acggtgcagc tgactccata   120
ttttcctact tgtggcagcg actgcatccg acataaagga acagttgtgc tctgcccaca   180
aacaggcgtc cctttccctc tggataacaa caaaagcaag ccggganggn ctgncctctc   240
ctcctgctgt ctctgctggt ggccacatgg gtgctggtgg cagggatcta tctaatgtgg   300
aggcacgaaa ggatcaagaa gacttccttt tctaaccacc acattactgc cccccattta   360
aggttcttgt ggttttaccc atctggaaat atgttttccc ttcacacatt tgtttatttc   420
attgatttnt ttcaaaacct tggcaggagt tt                                  452

<210> SEQ ID NO 91

<211> LENGTH: 465
<212> TYPE: DNA
<213> ORGANISM: Homo sapiens
<220> FEATURE:
<221> NAME/KEY: misc_feature
<222> LOCATION: (22)..(22)
<223> OTHER INFORMATION: a or g or c or t/u
<220> FEATURE:
<221> NAME/KEY: misc_feature
<222> LOCATION: (403)..(403)
<223> OTHER INFORMATION: a or g or c or t/u
<220> FEATURE:
<221> NAME/KEY: misc_feature
<222> LOCATION: (415)..(415)
<223> OTHER INFORMATION: a or g or c or t/u
<220> FEATURE:
<221> NAME/KEY: misc_feature
<222> LOCATION: (437)..(437)
<223> OTHER INFORMATION: a or g or c or t/u
<220> FEATURE:
<221> NAME/KEY: misc_feature
<222> LOCATION: (449)..(449)
<223> OTHER INFORMATION: a or g or c or t/u

<400> SEQUENCE: 91

```
gggtccagtg cagtggcttg cntgcagaaa gaaggcagca gacaaagtcg tcttccttct    60
ttccaatgac gtcaacagtg tgtgcgatgg tacctgtggc aagagcgagg gcagtcccag   120
tgagaactct caagacctct tcccccttgc ctttaacctt ttctgcagtg atctaagaag   180
ccagattcat ctgcacaaat acgtggtggt ctactttaga gagattgata caaaagacga   240
ttacaatgct ctcagtgtct gccccaagta ccacctcatg aaggatgcca ctgctttctg   300
tgcagaactt ctccatgtca agcagcaggt gtcagcagga aaaagattca caagcctgcc   360
acgatggctg cttgcttcct ttgtagccca cccatgagga agncaagaga ccttnaaagg   420
gttccttttc ccatcanttt acaggggana aaacgtgtga tgatc                   465
```

<210> SEQ ID NO 92
<211> LENGTH: 440
<212> TYPE: DNA
<213> ORGANISM: Homo sapiens
<220> FEATURE:
<221> NAME/KEY: misc_feature
<222> LOCATION: (13)..(13)
<223> OTHER INFORMATION: a or g or c or t/u
<220> FEATURE:
<221> NAME/KEY: misc_feature
<222> LOCATION: (16)..(16)
<223> OTHER INFORMATION: a or g or c or t/u
<220> FEATURE:
<221> NAME/KEY: misc_feature
<222> LOCATION: (18)..(19)
<223> OTHER INFORMATION: a or g or c or t/u
<220> FEATURE:
<221> NAME/KEY: misc_feature
<222> LOCATION: (77)..(77)
<223> OTHER INFORMATION: a or g or c or t/u
<220> FEATURE:
<221> NAME/KEY: misc_feature
<222> LOCATION: (175)..(175)
<223> OTHER INFORMATION: a or g or c or t/u
<220> FEATURE:
<221> NAME/KEY: misc_feature
<222> LOCATION: (277)..(277)
<223> OTHER INFORMATION: a or g or c or t/u
<220> FEATURE:
<221> NAME/KEY: misc_feature
<222> LOCATION: (330)..(330)
<223> OTHER INFORMATION: a or g or c or t/u
<220> FEATURE:
<221> NAME/KEY: misc_feature
<222> LOCATION: (336)..(336)
<223> OTHER INFORMATION: a or g or c or t/u
<220> FEATURE:
<221> NAME/KEY: misc_feature
<222> LOCATION: (420)..(420)
<223> OTHER INFORMATION: a or g or c or t/u

<400> SEQUENCE: 92

| | | | | | |
|---|---|---|---|---|---|
| ttttgtttgg | ctnatntnnt | tcttattgtt | gcattatcaa | aatggttata | gtttcaatt | 60 |
| aaaactgtaa | ttgattncta | tgtataaaac | agctttgaag | ttgtaaatgt | agtttccaat | 120 |
| cgttagttaa | tgctacatta | gttagcaata | tttgaaaatt | ttattggtat | aaaangtttt | 180 |
| aattactaag | gctgtttgta | ggctgcatag | taagcttcag | gatcatcaca | cgttttttccc | 240 |
| ctgtaattgg | tgggatagga | agcctttaag | gtctctngct | tctcatgggt | gggctacaag | 300 |
| gagcagcagc | catcgtggca | ggcttgtgan | cttttncctg | ctgacacctg | ctgcttgaca | 360 |
| tgggagaagt | tctgcacaga | aaggcagtgg | gcatccttca | tgaggtgggt | acttgggggn | 420 |
| cagacactga | ggagcattgt | | | | | 440 |

<210> SEQ ID NO 93
<211> LENGTH: 641
<212> TYPE: DNA
<213> ORGANISM: Homo sapiens

<400> SEQUENCE: 93

| | | | | | |
|---|---|---|---|---|---|
| actcaaaaga | aggcagcaga | caaagtcgtc | ttccttcttt | ccaatgacgt | caacagtgtg | 60 |
| tgcgatggta | cctgtggcaa | gagcgagggc | agtcccagtg | agaactctca | agacctcttc | 120 |
| cccttgcct | ttaaccttttt | ctgcagtgat | ctaagaagcc | agattcatct | gcacaaatac | 180 |
| gtggtggtct | actttagaga | gattgataca | aaagacgatt | acagtgctct | cagtgtctgc | 240 |
| cccaagtacc | acctcatgaa | ggatgccact | gctttctgtg | cagaacttct | ccatgtcaag | 300 |
| cagcaggtgt | cagcaggaaa | aagatcacaa | gcctgccacg | atggccgctg | ctccttgtag | 360 |
| cccacccatg | agaagcaaga | gaccttaaag | gcttcctatc | ccaccaatta | cagggaaaaa | 420 |
| acgtgtgatg | atcctgaagc | ttactatgca | gcctacaaac | agcctttagta | attaaaacat | 480 |
| tttataccaa | taaaatttc | aaatatgcta | actaatgtag | cattaactaa | cgattggaaa | 540 |
| ctacatttac | aacttcaaag | ctgttttata | catagaaatc | aattacagct | ttaattgaaa | 600 |
| actgtaaacca | ttttgataat | gcaacaataa | agcatcttca | g | | 641 |

<210> SEQ ID NO 94
<211> LENGTH: 468
<212> TYPE: DNA
<213> ORGANISM: Homo sapiens

<400> SEQUENCE: 94

| | | | | | |
|---|---|---|---|---|---|
| gtccagtgca | gtggcttgcc | actcaaaaga | aggcagcaga | caaagtcgtc | ttccttcttt | 60 |
| ccaatgacgt | caacagtgtg | tgcgatggta | cctgtggcaa | gagcgagggc | agtcccagtg | 120 |
| agaactctca | agacctcttc | cccttgcct | ttaaccttttt | ctgcagtgat | ctaagaagcc | 180 |
| agattcatct | gcacaaatac | gtggtggtct | actttagaga | gattgataca | aaagacgatt | 240 |
| acagtgctct | cagtgtctgc | cccaagtacc | acctcatgaa | ggatgccact | gctttctgtg | 300 |
| cagaacttct | ccatgtcaag | cagcaggtgt | cagcaggaaa | aagatcacaa | gcctgccacg | 360 |
| atggccgctg | ctccttgtag | cccacccatg | agaagcaaga | gaccttaaag | gcttcctatc | 420 |
| ccaccaatta | caggggaaaa | aacgtgtgat | gatcctgaag | cttactat | | 468 |

<210> SEQ ID NO 95

```
<211> LENGTH: 507
<212> TYPE: DNA
<213> ORGANISM: Homo sapiens
<220> FEATURE:
<221> NAME/KEY: misc_feature
<222> LOCATION: (215)..(215)
<223> OTHER INFORMATION: a or g or c or t/u
<220> FEATURE:
<221> NAME/KEY: misc_feature
<222> LOCATION: (427)..(427)
<223> OTHER INFORMATION: a or g or c or t/u
<220> FEATURE:
<221> NAME/KEY: misc_feature
<222> LOCATION: (438)..(438)
<223> OTHER INFORMATION: a or g or c or t/u
<220> FEATURE:
<221> NAME/KEY: misc_feature
<222> LOCATION: (445)..(445)
<223> OTHER INFORMATION: a or g or c or t/u
<220> FEATURE:
<221> NAME/KEY: misc_feature
<222> LOCATION: (454)..(454)
<223> OTHER INFORMATION: a or g or c or t/u
<220> FEATURE:
<221> NAME/KEY: misc_feature
<222> LOCATION: (459)..(459)
<223> OTHER INFORMATION: a or g or c or t/u
<220> FEATURE:
<221> NAME/KEY: misc_feature
<222> LOCATION: (471)..(471)
<223> OTHER INFORMATION: a or g or c or t/u
<220> FEATURE:
<221> NAME/KEY: misc_feature
<222> LOCATION: (477)..(477)
<223> OTHER INFORMATION: a or g or c or t/u
<220> FEATURE:
<221> NAME/KEY: misc_feature
<222> LOCATION: (486)..(486)
<223> OTHER INFORMATION: a or g or c or t/u
<220> FEATURE:
<221> NAME/KEY: misc_feature
<222> LOCATION: (499)..(499)
<223> OTHER INFORMATION: a or g or c or t/u
<220> FEATURE:
<221> NAME/KEY: misc_feature
<222> LOCATION: (507)..(507)
<223> OTHER INFORMATION: a or g or c or t/u

<400> SEQUENCE: 95
tattgttgca ttatcaaaat ggttatagtt ttcaattaaa actgtaattg atttctatgt     60
ataaaacagc tttgaagttg taaatgtagt ttccaatcgt tagttaatgc tacattagtt    120
agcaatattt gaaaatttta ttggtataaa atgttttaat tactaaggct gtttgtaggc    180
tgcatagtaa gcttcaggat catcacacgt ttttncgctg taattgggtg gggatagggs   240

Note: rechecking line 240: "tgcatagtaa gcttcaggat catcacacgt ttttncgctg taattgggtg gggataggga"

agcctttaag gtctcttgct tctcatgggg tggggctaca agggaggcag gcagccatcg    300
tgggcagggc ttgtgatctt tttccctgct gacacctgct gcttgacatg ggggaaggt    360 tctggcacag aaagcagtgg gcatccttca tgagggtggt acttgggggg cagacactga    420
ggaggcnttg taaatcgnct ttttngtatc caanctctnc taaagtaggg nccaccncgt    480
tttttnttgc aggtggatnc ggggctn                                        507

<210> SEQ ID NO 96
<211> LENGTH: 440
<212> TYPE: DNA
<213> ORGANISM: Homo sapiens
<220> FEATURE:
<221> NAME/KEY: misc_feature
<222> LOCATION: (22)..(22)
<223> OTHER INFORMATION: a or g or c or t/u
<220> FEATURE:
<221> NAME/KEY: misc_feature
```

```
<222> LOCATION: (24)..(24)
<223> OTHER INFORMATION: a or g or c or t/u
<220> FEATURE:
<221> NAME/KEY: misc_feature
<222> LOCATION: (364)..(364)
<223> OTHER INFORMATION: a or g or c or t/u
<220> FEATURE:
<221> NAME/KEY: misc_feature
<222> LOCATION: (382)..(382)
<223> OTHER INFORMATION: a or g or c or t/u
<220> FEATURE:
<221> NAME/KEY: misc_feature
<222> LOCATION: (414)..(414)
<223> OTHER INFORMATION: a or g or c or t/u
<220> FEATURE:
<221> NAME/KEY: misc_feature
<222> LOCATION: (424)..(424)
<223> OTHER INFORMATION: a or g or c or t/u
<220> FEATURE:
<221> NAME/KEY: misc_feature
<222> LOCATION: (430)..(430)
<223> OTHER INFORMATION: a or g or c or t/u

<400> SEQUENCE: 96
gggtccagtg cagtggcttg cntncaaaag aaggcagcag acaaagtcgt cttccttctt    60
tccaatgacg tcaacagtgt gtgcgatggt acctgtggca agagcgaggg cagtcccagt   120
gagaactctc aagacctctt ccccccttgcc tttaaccttt tctgcagtga tctaagaagc   180
cagattcatc tgcacaaata cgtggtggtc tactttagag agattgatac aaaagacgat   240
tacaatgctc tcagtgtctg ccccaagtac cacctcatga aggatgccac tgctttctgt   300
gcagaacttc tccatgtcaa gcagcaggtg tcagcaggaa aaagatcaca agcctgccac   360
gatngctgct gctccttgta gnccacccat gagaagcaag tgacctttaa aggntttcct   420
attnccaccn atttacaggg                                                440

<210> SEQ ID NO 97
<211> LENGTH: 630
<212> TYPE: DNA
<213> ORGANISM: Homo sapiens

<400> SEQUENCE: 97
gactagatgt ttggctgaag atgctttatt gttgcattat caaaatggtt atagttttca    60
attaaaactg taattgattt ctatgtataa aacagctttg aagttgtaaa tgtagttttcc   120 aatcgttagt taatgctaca ttagttagca atatttgaaa attttattgg tataaaatgt   180
tttaattact aaggctgttt gtaggctgca tagtaagctt caggatcatc acacgttttt   240
tccctgtaat tggtgggata ggaagccttt aaggtctctt gcttctcatg ggtgggctac   300
aaggagcagc agccatcgtg gcaggcttgt gatcttttttc ctgctgacac ctgctgcttg   360
acatggagaa gttctgcaca gaaagcagtg gcatccttca tgaggtggta cttggggcag   420
acactgagag cattgtaatc gtcttttgta tcaatctctc taaagtagac caccacgtat   480
ttgtgcagat gaatctggct tcttagatca ctgcagaaaa ggttaaaggc aagggggaag   540
aggtcttgag agttctcact gggactgccc tcgctcttgc cacaggtacc atcgcacaca   600
ctgttgacgt cattggaaaa gaaggaagac                                     630

<210> SEQ ID NO 98
<211> LENGTH: 788
<212> TYPE: DNA
<213> ORGANISM: Homo sapiens

<400> SEQUENCE: 98
```

```
gagttctcac tgggactgcc ctcgctcttg ccacaggtac catcgcacac actgttgacg    60
tcattggaaa gaaggaagac gaccttgtct gctaccttct tttgagtggc aagccactgc   120
actggaccca tctctgctat tttcttttc tgccacttt caaggatgac ctcacttctg   180
caatggtttt gaagaaattc agtgaagtaa caaattgtgt gatggaaaca tatttcagat   240
gggtaaacca caagaacctt aatgggggc agtagtgtgg tggtagaaaa ggaagtcttc   300
ttgatccttt ctgtgagagg agaaaagcat ttgttatctg taatagcaa acagcaggct   360 ttcactctgt aaaccatccc tgacaaatga tcccttgcta gagaatgtca gctgagcacc   420
aagggccttg ttagtgacag caaggaaaaa catcctgatg ttcctttga acacatcacc   480 tgaaacacac tgatgcttaa accttaactt ttttttttg ggggacatag tctcactctg   540
tcgcccaggc tggagtgcgt gggagaggac ctcggaaaga ctggcaagca tccgcataca   600
agggagtaac agcacaatac tccgtgaact tcggagccct ccaaaggaat actcaagggc   660
gggtaaagga tggcaagggt cgacggagag cccacgagga gagcggaagg tagagaggag   720
acaagcataa gacgcgagag gaactccaag gcggggccaa agagagaaac cacggtcacc   780
aacagaag                                                            788

<210> SEQ ID NO 99
<211> LENGTH: 307
<212> TYPE: DNA
<213> ORGANISM: Homo sapiens
<220> FEATURE:
<221> NAME/KEY: misc_feature
<222> LOCATION: (34)..(34)
<223> OTHER INFORMATION: a or g or c or t/u
<220> FEATURE:
<221> NAME/KEY: misc_feature
<222> LOCATION: (263)..(263)
<223> OTHER INFORMATION: a or g or c or t/u
<220> FEATURE:
<221> NAME/KEY: misc_feature
<222> LOCATION: (270)..(270)
<223> OTHER INFORMATION: a or g or c or t/u
<220> FEATURE:
<221> NAME/KEY: misc_feature
<222> LOCATION: (279)..(279)
<223> OTHER INFORMATION: a or g or c or t/u
<220> FEATURE:
<221> NAME/KEY: misc_feature
<222> LOCATION: (306)..(306)
<223> OTHER INFORMATION: a or g or c or t/u

<400> SEQUENCE: 99
agaagccaga ttcatctgca caaatacgtg gtgntctact ttagagagat tgatacaaaa    60
gacgattaca atgctctcag tgtctgcccc aagtaccacc tcatgaagga tgccactgct   120
ttctgtgcag aacttctcca tgtcaagcag caggtgtcag caggaaaaag atcacaagcc   180
tgccacgatg gctgctgctc cttgtagccc acccatgaga agcaagagac cttaaaggct   240
tcctatccca ccaattacag ggnaaaaacn gtagtgatna tccctgacag cttactatgc   300 cagccnt                                                             307

<210> SEQ ID NO 100
<211> LENGTH: 335
<212> TYPE: DNA
<213> ORGANISM: Homo sapiens
<220> FEATURE:
<221> NAME/KEY: misc_feature
<222> LOCATION: (67)..(67)
<223> OTHER INFORMATION: a or g or c or t/u
<220> FEATURE:
<221> NAME/KEY: misc_feature
```

```
<222> LOCATION: (315)..(315)
<223> OTHER INFORMATION: a or g or c or t/u
<220> FEATURE:
<221> NAME/KEY: misc_feature
<222> LOCATION: (333)..(333)
<223> OTHER INFORMATION: a or g or c or t/u

<400> SEQUENCE: 100
ttggctgaag atgctttatt gttgcattat caaaatcggt tacagttttc aattaaagct      60
gtaattngat ttctatgtat aaaacagctt tgaagttgta aatgtagttt ccaatcgtta     120
gttaatgcta cattagttag caatatttga aaattttatt ggtataaaat gttttaatta     180
ctaaggctgt ttgtaggctg catagtaagc ttcaggatca tcacacgttt tttccctgta     240
attgggtggg ataggaagcc tttaaggtct cttgcttctc attgggtggg ctacaaggag     300
cagcagccat ccgtnggcaa ggctttgtgg atnct                                335

<210> SEQ ID NO 101
<211> LENGTH: 639
<212> TYPE: DNA
<213> ORGANISM: Homo sapiens

<400> SEQUENCE: 101
ggaagagaaa gatcgtccag aggttccatc gcacacactg tatgacgtca ttggaaatga      60
aggaagacga ctttgtctgc tggcttcttg tgagtggcaa gccactgcag tggacccatc     120
tctgctattt tctttattct gccacttttc aaggatgacc tcacttctgc aatggttttg     180
aagaaagttc agtgaagtaa caaattgtgt gatggaaaca tatttcagat gggtaaacca     240
caagaacctt aatgggggc agtagtgtgg tggtagaaaa ggaagtcttc ttgatccttt     300
ctgtgagagg agaaaagcat tagttatctg tgaacagcaa acagcaggca tttcacatct     360
gtaaaccatc cctgacaaat gatcccttgc tagagaatgt cagctgagca ccaaggggcc     420
ttgttagtga cagcaaggac aaaacatcct gatgttcctt tgaacacat cagctgaaac     480 acactgatgc tctaaaccgt taactattta ttaatggggg aacataggtc tcaactcatg     540
tacgaccagg ctggagtgca gtggggttga acatcgacag acatagcaaa ccaccgatca     600
ctagggaaac aacgcacaga actccagact taaaacacc                             639

<210> SEQ ID NO 102
<211> LENGTH: 477
<212> TYPE: DNA
<213> ORGANISM: Homo sapiens
<220> FEATURE:
<221> NAME/KEY: misc_feature
<222> LOCATION: (365)..(365)
<223> OTHER INFORMATION: a or g or c or t/u

<400> SEQUENCE: 102
attcggcacc tgggggcag acactgagag cattgtaatc gtcttttgta tcaatctctc      60
taaagtagac caccacgtat ttgtgcagat gaatctggct tcttagatca ctgcagaaaa     120
ggttaaaggc aagggggaag aggtcttgag agttctcact gggactgccc tcgctcttgc     180
cacaggtacc atcgcacaca ctgttgacgt cattggaaag aaggaagacg actttgtctg     240
ctgccttctt tgagtggca agccactgca ctggacccat ctctgctatt ttcttttct      300 gccacttttc aaggatgacc tcacttctgc aatggttttg aagaaattca gtgaagtaac     360
aaatntgtgt gatggaaaca tatttcagat gggtaaacca caagaacctt aatgggggc     420 agtagtgtgg tggtagaaaa ggaagtcttc ttgatccttt ctgtgagagg agaaagc       477
```

<210> SEQ ID NO 103
<211> LENGTH: 432
<212> TYPE: DNA
<213> ORGANISM: Homo sapiens

<400> SEQUENCE: 103

```
ttttgatggt ccacttccat ttaatgaatt agtaaatatc ttttctcatg attttaatta      60 cattttttc tctagcttac tttattataa tacagcacat aatacaccta acatgcaaaa      120
tatgtgttaa ttggctgttt atgttattgg taagacttcc agtcaacagt aggctattag     180
aagttaagtt gtgggaaaat caaaggttat aggagatttt caactgcatg cagggccggt     240
gccctcccca ctgtgttgtt caagggtcag ctgtactctc taagggcttt gctaacttca     300
aaacatggag tatttgaata cagaaaccag agcatttaca tactcagctc aaggcagagc     360
tattaaaaaa actcctcttc tccatatgta ggaaaggaaa tacaaatgca tcctttgagt     420
catttgtgat gt                                                        432
```

<210> SEQ ID NO 104
<211> LENGTH: 316
<212> TYPE: DNA
<213> ORGANISM: Homo sapiens
<220> FEATURE:
<221> NAME/KEY: misc_feature
<222> LOCATION: (68)..(68)
<223> OTHER INFORMATION: a or g or c or t/u
<220> FEATURE:
<221> NAME/KEY: misc_feature
<222> LOCATION: (70)..(70)
<223> OTHER INFORMATION: a or g or c or t/u
<220> FEATURE:
<221> NAME/KEY: misc_feature
<222> LOCATION: (74)..(74)
<223> OTHER INFORMATION: a or g or c or t/u
<220> FEATURE:
<221> NAME/KEY: misc_feature
<222> LOCATION: (120)..(120)
<223> OTHER INFORMATION: a or g or c or t/u
<220> FEATURE:
<221> NAME/KEY: misc_feature
<222> LOCATION: (140)..(140)
<223> OTHER INFORMATION: a or g or c or t/u
<220> FEATURE:
<221> NAME/KEY: misc_feature
<222> LOCATION: (211)..(211)
<223> OTHER INFORMATION: a or g or c or t/u
<220> FEATURE:
<221> NAME/KEY: misc_feature
<222> LOCATION: (289)..(289)
<223> OTHER INFORMATION: a or g or c or t/u

<400> SEQUENCE: 104

```
aacagttgtg ctctgcccac aaacaggcgt ccctttccct ctggataaca acaaaagcaa      60
gccgggangn ctgncgctct cctcctgctg tctctgctgg tggccacatg ggtgctggtn     120
gcagggatct atctaatgtn gaggcacgaa agggatcaag aggacttcct tttctaccac     180
cacactactg cccccccatta aggttcttgt nggtttaccc atctgaaaat atgtttccat    240
cacacaattt gttacttcac tggaatttct tcaaaaccat tggcaggang tgagggtcat     300
ccttggaaaa gtgggc                                                    316
```

<210> SEQ ID NO 105
<211> LENGTH: 401
<212> TYPE: DNA
<213> ORGANISM: Homo sapiens
<220> FEATURE:
<221> NAME/KEY: misc_feature

```
<222> LOCATION: (274)..(274)
<223> OTHER INFORMATION: a or g or c or t/u

<400> SEQUENCE: 105
cctcacttct gcaatggttt tgaagaaatt cagtgaagta acaaattgtg tgatggaaac    60
atatttcaga tgggtaaacc acaagaacct taatgggggg cagtagtgtg gtggtagaaa   120
aggaagtctt cttgatcctt tcgtgcctcc acattagata gatccctgcc accagcaccc   180
atgtggccac cagcagagac agcaggagga gaggcagcca gcctcccggc tttgcttttg   240
ttgttatcca gaggggaaag gggacgcctg tttntggggc agagcacaac tgtttccctc   300
gtgcccgaat tctttgggcc ttcgaggggc caaatttccc tattaggtga ggtcgtattt   360
taaatttcgg taattcatgg tcataggctt gttttttcccc g                      401

<210> SEQ ID NO 106
<211> LENGTH: 516
<212> TYPE: DNA
<213> ORGANISM: Homo sapiens
<220> FEATURE:
<221> NAME/KEY: misc_feature
<222> LOCATION: (400)..(400)
<223> OTHER INFORMATION: a or g or c or t/u
<220> FEATURE:
<221> NAME/KEY: misc_feature
<222> LOCATION: (462)..(462)
<223> OTHER INFORMATION: a or g or c or t/u
<220> FEATURE:
<221> NAME/KEY: misc_feature
<222> LOCATION: (483)..(483)
<223> OTHER INFORMATION: a or g or c or t/u
<220> FEATURE:
<221> NAME/KEY: misc_feature
<222> LOCATION: (509)..(509)
<223> OTHER INFORMATION: a or g or c or t/u

<400> SEQUENCE: 106
gtttcaacac aattttggat cagctgcctg tttgcaaaaa cataatatat ttctgttaaa    60
cagttcttca cctaacagca tattgctctt ataactggta gagctgtttc aaaggaagtt   120
ggtttctggt ccaagttttg acctaaaacca tgtccatctt ctattaccag cacttacaag   180
cactgtgaaa actgatcatg acaaataagt aaaatttgct acattaaaca tattgcctca   240
gccattacta agcgtccact tgtaaagctg gacacagttt ttactttatg cttcattttg   300
attttttatc cgtaagacat aaattagaag gcatgaggtg gcccttttaag gataatctgc   360 aaatatacac attttaaata gtcatccatc tggaaatcgn tccaccattc caggggaagg   420
attccaggta ttggtgctgt ggtggaaata aagcattccc cngggaaaaa aaccatttta   480
tgnctaaata attaccacca ttaacctcnt ggggtt                              516

<210> SEQ ID NO 107
<211> LENGTH: 187
<212> TYPE: DNA
<213> ORGANISM: Homo sapiens

<400> SEQUENCE: 107
gaatactaac tctaagaacc cctcactgat tcactcaata gcatcttaag tgaaaaacct    60
tctattacat gcaaaaaatc attgttttta agataacaaa agtagggaat aaacaagctg   120
aacccacttt tactggacca aatgatctat tatatgtgta accacttgta tgatttggga   180
tttgcat                                                              187

<210> SEQ ID NO 108
```

```
<211> LENGTH: 156
<212> TYPE: DNA
<213> ORGANISM: Homo sapiens

<400> SEQUENCE: 108 tttttacaa cttcaaagct gttttataca tagaaatcaa ttacagtttt aattgaaaac      60
tataaccatt ttgataatgc aacaataaag catcttcagc caaacatcta gtcttccata   120
gaccatgcat tgcagtgtac ccagaactgt ttagct                              156

<210> SEQ ID NO 109
<211> LENGTH: 491
<212> TYPE: DNA
<213> ORGANISM: Homo sapiens
<220> FEATURE:
<221> NAME/KEY: misc_feature
<222> LOCATION: (478)..(478)
<223> OTHER INFORMATION: a or g or c or t/u
<220> FEATURE:
<221> NAME/KEY: misc_feature
<222> LOCATION: (491)..(491)
<223> OTHER INFORMATION: a or g or c or t/u

<400> SEQUENCE: 109
ctgagtgtga tggtgtaagc ctgtggtccc agctactagg gaggctgaga tgggattaca     60
ggtgtgagcc acggcgcctg gcctaaaagc atcttttctt taacgcaga ggttatgttg    120 tattattagc ataaatgttt ttttctggga atgcttattt cacacagcac aatactgaat   180
cttctctgga atgtggatcg atttcagatg gatgactatt aaaatgtgta tatttgcaga   240
ttatccttaa agggccacct catgccttct aatttatgtc ttacggataa aaaatcaaaa    300
tgaagcataa agtaaaaact gtgtccagct ttacaagtgg acgcttagta atggctgagg   360
caatatgttt aatgtagcca aattttactt atttgtccat gatccagttt ttcacagtgc   420
ttgttaagtg ctggtaatta ggaaggtggg acatgggtta ggtcaaaact tgggaccnga   480
aaccaacttg n                                                       491

<210> SEQ ID NO 110
<211> LENGTH: 270
<212> TYPE: DNA
<213> ORGANISM: Homo sapiens

<400> SEQUENCE: 110
tttttttttt acaacttcaa agctgtttta tacatagaaa tcaattacag ttttaattga     60
aaactataac cattttgata atgcaacaat aaagcatctt cagccaaaca tctagtcttc   120
catagaccat gcattgcatt gtacccagaa ctgtttagct aatattctat gtttaattaa   180
tgaatactaa ctctaagaac ccctcactga ttcactcaat agcatcttaa gtgaaaaacc   240
ttctattaca tgcaaaaaat cattggtttt                                   270

<210> SEQ ID NO 111
<211> LENGTH: 478
<212> TYPE: DNA
<213> ORGANISM: Homo sapiens

<400> SEQUENCE: 111
ttttctgagt aagaacaggc tttatttgta aaaccactcg tgactcttta caaagcagga     60
tacacagaag ggaaaaaaat acacagtgca aaatggatgt tctgagtgcc acaaggatct   120
gctgaaaaaa gccaaagatg taagatggct gggtatatat gagaatgaat atttcactat   180
attctgattc aattaccagt ctcagtggcc caggatgagc ttttggtgtg gtcacatggc   240
```

```
caacatttgg ataacaaatg aggaataatg gtaccgcctc actagtgcct gagaacagca    300
tgttctggaa aatgtctctg gagttagaga tgtgttagct ttttcattac agatggagaa    360
atacaatgtt tacacaacag tccagggggtg gggtcaaaag ttggaaggtg tcattagacg    420
cagccaaata aagtgaagac aacccaggtg actggcagcc ctgacttgtg cgtgggcg      478
```

<210> SEQ ID NO 112
<211> LENGTH: 263
<212> TYPE: DNA
<213> ORGANISM: Homo sapiens

<400> SEQUENCE: 112

```
tttctgagta agaacaggct ttatttgtaa aaccactcgt gactctttac aaagcaggat     60
acacagaagg gaaaaaaata cacagtgcaa aatggatgtt ctgagtgcca caaggatctg    120
ctgaaaaaag ccaaagatgt aagatggctg gtatatatg agaatgaata tttcactata    180
ttctgattca attaccagtc tcagtggccc aggatgagct ttggtggtgg tcacatggcc    240
aacatttgga taacaaatga gga                                            263
```

<210> SEQ ID NO 113
<211> LENGTH: 388
<212> TYPE: DNA
<213> ORGANISM: Homo sapiens

<400> SEQUENCE: 113

```
gagatggagg tctcgctttg tgacgtagcc tggtcttgag cgatcctttt gccttggcct     60
tgccaaagtg ctgggattgg aggcatgagc cactgcaccc accctgtttt ttttttaag    120 taaaccatta taataactca tttataaaaa ggttacttca agagggcttt caacttaaga    180
attattttca ttttgaacat gaaaagttaa atagtaacta agaaactgag aactctgaca    240
gtgacctcta ataggtaact ttaggcaaaa gtagacaagt ttgtgggtat tttgttgttc    300
atgttaaaag gcacctgtac aagaatcaag atatgaatct agtttgtaga gggaaggtct    360
tatgcaaata ccaaatcata caagtggt                                      388
```

<210> SEQ ID NO 114
<211> LENGTH: 450
<212> TYPE: DNA
<213> ORGANISM: Homo sapiens

<400> SEQUENCE: 114

```
agagatgttg gtctcgcttt gtgacgtagc ctgggcttga gcgatccttt tgccttggcc     60
ttgccaaagt gctgggattg gaggcatgag ccactgcacc cacccctgtt ttttttttaa    120
gtaaaccatt ataataactc atttataaaa aggttacttc aagagggctt tcaacttaag    180
aattattttc attttgaaca tgaaaagtta aatagtaact aagaaactga gaactctgac    240
agtgacctct aataggtaac tttaggcaaa agtagacaag tttgtgggta ttttgttgtt    300
catgttaaaa ggcacctgta caagaatcaa gatatgaatc tagtttgtag agggaaggtc    360
ttatgcaaat accaaatcat acaagtggtt acacatataa tagatcattt ggtccagtaa    420
aagtgggttc agcttgttta ttccctactt                                    450
```

<210> SEQ ID NO 115
<211> LENGTH: 162
<212> TYPE: DNA
<213> ORGANISM: Homo sapiens

```
<400> SEQUENCE: 115
gagatggagg tctcgctttg tgacgtagcc tggtcttgag cgatcctttt gccttggctt    60
gcaaagtgct gggattggag gcatgagcac tgcacccacc cctgttttttt ttttaagta   120 aaccattata ataactcatt tataaaaagg ttacttcaag ag                      162

<210> SEQ ID NO 116
<211> LENGTH: 392
<212> TYPE: DNA
<213> ORGANISM: Homo sapiens
<220> FEATURE:
<221> NAME/KEY: misc_feature
<222> LOCATION: (117)..(117)
<223> OTHER INFORMATION: a or g or c or t/u
<220> FEATURE:
<221> NAME/KEY: misc_feature
<222> LOCATION: (345)..(345)
<223> OTHER INFORMATION: a or g or c or t/u
<220> FEATURE:
<221> NAME/KEY: misc_feature
<222> LOCATION: (378)..(378)
<223> OTHER INFORMATION: a or g or c or t/u
<220> FEATURE:
<221> NAME/KEY: misc_feature
<222> LOCATION: (388)..(388)
<223> OTHER INFORMATION: a or g or c or t/u

<400> SEQUENCE: 116
ttcactcaat agcatcttaa gtgaaaaacc ttctattaca tgcaaaaaat cattgttttt    60
aagataacaa agtagggaa taaacaagct gaacccactt ttactggacc aaatgancta   120
ttatatgtat aaccacttgt atgatttggt atttgcataa gaccttccct ctacaaacta  180
gattcatatc ttgattcttg tacaggtgcc ttttaatat tctgtgatga aatcgttcac   240
agtcagagta catgtctgct gcatatggga aatagggact gttgttctga gggacaaggc  300
actcaattca gccgtaaagg ctgacccggg ctacttttt tccangggaa tacaatttttt  360 ttaccttgga ataaaatngg gcccgacngg ac                                 392

<210> SEQ ID NO 117
<211> LENGTH: 428
<212> TYPE: DNA
<213> ORGANISM: Homo sapiens

<400> SEQUENCE: 117
tttttttttt tgagtaagaa caggctttat ttgtaaaacc actcgtgact ctttacaaag    60
caggatacac agaagggaaa aaatacaca gtgcaaaatg gatgttctga gtgccacaag   120
gatctgctga aaaaaagcca aagatgtaag atggctgggt atatatgaga atgaatattt   180
cactatattc tgattcaatt accagtctca gtggcccagg atgagctttt ggtgtggtca   240
catggccaac atttggataa caatgagga ataatggtac cgcctcacta gtgcctgaga   300
acagcatgtt ctggaaaatg tctctggagt tagagatgtg ttagcttttt cattacagat   360
ggagaaatac aatgtttaca caacagtcca ggggtggggt caaaagttgg aaggtgtcat   420
tagacgca                                                           428

<210> SEQ ID NO 118
<211> LENGTH: 430
<212> TYPE: DNA
<213> ORGANISM: Homo sapiens

<400> SEQUENCE: 118
aaatttttaa cttttaatag ttaaaatagt taactattgg tatggtagga aatgataaag    60
```

```
tagactagta tctgtataca ttttctgcat ttatgacata ccttttctt cattttttc      120 aatattttaa ttgaaaagtt catccgagtt tcatctaagt tttttcaaag tgatacaaat     180
ctccaaaaaa ttttccaata tatgtattga aaaatccag gtgtaagtgg ctctgcgcag      240
tccaaacctg tgttgttcaa gggtcaactg tgtatgaatc caagcgaaag cttttcttaa     300
cacctcataa gaactatttt ttaaaaaaca ggaactagca tagagtaacc atcacaggta     360
aagtgtaatt tgttatcagc catcttttgc ccatttcagt actggtagaa ggctcaatgg     420
taaaaataaa                                                            430
```

<210> SEQ ID NO 119
<211> LENGTH: 368
<212> TYPE: DNA
<213> ORGANISM: Homo sapiens

<400> SEQUENCE: 119

```
tttttttttt tttttttttt ttttctgact gtcccgtttt tattttacc attgagcctt      60 ctaccagtac tgaaatgggc aaaagatggc tgataacaaa ttacacttta cctgtgatgg     120
ttactctatg ctagttcctg tttttaaaa aatagttctt atgaggtgtt aagaaaagct      180
ttcgcttgga ttcatacaca gttgacccct gaacaacaca ggtttggact gcgcagacca     240
cttacacctg gatttttca atacatatat tggaaaattt ttgggggatt tgtatcactt      300
tgaaaaaact tagatgaaac tcggatggac ttttccatta aaatattgga aaaatgaag      360 aaaaaggt                                                              368
```

<210> SEQ ID NO 120
<211> LENGTH: 435
<212> TYPE: DNA
<213> ORGANISM: Homo sapiens

<400> SEQUENCE: 120

```
tttttttttt tttttttttt ttttctgact ggcccgtttt tattttacc attgagcctt      60 ctaccagtac tgaaatgggc aaaagatggc tgataacaaa ttacacttta cctgggatgg     120
ttactctatg ctagttcctg tttttaaaa aatagttctt atgaggggtt aaaaaagct       180 ttcgcttgga ttcatacaca gttgacccct gaacaacaca ggtttggact gcgcagagcc     240
acttacacct ggattttttc aatacatata ttggaaaatt ttttggagat tgtatcact      300 ttgaaaaaac ttagatgaaa ctcggatgaa cttttcaatt aaaatattga aaaaatgaa      360 gaaaaaggta tgtcataaat gcagaaaatg tatacagata ctagtctact ttatcatttc     420
ctaccatacc aatag                                                      435
```

<210> SEQ ID NO 121
<211> LENGTH: 880
<212> TYPE: DNA
<213> ORGANISM: Homo sapiens
<220> FEATURE:
<221> NAME/KEY: misc_feature
<222> LOCATION: (788)..(788)
<223> OTHER INFORMATION: a or g or c or t/u

<400> SEQUENCE: 121

```
taaaggaaca gttgtgctct gcccacaaac aggcgtccct ttccctctgg ataacagtaa      60
gtgcccagta acttcaacca gatgatcaaa gtggctcaca cacagtcact gcccccact     120 cagtatgtgg aagggttgtg tgtatgtggg cagtgcaagg ggtcgctgcc tgtgtacact     180
```

-continued

| | |
|---|---|
| gaactggggt gcagagaaag ccaacagtgc tgtcccagag aacctagaat ctgagtaaga | 240 |
| acaggcttta tttgtaaaac cactcgtgac tctttacaaa gcaggataca cagaagggaa | 300 |
| aaaaatacac agtgcaaaat ggatgttctg agtgccacaa ggatctgctg aaaaaagcca | 360 |
| aagatgtaag atggctgggt atatatgaga atgaatattt cactatattc tgattcaatt | 420 |
| accagtctca gtggcccagg atgagctttt ggtgtggtca catggccaac atttggataa | 480 |
| caaatgagga ataatggtac cgcctcacta gtgcctgaga acagcatgtt ctggaaaatg | 540 |
| tctctggagt tagagatgtg ttagctttt cattacagat ggagaaatac aatgtttaca | 600 |
| caacagtcca ggggtggggg tcaaaagttg aaggtgtca ttagacgcag ccaaataaag | 660 |
| tgaagaccac ccaggtgact ggcagccctg acttgtgcgt gggcgaaacc ttacagattc | 720 |
| ctggggcact ctgtgcctga acttacctgg atggtctttg tgaggcgggt gggcacttat | 780 |
| cctccatnaa tggtcagtct aacaagaccg gcctgtaaaa atggcatcta ataggggcta | 840 |
| tggaatggaa aacagttggt acccagaaat aactttaatt | 880 |

<210> SEQ ID NO 122
<211> LENGTH: 437
<212> TYPE: DNA
<213> ORGANISM: Homo sapiens
<220> FEATURE:
<221> NAME/KEY: misc_feature
<222> LOCATION: (34)..(34)
<223> OTHER INFORMATION: a or g or c or t/u
<220> FEATURE:
<221> NAME/KEY: misc_feature
<222> LOCATION: (192)..(192)
<223> OTHER INFORMATION: a or g or c or t/u

<400> SEQUENCE: 122

| | |
|---|---|
| gacagtctgg gagcccagag ctctgggagg agtngggaaa atgctgcttc ctgctgcttg | 60 |
| cttctaggca cctgcttccg ccatctcact taccatggct agagatgggg gtgagactgg | 120 |
| ggaaggacaa aagcagggaa cagataaggg atggaaatca aagggaata tagaaagaac | 180 |
| tctggatatg cnagaaatgc cggtacctga gcattttgta tcaatgggag taccctctgt | 240 |
| aactgctcag taggttacaa atgaagagtc caccagtatt agaaacaatt taaacttgcc | 300 |
| agtaccaact gggatgtgtg ccttcaattt gaaaattgta tgtttattt tttaaatttg | 360 |
| gttaacagca ttaatttata gagtatttga tgtcatttat ggttcccgag gtgtttccaa | 420 |
| cacaattttt gggatca | 437 |

<210> SEQ ID NO 123
<211> LENGTH: 1107
<212> TYPE: DNA
<213> ORGANISM: Homo sapiens
<220> FEATURE:
<221> NAME/KEY: misc_feature
<222> LOCATION: (893)..(893)
<223> OTHER INFORMATION: a or g or c or t/u

<400> SEQUENCE: 123

| | |
|---|---|
| cttttaatag ttaaaatagt taactattgg tatggtagga aatgataaag tagactagta | 60 |
| tctgtataca ttttctgcat ttatgacata ccttttttctt catttttttc aatattttaa | 120 |
| ttgaaaagtt catccgagtt tcatctaagt tttttcaaag tgatacaaat ctccaaaaaa | 180 |
| ttttccaata tatgtattga aaaaatccag gtgtaagtgg ctctgcgcag tccaaacctg | 240 |
| tgttgttcaa gggtcaactg tgtatgaatc caagcgaaag cttttcttaa cacctcataa | 300 |
| gaactatttt ttaaaaaaca ggaactagca tagagtaacc atcacaggta aagtgtaatt | 360 |

```
tgttatcagc catcttttgc ccatttcagt actggtagaa ggctcaatgg taaaaataaa      420
aacgggacag tcagaagatc tggaagtcct gaccctgctt tcacctggca tgtgtaatcc      480
agtcatgctc gtatcagtct ctgtaggagc acttgaaggt attacataaa tgctatctaa      540
ctctgggaaa cgccaacatg tgattgcctc cagaggaatc ttctttaaaa aaaaattcaa      600
aatgttattt ccttactagg atgtctttaa agaattataa cccttaccgt gcctccacat      660
tagatagatc cctgccacca gcacccatgt ggccaccagc agagacagca ggaggagagg      720
cagccagcct cccggcttgc ttttgtctgg aaaaaaacaa agcttattca cctttggaaa      780
aaaatccaca cttatctctt aatttaaaaa ctaagacttg gtatacttta tagagggtta      840
tttatttttt attattttt agttttgaga cagagtctcg ctttgttgcc tangctggag      900
tgcagtggcg caatctcggt tcactgcagc ctccgttctc cggggttcaa ggcatgctgg      960
ctcagcctcc tgtatagctg ggattaaag gcatgtgttc acgcggccca gcccctttg     1020 taaaagattt agatcccttt taaaaccatc agtcaggagg ctccttaaa aagtctggcc     1080 atctaatctt ttttcccca aagggg                                         1107

<210> SEQ ID NO 124
<211> LENGTH: 290
<212> TYPE: DNA
<213> ORGANISM: Homo sapiens

<400> SEQUENCE: 124
tttttttttt tctttttct gagtaagaac aggctttatt tgtaaaacca ctcgtgactc      60
tttacaaagc aggatacaca gaagggaaaa aaatacacag tgcaaaatgg atgttctgag     120
tgccacaagg atctgctgaa aaaagccaaa gatgtaagat ggctgggtat atatgagaat     180
gaatatttca ctatattctg attcaattac cagtctcagt ggcccaggat gagcttttgg     240
tgtggtcaca tggccaacat ttggataaca atgaggaat aatctcgtgc                290

<210> SEQ ID NO 125
<211> LENGTH: 812
<212> TYPE: DNA
<213> ORGANISM: Homo sapiens

<400> SEQUENCE: 125
aatttataga gtattgatgt catttatgtt tctgaggtgt ttcaacacaa ttttggatca      60
gctgcctgtt tgcaaaaaca taatatattt ctgttaaaca gttcttcacc taacagcata     120
ttgctcttat aactggtaga gctgtttcaa aggaagttgg tttctggtcc aagttttgac     180
ctaaaccatg tccatcttct attaccagca cttacaagca ctgtgaaaac tgatcatgac     240
aaataagtaa aatttgctac attaaacata ttgcctcagc cattactaag cgtccacttg     300
taaagctgga cacagttttt actttatgct tcattttgat ttttatccg taagacataa     360 attgaaggc atgaggtggc cctttaagga taatctgcaa atatacacat tttaatagtc     420
atccatctga aatcgatcca cattccagag aagattcagt attgtgctgt gtgaaataag     480
cattcccaga aaaaaaacat ttatgctaat aatacaacat aacctctgca ttaaagaaaa     540
agatgctttt aggccaggcg ccgtggctca cgcctgtaat ccctgcactt tgagaggctg     600
aggtgggtgg atcatgaggt caggagatca agaccatcct ggctaacagg gtgaaacccc     660
gtctctactg gggatataac aaagttagct gggtgtggtg gtgggtgctt gtggtcccag     720
ctactcagga ggctgaggca ggagaatggc gtgaacccgg aaggcagagg ttgtagtgac     780
```

```
gcgaggttca cgccactgca ttccagtctg gg                                     812
```

<210> SEQ ID NO 126
<211> LENGTH: 679
<212> TYPE: DNA
<213> ORGANISM: Homo sapiens
<220> FEATURE:
<221> NAME/KEY: misc_feature
<222> LOCATION: (8)..(8)
<223> OTHER INFORMATION: a or g or c or t/u

<400> SEQUENCE: 126

```
caggaagnta agaacagtcc taaaatctct ttggcttctt tgtcctgata tgcaccggca        60
ttttcacagt aggaactagg gtttctgtcc agttttttttg gttctttaag gaattaatgt     120
tattctgggt acaactgctt acatacatag cacatataga tgacatttttt acaggccgtc    180
ttgttagact gacatacatg gaggatagtg ccacccgcct cacaagaaca tcaggtaagc     240
tcaggcacag agtgcccagg aatctgtaag gcttcgccca cgcacaagtc agggctgcca     300
gtcacctggg ttgtcttcac tttatttggc tgcgtctaat gacaccttcc aacttttgac     360
cccaccctg gactgttgtg taaacattgt atttctccat ctgtaatgaa aaagctaaca      420
catctctaac tccagagaca ttttccagaa catgctgttc tcaggcacta gtgaggcggt     480
accattattc ctcatttgtt atccaaatgt tggccatgtg accacaccaa aagctcatcc    540
tgggccactg agactggtaa ttgaatcaga atatagtgaa atattcattc tcatatatac     600
ccagccatct tacatctttg gcttttttca gcagatcctt gtggcactca gaacatccat     660
tttgcactgt gtattttttt                                                  679
```

<210> SEQ ID NO 127
<211> LENGTH: 449
<212> TYPE: DNA
<213> ORGANISM: Homo sapiens

<400> SEQUENCE: 127

```
aaattttttaa cttttaatag ttaaaatagt taactattgg tatggtagga aatgataaag       60
tagactagta tctgtataca ttttctgcat ttatgacata ccttttttctt catttttttc    120
aatatttttaa ttgaaaagtt catccgagtt tcatctaagt tttttcaaag tgatacaaat     180
ctccaaaaaa ttttccaata tatgtattga aaaaatccag gtgtaagtgg ctctgcgcag      240
tccaaacctg tgttgttcaa gggtcaactg tgtatgaatc caagcgaaag cttttcttaa    300
cacctcataa gaactatttt ttaaaaaaca ggaactagca tagagtaacc atcacaggta   360
aagtgtaatt tgttatcagc catcttttgc ccatttcagt actggtagaa ggctcaatgg    420
taaaaataaa aacgggacag tcagaaaaa                                       449
```

<210> SEQ ID NO 128
<211> LENGTH: 396
<212> TYPE: DNA
<213> ORGANISM: Homo sapiens

<400> SEQUENCE: 128

```
tctgagtaag aacaggcttt atttgtaaaa ccactcgtga ctctttacaa agcaggatac      60
acagaaggga aaaaaataca cagtgcaaaa tggatgttct gagtgccaca aggatctgct    120
gaaaaaagcc aaagatgtaa gatggctggg tatatatgag aatgaatatt tcactatatt     180
ctgattcaat taccagtctc agtgggccag gatgagcttt tggtgtggtc acatggccaa    240
catttggata acaaatgagg aataatggta ccgcctcact agtgcctgag aacagcatgt     300
```

```
tctggaaaat gtctctggag ttagagatgt gttagctttt tcattacaga tggagaaata    360
caatgtttac acaacagtcc aggggtgggg tcaaag                              396

<210> SEQ ID NO 129
<211> LENGTH: 232
<212> TYPE: DNA
<213> ORGANISM: Homo sapiens

<400> SEQUENCE: 129
ctgactgtcc cgttttatt tttaccattg agccttctac cagtactgaa atgggcaaaa     60
gatggctgat aacaaattac actttacctg tgatggttac tctatgctag ttcctgtttt   120
ttaaaaaata gttcttatga ggtgttaaga aaagctttcg cttggattca tacacagttg   180
acccttgaac aacacaggtt tggactgcgc agagccaccc tcgtgccgaa tt           232

<210> SEQ ID NO 130
<211> LENGTH: 185
<212> TYPE: DNA
<213> ORGANISM: Homo sapiens

<400> SEQUENCE: 130
ctgactgtcc cgttttatt tttaccattg agccttctac cagtactgaa atgggcaaaa     60
gatggctgat aacaaattac actttacctg tgatggttac tctatgctag ttcctgtttt   120
ttaaaaaata gttcttatga ggtgttaaga aaagctttcg cttggattca tacacagttg   180
accct                                                                185

<210> SEQ ID NO 131
<211> LENGTH: 726
<212> TYPE: DNA
<213> ORGANISM: Homo sapiens

<400> SEQUENCE: 131
ggaaatgata aagtagacta gtatctgtat acattttctg catttatgac ataccttttt     60
cttcattttt ttcaatattt taattgaaaa gttcatccga gtttcatcta agttttttca   120
aagtgataca aatctccaaa aaattttcca atatatgtat tgaaaaaatc caggtgtaag   180
tggctctgcg cagtccaaac ctgtgttgtt caagggtcaa ctgtgtatga atccaagcga   240
aagcttttct taacacctca taagaactat ttttaaaaa acaggaacta gcatagagta   300
accatcacag gtaaagtgta atttgttatc agccatcttt gcccatttca gtactggtag   360
aaggctcaat ggtaaaaata aaacgggac agtcagaaga tctggaagtc ctgaccctgc   420
tttcacctgg catgtgtaat ccagtcatgc tcgtatcagt ctctgtagga gcacttgaag   480
gtattacata aatgctatct aactctggga acgccaaca tgtgattgcc tccagaggaa   540
tcttctttaa aaaaaattc aaaatgttat ttccttacta ggatgtcttt aaagaattat   600
aacccttacc gtgcctccac attagataga tccctgcaac agacccatgt ggcaccagca   660
gagacagcag gaggagaggc agcagctccc ggttgtttgt ctggaaaaac aaaggttatc   720
actttg                                                               726

<210> SEQ ID NO 132
<211> LENGTH: 185
<212> TYPE: DNA
<213> ORGANISM: Homo sapiens

<400> SEQUENCE: 132
```

```
ctgactgtcc cgttttttatt tttaccattg agccttctac cagtactgaa atgggcaaaa    60
gatggctgat aacaaattac acttacctg tgatggttac tctatgctag ttcctgtttt   120
ttaaaaaata gttcttatga ggtgttaaga aaagctttcg cttggattca tacacagttg   180
accct                                                               185

<210> SEQ ID NO 133
<211> LENGTH: 291
<212> TYPE: DNA
<213> ORGANISM: Homo sapiens

<400> SEQUENCE: 133
gcacgagatt attcctcatt tgttatccaa atgttggcca tgtgaccaca ccaaaagctc    60
atcctgggcc actgagactg gtaattgaat cagaatatag tgaaatattc attctcatat   120
atacccagcc atcttacatc tttggctttt ttcagcagat ccttgtggca ctcagaacat   180
ccattttgca ctgtgtattt tttcccttc tgtgtatcct gctttgtaaa gagtcacgag   240
tggttttaca aataaagcct gttcttactc agaaaaaaaa aaaaaaaaa a             291

<210> SEQ ID NO 134
<211> LENGTH: 795
<212> TYPE: DNA
<213> ORGANISM: Homo sapiens
<220> FEATURE:
<221> NAME/KEY: misc_feature
<222> LOCATION: (1)..(2)
<223> OTHER INFORMATION: a or g or c or t/u
<220> FEATURE:
<221> NAME/KEY: misc_feature
<222> LOCATION: (770)..(770)
<223> OTHER INFORMATION: a or g or c or t/u

<400> SEQUENCE: 134
nnttgaacag gcgtgacggt ccggattccc gggatgttgt gctctgccca caaacaggcg    60
tccctttccc tctggataac aacaaaagca agccggagg ctggctgcct ctcctcctgc   120
tgtctctgct ggtggccaca tgggtgctgg tggcagggat ctatctaatg tggaggcacg   180
aaaggatcaa gaagacttcc ttttctacca ccacactact gccccccatt aaggttcttg   240
tggtttaccc atctgaaata tgtttccatc acacaatttg ttacttcact gaatttcttc   300
aaaaccattg cagaagtgag gtcatccttg aaaagtggca gaaaagaaa atagcagaga   360 tgggtccagt gcagtggctt gccactcaaa agaaggcagc agacaaagtc gtcttccttc   420
tttccaatga cgtcaacagt gtgtgcgatg gtacctgtgg caagagcgag ggcagtccca   480
gtgagaactc tcaagacctc ttcccccttg cctttaacct tttctgcagt gatctaagaa   540
gccagattca tctgcacaaa tacgtggtgg tctactttag agagattgat acaaaagacg   600
attacaatgc tctcagtgtc tgccccaagt accacctcat gaaggatgcc actgcttttct   660 gtgcagaact tctccatgtc aagcagcagg tgtcagcagg aaaaagatca caagcctgcc   720
acgatggctg ctgctccttg tagcccaccc atgagaagca agagaccttn aaggcttcct   780
atcccaccat tacag                                                    795

<210> SEQ ID NO 135
<211> LENGTH: 387
<212> TYPE: DNA
<213> ORGANISM: Homo sapiens

<400> SEQUENCE: 135
tttttttttt tttctgagta agaacaggct ttatttgtaa aaccactcgt gactctttac    60
```

| | | |
|---|---|---|
| aaagcaggat acacagaagg gaaaaaaata cacagggcaa aatggatgtt ctgagtgcca | 120 | |
| caaggatctg ctgaaaaaag ccaaagatgt aagatggctg ggtatatatg agaatgaata | 180 | |
| tttcactata ttctgattca attaccagtc tcagtggccc aggatgagct tttggtgtgg | 240 | |
| tcacatggcc aacatttgga taacaaatga ggaataatgg taccgcctca ctagtgcctg | 300 | |
| agaacagcat gttctggaaa atgtctctgg agttagagat gtgttagctt tttcattaca | 360 | |
| gatggagaaa tacaatgttt acacaac | 387 | |

<210> SEQ ID NO 136
<211> LENGTH: 561
<212> TYPE: DNA
<213> ORGANISM: Homo sapiens

<400> SEQUENCE: 136

| | | |
|---|---|---|
| catgatgttc agtatgatca gttaacctta acctctgagc atcctgaagc aaaatctaaa | 60 | |
| taatgcagct attaccactg gtggtccagg ctctggtgaa gccctctgag cccaggagga | 120 | |
| agagaaagca ttgtccagag gtaggaacac agtctgggag cccagagctc tgggaggagt | 180 | |
| gggaaaatgc tgcttcctgc tgcttgcttc taggcacctg cttccgccat ctcacttacc | 240 | |
| atggctagag atgggggtga gactggggaa ggacaaaagc agggaacaga taagggatgg | 300 | |
| aaatcagaag ggaatataga aagaactctg gatgtggaga aatgccggta cctgagcatt | 360 | |
| ttgtatcaat gggagtaccc tctgtaactg ctcagtaggt tacaaatgaa gagtccacca | 420 | |
| gtattagaaa caatttaaac ttgccagtac caactgggat gtgtgccttc aatttgaaaa | 480 | |
| ttgtatgttt tattttttaa atttgttaac agcattaatt tatagagtat tgatgtcatt | 540 | |
| tatgtttctg aggtgtttca a | 561 | |

<210> SEQ ID NO 137
<211> LENGTH: 476
<212> TYPE: DNA
<213> ORGANISM: Homo sapiens

<400> SEQUENCE: 137

| | | |
|---|---|---|
| tctgagtaag aacaggcttt atttgtaaaa ccactcgtga ctctttacaa agcaggatac | 60 | |
| acagaaggga aaaaaataca cagtgcaaaa tggatgttct gagtgccaca aggatctgct | 120 | |
| gaaaaaagcc aaagatgtaa gatggctggg tatatatgag aatgaatatt tcactatatt | 180 | |
| ctgattcaat taccagtctc agtgcccag gatgagcttt tggtgtggtc acatggccaa | 240 | |
| catttggata caaatgagg aataatggta ccgcctcact agtgcctgag aacagcatgt | 300 | |
| tctggaaaat gtctctggag ttagagatgt gttagctttt tcattacaga tggagaaata | 360 | |
| caatgtttac acacagtcc agggggtgggg tcaaagttg gaaggtgtca ttagacgcag | 420 | |
| ccaaataaag tgaagacaac ccaggtgact ggcagccctg acttgtgcgt gggcga | 476 | |

<210> SEQ ID NO 138
<211> LENGTH: 186
<212> TYPE: DNA
<213> ORGANISM: Homo sapiens

<400> SEQUENCE: 138

| | | |
|---|---|---|
| ctgactgtcc cgttttattt tttaccattg agccttctac cagtactgaa atgggcaaaa | 60 | |
| gatggctgat aacaaattac actttacctg tgatggttac tctatgctag atcctgtttt | 120 | |
| tttaaaaaat agttcttatg aggtgttaag aaaagctttc gcttggattc atacacagtt | 180 | | gaccct                                                                          186

<210> SEQ ID NO 139
<211> LENGTH: 456
<212> TYPE: DNA
<213> ORGANISM: Homo sapiens
<220> FEATURE:
<221> NAME/KEY: misc_feature
<222> LOCATION: (255)..(255)
<223> OTHER INFORMATION: a or g or c or t/u
<220> FEATURE:
<221> NAME/KEY: misc_feature
<222> LOCATION: (260)..(260)
<223> OTHER INFORMATION: a or g or c or t/u
<220> FEATURE:
<221> NAME/KEY: misc_feature
<222> LOCATION: (307)..(307)
<223> OTHER INFORMATION: a or g or c or t/u
<220> FEATURE:
<221> NAME/KEY: misc_feature
<222> LOCATION: (350)..(350)
<223> OTHER INFORMATION: a or g or c or t/u
<220> FEATURE:
<221> NAME/KEY: misc_feature
<222> LOCATION: (406)..(406)
<223> OTHER INFORMATION: a or g or c or t/u
<220> FEATURE:
<221> NAME/KEY: misc_feature
<222> LOCATION: (431)..(431)
<223> OTHER INFORMATION: a or g or c or t/u
<220> FEATURE:
<221> NAME/KEY: misc_feature
<222> LOCATION: (446)..(446)
<223> OTHER INFORMATION: a or g or c or t/u

<400> SEQUENCE: 139
aggaagttaa gaacagtcct aaaatctctt tggcttcttt gtcctgatat gcaccggcat     60
tttcacagta ggaactaggg tttctgtcca gttttttttgg ttctttaagg aattaatgtt    120
attctgggta caactgctta catacatagc acatatagat gacatttttta caggccgtct    180 tgttagactg acatacatgg aggatagtgc cacccgcctc acaagaacat caggtaagct    240
caggcacaga gtccnagggn atctgtaagg gcttcgccca cgcacaagtc agggctgcca    300
gtcaccnggg ttgtcttcac tttatttggg ctgcgtctaa tgacaccttn ccaacttttt    360
gaccccaccc tggggcttgt tgtgtaaacc attgttattt ctcccntctg taatggaaaa    420
aggttaacac nttttttaact tccggngaca ttttttc                              456

<210> SEQ ID NO 140
<211> LENGTH: 1816
<212> TYPE: DNA
<213> ORGANISM: Homo sapiens

<400> SEQUENCE: 140
gcacgagcga tgtcgctcgt gctgctaagc ctggccgcgc tgtgcaggag cgccgtaccc     60
cgagagccga ccgttcaatg tggctctgaa actgggccat ctccagagtg gatgctacaa    120
catgatctaa tccccggaga cttgagggac ctccgagtag aacctgttac aactagtgtt    180
gcaacagggg actattcaat tttgatgaat gtaagctggg tactccgggc agatgccagc    240
atccgcttgt tgaaggccac caagatttgt gtgacgggca aaagcaactt ccagtcctac    300
agctgtgtga ggtgcaatta cacagaggcc ttccagactc agaccagacc ctctggtggt    360
aaatggacat ttcctacat cggcttccct gtagagctga acacagtcta tttcattggg    420
gcccataata ttcctaatgc aaatatgaat gaagatggcc cttccatgtc tgtgaatttc    480
acctcaccag gctgcctaga ccacataatg aaatataaaa aaagtgtgt caaggccgga    540

```
agcctgtggg atccgaacat cactgcttgt aagaagaatg aggagacagt agaagtgaac    600
ttcacaacca ctcccctggg aaacagatac atggctctta tccaacacag cactatcatc    660
gggttttctc aggtgtttga gccacaccag aagaaacaaa cgcgagcttc agtggtgatt    720
ccagtgactg gggatagtga aggtgctacg gtgcagctga ctccatattt tcctacttgt    780
ggcagcgact gcatccgaca taaaggaaca gttgtgctct gcccacaaac aggcgtccct    840
ttccctctgg ataacaacaa aagcaagccg ggaggctggc tgcctctcct cctgctgtct    900
ctgctggtgg ccacatgggt gctggtggca gggatctatc taatgtggag gcacgaaagg    960
atcaagaaga cttccttttc taccaccaca ctactgcccc ccattaaggt tcttgtggtt   1020
tacccatctg aaatatgttt ccatcacaca atttgttact tcactgaatt tcttcaaaac   1080
cattgcagaa gtgaggtcat ccttgaaaag tggcagaaaa agaaaatagc agagatgggt   1140
ccagtgcagt ggcttgccac tcaaaagaag gcagcagaca aagtcgtctt ccttctttcc   1200
aatgacgtca acagtgtgtg cgatggtacc tgtggcaaga gcgagggcag tcccagtgag   1260
aactctcaag actcttcccc ttgcctttaa ccttttctgc agtgatctaa gaagccagat   1320
tcatctgcac aaatacgtgg tggtctactt tagagagatt gatacaaaag acgattacaa   1380
tgctctcagt gtctgcccca agtaccacct catgaaggat gccactgctt tctgtgcaga   1440
acttctccat gtcaagtagc aggtgtcagc aggaaaaaga tcacaagcct gccacgatgg   1500
ctgctgctcc ttgtagccca cccatgagaa gcaagagacc ttaaaggctt cctatcccac   1560 caattcagg gaaaaaacgt gtgatgatcc tgaagcttac tatgcagcct acaaacagcc   1620
ttagtaatta aaacatttta taccaataaa attttcaaat attgctaact aatgtagcat   1680
taactaacga ttggaaacta catttacaac ttcaaagctg ttttatacat agaaatcaat   1740
tacagtttta attgaaaact ataaccattt tgataatgca acaataaagc atcttcagcc   1800
aaaaaaaaaa aaaaaa                                                   1816
```

<210> SEQ ID NO 141
<211> LENGTH: 1828
<212> TYPE: DNA
<213> ORGANISM: Homo sapiens

<400> SEQUENCE: 141

```
cggcgatgtc gctcgtgctg ataagcctgg ccgcgctgtg caggagcgcc gtaccccgag     60
agccgaccgt tcaatgtggc tctgaaactg ggccatctcc agagtggatg ctacaacatg    120
atctaatccc cggagacttg agggacctcc gagtagaacc tgttacaact agtgttgcaa    180
caggggacta ttcaattttg atgaatgtaa gctgggtact ccgggcagat gccagcatcc    240
gcttgttgaa ggccaccaag atttgtgtga cgggcaaaag caacttccag tcctacagct    300
gtgtgaggtg caattacaca gaggccttcc agactcagac cagaccctct ggtggtaaat    360
ggacattttc ctatatcggc ttccctgtag agctgaacac agtctatttc attggggccc    420
ataatattcc taatgcaaat atgaatgaag atggcccttc catgtctgtg aatttcacct    480
caccaggctg cctagaccac ataatgaaat ataaaaaaaa gtgtgtcaag gccggaagcc    540
tgtgggatcc gaacatcact gcttgtaaga agaatgagga gacagtagaa gtgaacttca    600
caaccactcc cctgggaaac agatacatgg ctcttatcca acacagcact atcatcgggt    660
tttctcaggt gtttgagcca caccagaaga aacaaacgcg agcttcagtg gtgattccag    720
tgactgggga tagtgaaggt gctacggtgc agctgactcc atattttcct acttgtggca    780
```

```
gcgactgcat ccgacataaa ggaacagttg tgctctgccc acaaacaggc gtcccttttcc    840
ctctggataa caacaaaagc aagccgggag gctggctgcc tctcctcctg ctgtctctgc    900
tggtggccac atgggtgctg gtggcaggga tctatctaat gtggaggcac gaaaggatca    960
agaagacttc cttttctacc accacactac tgcccccat taaggttctt gtggtttacc   1020
catctgaaat atgtttccat cacacaattt gttacttcac tgaatttctt caaaaccatt   1080
gcagaagtga ggtcatcctt gaaaagtggc agaaaaagaa aatagcagag atgggtccag   1140
tgcagtggct tgccactcaa agaaggcag cagacaaagt cgtcttcctt ctttccaatg    1200
acgtcaacag tgtgtgcgat ggtacctgtg gcaagagcga gggcagtccc agtgagaact   1260
ctcaagacct cttccccctt gccttttaacc ttttctgcag tgatctaaga agccagattc   1320
atctgcacaa atacgtggtg gtctacttta gagagattga tacaaaagac gattacaatg   1380
ctctcagtgt ctgccccaag taccacttca tgaaggatgc cactgctttc tgtgcagaac   1440
ttctccatgt caagcagcag gtgtcagcag gaaaaagatc acaagcctgc cacgatggct   1500
gctgctcctt gtagcccacc catgagaagc aagagacctt aaaggcttcc tatcccacca   1560
attacaggga aaaacgtgt gatgatcctg aagcttacta tgcagcctac aaacagcctt    1620
agtaattaaa acattttata ccaataaaat tttcaaatat tactaactaa tgtagcatta   1680
actaacgatt ggaaactaca tttacaactt caaagctgtt ttatacatag aaatcaatta   1740
cagctttaat tgaaaactgt aaccattttg ataatgcaac aataaagcat cttccaaaaa   1800
aaaaaaaaaa aaaaaaaaaa aaaaaaa                                       1828
```

<210> SEQ ID NO 142
<211> LENGTH: 2856
<212> TYPE: DNA
<213> ORGANISM: Homo sapiens
<220> FEATURE:
<221> NAME/KEY: misc_feature
<222> LOCATION: (1325)..(1325)
<223> OTHER INFORMATION: a or g or c or t/u

<400> SEQUENCE: 142

```
cggcgatgtc gctcgtgctg ataagcctgg ccgcgctgtg caggagcgcc gtaccccgag     60
agccgaccgt tcaatgtggc tctgaaactg ggccatctcc agagtggatg ctacaacatg    120
atctaatccc cggagacttg agggacctcc gagtagaacc tgttacaact agtgttgcaa    180
caggggacta ttcaattttg atgaatgtaa gctgggtact ccgggcagat gccagcatcc    240
gcttgttgaa ggccaccaag atttgtgtga cgggcaaaag caacttccag tcctacagct    300
gtgtgaggtg caattacaca gaggccttcc agactcagac cagaccctct ggtggtaaat    360
ggacattttc ctatatcggc ttccctgtag agctgaacac agtctatttc attggggccc    420
ataatattcc taatgcaaat atgaatgaag atggcccttc catgtctgtg aatttcaccct    480
caccaggctg cctagaccac ataatgaaat ataaaaaaaa gtgtgtcaag gccggaagcc    540
tgtgggatcc gaacatcact gcttgtaaga agaatgagga gacagtagaa gtgaacttca    600
caaccactcc cctgggaaac agatacatgg ctcttatcca acacagcact atcatcgggt    660
tttctcaggt gtttgagcca caccagaaga acaaacgcg agcttcagtg gtgattccag    720
tgactgggga tagtgaaggt gctacggtgc aggtaaagtt cagtgagctg ctctggggag    780
ggaagggaca tagaagactg ttccatcatt cattgctttt aaggatgagt tctctcttgt    840
caaatgcact tctgccagca gacaccagtt aagtggcgtt catgggggtt ctttcgctgc    900
agcctccacc gtgctgaggt caggaggccg acgtggcagt tgtggtccct tttgcttgta    960
```

```
ttaatggctg ctgaccttcc aaagcacttt ttattttcat tttctgtcac agacactcag   1020
ggatagcagt accattttac ttccgcaagc ctttaactgc aagatgaagc tgcaaagggt   1080
ttgaaatggg aaggtttgag ttccaggcag cgtatgaact ctggagaggg gctgccagtc   1140
ctctctgggc cgcagcggac ccagctggaa cacaggaagt tggagcagta ggtgctcctt   1200
cacctctcag tatgtctctt tcaactctag tttttgaagt ggggacacag gaagtccagt   1260
ggggacacag ccactcccca aagaataagg aacttccatg cttcattccc tggcataaaa   1320
agtgntcaaa cacaccagag ggggcaggca ccagccaggg tatgatgggt actacccttt   1380
tctggagaac catagacttc ccttactaca gggacttgca tgtcctaaag cactggctga   1440
aggaagccaa gaggatcact gctgctcctt ttttgtagag gaaatgtttg tgtacgtggt   1500
aagatatgac ctagcccttt taggtaagcg aactggtatg ttagtaacgt gtacaaagtt   1560
taggttcaga ccccgggagt cttgggcatg tgggtctcgg gtcactggtt ttgactttag   1620
ggctttgtta cagatgtgtg accaagggga aaatgtgcat gacaacacta gaggtagggg   1680
cgaagccaga aagaagggaa gttttggctg aagtaggagt cttggtgaga ttttgctgtg   1740
atgcatggtg tgaactttct gagcctcttg ttttcctca gctgactcca tattttccta   1800
cttgtggcag cgactgcatc cgacataaag gaacagttgt gctctgccca caaacaggcg   1860
tccctttccc tctggataac aacaaaagca agccggagg ctgctgcct ctcctcctgc   1920 tgtctctgct ggtggccaca tgggtgctgg tggcagggat ctatctaatg tggaggcacg   1980
aaaggatcaa gaagacttcc ttttctacca ccacactact gcccccatt aaggttcttg   2040 tggtttaccc atctgaaata tgtttccatc acacaatttg ttacttcact gaatttcttc   2100
aaaaccattg cagaagtgag gtcatccttg aaaagtggca gaaaaagaaa atagcagaga   2160
tgggtccagt gcagtggctt gccactcaaa agaaggcagc agacaaagtc gtcttccttc   2220
tttccaatga cgtcaacagt gtgtgcgatg gtacctgtgg caagagcgag ggcagtccca   2280
gtgagaactc tcaagacctc ttccccttg cctttaacct tttctgcagt gatctaagaa   2340
gccagattca tctgcacaaa tacgtggtgg tctactttag agagattgat acaaaagacg   2400
attacaatgc tctcagtgtc tgccccaagt accacttcat gaaggatgcc actgctttct   2460
gtgcagaact tctccatgtc aagcagcagg tgtcagcagg aaaaagatca caagcctgcc   2520
acgatggctg ctgctccttg tagcccaccc atgagaagca agagacctta aaggcttcct   2580
atcccaccaa ttacagggaa aaaacgtgtg atgatcctga agcttactat gcagcctaca   2640
aacagcctta gtaattaaaa cattttatac caataaaatt ttcaaatatt actaactaat   2700
gtagcattaa ctaacgattg gaaactacat ttacaacttc aaagctgttt tatacataga   2760
aatcaattac agctttaatt gaaaactgta accattttga taatgcaaca ataaagcatc   2820
ttccaaaaaa aaaaaaaaaa aaaaaaaaa aaaaaa                              2856
```

<210> SEQ ID NO 143
<211> LENGTH: 1583
<212> TYPE: DNA
<213> ORGANISM: Homo sapiens

<400> SEQUENCE: 143

```
atgtcgctcg tgctgctaag cctggccgcg ctgtgcagga gcgccgtacc ccgagagccg     60
accgttcaat gtggctctga aactgggcca tctccagagt ggatgctaca acatgatcta    120
atcccgggag acttgaggga cctccgagta gaacctgtta caactagtgt tgcaacaggg    180
```

```
gactattcaa ttttgatgaa tgtaagctgg gtactccggg cagatgccag catccgcttg      240
ttgaaggcca ccaagatttg tgtgacgggc aaaagcaact tccagtccta cagctgtgtg      300
aggtgcaatt acacagaggc cttccagact cagaccagac cctctggtgg taaatggaca      360
ttttcctata tcggcttccc tgtagagctg aacacagtct atttcattgg gcccataat       420 attcctaatg caaatatgaa tgaagatggc ccttccatgt ctgtgaattt cacctcacca      480
ggctgcctag accacataat gaaatataaa aaaaagtgtg tcaaggccgg aagcctgtgg      540
gatccgaaca tcactgcttg taagaagaat gaggagacag tagaagtgaa cttcacaacc      600
actcccctgg gaaacagata catggctctt atccaacaca gcactatcat cgggttttct      660
caggtgtttg agccacacca aagaaacaa acgcgagctt cagtggtgat tccagtgact       720
ggggatagtg aaggtgctac ggtgcagctg actccatatt ttcctacttg tggcagcgac      780
tgcatccgac ataaaggaac agttgtgctc tgcccacaaa caggcgtccc tttccctctg      840
gataacaaca aaagcaagcc gggaggctgg ctgcctctcc tcctgctgtc tctgctggtg      900
gccacatggg tgctggtggc agggatctat ctaatgtgga ggcacgaaag gatcaagaag      960
acttcctttt ctaccaccac actactgccc ccattaagg ttcttgtggt ttacccatct      1020
gaaatatgtt tccatcacac aatttgttac ttcactgaat ttcttcaaaa ccattgcaga      1080
agtgaggtca tccttgaaaa gtggcagaaa aagaaaatag cagagatggg tccagtgcag      1140
tggcttgcca ctcaaaagaa ggcagcagac aaagtcgtct tccttctttc caatgacgtc      1200
aacagtgtgt gcgatggtac ctgtggcaag agcgagggca gtcccagtga aactctcaa       1260 gacctcttcc cccttgcctt taacctttc tgcagtgatc taagaagcca gattcatctg      1320
cacaaatacg tggtggtcta ctttagagag attgatacaa aagacgatta caatgctctc      1380
agtgtctgcc ccaagtacca cctcatgaag gatgccactg ctttctgtgc agaacttctc      1440
catgtcaagc agcaggtgtc agcaggaaaa agatcacaag cctgccacga tggctgctgc      1500
tccttgtagc ccacccatga gaagcaagag accttaaagg gttccttttc ccatcattta      1560 cagggggaaaa acgtgtgatg atc                                              1583

<210> SEQ ID NO 144
<211> LENGTH: 2584
<212> TYPE: DNA
<213> ORGANISM: Homo sapiens

<400> SEQUENCE: 144
catattagag tctacagata tgcctttctt acagcaatcc tgcacccaca taaaagctac       60
attttcaata caagattaaa aggtattctg caaaatgtgc aaggttttca tgtctgctgg      120
tgtagctgta gtgatggctt catgaatttt tttctttttt gactatggtc cttacgctgg      180
attcatttat cttgaaatgg tgaacaatca cagctgcaga ccctcaattt atggtacata      240
tcaagcaatt tggcttttt tcttgtaatg aaaaaaaaaa gttttttttg cttttttca       300 tgacactgct tcttgggagc actgccagca ttactagtgg cacttcgtat gggtcctaag      360
gtgttattga aggtttacga tattgcacta aacacgaaaa ataccagaga accactggag      420
atacttttta ctgtgatatg taatttactg gagacaggaa ctgctcgttt ggagatggtt      480
agcatcacag ggtgttttaa gtcgatactt gcaacccttg agctcaccac agtagcaaca      540
ggaggtggct aggaaattat tcacagcagg acagtacgca ctgcaattaa ttgtatgcag      600
ttatgattta ataccacatc tttatgctca cgtttctctc aactgtgaat ggtgccatgt      660
acagttggta tgtgtgtgtt taagtttgga taaattttta acttttaata gttaaaatag      720
```

```
ttaactattg gtatggtagg aaatgataaa gtagactagt atctgtatac attttctgca    780
tttatgacat acctttttct tcattttttt caatatttta attgaaaagt tcatccgagt    840
ttcatctaag ttttttcaaa gtgatacaaa tctccaaaaa attttccaat atatgtattg    900
aaaaaatcca ggtgtaagtg gctctgcgca gtccaaacct gtgttgttca agggtcaact    960
gtgtatgaat ccaagcgaaa gcttttctta cacctcata agaactattt tttaaaaaac   1020
aggaactagc atagagtaac catcacaggt aaagtgtaat ttgttatcag ccatcttttg   1080
cccatttcag tactggtaga aggctcaatg gtaaaaataa aaacgggaca gtcagaagat   1140
ctggaagtcc tgaccctgct ttacctggc atgtgtaatc cagtcatgct cgtatcagtc   1200
tctgtaggag cacttgaagg tattacataa atgctatcta actctgggaa acgccaacat   1260
gtgattgcct ccagaggaat cttctttaaa aaaaaattca aatgttatt tccttactag   1320
gatgtcttta agaattata accttaccg tgcctccaca ttagatagat ccctgccacc   1380
agcacccatg tggccaccag cagagacagc aggaggagag gcagccagcc tcccggcttg   1440
cttttgtctg gaaaaacaa agcttattca cctttggaaa acaaatccac acttatctct   1500
taatttaaaa actaagactt ggtatacttt atagaggttt atttattttt tattattttt   1560
tagttttgag acagagtctc gctttgttgc ctaggctgga gtgcagtggc gcaatctcgg   1620
ttcactgcag cctccgtctc ccgggttcaa gcaatgctgc ctcagcctcc tgagtagctg   1680
ggattacagg catgtgtcac cgcgcccagc cactttgtag agatttagat ccctttaaaa   1740
ccatcagtca gaagctcttt agatagtctg ccaatcatat cttttccct agagtgtgca   1800
ggtcttgcat tagattctca aaagggatat gggacccagg aagttaagaa cagtcctaaa   1860
atctctttgg cttctttgtc ctgatatgca ccggcatttt cacagtagga actagggttt   1920
ctgtccagtt ttttggttc tttaaggaat taatgttatt ctgggtacaa ctgcttacat   1980
acatagcaca tatagatgac attttacag gccgtcttgt tagactgaca tacatggagg   2040
atagtgccac ccgcctcaca agaacatcag gtaagctcag gcacagagtg cccaggaatc   2100
tgtaaggctt cgcccacgca caagtcaggg ctgccagtca cctgggttgt cttcacttta   2160
tttggctgcg tctaatgaca ccttccaact tttgaccccca ccctggact gttgtgtaaa   2220
cattgtattt ctccatctgt aatgaaaaag ctaacacatc tctaactcca gagacatttt   2280
ccagaacatg ctgttctcag gcactagtga ggcggtacca ttattcctca tttgttatcc   2340
aaatgttggc catgtgacca caccaaaagc tcatcctggg ccactgagac tagtaattga   2400
atcagaatat agtgaaatat tcattctcat atatacccag ccatcttaca tctttggctt   2460
ttttcagcag atccttgtgg cactcagaac atccattttg cactgtgtat tttttttccct   2520
tctgtgtatc ctgctttgta aagagtcacg agtggtttta caaataaagc ctgttcttac   2580
tcag                                                                 2584
```

<210> SEQ ID NO 145
<211> LENGTH: 665
<212> TYPE: DNA
<213> ORGANISM: Homo sapiens

<400> SEQUENCE: 145

```
ttttttttttt ttttttctga gtaagaacag gctttatttg taaaaccact cgtgactctt      60
tacaaagcag gatacacaga agggaaaaaa atacacagtg caaatggat gttctgagtg     120
ccacaaggat ctgctgaaaa aagccaaaga tgtaagatgg ctgggtatat atgagaatga     180
```

| | |
|---|---|
| atatttcact atattctgat tcaattacca gtctcagtgg cccaggatga gcttttggtg | 240 |
| tggtcacatg gccaacattt ggataacaaa tgaggaataa tggtaccgcc tcactagtgc | 300 |
| ctgagaacag catgttctgg aaaatgtctc tggagttaga gatgtgttag cttttcatt | 360 |
| acagatggag aaatacaatg tttacacaac agtccagggg tggggtcaaa agttggaagg | 420 |
| tgtcattaga cgcagccaaa taaagtgaag acaacccagg tgactggcag ccctgacttg | 480 |
| tgcgtgggcg aagccttaca gattcctggg cactctgtgc ctgagcttac ctgatgttct | 540 |
| tgtgaggcgg gtggcactat cctccatgta tgtcagtcta acaagacggc ctgtaaaaat | 600 |
| gtcatctata tgtgctatgt atgtaagcag ttgtacccag aataacatta atcctcgtgc | 660 |
| cgaat | 665 |

<210> SEQ ID NO 146
<211> LENGTH: 664
<212> TYPE: DNA
<213> ORGANISM: Homo sapiens
<220> FEATURE:
<221> NAME/KEY: misc_feature
<222> LOCATION: (613)..(613)
<223> OTHER INFORMATION: a or g or c or t/u

<400> SEQUENCE: 146

| | |
|---|---|
| tttttttttt tttttgttgg gctgaagatg ctttattatt gcattatcaa aatggttata | 60 |
| gtttcaatt aaaactgtaa ttgatttcta tgtataaaac agcttgaag ttgtaaatgt | 120 |
| agtttccaat cgttagttaa tgctacatta gttagcaata tttgaaaatt ttattggtat | 180 |
| aaaatgtttt aattactaag gctgtttgta ggctgcatag taagcttcag gatcatcaca | 240 |
| cgttttttcc ctgtaattgg tgggatagga agcctttaag gtctcttgct tctcatgggt | 300 |
| gggctacaag gagcagcagc catcgtggca ggcttgtgat cttttcctg ctgacacctg | 360 |
| ctgcttgaca tggagaagtt ctgcacagaa agcagtggca tccttcatga ggtggtactt | 420 |
| ggggcagaca ctgagagcat tgtaatcgtc ttttgtatca atctctctaa agtagaccac | 480 |
| cacgtatttg tgcagatgaa tctggcttct tagatcactg cagaaaaggt taaaggcaag | 540 |
| ggggaagagg tcttgagagt tctcactggg actgccctcg ctcttgccac aggtaccatc | 600 |
| gcacacactg ttnacgtcat tggaaagaag gaagacgact ttgtctgctg ccttcttttg | 660 |
| agtg | 664 |

<210> SEQ ID NO 147
<211> LENGTH: 739
<212> TYPE: DNA
<213> ORGANISM: Homo sapiens

<400> SEQUENCE: 147

| | |
|---|---|
| tggttttgt ttttttttca ttttctgttg gattacagaa aaagaatggg acccattcag | 60 |
| gtctcgattt ccaaaggtaa agatggaagg ctgggcagac tggcttttgt tacctgacat | 120 |
| gccgtagggt gagcttagag gaagaaagaa acaatttttt atttggccaa aacagaacaa | 180 |
| atgctgaaaa ggaaatcttg ttttttttcct aaagccaaat agaaatgatt tgggtataat | 240 |
| ttaagagtcc ttgtgttgta cagatatggt gactgatgta gttattaata ctaccaactt | 300 |
| agtcatcaag cctcaatttt cctttacctg aaggattaag tgaaagcttt tggagttcat | 360 |
| gatgttcagt atgatcagtt aaccttaacc tctgagcatc ctgaagcaaa atctaaataa | 420 |
| tgcagctatt accactggtg gtccaggctc tggtgaagcc ctctgagccc aggaggaaga | 480 |
| gaaagcattg tccagaggta ggaacacagt ctgggagccc agagctctgg gaggagtggg | 540 |

```
aaaatgctgc ttcctgctgc ttgcttctag gcacctgctt ccgccatctc acttaccatg    600
gctagagatg ggggtgagac tggggaagga cacaagcagg gaacagataa gggatggaaa    660
tcagaaggga atatagaaag aactctggat gtggagacat gccggtacct gagcattttg    720
tatcaatggg agtacctct                                                 739
```

<210> SEQ ID NO 148
<211> LENGTH: 657
<212> TYPE: DNA
<213> ORGANISM: Homo sapiens

<400> SEQUENCE: 148

```
tttttttttt ttttttttgg ctgaagatgc tttattgttg cattatcaaa atggttacag     60
ttttcaatta aagctgtaat tgatttctat gtataaaaca gctttgaagt tgtaaatgta    120
gtttccaatc gttagttaat gctacattag ttagcaatat ttgaaaattt tattggtata    180
aaatgtttta attactaagg ctgtttgtag gctgcatagt aagcttcagg atcatcacac    240 gttttttttcc ctgtaattgg tgggatagga agcctttaag gtctcttgct tctcatgggt    300
gggctacaag gagcagcagc catcgtggca ggcttgtgat cttttttcctg ctgacacctg    360 ctgcttgaca tggagaagtt ctgcacagaa agcagtggca tccttcatga ggtggtactt    420
ggggcagaca ctgagagcat tgtaatcgtc ttttgtatca atctctctaa gtagaccac    480 cacgtatttg tgcagatgaa tctggcttct tagatcactg cagaaaaggt taaaggcaag    540
ggggaagagg tcttgagagt tctcactggg acttgcctcg ctcttgccac aggtaccatc    600
gcacacactg ttgacgtcat tggaaagaaa gaagacgact ttgtctgctg ccttctt       657
```

<210> SEQ ID NO 149
<211> LENGTH: 102
<212> TYPE: DNA
<213> ORGANISM: Homo sapiens

<400> SEQUENCE: 149

```
gctgaagatg ctttattgtt gcattatcaa aatggttaca gttttcaatt aaagctgtaa     60
ttgatttcta tgtataaaac agctttgaag ttgtaaatgt ag                      102
```

<210> SEQ ID NO 150
<211> LENGTH: 187
<212> TYPE: DNA
<213> ORGANISM: Homo sapiens

<400> SEQUENCE: 150

```
cacgcgtccg attttatacc aataaaattt tcaaatattg ctaactaatg tagcattaac     60
taacgattgg aaactacatt tacaacttca aagctgtttt atacatagaa atcaattaca    120
gctttaattg aaaactgtaa ccatttgat aatgcaacaa taaagcatct tcagccaaaa    180
aaaaaaa                                                              187
```

<210> SEQ ID NO 151
<211> LENGTH: 361
<212> TYPE: DNA
<213> ORGANISM: Homo sapiens

<400> SEQUENCE: 151

```
agaaaaagaa aatagcagag atgggtccag tgcagtggct tgcataaaaa agaaggcagc     60
agacaaagtc gtcttccttc tttccaatga cgtcaacagt gtgtgcgatg gtacctgtgg    120
```

| | |
|---|---|
| caagagcgag ggcagtccca gtgagaactc tcaagacctc ttccccctt gcctttaacc | 180 |
| ttttctgcag tgatctaaga agccagattc atctgcacaa atacgtggtg gtctacttta | 240 |
| gagagattga tacaaaagac gattacaatg ctctcagtgt ctgccccaag taccacctca | 300 |
| tgaaggatgc cactgctttc tgtgcagaac ttctccatgt caagcagcag gtttcagcag | 360 |
| g | 361 |

<210> SEQ ID NO 152
<211> LENGTH: 783
<212> TYPE: DNA
<213> ORGANISM: Homo sapiens
<220> FEATURE:
<221> NAME/KEY: misc_feature
<222> LOCATION: (707)..(707)
<223> OTHER INFORMATION: a or g or c or t/u

<400> SEQUENCE: 152

| | |
|---|---|
| tttttttttt tttgtttgg ctgaagatgc tttattgttg cattatcaaa atggttacag | 60 |
| ttttcaatta aagctgtaat tgatttctat gtataaaaca gctttgaagt tgtaaatgta | 120 |
| gtttccaatc gttagttaat gctacattag ttagcaatat ttgaaaattt tattggtata | 180 |
| aaatgtttta attactaagg ctgtttgtag gctgcatagt aagcttcagg atcatcacac | 240 |
| gttttttccc tgtaattggt gggataggaa gcctttaagg tctcttgctt ctcatgggtg | 300 |
| ggctacaagg agcagcagcc atcgtggcag gcttgtgatc tttttcctgc tgacacctgc | 360 |
| tgcttgacat ggagaagttc tgcacagaaa gcagtggcat ccttcatgag gtggtacttg | 420 |
| gggcagacac tgagagcatt gtaatcgtct tttgtatcaa tctctctaaa gtagaccacc | 480 |
| acgtatttgt gcagatgaat ctggcttctt agatcactgc agaaaaggtt aaaggcaagg | 540 |
| gggaagaggt cttgagagtt ctcactggga ctgccctcgc tcttgccaca ggtaccatcg | 600 |
| cacacactgt tgacgtcatt ggaaagaagg aagacgactt tgtctgctgc cttcttttga | 660 |
| gtggcaagcc actgcactgg acccatctct gctattttct ttttctngca cttttcaagg | 720 |
| atgactcact tctgcaatgg tttttgagaa ttcagtgaag tacaaatgtg tgatggaaca | 780 |
| tat | 783 |

<210> SEQ ID NO 153
<211> LENGTH: 399
<212> TYPE: DNA
<213> ORGANISM: Homo sapiens

<400> SEQUENCE: 153

| | |
|---|---|
| cgctcgtgct gctaagcctg gccgcgctgt gcaggagcgc cgtaccccga gagccgaccg | 60 |
| ttcaatgtgg ctctgaaact gggccatctc cagagtggat gctacaacat gatctaatcc | 120 |
| ccggagactt gagggacctc cgagtagaac ctgttacaac tagtgttgca acaggggact | 180 |
| attcaatttt gatgaatgta agctgggtac tccgggcaga tgccacacca gaagaaacaa | 240 |
| acgcgagctt cagtggtgat tccagtgact ggggatagtg aaggtgctac ggtgcagctg | 300 |
| actccatatt ttcctacttg tggcagcgac tgcatccgac ataaaggaac agttgtgctc | 360 |
| tgcccacaaa caggcgtccc tttccctctg gataacaac | 399 |

<210> SEQ ID NO 154
<211> LENGTH: 518
<212> TYPE: DNA
<213> ORGANISM: Homo sapiens
<220> FEATURE:
<221> NAME/KEY: misc_feature
<222> LOCATION: (503)..(503)
<223> OTHER INFORMATION: a or g or c or t/u

<400> SEQUENCE: 154

| | | | | | |
|---|---|---|---|---|---|
| gctgagtgtg | atggtgtaag | cctgtggtcc | cagctactag | ggaggctgag | atgggattac | 60 |
| aggtgtgagc | cacggcgcct | ggcctaaaag | catctttttc | tttaacgcag | aggttatgtt | 120 |
| gtattattag | cataaatgtt | tttttctggg | aatgcttatt | tcacacagca | caatactgaa | 180 |
| tcttctctgg | aatgtggatc | gatttcagat | ggatgactat | taaaatgtgt | atatttgcag | 240 |
| attatcctta | aagggccacc | tcatgccttc | taatttatgt | cttacggata | aaaaatcaaa | 300 |
| atgaagcata | aagtaaaaac | tgtgtccagc | tttacaagtg | gacgcttagt | aatggctgag | 360 |
| gcaatatgtt | taatgtagca | aattttactt | atttgtcatg | atcagttttc | acagtgcttg | 420 |
| taagtgctgg | taatagaaga | tggacatggt | ttaggtcaaa | acttggacca | gaaaccaact | 480 |
| tcctttgaaa | cagctctacc | agntataaga | gcaatatg | | | 518 |

<210> SEQ ID NO 155
<211> LENGTH: 490
<212> TYPE: DNA
<213> ORGANISM: Homo sapiens

<400> SEQUENCE: 155

| | | | | | |
|---|---|---|---|---|---|
| ctgttgacgt | cattggaaag | aaggaagacg | actttgtctg | ctgccttctt | ttgagtggca | 60 |
| agccactgca | ctggacccat | ctctgctatt | ttcttttttct | gccactttttc | aaggatgacc | 120 |
| tcacttctgc | aatggttttg | aagaaattca | gtgaagtaac | aaattgtgtg | atggaaacat | 180 |
| atttcagatg | ggtaaaccac | aagaacctta | atggggggca | gtagtgtggt | ggtagaaaag | 240 |
| gaagtcttct | tgatcctttc | tgtgagagga | gaaaagcatt | tgttatctgt | gaacagcaaa | 300 |
| cagcaggctt | tcactctgta | aaccatccct | gacaaatgat | cccttgctag | agaatgtcag | 360 |
| ctgagcacca | agggccttgt | tagtgacagc | aaggaaaaac | atcctgatgt | tccttttgaa | 420 |
| cacatcacct | gaaacacact | gatgcttaaa | ccttaacttt | tttttttttg | agacacagt | 480 |
| ctcactctgt | | | | | | 490 |

<210> SEQ ID NO 156
<211> LENGTH: 421
<212> TYPE: DNA
<213> ORGANISM: Homo sapiens

<400> SEQUENCE: 156

| | | | | | |
|---|---|---|---|---|---|
| tttttttttt | ttttttttct | gagtaagaac | aggcttatt | tgtaaaacca | ctcgtgactc | 60 |
| tttacaaagc | aggatacaca | gaagggaaaa | aaatacacag | tgcaaaatgg | atgttctgag | 120 |
| tgccacaagg | atctgctgaa | aaagccaaa | gatgtaagat | ggctgggtat | atatgagaat | 180 |
| gaatatttca | ctatattctg | attcaattac | cagtctcagt | ggcccaggat | gagcttttgg | 240 |
| tgtggtcaca | tggccaacat | ttggataaca | atgaggaat | aatggtaccg | cctcactagt | 300 |
| gcctgagaac | agcatgttct | ggaaaatgtc | tctggagtta | gagatgtgtt | agcttttca | 360 |
| ttacagatgg | agaaatacaa | tgtttacaca | acagtccagg | ggtggggtca | aaagttggaa | 420 |
| g | | | | | | 421 |

<210> SEQ ID NO 157
<211> LENGTH: 547
<212> TYPE: DNA
<213> ORGANISM: Homo sapiens

<400> SEQUENCE: 157

```
ttttttttttt ttttttttgg ctgaagatgc tttattgttg cattatcaaa atggttatag      60
ttttcaatta aaactgtaat tgatttctat gtataaaaca gctttgaagt tgtaaatgta     120
gtttccaatc gttagttaat gctacattag ttagcaatat ttgaaaattt tattggtata     180
aaatgtttta attactaagg ctgtttgtag gctgcatagt aagcttcagg atcatcacac     240
gtttttttccc tgtaattggt gggataggaa gcctttaagg tctcttgctt ctcatgggtg    300
ggctacaagg agcagcagcc atcgtggcag gcttgtgatc ttttcctgc tgacacctgc      360
tgcttgacat ggagaagttc tgcacagaaa gcagtggcat ccttcatgag gtggtacgtg     420
gggcagacac tgagagcatt gtaatcgtct tttgtatcaa tctctctaaa gtagaccacc     480
acgtatttgt gcagatgaat ctggcttctt agatcactgc agaaaaggtt aaaggcaagg     540
gggaaga                                                               547
```

<210> SEQ ID NO 158
<211> LENGTH: 644
<212> TYPE: DNA
<213> ORGANISM: Homo sapiens

<400> SEQUENCE: 158

```
ttttttttttt ttttttttga aagggtcagg acttccagat cttctgactg tcccgttttt    60
attttttacca ttgagccttc taccagtact gaaatgggca aagatggct gataacaaat     120
tacactttac ctgtgatggt tactctatgc tagttcctgt tttttaaaaa atagttctta    180
tgaggtgtta agaaaagctt tcgcttggat tcatacacag ttgacccttg aacaacacag    240
gtttggactg cgcagagcca cttacacctg gatttttttca atacatatat tggaaaattt   300
tttggagatt tgtatcactt tgaaaaaact tagatgaaac tcggatgaac ttttcaatta   360
aaatattgaa aaaaatgaag aaaaaggtat gtcataaatg cagaaaatgt atacagatac   420
tagtctactt tatcattttcc taccatacca atagttaact attttaacta ttaaaagtta   480
aaaatttatc aaaacttaaa cacacacata ccaactgtac atggcaccat tcacagttga   540
gagaaacgtg agcataaaga tgtggtatta atcataact gcatacaatt aattgcagtg    600
cgtactgtcc tgctgtgaat atttcctagc cctcgtgccg aatc                    644
```

<210> SEQ ID NO 159
<211> LENGTH: 470
<212> TYPE: DNA
<213> ORGANISM: Homo sapiens

<400> SEQUENCE: 159

```
gtgggtgacc gtggcttgcc actcaaaaga aggcagcaga caaagtcgtc ttccttctttt    60
ccaatgacgt caacagtgtg tgcgatggta cctgtggcaa gagcgagggc agtcccagtg    120
agaactctca agacctcttc cccttgcct ttaaccttttt ctgcagtgat ctaagaagcc     180
agattcatct gcacaaatac gtggtggtct actttagaga gattgataca aaagacgatt    240
acaatgctct cagtgtctgc cccaagtacc acctcatgaa ggatgccact gctttctgtg    300
cataacttct ccatgtcaag cagcaggtgt cagcaggaaa aagatcacaa gcctgccacg    360
atggctgctg ctccttgtag cccacccatg agaagcaaga gaccttaaag gcttcctatc     420
ccaccaatta cagggaaaaa aacgtgtgat gatcctgaag ccacggtcaa                470
```

<210> SEQ ID NO 160
<211> LENGTH: 499

<212> TYPE: DNA
<213> ORGANISM: Homo sapiens

<400> SEQUENCE: 160

```
tagaggatcc cggtcgacgg tggttcagtg atcatcacac tttttccctg taataggtgg      60
gataggaagc ctttaaggtc tcttgcttct catgggtggg ctacaaggag cagcagccat     120
cgtggcaggc ttgtgatctt tttcctgctg acacctgctg cttgacatgg agaagttatg     180
cacagaaagc agtggcatcc ttcatgaggt ggtacttggg gcagacactg agagcattgt     240
aatcgtcttt tgtatcaatc tctctaaagt agaccaccac gtatttgtgc agatgaatct     300
ggcttcttag atcactgcag aaaaggttaa aggcaagggg gaagaggtct tgagagttct     360
cactgggact gccctcgctc ttgccacagg taccatcgca cacactgttg acgtcattgg     420
aaagaaggaa gacgactttg tctgctgcct tcttttgagt ggcaagccac ggtcaaccca     480
caagccacgg tcaacccac                                                  499
```

<210> SEQ ID NO 161
<211> LENGTH: 615
<212> TYPE: DNA
<213> ORGANISM: Homo sapiens

<400> SEQUENCE: 161

```
tctacgtggt aagatatgac ctagcccttt taggtaagcg aactggtatg ttagtaacgt      60
gtacaaagtt taggttcaga ccccgggagt cttgggcatg tgggtctcgg gtcactggtt     120
ttgactttag ggcttttgtta cagatgtgtg accaagggga aaatgtgcat gacaacacta     180
gaggtagggg cgaagccaga aagaagggaa gttttggctg aagtaggagt cttgcgactg     240
catccgacat aaaggaacag ttgtgctctg cccacaaaca ggcgtccctt tccctctgga     300
taacaacaaa agcaagccgg gaggctggct gcctctcctc ctgctgtctc tgctggtggc     360
cacatgggtg ctggtggcag ggatctatct aatgtggagg cacgaaagga tcaagaagac     420
ttccttttct accaccacac tactgccccc cattaaggtt cttgtggttt acccatctga     480
aatatgtttc catcacacaa tttgttactt cactgaattt cttcaaaacc attgcagaag     540
tgaggtcatc cttgaaagtg gcagagtagc agagatgggt ccagtgcagt ggcttgccac     600
tcgtgcgatg gtctt                                                      615
```

<210> SEQ ID NO 162
<211> LENGTH: 636
<212> TYPE: DNA
<213> ORGANISM: Homo sapiens
<220> FEATURE:
<221> NAME/KEY: misc_feature
<222> LOCATION: (50)..(50)
<223> OTHER INFORMATION: a or g or c or t/u
<220> FEATURE:
<221> NAME/KEY: misc_feature
<222> LOCATION: (203)..(203)
<223> OTHER INFORMATION: a or g or c or t/u
<220> FEATURE:
<221> NAME/KEY: misc_feature
<222> LOCATION: (323)..(323)
<223> OTHER INFORMATION: a or g or c or t/u
<220> FEATURE:
<221> NAME/KEY: misc_feature
<222> LOCATION: (463)..(463)
<223> OTHER INFORMATION: a or g or c or t/u
<220> FEATURE:
<221> NAME/KEY: misc_feature
<222> LOCATION: (467)..(467)
<223> OTHER INFORMATION: a or g or c or t/u
<220> FEATURE:

```
<221> NAME/KEY: misc_feature
<222> LOCATION: (502)..(502)
<223> OTHER INFORMATION: a or g or c or t/u
<220> FEATURE:
<221> NAME/KEY: misc_feature
<222> LOCATION: (507)..(507)
<223> OTHER INFORMATION: a or g or c or t/u
<220> FEATURE:
<221> NAME/KEY: misc_feature
<222> LOCATION: (595)..(595)
<223> OTHER INFORMATION: a or g or c or t/u
<220> FEATURE:
<221> NAME/KEY: misc_feature
<222> LOCATION: (600)..(600)
<223> OTHER INFORMATION: a or g or c or t/u

<400> SEQUENCE: 162
ggcacgagca ctggctgaag gaagccaaga ggatcactgc tgctcctttn ttctagagga      60
aatgtttgtc tacgtggtaa gatatgacct agccctttta ggtaagcgaa ctggtatgtt     120
agtaacgtgt acaaagttta ggttcagacc ccgggagtct tgggcatgtg gtctcgggt     180 cactggtttt gactttaggg ctntgttaca gatgtgtgac caaggggaaa atgtgcatga     240
caacactaga gctgactcca tattttccta cttgtggcag cgactgcatc cgacataaag     300
gaacagttgt gctctgccca canacaggcg tcccttccc tctggataac aacataagca     360
agccgggagg ctggctgcct ctcctcctgc tgtctctgct ggtggcacat gggtgctggt     420
ggagggatct atctaatgtg gaggcacgga tcaagaagac ttncttntct accaccacac     480
tactggcccc aataagggtc tngtggntac cccatctgaa tatgttcata cacaatttgt     540
actcactgaa ttctcaaaac attgagagtg aggcatcctg aaagtgcgaa aaganatgcn     600
aatggtcagt gcatgctgca ctagcagcat ggactt                               636

<210> SEQ ID NO 163
<211> LENGTH: 676
<212> TYPE: DNA
<213> ORGANISM: Homo sapiens

<400> SEQUENCE: 163
gatcccgcgc agtggcccgg cgatgtcgct cgtgctgcta agcctggccg cgctgtgcag      60
gagcgccgta ccccgagagc cgaccgttca atgtggctct gaaactgggc catctccaga     120
gtggatgcta caacatgatc taatcccggg agacttgagg gacctccgag tagaaccgtt     180
tacaactagt gttgcaacag gggactattc aattttgatg aatgtaagct gggtactccg     240
ggcagatgcc agcatccgct tgttgaaggc caccaagatt tgtgtgacgg gcaaaagcaa     300
cttccagtcc tacagctgtg tgaggtgcaa ttacacagag gccttccaga ctcagaccag     360
accctctggt ggtaaatgga catttttccta catcggcttc cctgtagagc tgaacacagt     420
ctatttcatt ggggcccata atattcctaa tgcaaatatg aatgaagatg gcccttccat     480
gtctgtgaat ttcacctcac caggctgcct agaccacata atgaaatata aaaaaaagtg     540
tgtcaaggcc ggaagcctgt gggatccgaa catcactgct tgtaagaaga atgaggagac     600
agtagaagtg aacttcacaa ccactcccct gggaaacaga tacatggctc ttatccaaca     660
cagcactatc attcgg                                                      676

<210> SEQ ID NO 164
<211> LENGTH: 722
<212> TYPE: DNA
<213> ORGANISM: Homo sapiens

<400> SEQUENCE: 164
```

```
gtcttgcatt agattctcaa aagggatatg ggacccagga agttaagaac agtcctaaaa    60
tctctttggc ttctttgtcc tgatatgcac cggcattttc acagtaggaa ctagggtttc   120
tgtccagttt ttttggttct taaggaatt aatgttattc tgggtacaac tgcttacata   180
catagcacat atagatgaca tttttacagg ccgtcttgtt agactgacat acatggagga   240
tagtgccacc cgcctcacaa gaacatcagg taagctcagg cacagagtgc ccaggaatct   300
gtaaggcttc gccacgcac aagtcagggc tgccagtcac ctgggttgtc ttcactttat   360
ttggctgcgt ctaatgacac cttccaactt ttgaccccac ccctggactg ttgtgtaaac   420
attgtatttc tccatctgta atgaaaaagc taacacatct ctaactccag agacattttc   480
cagaacatgc tgttctcagg cactagtgag gcggtaccat tattcctcat ttgttatcca   540
aatgttggcc atgtgaccac accaaaagct catcctgggc cactgagact ggtaattgaa   600
tcagaatata gtgaaatatt cattctcata tatacccagc catcttacat ctttggcttt   660
tttcagcaga tccttgtggc actcagaaca tccattttgc actgtgtatt tttttccctt   720
ct                                                                  722

<210> SEQ ID NO 165
<211> LENGTH: 335
<212> TYPE: DNA
<213> ORGANISM: Homo sapiens

<400> SEQUENCE: 165
tgtgtaactc tcaagacctc ttccccctttg cctttaacct tttctgcagt gatctaagaa    60
gccagattca tctgcacaaa tacgtggtgg tctactttag agagattgat acaaaagacg   120
attacaatgc tctcagtgtc tgccccaagt accacctcat ggaggatgcc actgcttttct   180 gtgcagaact tctccatgtc aagtagcagg tgtcagcagg aaaaagatca caagcctgcc   240
acgatggctg ctgctccttg tagcccaccc atgagaagca agagacctta aaggcttcct   300
atcccaccaa ttacagggaa aaaacgtgtg atgat                              335

<210> SEQ ID NO 166
<211> LENGTH: 680
<212> TYPE: DNA
<213> ORGANISM: Homo sapiens
<220> FEATURE:
<221> NAME/KEY: misc_feature
<222> LOCATION: (591)..(591)
<223> OTHER INFORMATION: a or g or c or t/u

<400> SEQUENCE: 166
ctgaaatatg tttccatcac acaatttgtt acttcactga atttcttcaa aaccattgca    60
gaagtgaggt catccttgaa aagtggcaga aaaagaaaat agcagagatg ggtccagtgc   120
agtggcttgc cactcaaaag aaggcagcag acaaagtcgt cttccttctt tccaatgacg   180
tcaacagtgt gtgcgatggt acctgtggca agagcgaggg cagtcccagt gagaactctc   240
aagacctctt ccccctttgcc tttaaccttt tctgcagtga tctaagaagc cagattcatc   300
tgcacaaata cgtggtggtc tactttagag agattgatac aaaagacgat tacaatgctc   360
tcagtgtctg ccccaagtac cacctcatga ggatgccac tgctttctgt gcagaacttc   420
tccatgtcaa gtagcaggtg tcagcaggaa aaagatcaca agcctgccac gatggctgct   480
gctccttgta gcccacccat gagaagcaag agaccttaaa ggcttcctat cccaccaatt   540
acagggaaaa aaacgtgtga tgatccctga agcttactat gcagcctaca nacagcctta   600
```

```
gtaataaaac attttatcca ataaaatttc aaattttgct taactatgtg cataaactac      660
gattgaaaac tctttacact                                                  680

<210> SEQ ID NO 167
<211> LENGTH: 491
<212> TYPE: DNA
<213> ORGANISM: Homo sapiens

<400> SEQUENCE: 167
cattgtggtt gcagctgcat agtaagcttc aggatcatca cacgttttt ccctgtaatt       60 ggtgggatag gaagccttta aggtctcttg cttctcatgg gtgggctaca aggagcagca     120
gccatcgtgg caggcttgtg atctttttcc tgctgacacc tgctgcttga catggagaag     180
ttctgcacag aaagcagtgg catccttcat gaggtggtac ttggggcaga cactgagagc     240
attgtaatcg tcttttgtat caatctccct aaagtagacc accacgtatt tgtgcagatg     300
aatctggctt cttagatcac tgcagaaaag gttaaaggca aggggaaga ggtcttgaga      360 gttctcactg ggactgccct cgctcttgcc acaggtacca tcgcacacac tgttgacgtc     420
attggaaaga aggaagacga ctttgtctgc tgccttcttt tgagtggcaa gccactgcac     480
tggacccatc t                                                          491

<210> SEQ ID NO 168
<211> LENGTH: 533
<212> TYPE: DNA
<213> ORGANISM: Homo sapiens

<400> SEQUENCE: 168
gtgaataagc tttgtttttt ccagacaaaa gcaagccagg aggctggctg cctctcctcc      60
tgctgtctct gctggtggcc acatggttgc tggtggcagg gatctatcta atgtggaggc     120
acggtaaggg ttataattct ttaaagtcat cctagtaagg aaataacatt tggaatttt      180 ttttaaagaa gattcctctg gaggcaatca cctgttggcg tttcccagag ttagatagca     240
tttatgtaat accttcaagt gctcctacag agactgatac gagcatgact ggattacaca     300
tgccaggtga aagcagggcc aggacttcca gatcttctga ctgtcccgtt tttatttta      360 ccattgagcc ttctaccaga actgaaatgg gcaaagatg gctgataaca aattacactt      420
tacctgtgat ggttactcta tgctagttcc tgtttttaaa aaaatagttc ttatgaggtg     480
tcaagaaaag ctttcgcttg gattcataca cagttgaccc ttgaacaaca cag            533

<210> SEQ ID NO 169
<211> LENGTH: 218
<212> TYPE: DNA
<213> ORGANISM: Homo sapiens
<220> FEATURE:
<221> NAME/KEY: misc_feature
<222> LOCATION: (119)..(120)
<223> OTHER INFORMATION: a or g or c or t/u
<220> FEATURE:
<221> NAME/KEY: misc_feature
<222> LOCATION: (199)..(199)
<223> OTHER INFORMATION: a or g or c or t/u

<400> SEQUENCE: 169
gatcctgaag cttactatgc agcctacaaa cagccttagt aattaaaaca ttttatacca      60
ataaaatttt caaatattgc taactaatgt agcattaact aacgattgga aactacatnn     120
acaacttcaa agctgtttta tacatagaaa tcaattacag ctttaattga aaactataac     180 catttgata atgcaacant aaagcatctt cagccaaa                              218
```

<210> SEQ ID NO 170
<211> LENGTH: 703
<212> TYPE: DNA
<213> ORGANISM: Homo sapiens
<220> FEATURE:
<221> NAME/KEY: misc_feature
<222> LOCATION: (554)..(554)
<223> OTHER INFORMATION: a or g or c or t/u
<220> FEATURE:
<221> NAME/KEY: misc_feature
<222> LOCATION: (703)..(703)
<223> OTHER INFORMATION: a or g or c or t/u

<400> SEQUENCE: 170

| | | | | | |
|---|---|---|---|---|---|
| gcaacttcca | gtcctacagc | tgtgtgaggt | gcaattacac | agaggccttc | cagactcaga | 60 |
| ccagaccctc | tggtggtaaa | tggacatttt | cctatatcgg | cttccctgta | gagctgaaca | 120 |
| cagtctattt | cattggggcc | cataatattc | ctaatgcaaa | tatgaatgaa | gatggccctt | 180 |
| ccatgtctgt | gaatttcacc | tcaccaggct | gcctagacca | cataatgaaa | tataaaaaaa | 240 |
| agtgtgtcaa | ggccggaagc | ctgtgggatc | cgaacatcac | tgcttgtaag | aagaatgagg | 300 |
| agacagtaga | agtgaacttc | acaaccactc | ccctgggaaa | cagatacatg | gctcttatcc | 360 |
| aacacagcac | tatcatcggg | ttttctcagg | tgtttgagcc | acaccagaag | aaacaaacgc | 420 |
| gagcttcagt | ggtgattcca | gtgactgggg | atagtgaagg | tgctacggtg | cagctgactc | 480 |
| catattttcc | tacttgtggc | agcgactgca | tccgacataa | aggaacagtt | gtgctctgcc | 540 |
| cacaaacagg | cgtnccttttt | cctctggata | caacaaaag | caagccggga | ggcttggctg | 600 |
| ctctccttct | gctggccttt | gctgtggcca | cattggtgct | ggtggcaggg | atctatctaa | 660 |
| tgtggatgca | cgtctcgtgg | tttacccatc | tgaaatatgt | tcn | | 703 |

<210> SEQ ID NO 171
<211> LENGTH: 893
<212> TYPE: DNA
<213> ORGANISM: Homo sapiens
<220> FEATURE:
<221> NAME/KEY: misc_feature
<222> LOCATION: (798)..(798)
<223> OTHER INFORMATION: a or g or c or t/u
<220> FEATURE:
<221> NAME/KEY: misc_feature
<222> LOCATION: (805)..(805)
<223> OTHER INFORMATION: a or g or c or t/u

<400> SEQUENCE: 171

| | | | | | |
|---|---|---|---|---|---|
| attttccctc | ttgtggcagc | gactggcatc | cgacataaag | gaacagttgt | gctctgccca | 60 |
| caaacaggcg | tcccttttcc | tctggataac | aacaaaagca | agccgggagg | ctggctgcct | 120 |
| ctcctcctgc | tgtctctgct | ggtggccaca | tgggtgctgg | tggcagggat | ctatctaatg | 180 |
| tggaggcacg | aaaggatcaa | gaagacttcc | ttttctacca | ccacactact | gcccccatt | 240 |
| aaggttcttg | tggtttaccc | atctgaaata | tgtttccatc | acacaatttg | ttacttcact | 300 |
| gaatttcttc | aaaaccattg | cagaagtgag | gtcatccttg | aaaagtggca | gaaaaagaaa | 360 |
| atagcagaga | tgggtccagt | gcagtggctt | gccactcaaa | agaaggcagc | agacaaagtc | 420 |
| gtcttccttc | tttccaatga | cgtcaacagt | gtgtgcgatg | gtacctgtgg | caagagcgag | 480 |
| ggcagtccca | gtgagaactc | tcaagacctc | ttcccccttg | cctttaacct | tttctgcagt | 540 |
| gatctaagaa | gccagattca | tctgcacaaa | tacgtggtgg | tctactttag | agagattgat | 600 |
| acaaaagacg | attacaatgc | tctcagtgtc | tgccccaagt | accacctcat | gaaggatgcc | 660 |

```
actgctttct gtgcagaact tctccatgtc aagcagcagg tgtcagcagg aaaaagatca    720
caagcctgcc acgatggctg ctgctccttg tagcccaccc atgagaagca agagaccttg    780
aggcttctat cccaccanta caggnaaaaa cgtgtgatga tcctgaagct tactatgcag    840
cctacaacag gcttagtatt aaaacattta tacccataaa ttttcaaatt gct           893
```

<210> SEQ ID NO 172
<211> LENGTH: 959
<212> TYPE: DNA
<213> ORGANISM: Homo sapiens

<400> SEQUENCE: 172

```
taggtgacac tatagaacaa gtttgtacaa aaaagcaggc tggtaccggt ccggaattcc     60
cgggatagtg gmccggcgak gtcgctcgtg ctgctaagcc tggccgcgct gtgcaggagc    120
gccgtacccc gagagccgac cgttcaatgt ggctctgaaa ctgggccatc tccaragtgg    180
atgskacaac atgatctaat cccgggagac ttgagggacc tccgagtaga acctgttaca    240
actagtgttg caacagggga ctattcaatt ttgatgaatg taagctgggt actccgggsa    300
gatgccagca tccgcttgtt gaaggccacc aagatttgtg tgamgggcaa aagcaacwtc    360
cagtcctaca gcwgtgtgag gtagcaatta cacagagagc acatatccag actctagacc    420
agaccctctg gwggtaaatg gacattttcc tatatcggct tccctgtaga gctgaacaca    480
gtctatattc attggggccc awaatawwcc taatgcaaat atgaatgaag atggcccttc    540
catgtctgtg aatttcacct caccaggctg cctagaccac ataatgaaat awaaaaaaaa    600
gtgtgtcaag gccggaagcc tgtgggatcc gaacatcact gcttgtaaga agaatgarga    660
gacagtagaa gtgaacttca caaccactcc cctgggaaac agatamatkg ctcttatcca    720
acacarmact atcatcgggt tttctcaggt gtttgagcca caccagaaga aacaaacgcg    780
agcttcagtg gtgattccag tgactgggga tagtgaaggt gctacggtgc agctgactcc    840
atattttcct acttgtggca gcgwctgcat ccgacataaa ggaacagttg tgctctgccc    900
acaaacaggc gtcccttttyc ctctggataa caacaaaagc aacygggags tggytgyct    959
```

<210> SEQ ID NO 173
<211> LENGTH: 1200
<212> TYPE: DNA
<213> ORGANISM: Homo sapiens
<220> FEATURE:
<221> NAME/KEY: misc_feature
<222> LOCATION: (15)..(15)
<223> OTHER INFORMATION: a or g or c or t/u
<220> FEATURE:
<221> NAME/KEY: misc_feature
<222> LOCATION: (35)..(35)
<223> OTHER INFORMATION: a or g or c or t/u
<220> FEATURE:
<221> NAME/KEY: misc_feature
<222> LOCATION: (43)..(43)
<223> OTHER INFORMATION: a or g or c or t/u
<220> FEATURE:
<221> NAME/KEY: misc_feature
<222> LOCATION: (45)..(45)
<223> OTHER INFORMATION: a or g or c or t/u
<220> FEATURE:
<221> NAME/KEY: misc_feature
<222> LOCATION: (48)..(48)
<223> OTHER INFORMATION: a or g or c or t/u

<400> SEQUENCE: 173

```
waatwakadd ratanhtgaa aactataacc atttntgata atngnaanaa taaagcatct     60
tcagccaaac atctagtctt ccatagacca tgcattgcag tgtacccaga wctgtttagc    120
```

```
taatattcta tgtttaatta atgaatacta actctaagaa cccctcactg attcactcaa      180
tagcatctta agtgaaaaac cttctattac atgcaaaaaa tcattgtttt taagataaca      240
aaagtaggga ataaacaagc tgaacccact tttactggac caaatgatct attatatgtg      300
taaccacttg tatgatttgg tatttgcata agaccttccc tctacaaact agattcatat      360
cttgattctt gtacaggtgc cttttaacat gaacaacaaa atacccacaa acttgtctac      420
ttttgcctaa agttacctat tagaggtcac tgtsagagtk ctcagtttct tagttactat      480
ttaastttts atgttcaaaa tgaaaataat tctkaagtkg aaagsgctct gaagtaacc       540 tttttataaa tgagttatta taatggttta cttaaataaa avagaggggk ttttgcggtg      600
gctcatgcct ccaatcccag cactttggca aggccaaggc aaaavgatcg ctcaagacca      660
ggctacgtca caaagcgaga cctccatctc tacaaaagat ttaaaaaatt agctgagtgt      720
gatggtgtga gcctgtggtc ccagctacta gggaggctga gatgggagga tcacttgagc      780
cctggaggtc aagggtgcag taaacggtga ttgtgccact gcactccatc ctgggtgaga      840
gcagaccctg tctaaaacaa acaaacgaaa aaaccccac agaatgacag aacataaaag       900
atgcacattt tgtcttccaa cttttttactc ttctaaaagc atcttttta aattttttaa       960 atttttttt ttttgagaca gagtttcact ctgtcacaca ggctggagtg mgtggcgtga      1020
ctcggctcac tamaactctg cytccggggt yacscatctc ctgcwcagct cctgagaagc     1080
kggayamagg mccacacaaa ccagtaaytt tatwttttga aaaagggtty acctgtasma     1140
graggctgaa tccgacmaar tmaccmccac yycaaadgag gawaagkgkr smggscbggc     1200
```

<210> SEQ ID NO 174
<211> LENGTH: 899
<212> TYPE: DNA
<213> ORGANISM: Homo sapiens
<220> FEATURE:
<221> NAME/KEY: misc_feature
<222> LOCATION: (483)..(483)
<223> OTHER INFORMATION: a or g or c or t/u
<220> FEATURE:
<221> NAME/KEY: misc_feature
<222> LOCATION: (485)..(485)
<223> OTHER INFORMATION: a or g or c or t/u

<400> SEQUENCE: 174

```
ttatgggggg cagtagtgtg gtggtagaaa aggaagtctt cttgatcctt tcgtgcctcc       60
cattagatag atccctgcca ccagcaccca tgtggccacc agcagagaca gcaggaggag      120
aggcagccag cctcccggct tgcttttgtt gttatccaga gggaaaggga cgcctgtttg      180
tgggcagagc acaactgttc ctttatgtcg gatgcagtcg ctgccacaag taggaaaata      240
tggagtcagc tgcaccgtag caccttcact atccccagtc actggaatca ccactgaagc      300
tcgcgtttgt ttcttctggt gtggctcaaa cacctgagaa aacccgatga tagtgctgtg      360
ttggataaga gccatgtatc tgtttcccag gggagtggtt gtgaagttca cttctactgt      420
ctcctcattc ttcttacaag cagtgatgtt cggatcccac aggcttccgg ccttgacaca      480
ctntntttta tatttcatta tgtggtctag gcagcctggt gaggtgaaat tcacagacat      540
ggaagggcca tcttcattca tatttgcatt aggaatatta tgggccccaa tgaaatagac      600
tgtgttcagc tctacagggg aagccgatat aggaaaatgt ccatttacca ccagagggtc      660
tggtctgagt cttgaaggcc ttttgtgtta ttgcacctta cacagctgtt agactgggaa      720
gttgcttttg ccccgcacac aaatcttgtg ggccttcaac agcggatgct gccatttgcc      780
```

```
ccgaagtccc cagctcaatt cattaaaaat tgaataggcc ccttgtggca accctagttg    840
gtacagggtt ttacttgggg ggcccctcta agtttccccg ggatataaac aaagtgtgg     899

<210> SEQ ID NO 175
<211> LENGTH: 877
<212> TYPE: DNA
<213> ORGANISM: Homo sapiens

<400> SEQUENCE: 175
ttatgggggg cagtagtgtg gtggtagaaa aggaagtctt cttgatcctt tcgtgcctcc     60
acattagata gatccctgcc accagcaccc atgtggccac cagcagagac agcaggagga    120
gaggcagcca gcctcccggc ttgcttttgt tgttatccag agggaaaggg acgcctgttt    180
gtgggcagag cacaactgtt cctttatgtc ggatgcagtc gctgccacaa gtaggaaaat    240
atggagtcag ctgcaccgta gcaccttcac tatccccagt cactggaatc accactgaag    300
ctcgcgtttg tttcttctgg tgtggctcaa acacctgaga aaacccgatg atagtgctgt    360
gttggataag agccatgtat ctgtttccca ggggagtggt tgtgaagttc acttctactg    420
tctcctcatt cttcttacaa gcagtgatgt tcggatccca caggcttccg gccttgacac    480 acttttttt atatttcatt atgtggtcta ggcagcctgg tgaggtgaaa ttcacagaca      540
tggaagggcc atcttcattc atatttgcat taggaatatt atgggcccca atgaaataga    600
ctgtgttcag ctctacaggg aagccgatat aggaaaatgt ccatttacca ccagagggtc    660
tggtctgagt ctggaaggcc tctgtgtaat tgcacctcac acagctgtag gactgggagt    720
tgcttttgcc cgtacacaaa tcttgttggc cttcaacaag cggatgctgg catctggcgg    780
gggtacccag cttacattca tcaaaattga atagtcccct tgttgcaaca ctagtttgta    840
aacaggttct actccggggg tccctcagt ctcccgg                              877

<210> SEQ ID NO 176
<211> LENGTH: 419
<212> TYPE: DNA
<213> ORGANISM: Homo sapiens

<400> SEQUENCE: 176
caaatatgaa tgaagatggc ccttccatgt ctgtgaattt cacctcacca ggctgcctag     60
accacataat gaaatataaa aaaaagtgtg tcaaggccgg aagcctgtgg gatccgaaca    120
tcactgcttg taagaagaat gaggagacag tagaagtgaa cttcacaacc actcccctgg    180
gaaacagata catggctctt atccaacaca gcactatcat cgggttttct caggtgtttg    240
agccacacca gaagaaacaa acgcgagctt cagtggtgat tccagtgact ggggatagtg    300
aaggtgctac ggtgcaactg actccatatt ttcctacttg tggcagcgac tgcatccgac    360
ataaaggaac agttgtgctc tgcccacaaa caggcgtccc tttccctctg gataacaac    419

<210> SEQ ID NO 177
<211> LENGTH: 420
<212> TYPE: DNA
<213> ORGANISM: Homo sapiens

<400> SEQUENCE: 177
gcaaatatga atgaagatgg cccttccatg tctgtgaatt tcacctcacc aggctgccta     60
gaccacataa tgaaatataa aaaaaagtgt gtcaaggccg gaagcctgtg ggatccgaac    120
atcactgctt gtaagaagaa tgaggagaca gtagaagtga acttcacaac cactcccctg    180
ggaaacagat acatggctct tatccaacac agcactatca tcgggttttc tcaggtgttt    240
```

```
gagccacacc agaagaaaca aacgcgagct tcagtggtga ttccagtgac tggggatagt    300
gaaggtgcta cggtgcagct gactccatat tttcctactt gtggcagcga ctgcatccga    360
cataaaggaa cagttgtgct ctgcccacaa acaggcgtcc ctttccctct ggataacaac    420
```

<210> SEQ ID NO 178
<211> LENGTH: 676
<212> TYPE: DNA
<213> ORGANISM: Homo sapiens

<400> SEQUENCE: 178

```
gcaaatatga atgaagatgg cccttccatg tctgtgaatt tcacctcacc aggctgccta     60
gaccacataa tgaaatataa aaaaaagtgt gtcaaggccg gaagcctgtg ggatccgaac    120
atcactgctt gtaagaagaa tgaggagaca gtagaagtga acttcacaac cactcccctg    180
ggaaacagat acatggctct tatccaacac agcactatca tcgggttttc tcaggtgttt    240
gagccacacc agaagaaaca aacgcgagct tcagtggtga ttccagtgac tggggatagt    300
gaaggtgcta cggtgcagct gactccatat tttcctactt gtggcagcga ctgcatccga    360
cataaaggaa cagttgtgct ctgcccacaa acaggcgtcc ctttccctct ggataacaac    420
aaaagcaagc cgggaggctg gctgcctctc ctcctgctgt ctctgctggt ggccacatgg    480
gtgctggtgg cagggatcta tctaatgtgg aggcacgaaa ggatcaagaa gacttccttt    540
tttaccacca cactactgtc tcccattaaa gatcttgtgg tttatccatc tgaaatattg    600
ttccattaca catattggta cctaactgaa attctttaaa accattgcaa attgaggtca    660
ctcttgaaag ggcgtg                                                    676
```

<210> SEQ ID NO 179
<211> LENGTH: 517
<212> TYPE: DNA
<213> ORGANISM: Homo sapiens

<400> SEQUENCE: 179

```
cggctcctac cttttgcccg atccccttcc ccattccgcc ccgcccaa cgcagtgcac      60 agtgccctgc acacagtagt cgctcaataa atgttcgtgg atgatgatga tgatgatgat   120
gaaaaaaatg cagcatcaac ggcagcagca agcggaccac gcgaacgagg caaactatgc   180
aagaggcacc agacttcctc tttctggtga aggaccaact tctcagctga atagctccaa   240
gcaaactgtc ctgtcttggc aagctgcaat cgatgctgct agacaggcca aggctgccca   300
aactatgagc acctctgcac ccccacctgt aggatctctc tcccaaagaa aacgtcagca   360
atacgccaag agcaaaaaac agggtaactc gtccaacagc cgacctgccc gcgccctttt   420
ctgtttatca ctcaataacc ccatccgaag agcctgcatt agtatagtgg aatggaaaca   480
tttgacatat ttatattatt ggctatttt tgccaat                             517
```

<210> SEQ ID NO 180
<211> LENGTH: 860
<212> TYPE: DNA
<213> ORGANISM: Homo sapiens

<400> SEQUENCE: 180

```
gaatatgacc ctgaggcaaa gggaaggata acaccttga tgtggtcact ctgcttcgac     60
gcatccagcc tcccctgggg tttgggaagt tatgtccaca cagggtagcg tgcaagagat   120
tagttgccat gaacatgcct ctcaacagtg acgggacagt catgtttaat gcaaccctgt   180
```

```
ttgctttggt tcgaacggct cttaagatca agaccgaagg gaacctggag caagctaatg    240
aagaacttcg ggctgtgata aagaaaattt ggaagaaaac cagcatgaaa ttacttgacc    300
aagttgtccc tccagctggt gatgatgagg taaccgtggg gaagttctat gccactttcc    360
tgatacagga ctactttagg aaattcaaga acggaaaga acaaggactg gtgggaaagt    420
accctgcgaa gaacaccaca attgccctac aggcgggatt aaggacactg catgacattg    480
ggccagaaat ccggcgtgct atatcgtgtg atttgcaaga tgacgagcct gaggaaacaa    540
aacgagaaga agaagatgat gtgttcaaaa gaaatggtgc cctgcttgga aaccatgtca    600
atcatgttaa tagtgatagg agagattccc ttcagcagac caatagcacc accgtccccct   660 gcattgtcca aaggccttca attccacctg caagtgatac tgagaaaccg ctgtttcctc    720
cagcaggaaa ttcggggtgt cataaccatc ataaccatta attccatagg aaagcaaggt    780
tcccacttca acaatgccag tctcgaatag tgccaatatg tccaaagctt gccatggtaa    840
gcgggccagc attgggaacc                                               860

<210> SEQ ID NO 181
<211> LENGTH: 495
<212> TYPE: DNA
<213> ORGANISM: Homo sapiens

<400> SEQUENCE: 181
gcacgagatt aattagactt ttgtataaga gatgtcatgc ctcaagaaag ccataaacct     60
ggtaggaaca ggtcccaagc ggttgagcct ggcagagtac catgcgctcg ccccagctg    120 caggaaacag caggccccgc cctctcacag aggatgggtg aggaggccag acctgccctg   180
ccccattgtc cagatgggca ctgctgtgga gtctgcttct cccatgtacc agggcaccag   240
gcccacccaa ctgaaggcat ggcggcgggg tgcaggggaa agttaaaggt gatgacgatc   300
atcacacctg tgtcgttacc tcagccatcg gtctagcata tcagtcactg ggcccaacat   360
atccattttt aaacccttc ccacaaatac actgcgtcct ggttcctgtt tagctgttct    420
gaaatacggt gtgtaagtaa gtcagaaccc agctaccagt gattattgcg agggcaatgg    480
gacctcataa ataag                                                    495

<210> SEQ ID NO 182
<211> LENGTH: 557
<212> TYPE: DNA
<213> ORGANISM: Homo sapiens

<400> SEQUENCE: 182
tttttttttt tttttttag tggggaacta caattattag gacccatgga tattgctgca     60
gttcaaatac aatacagtaa ttacaaaata tagaccatct ctttacaaat acaaattata   120
gtatattaca agtcatgtac agtaaatcta aattttaaa caaactagtg tatctaagtt    180
tacctggttg cgagtgcatt attattccag tttacagttg cccttagcgt gacagtcaga   240
aaccgaccat cggagtgata ttctcttatg taaactggcg tcacatcaca gaaaaccta    300 tttatgaggt cccattgccc tcgcaataat cactggtagc tgggttctga cttacttaca   360
caccgtattt cagaacagct aaacaggaac caggacgcag tgtatttgtg ggaaagggtt    420
taaaaatgga tatgttgggc ccagtgactg atatgctaga ccgatggctg aggtaacgac    480
acaggtgtga tgatcgtcat cacctttaac tttccctgc acccgccgc catgccttcc      540 agttgggtgg gcctggt                                                  557
```

<210> SEQ ID NO 183
<211> LENGTH: 416
<212> TYPE: DNA
<213> ORGANISM: Homo sapiens

<400> SEQUENCE: 183

| | | | | | |
|---|---|---|---|---|---|
| ctctgagcac | tacaatcagc | cagattggtt | gacacagatt | caagatattg | ccaacaaagt | 60 |
| cctcttggct | ctgttcacct | gcgagatgct | ggtaaaaatg | tacagcttgg | gcctccaagc | 120 |
| atactcttgt | tctctttaca | accggtttga | ttgcttcgtg | gtgtgtggtg | gaatcactga | 180 |
| gacgatcttg | gtggaactgg | aaatcatgtc | tccctgggg | atctctgtgt | tcggtgtgt | 240 |
| gcgcctctta | agaatcttca | aagtgaccag | gcactggact | tccctgagca | acttagtggc | 300 |
| atccttatta | aactccatga | agtccatcgc | ttcgctgttg | cttctgcttt | ttctcttcat | 360 |
| tatcatcttt | tccttgcttg | ggatgcagct | gtttggcggc | aagtttaatt | ttgatg | 416 |

<210> SEQ ID NO 184
<211> LENGTH: 401
<212> TYPE: DNA
<213> ORGANISM: Homo sapiens
<220> FEATURE:
<221> NAME/KEY: misc_feature
<222> LOCATION: (365)..(365)
<223> OTHER INFORMATION: a or g or c or t/u

<400> SEQUENCE: 184

| | | | | | |
|---|---|---|---|---|---|
| accagcagac | ctgactgtcc | ccagcagctt | ccggaacaaa | aacagcgaca | agagaggagt | 60 |
| gcggacagtt | ggtggaggca | gtcctgatat | ccgaagcttg | ggacgctatg | caagggaccc | 120 |
| aaaatttgtg | tcagcaacaa | aacacgaaat | cgctgatgcc | tgtgacctca | ccatcgacga | 180 |
| gatggagagt | gcagccagca | ccctgcttaa | tgggaacgtg | cgtccccgag | ccaacgggga | 240 |
| tgtgggcccc | ctctcacacc | ggcagactat | gagctacagg | actttggtcc | tgggcttaca | 300 |
| gcgacgaaga | gccagaccct | ggggagggat | tgagggagga | cctgggcgga | tgaattgatt | 360 |
| ttgcntcacc | acctttgtta | ggcccccagg | cgaggggcaa | g | | 401 |

<210> SEQ ID NO 185
<211> LENGTH: 186
<212> TYPE: DNA
<213> ORGANISM: Homo sapiens
<220> FEATURE:
<221> NAME/KEY: misc_feature
<222> LOCATION: (11)..(11)
<223> OTHER INFORMATION: a or g or c or t/u
<220> FEATURE:
<221> NAME/KEY: misc_feature
<222> LOCATION: (172)..(172)
<223> OTHER INFORMATION: a or g or c or t/u

<400> SEQUENCE: 185

| | | | | | |
|---|---|---|---|---|---|
| tttttttttt | nttttttttt | ttgtggaaag | atgataggtt | tatagtgact | caaatatttt | 60 |
| tagaaaaatt | tctgtagtgt | caagttcttt | caaacttaaa | attttaaccc | cagaggattt | 120 |
| tcgctgaata | aatgagaatt | ggctctattt | cttctacttc | tggatagccc | gngtaaaaat | 180 |
| actaat | | | | | | 186 |

<210> SEQ ID NO 186
<211> LENGTH: 433
<212> TYPE: DNA
<213> ORGANISM: Homo sapiens
<220> FEATURE:
<221> NAME/KEY: misc_feature
<222> LOCATION: (45)..(45)

```
<223> OTHER INFORMATION: a or g or c or t/u
<220> FEATURE:
<221> NAME/KEY: misc_feature
<222> LOCATION: (296)..(296)
<223> OTHER INFORMATION: a or g or c or t/u
<220> FEATURE:
<221> NAME/KEY: misc_feature
<222> LOCATION: (303)..(303)
<223> OTHER INFORMATION: a or g or c or t/u
<220> FEATURE:
<221> NAME/KEY: misc_feature
<222> LOCATION: (345)..(345)
<223> OTHER INFORMATION: a or g or c or t/u
<220> FEATURE:
<221> NAME/KEY: misc_feature
<222> LOCATION: (366)..(366)
<223> OTHER INFORMATION: a or g or c or t/u
<220> FEATURE:
<221> NAME/KEY: misc_feature
<222> LOCATION: (386)..(386)
<223> OTHER INFORMATION: a or g or c or t/u
<220> FEATURE:
<221> NAME/KEY: misc_feature
<222> LOCATION: (391)..(391)
<223> OTHER INFORMATION: a or g or c or t/u
<220> FEATURE:
<221> NAME/KEY: misc_feature
<222> LOCATION: (420)..(420)
<223> OTHER INFORMATION: a or g or c or t/u
<220> FEATURE:
<221> NAME/KEY: misc_feature
<222> LOCATION: (428)..(428)
<223> OTHER INFORMATION: a or g or c or t/u

<400> SEQUENCE: 186
tttttttttt tttttttttt tgtggaaaga tgataggttt atagngactc aaaatatttt      60
agaaaaattt ctgtagtgtc aagttctttc aaacttaaaa ttttaacccc agaggatttt     120
cgctgaataa atgagaattg ctctatttc ttctacttct ggatagcccg agtaaaata      180 ctaataattt ctagatttta gtggggaact acaattatta ggacccatgg atattgctgc    240
agttcaaata caatacagta attacaaaat atagaccatc tctttacaaa tacaanttat    300
agnatattac aagtcatgta cagtaaatct ataattttgg acaanctagt gtatctaagt    360
ttaccngggg tgcgagtgcc ttattnttcc ngtttacagt tgcccttagc gtgacagtcn    420
ggaaccgncc ttc                                                       433

<210> SEQ ID NO 187
<211> LENGTH: 331
<212> TYPE: DNA
<213> ORGANISM: Homo sapiens
<220> FEATURE:
<221> NAME/KEY: misc_feature
<222> LOCATION: (61)..(61)
<223> OTHER INFORMATION: a or g or c or t/u

<400> SEQUENCE: 187
gcctgactgt ccccagcagc ttccggaaca aaaacagcga caagcagagg agtgcggaca      60
ntttggtgga ggcagtcctg atatccgaag cttgggacgc tatgcaaggg acccaaaatt    120
tgtgtcagca acaaaacacg aaatcgctga tgcctgtgac ctcaccatcg acgagatgga    180
gagtgcagcc agcaccctgc ttaatgggaa cgtgcgtccc cgagccaacg gggatgtggg    240 cccccctctca caccggcaga ctatgagcta caggactttg gtcctgggct acagcgacga    300
agagccagac cctgggaggg atgaggagga c                                    331

<210> SEQ ID NO 188
<211> LENGTH: 643
```

<212> TYPE: DNA
<213> ORGANISM: Homo sapiens

<400> SEQUENCE: 188

```
agcggtcgta ataatgtagt tccccactaa aatctagaaa ttattagtat tttactcgg      60
gctatccaga agtagaagaa atagagcaaa ttctcattta ttcagcgaaa atcctctggg    120
gttaaaattt taagttgaaa gaacttgaca ctacagaaat ttttctaaaa tatttgagtc    180
actataaacc tatcatcttt ccacaagata taccagatga ctattgcagt cttctcttgg    240
gcaagagttc catgatttga tactgtacct tggatccacc atgggtgcaa ctgtcttggt    300
ttgttgttga cttgaaccac cctctggtaa gtaagtgaat tacagagcag gtctagctgg    360
ctgctctgcc ccttgggtat ccatagttac ggttttctct gtggcccacc caggtgtttt    420
tgcatcgctg gtgcagaaat gcacaggtgg atgagatata gctgctcttg tcctctgggg    480
actggtggtg ctgcttaaga aataaggggt gctggggaca gaggagcaac gtggtgatct    540
ataggattgg agtgtcgggg tctgtacaaa tcgtattgtt gccttttaca aaactgtgta    600
ctgtatgttc tctttgaggg cttttgtatg caattgaatg agg                      643
```

<210> SEQ ID NO 189
<211> LENGTH: 357
<212> TYPE: DNA
<213> ORGANISM: Homo sapiens

<400> SEQUENCE: 189

```
ttttcttgtg gaaagatgat aggtttatag tgactcaaaa tattttagaa aaatttctgt     60
agtgtcaagt tctttcaaac ttaaaatttt aaccccagag gattttcgct gaataaatga    120
gaattggctc tatttcttct acttctggat agcccgagta aaaatactaa taatttctag    180
attttagtgg ggaactacaa ttattaggac ccatggatat tgctgcagtt caaatacaat    240
acagtaatta caaatatag accatctctt tacaaataca aattatagta tattacaagt    300
catgtacagt aaatctataa ttttaaacaa acctgtgtat ctaagtttac ctggttg      357
```

<210> SEQ ID NO 190
<211> LENGTH: 420
<212> TYPE: DNA
<213> ORGANISM: Homo sapiens

<400> SEQUENCE: 190

```
gacaaataaa gcaattataa atgtatctca ctttagaaca gacaaaaaaa gggcatgcta     60
tggaaattgt ttaaatctca agcaacaatg ctgattaatt tctggtcaat aatcgttcta    120
tagttctcct tcatgaagcc tggtgaggtt ccaggaaaca gcttgatttg ggaagcctca    180
gcagaaaaga aagcatctca gaggacacat aaaatgtctg caacccctc ttggcggccc     240
tcatccagca aagcttgtgt ggtcttggca actgtcctca ggactctgct tcaagatga     300
aagaggtgta gcttacccgc tcaatacacc aagtacaaga tttagtacga aaaatgaccc    360
aaagatgacg agactgacaa gatacaccca gggcaattcc aatcccatag catcattcat    420
```

<210> SEQ ID NO 191
<211> LENGTH: 465
<212> TYPE: DNA
<213> ORGANISM: Homo sapiens

<400> SEQUENCE: 191

```
tttatattat tcaccacttt gttatgaaga ccttacaaac ctcttcttaa gacattctta     60
```

| | | | |
|---|---|---|---|
| ctctgatcca | ggcaaaaaca | cttcaaggtt tgtaaatgac tctttcctga cataaatcct | 120 |
| tttttattaa | aatgcaaaat | gttcttcaga ataaaactgt gtaataattt ttatacttgg | 180 |
| gagtgctcct | tgcacagagc | tgtcatttgc cagtgagagc ctccgacagg gcaggtactg | 240 |
| tgccagggca | gctctgaaat | tatggatatt cttatcctcc tggttccttc ggtgccaatg | 300 |
| gtaacctaat | accagccgca | gggagcgcca tttctcctaa agggctacac cactgtcaac | 360 |
| attatcctgg | actctgtgtc | tctctctgtt gggtcttgtg gcatcacatc aggccaaaat | 420 |
| tgccagacca | ggaccctaag | tgtctgatag aggcgatgat ctttt | 465 |

<210> SEQ ID NO 192
<211> LENGTH: 330
<212> TYPE: DNA
<213> ORGANISM: Homo sapiens

<400> SEQUENCE: 192

| | | | |
|---|---|---|---|
| tttttttttt | tttttttttt | tcttacaaag aaaaatttaa tattcgatga gaggttgaac | 60 |
| caggcttaaa | gcaaacatac | taggaaatgg ggcagcctgt aagaatgcca gtttgtaagt | 120 |
| actgactttg | gaaagatca | tcgcctctat cagacactta gggtcctggt ctggcaattt | 180 |
| tggcctgatg | tgatgccaca | agacccaaca gagagagaca cagagtccag gataatgttg | 240 |
| acaggggta | gcccttagg | agaaatggcg ctccctgcgg ctggtattag gttaccattg | 300 |
| gcaccgaagg | aaccaggagg | ataagaatat | 330 |

<210> SEQ ID NO 193
<211> LENGTH: 502
<212> TYPE: DNA
<213> ORGANISM: Homo sapiens

<400> SEQUENCE: 193

| | | | |
|---|---|---|---|
| tgtaaataac | aaacaccact | ttgttatgaa gaccttacaa acctcttctt aagacattct | 60 |
| tactctgatc | caggcaaaaa | cacttcaagg tttgtaaatg actcttttcct gacataaatc | 120 |
| cttttttatt | aaaatgcaaa | atgttcttca gaataaaact gtgtaataat tttatactt | 180 |
| gggagtgctc | cttgcacaga | gctgtcattt gccagtgaga gcctccgacg ggcaggtac | 240 |
| tgtgccaggg | cagctctgaa | attatggata ttcttatcct cctggttcct tcggtgccaa | 300 |
| tggtaaccta | ataccagccg | cagggagcgc catttctcct aaagggctac accactgtca | 360 |
| acattatcct | ggactctgtg | tctctctctg ttgggtcttg tggcatcaca tcaggccaaa | 420 |
| attgccagac | caggacccta | agtgtctgat agaggcgatg atcttttcca aagtcagtac | 480 |
| ttacaaactg | gcattcttac | ag | 502 |

<210> SEQ ID NO 194
<211> LENGTH: 410
<212> TYPE: DNA
<213> ORGANISM: Homo sapiens

<400> SEQUENCE: 194

| | | | |
|---|---|---|---|
| tttttttttt | tgtaaataac | aaacaccact ttgttatgaa gaccttacaa acctcttctt | 60 |
| aagacattct | tactctgatc | caggcaaaaa cacttcaagg tttgtaaatg actcttttcct | 120 |
| gacataaatc | cttttttatt | aaaatgcaaa atgttcttca gaataaaact gtgtaataat | 180 |
| ttttatactt | gggagtgctc | cttgcacaga gctgtcattt gccagtgaga gcctccgacg | 240 |
| ggcaggtac | tgtgccaggg | cagctctgaa attatggata ttcttatcct cctggttcct | 300 |
| tcggtgccaa | tggtaaccta | ataccagccg cagggagcgc catttctcct aaagggctac | 360 |

```
accactgtca acattatcct ggactctgtg tctctctctg ttgggtcttg            410
```

<210> SEQ ID NO 195
<211> LENGTH: 333
<212> TYPE: DNA
<213> ORGANISM: Homo sapiens

<400> SEQUENCE: 195

```
gtaaataaca acaccactt tgttatgaag accttacaaa cctcttctta agacattctt    60
actctgatcc aggcaaaaac acttcaaggt ttgtaaatga ctctttcctg acataaatcc   120
ttttttatta aaatgcaaaa tgttcttcag aataaaactg tgtaataatt tttatacttg   180
ggagtgctcc ttgcacagag ctgtcatttg ccagtgagag cctccgacgg gcaggtactg   240
tgccagggca gctctgaaat atggatattc ttacctcctg gttctttcgg tgcaaatggt   300
aacctaatac cagccgcagg gagcgccatt tct                                 333
```

<210> SEQ ID NO 196
<211> LENGTH: 282
<212> TYPE: DNA
<213> ORGANISM: Homo sapiens
<220> FEATURE:
<221> NAME/KEY: misc_feature
<222> LOCATION: (231)..(231)
<223> OTHER INFORMATION: a or g or c or t/u

<400> SEQUENCE: 196

```
gtaaataaca acaccactt tgttatgaag accttacaaa cctcttctta agacattctt    60
actctgatcc aggcaaaaac acttcaaggt ttgtaaatga ctctttcctg acataaatcc   120
ttttttatta aaatgcaaaa tgttcttcag aataaaactg tgtaataatt tttatacttg   180
ggagtgctcc ttgcacagag ctgtcatttg ccagtgagag cctccgacgg ngcaggtact   240
gtgccagggc agctctgaat tatggatatt cttatcctcc tg                      282
```

<210> SEQ ID NO 197
<211> LENGTH: 400
<212> TYPE: DNA
<213> ORGANISM: Homo sapiens

<400> SEQUENCE: 197

```
tttttcttac aaagaaaaat ttaatattcg atgagaggtt gaaccaggct taaagcagac    60
atactaggaa atggtgcagc ctgtaagaat gccagtttgt aagtactgac tttggaaaag   120
atcatcgcct ctatcagaca cttagggtcc tggtctggca atttggcct gatgtgatgc    180 cacaagaccc aacagagaga gacacagagt ccaggataat gttgacagtg gtgtagccct   240
ttaggagaaa tggcgctccc tgcggctggt attaggttac cattggcacc gaaggaacca   300
ggaggataag aatatccata atttcagagc tgccctggca cagtacctgc cccgtcggag   360
gctctcactg gcaaatgaca gctctgtgca aggagcactc                         400
```

<210> SEQ ID NO 198
<211> LENGTH: 482
<212> TYPE: DNA
<213> ORGANISM: Homo sapiens

<400> SEQUENCE: 198

```
ttatcttgtg gaaagatgat aggtttatag tgactcaaaa tattttagaa aaatttctgt    60
agtgtcaagt tctttcaaac ttaaaatttt aaccccagag gattttcgct gaataaatga   120
```

```
gaattggctc tatttcttct acttctggat agcccgagta aaaatactaa taatttctag    180
attttagtgg ggaactacaa ttattaggac ccatggatat tgctgcagtt caaatacaat    240
acagtaatta caaaatatag accatctctt tacaaataca aattatagga tattacaagg    300
catgtacagt aaatctataa ttttaaacaa actagtgtat ctaagtttac ctggttgcga    360
gtgcattatt attccagttt acagttgccc ttagcgtgac agtcagaaac cgaccatcgg    420
agtgatattc tcttatgtaa actggcgtca catcacagaa aaccttattt atgaggtccc    480
at                                                                   482
```

<210> SEQ ID NO 199
<211> LENGTH: 459
<212> TYPE: DNA
<213> ORGANISM: Homo sapiens

<400> SEQUENCE: 199

```
gccctcacag cccaccacgc ctggccttcg cccaattctg aaacttcgta ggatagagct     60
ggaaagtgcc acatggtgaa gcgagatcca gctgtctggg tggatgtcgg agtccatagg    120
ctgagcagag atggttctta gtgaggttct cgctgccagt tgacggtgaa atcatagctg    180
ccatttacat tttgtgagat tatgaaaaac ataagactaa agaaactaaa tgtgttattc    240
ctgtggacac aaaaatgtgt gttttttcaga tggggagggg accaaaaagg aaaaacattt    300
catcttaaaa ctttcctaag acaaaggaaa acaaaaaacc atgctcctac aacttcaaat    360
ttttcttacc aaagaaaaat ttaatattcg atgagaggtt gaaccaggct taaagcagac    420
atactaggga atgggtgcag cctgtaagaa tgccagttt                           459
```

<210> SEQ ID NO 200
<211> LENGTH: 487
<212> TYPE: DNA
<213> ORGANISM: Homo sapiens

<400> SEQUENCE: 200

```
gtaaataaca aacaccactt tgttatgaag accttacaaa cctcttctta agacattctt     60
actctgatcc aggcaaaaac acttcaaggt ttgtaaatga ctctttcctg acataaatcc    120
ttttttatta aaatgcaaaa tgttcttcag aataaaactg tgtaataatt tttatacttg    180
ggagtgctcc ttgcacagag ctgtcatttg ccagtgagag cctccgacgg ggcaggtact    240
gtgccagggc agctctgaaa ttatggatat tcttatcctc ctggttcctt cggtgccaat    300
ggtaacctaa taccagccgc aggagcgcca tttctcctaa agggctacac cactgtcaac    360
attatcctgg gactctgtgt ctctctctgt tgggtcttgt ggcatcacat caggccaaaa    420
ttggccagac caggacccca agtggtctga tagaaggcga tgatcttttc caaagtcagt    480
acttaca                                                              487
```

<210> SEQ ID NO 201
<211> LENGTH: 445
<212> TYPE: DNA
<213> ORGANISM: Homo sapiens

<400> SEQUENCE: 201

```
gtttaaaatt atagatttac tgtacatgac ttgtaatata ctataatttg tatttgtaaa     60
gagatggtct atattttgta attactgtat tgtatttgaa ctgcagcaat atccatgggt    120
cctaataatt gtagttcccc actaaaatct agaaattatt agtatttttta ctcgggctat    180 ccagaagtag aagaaataga gccaattctc atttattcag cgaaaatcct ctggggttaa    240
```

```
aattttaagt tgaaagaac ttgacactac agaaatttt ctaaatatatt ttgagtcact        300 ataaacctat catctttcca caagatatac cagatgacta tttgcagtct tttctttggg        360
caagagttcc atgatttga tactgtacct ttggatccac catgggttgc aactgtctt         420 ggttttgttt gtttgacttg aacca                                             445
```

<210> SEQ ID NO 202
<211> LENGTH: 313
<212> TYPE: DNA
<213> ORGANISM: Homo sapiens

<400> SEQUENCE: 202

```
ttcgctgaat aaatgagaat tggctctatt tcttctactt ctggatagcc cgagtaaaaa        60
tactaataat ttctagattt tagtggggaa ctacaattat taggacccat ggatattgct       120
gcagttcaaa tacaatacag taattacaaa atatagacca tctctttaca aatacaaatt       180
atagtatatt acaagtcatg tacagtaaat ctataatttt aaacaaacta gtgtatctaa       240
gtttacctgg ttgcgagtgc attattattc cagtttacag ttgcccttag cgtgacagtc       300
agaaaccgac cat                                                          313
```

<210> SEQ ID NO 203
<211> LENGTH: 413
<212> TYPE: DNA
<213> ORGANISM: Homo sapiens

<400> SEQUENCE: 203

```
ttttatcttg tggaaagatg ataggtttat agtgactcaa aatattttag aaaaatttct        60
gtagtgtcaa gttcttcaa acttaaaatt ttaaccccag aggattttcg ctgaataaat       120
gagaattggc tctatttctt ctacttctgg atagcccgag taaaaatact aataatttct       180
agattttagt ggggaactac aattattagg acccatggat attgctgcag ttcaaataca       240
atacagtaat tacaaaatat agaccatctc tttacaaata caattatag tatattacaa       300 gtcatgtaca gtaaatctat aattttaaac aaactagtgt atctaagttt acctggttgc       360
gagtgcatta ttattccagt ttacagttgc ccttagcgtg acagtcagaa acc              413
```

<210> SEQ ID NO 204
<211> LENGTH: 476
<212> TYPE: DNA
<213> ORGANISM: Homo sapiens

<400> SEQUENCE: 204

```
ttttatcttg tggaaagatg ataggtttat agtgactcaa aatattttag aaaaatttct        60
gtagtgtcaa gttcttcaa acttaaaatt ttaaccccag aggattttcg ctgaataaat       120
gagaattggc tctatttctt ctacttctgg atagcccgag taaaaatact aataatttct       180
agattttagt ggggaactac aattattagg acccatggat attgctgcag ttcaaataca       240
atacagtaat tacaaaatat agaccatctc tttacaaata caattatag tatattacaa       300 gtcatgtaca gtaaatctat aattttaaac aaactagtgt atctaagttt acctggttgc       360
gagtgcatta ttattccagt ttacagttgc ccttagcgtg acagtcagaa accgaccatc       420
ggagtgatat tctcttatgt aaactggcgt cacatcacag aaaaccttat ttattt           476
```

<210> SEQ ID NO 205
<211> LENGTH: 406
<212> TYPE: DNA

<213> ORGANISM: Homo sapiens

<400> SEQUENCE: 205

| | | | | | |
|---|---|---|---|---|---|
| tttttttttt | agagccaatt | ctcatttatt | cagcgaaaat | cctctggggt | taaaattta | 60 |
| agtttgaaag | aacttgacac | tacagaaatt | tttctaaaat | attttgagtc | actataaacc | 120 |
| tatcatcttt | ccacaagata | taccagatga | ctatttgcag | tcttttcttt | gggcaagagt | 180 |
| tccatgattt | tgatactgta | cctttggatc | caccatgggt | tgcaactgtc | tttggttttg | 240 |
| tttgtttgac | ttgaaccacc | ctctggtaag | taagtgaatt | acagagcagg | tccagctggc | 300 |
| tgctctgccc | cttgggtatc | catagttacg | gttttctctg | tggcccaccc | agggtgtttt | 360 |
| ttgcatcgct | ggtgcagaaa | tgcacaggtg | gatgagatat | agctgc | | 406 |

<210> SEQ ID NO 206
<211> LENGTH: 473
<212> TYPE: DNA
<213> ORGANISM: Homo sapiens

<400> SEQUENCE: 206

| | | | | | |
|---|---|---|---|---|---|
| ttttttttg | taaataacaa | acaccacttt | gttatgaaga | ccttacaaac | ctcttcttaa | 60 |
| gacattctta | ctctgatcca | ggcaaaaaca | cttcaaggtt | tgtaaatgac | tctttcctga | 120 |
| cataaatcct | tttttattaa | aatgcaaaat | gttcttcaga | ataaaactgt | gtaataattt | 180 |
| ttatacttgg | gagtgctcct | tgcacagagc | tgtcatttgc | cagtgagagc | ctccgacagg | 240 |
| gcaggtactg | tgccagggca | gctctgaaat | tatggatatt | cttatcctcc | tggttccttc | 300 |
| ggtgccaatg | gtaacctaat | accagccgca | gggagcgcca | tttctcctaa | agggctacac | 360 |
| cactgtcaac | attatcctgg | actctgtgtc | tctctctgtt | gagtcttgtg | gcatcacatc | 420 |
| aggccaaaat | tgccagacca | ggaccctaag | tgtctgatag | aggcgatgat | ctt | 473 |

<210> SEQ ID NO 207
<211> LENGTH: 463
<212> TYPE: DNA
<213> ORGANISM: Homo sapiens

<400> SEQUENCE: 207

| | | | | | |
|---|---|---|---|---|---|
| tttagagcca | attctcattt | attcagcgaa | atcctctggg | gttaaaatt | ttaagtttga | 60 |
| aagaacttga | cactacagaa | attttttctaa | aatattttga | gtcactataa | acctatcatc | 120 |
| tttccacaag | atataccaga | tgactatttg | cagtcttttc | tttgggcaag | agttccatga | 180 |
| ttttgatact | gtacctttgg | atccaccatg | ggttgcaact | gtctttggtt | ttgtttgttt | 240 |
| gacttgaacc | accctctggt | aagtaagtga | attacagagc | aggtccagct | ggctgctctg | 300 |
| cccttgggt | atccatagtt | acggttttct | ctgtggccca | cccagggtgt | tttttgcatc | 360 |
| gctggtgcag | aaatgcacag | gtggatgaga | tatagctgct | cttgtcctct | ggggactggt | 420 |
| ggtgctgctt | aagaaataag | gggtgctggg | gacagaggag | caa | | 463 |

<210> SEQ ID NO 208
<211> LENGTH: 140
<212> TYPE: DNA
<213> ORGANISM: Homo sapiens

<400> SEQUENCE: 208

| | | | | | |
|---|---|---|---|---|---|
| tttttttttt | ttttgtaaat | aacaaacacc | actttgttat | gaagacctta | caaacctctt | 60 |
| cttaagacat | tcttactctg | atccaggcaa | aaacacttca | aggtttgtaa | atgactcttt | 120 |
| cctgacataa | atccttttg | | | | | 140 |

<210> SEQ ID NO 209
<211> LENGTH: 237
<212> TYPE: DNA
<213> ORGANISM: Homo sapiens
<220> FEATURE:
<221> NAME/KEY: misc_feature
<222> LOCATION: (208)..(208)
<223> OTHER INFORMATION: a or g or c or t/u
<220> FEATURE:
<221> NAME/KEY: misc_feature
<222> LOCATION: (221)..(221)
<223> OTHER INFORMATION: a or g or c or t/u
<220> FEATURE:
<221> NAME/KEY: misc_feature
<222> LOCATION: (229)..(229)
<223> OTHER INFORMATION: a or g or c or t/u

<400> SEQUENCE: 209

| | | | | | |
|---|---|---|---|---|---|
| acaaagaaaa | atttaatatt | cgatgagagg | ttgaaccagg | cttaaagcag | acatactagg | 60 |
| aaatggtgca | gcctgtaaga | atgccagttt | gtaagtactg | actttggaaa | agatcatcgc | 120 |
| ctctatcaga | cacttagggt | cctggtctgg | caattttggc | ctgatgtgat | gccacaagac | 180 |
| ccaacagaga | gagacacaga | gtccaggnta | atattgacag | naggtggang | ccccccct | 237 |

<210> SEQ ID NO 210
<211> LENGTH: 292
<212> TYPE: DNA
<213> ORGANISM: Homo sapiens

<400> SEQUENCE: 210

| | | | | | |
|---|---|---|---|---|---|
| tttttttttt | tttttttttt | ggtccaaaat | ttttaatagt | atacagacaa | cctgttaatt | 60 |
| tttttttttt | tttttttttgg | aaataacaaa | caccactttg | ttatgaagac | cttacaaacc | 120 |
| tcttcttaag | acattcttac | tctgatccag | gcaaaaacac | ttcaaggttt | ggaaatgact | 180 |
| ctttcctgac | ataaatcctt | ttttattaaa | atgcaaaagg | ttcttcagaa | taaaactgtg | 240 |
| taataatttt | tatacttggg | agtgctcctt | gcacagagct | gtcatttgcc | ag | 292 |

<210> SEQ ID NO 211
<211> LENGTH: 434
<212> TYPE: DNA
<213> ORGANISM: Homo sapiens

<400> SEQUENCE: 211

| | | | | | |
|---|---|---|---|---|---|
| tttttcttac | aaagaaaaat | ttaatattcg | atgagaggtt | gaaccaggct | taaagcagac | 60 |
| atactaggaa | atggtgcagc | ctgtaagaat | gccagtttgt | aagtactgac | tttgaaaaag | 120 |
| atcatcgcct | ctatcagaca | cttagggtcc | tggtctggca | attttggcct | gatgtgatgc | 180 |
| cacaagaccc | aacagagaga | gacacagagt | ccaggataat | gttgacagtg | gtgtagccct | 240 |
| ttaggagaaa | tggcgctccc | tgcggctggt | attaggttac | cattggcacc | gaagagacca | 300 |
| ggaggataag | aatatccata | atttcagagc | tgccctggca | cagtacctgc | cccgtcggag | 360 |
| gctctcactg | gcaaatgaca | gctctgtgca | aggagcactc | ccaagtataa | aaattattac | 420 |
| acagttttat | tctg | | | | | 434 |

<210> SEQ ID NO 212
<211> LENGTH: 451
<212> TYPE: DNA
<213> ORGANISM: Homo sapiens

<400> SEQUENCE: 212

| | |
|---|---|
| taaataacaa acaccacttt gttatgaaga ccttacaaac ctcttcttaa gacattctta | 60 |
| ctctgatcca ggcaaaaaca cttcaaggtt tgtaaatgac tctttcctga cataaatcct | 120 |
| tttttattaa aatgcaaaat gttcttcaga ataaaactgt gtaataattt ttatacttgg | 180 |
| gagtgctcct tgcacagagc tgtcatttgc cagtgagagc ctccgacggg gcaggtactg | 240 |
| tgccagggca gctctgaaat tatggatatt cttatcctcc tggttccttc ggtgccaatg | 300 |
| gtaacctaat accagccgca gggagcgcca tttctcctaa agggctacac cactgtcaac | 360 |
| attatcctgg actctgtgtc tctctctgtt gggtcttgtg gcatcacatc aggccaaaat | 420 |
| tgccagacca ggaccctaag tgtctgatag a | 451 |

<210> SEQ ID NO 213
<211> LENGTH: 231
<212> TYPE: DNA
<213> ORGANISM: Homo sapiens

<400> SEQUENCE: 213

| | |
|---|---|
| tttgtaaata acaaacacca ctttgttatg aagaccttac aaacctcttc ttaagacatt | 60 |
| cttactctga tccaggcaaa aacacttcaa ggtttgtaaa tgactctttc ctgacataaa | 120 |
| tccttttttta ttaaaatgca aaatgttctt cagaataaaa ctgtgtaata attttttatac | 180 |
| ttgggagtgc tccttgcaca gagctgtcat ttgccagtga gagcctccga c | 231 |

<210> SEQ ID NO 214
<211> LENGTH: 483
<212> TYPE: DNA
<213> ORGANISM: Homo sapiens

<400> SEQUENCE: 214

| | |
|---|---|
| ttgtaaataa caaacaccac tttgttatga agaccttaca aacctcttct taagacattc | 60 |
| ttactctgat ccaggcaaaa acacttcaag gtttgtaaat gactctttcc tgacataaat | 120 |
| ccttttttat taaaatgcaa aatgttcttc agaataaaac tgtgtaataa ttttttatact | 180 |
| tgggagtgct ccttgcacag agctgtcatt tgccagtgag agcctccgaa ggggcaggta | 240 |
| ctgtgccagg gcagctctga aattatggat attcttatcc tcctggttcc ttcggtgcca | 300 |
| atggtaacct aataccagcc gcaggagcgc catttctcct aaagggctac accactgtca | 360 |
| acattatcct ggactctgtg tctctctctg ttgggtcttg tggcatcaca tcaggccaaa | 420 |
| attgccagac caggacccta gtgtctgat agaggcgatg atcttttcca aagtcagtac | 480 |
| tta | 483 |

<210> SEQ ID NO 215
<211> LENGTH: 507
<212> TYPE: DNA
<213> ORGANISM: Homo sapiens

<400> SEQUENCE: 215

| | |
|---|---|
| gctcgacttt tttttggggg gaacgttttc attaggttaa cagtgtttgg caagcattgg | 60 |
| aaacacggaa tctcacagac agatacaggc agaaagaatc acagttcaat ccaaaagcaa | 120 |
| cacactgaga ggacatcaga gtccaaacac atgcagaaga gctgtcaggg agcagctagg | 180 |
| agacacgcag agttgcctca cacgtggcag caggagaagg tgcaacacgg atccgactgc | 240 |
| ttacccacta aggacaccaa gaaccaggtt aaggacgaaa atgagccaa ggatgatcag | 300 |
| actaacaaaa tacacccatg gccattccca tcctatcgca tcatttaccc agtagagcac | 360 |
| gtctgtccag ccctccatgg tgatgcactg aaacacagta agcatggcaa aggcaaagtt | 420 |

```
atcaaagttg gtgatgcctc cgttcgggcc aacccagcca ctcctacatt ccgtgccatt    480
ggcagtacac tggcgtccat tccctgt                                        507

<210> SEQ ID NO 216
<211> LENGTH: 443
<212> TYPE: DNA
<213> ORGANISM: Homo sapiens

<400> SEQUENCE: 216
tttttttttt ttttttggt ccaaaatttt taatagtata cagacaacct gttaatttt     60 tttttttttt ttttttgtaaa taacaaacac cactttgtta tgaagacctt acaaacctct  120
tcttaagaca ttcttactct gatccaggca aaaacacttc aaggtttgta atgactctt    180 tcctgacata aatccttttt tattaaaatg caaaatgttc ttcagaataa aactgtgtaa   240
taatttttat acttgggagt gctccttgca cagagctgtc atttgccagt gagagcctcc   300
gacggggcag gtactgtgcc agggcagctc tgaaattatg gatattctta tcctcctggt   360
tccttcggtg ccaatggtaa cctaatacca gccgcaggga gcgccatttc tcctaaaggg   420
ctacaccact gtcaacatta tcc                                           443

<210> SEQ ID NO 217
<211> LENGTH: 305
<212> TYPE: DNA
<213> ORGANISM: Homo sapiens

<400> SEQUENCE: 217
tttttttttt ttttttttct tacaaagaaa aatttaatat tcgatgagag gttgaaccag   60
gcttaaagca gacatactag gaaatggtgc agcctgtaag aatgccagtt tgtaagtact   120
gactttggaa aagatcatcg cctctatcag acacttaggg tcctggtctg gcaattttgg   180
cctgatgtga tgccacaaga cccaacagag agagacacag agtccaggat aatgttgaca   240
gtggtgtagc cctttaggag aaatggcgct cccctgcggct ggtattaggt taccattggc   300
accga                                                               305

<210> SEQ ID NO 218
<211> LENGTH: 376
<212> TYPE: DNA
<213> ORGANISM: Homo sapiens

<400> SEQUENCE: 218
tgtaaataac aaacaccact tggttatgaa gaccttacaa acctcttctt aagacattct    60
tactctgatc caggcaaaaa cacttcaagg tttgtaaatg actctttcct gacataaatc   120
cttttttatt aaaatgcaaa atgttcttca gaataaaact gtgtaataat ttttatactt   180
gggagtgctc cttgcacaga gctgtcattt gccagtgaga gcctccgacg gggcaggtac   240
tgtgccaggg cagctctgaa attatggata ttcttatcct cctggttcct tcggtgccaa   300
tggtaaccta ataccagccg cagggagcgc catttctcct aaagggctac accactgtca   360
acattatcct ggactc                                                   376

<210> SEQ ID NO 219
<211> LENGTH: 544
<212> TYPE: DNA
<213> ORGANISM: Homo sapiens

<400> SEQUENCE: 219
```

```
attcctgtta attttgacaa gctcaacggc tgaaatctag gaatggttac taccaaaagc      60
ccacccaatc cagctcattt tgctatcgtt ttataacaat taatctgcat tatatttgga     120
tccagacaaa taaagcaatt ataaatgtat ctcactttac aacagacaaa aaaagggcat     180
gctatggaaa ttgtttaaat ctcaagcaac aatgctgatt aatttctggt caataatcgt     240
tctatagttc tccttcatga agcctggtga ggttccagga acagcttga tttgggaagc     300 ctcagcagaa aagaaagcat ctcagaggac acataaaatg tctggcaacc cctcttggcg     360
gccctcatcc agcaaagctt gtgtggtctt ggcaactgtc ctcaggactc tgctttcaag     420
atgaaagagg tgtagcttac ccgctcaata caccaagtac aagatttagt acgaaaaatg     480
acccaaagat gacgagactg acacaataca cccagggcaa ttcaaatccc atagcatcat     540
tcat                                                                 544
```

```
<210> SEQ ID NO 220
<211> LENGTH: 308
<212> TYPE: DNA
<213> ORGANISM: Homo sapiens

<400> SEQUENCE: 220
```

```
ggtcgacgta tttgtaaaga gatggtctat atcttgtaat tactgtattg tatttgaact      60
gcagcaatat ccatgggtcc taataattgt agttccccac taaaatctag aaattattag     120 tattttact cgggctatcc agaagtagaa gaaatagagc caattctcat ttattcagcg      180
aaaatcctct ggggttaaaa ttttaagttt gaaagaactt gacactacag aaattttttct    240 aaaatatttt gagtcactat aaacctatca tctttccaca agaaaaaaaa acaaaaaaaa     300
agtcgacg                                                             308
```

```
<210> SEQ ID NO 221
<211> LENGTH: 939
<212> TYPE: DNA
<213> ORGANISM: Homo sapiens
<220> FEATURE:
<221> NAME/KEY: misc_feature
<222> LOCATION: (674)..(674)
<223> OTHER INFORMATION: a or g or c or t/u
<220> FEATURE:
<221> NAME/KEY: misc_feature
<222> LOCATION: (684)..(684)
<223> OTHER INFORMATION: a or g or c or t/u
<220> FEATURE:
<221> NAME/KEY: misc_feature
<222> LOCATION: (687)..(687)
<223> OTHER INFORMATION: a or g or c or t/u
<220> FEATURE:
<221> NAME/KEY: misc_feature
<222> LOCATION: (781)..(781)
<223> OTHER INFORMATION: a or g or c or t/u
<220> FEATURE:
<221> NAME/KEY: misc_feature
<222> LOCATION: (795)..(795)
<223> OTHER INFORMATION: a or g or c or t/u

<400> SEQUENCE: 221
```

```
caaagtactt ccccacattt agctggattt gtctttggtt tgaagaggct aatacgtgaa      60
agatttgttc acagttggat gtccccttt ctgaaccatg aagtaatatt gtgaatggag      120
ttgaatgctg aggttagggt gccggaaaga ttcagggtcc ttcggtaccc tcacatggct     180 tggcttttggt agaacaagaa actaagctct gatttggctt taaatgagag tgctaaattt    240
ccttttctta ataagaaacc tagctaaaca tttatatata cttttgaaca ctgaactttc     300
ttgttgcaga gttaacagct gttggggta gctgacagct ggatcctggt gctgttggta      360
```

```
ccatggtacc tgaagtgcac aggctggtag ccacacctga cattaacaag tgagtggtaa    420
cctctctgcc gctggctcac agctactgtt tccatagaaa tggctgtcgg gatcagtgga    480
aacgaggtaa gtgaaagttt tcgctgatcc ttgtttccat caagctgacg tctgtttccc    540
tggcaacagc agtggacagc agccaggcgc tagcaacaga ttcagtagag ctctcacttg    600
tcagctgtgg ctatcatctg ttcctgacca agttcttttt ttttttttta ataatgtaca    660
gaaagacctc tganggacca ggangcnact ctggccacat gtgccctcct ggatgctcgt    720
tttgcaaatg gagagctgtg tgctgagttg acttctctgt ccgcagttcc cctccactg     780 nggctctggg gttgntgatg tgcaggtaaa aaaaggagg gttgttgaag gttattagtt      840
gttccaaggg gaagcctgtt gaaacctggt tgatccccaa tccctatggg gaagaaaaat    900
ctctttaagg ggcttttcat gcccagagac ccaaatttt                           939

<210> SEQ ID NO 222
<211> LENGTH: 966
<212> TYPE: DNA
<213> ORGANISM: Homo sapiens

<400> SEQUENCE: 222
ggtggcgatt cggacgaggg caaagacttc ccccatttag ctggatttgt ctttggtttg     60
aagaggctaa tacgtgaaag atttgttcac agttggatgt cccctttct gaaccatgaa    120 gtaatattgt gaatggagtt gaatgctgag gttagggtgc cggaaagatt cagggtcctt    180
cggtaccctc acatggcttg gctttggtag aacaagaaac taagctctga tttggcttta    240
aatgagagtg ctaaatttcc ttttctaat aaagaaccta gctaaacatt tatatatact    300
tttgaacact gaacttttctt gttgcagagt taacagctgt tgggggtagc tgacagctgg    360
atcctggtgc tgttggtacc atggtacctg aagtgcacag gctggtagcc acacctgaca    420
ttaacaagtg agtggtaacc tctctgccgc tggctcacag ctactgtttc catagaaatg    480
gctgtcggga tcagtggaaa cgaggtaagt gaaagttttc gctgatcctt gtttccatca    540
agctgacgtc tgtttccctg gcaacagcag tggacagcag ccaggcgcta gcaacagatt    600
caggagagct ctcacttgtc agctgtggct atcatctgtt cctgaccaag ttctttttt    660 tttttttaat aatggacaga aagacctctg aggacccagg aggcacctct gggcacatgt    720
gccctcctgg atgctccttt tgcagatgga gacctgggg ctgagttgac ttctctggcc     780
gcagttcccc ctccacctgg ggctcctggg tggtgagggg ccaggtaaaa aagggaagg    840 tgtttgaggg tattaatggg tccccggcg ggctgatcga atcctgggga ctccacgtcc    900 ctgggggac aagaatctct tcaacggggt tttccggccg ggagccggag ttttttattc    960
agcggg                                                              966

<210> SEQ ID NO 223
<211> LENGTH: 692
<212> TYPE: DNA
<213> ORGANISM: Homo sapiens

<400> SEQUENCE: 223
tttttttttt tttttttct tgtggaaaga tgataggttt atagtgactc aaaatatttt      60
agaaaaattt ctgtagtgtc aagttctttc aaacttaaaa ttttaacccc agaggatttt    120
cgctgaataa atgagaattg gctctatttc ttctacttct ggatagcccg agtaaaaata    180
ctaataattt ctagatttta gtggggaact acaattatta ggacccatgg atattgctgc    240
```

| | |
|---|---:|
| agttcaaata caatacagta attacaaaat atagaccatc tctttacaaa tacaaattat | 300 |
| agtatattac aagtcatgta cagtaaatct ataattttaa acaaactagt gtatctaagt | 360 |
| ttacctggtt gcgagtgcat tattattcca gtttacagtt gcccttagcg tgacagtcag | 420 |
| aaaccgacca tcggagtgat attctcttat gtaaactggc gtcacatcac agaaaacctt | 480 |
| atttatgagg tcccattgcc ctcgcaataa tcactggtag ctgggttctg acttacttac | 540 |
| acaccgtatt tcagaacagc taaacaggaa ccaggacgca gtgtatttgg gggaaagggt | 600 |
| ttacaaatgg atatgttggg cccagtgact gatatgctag accgatggct gaggtaacga | 660 |
| cacaggtgtg atgatcgtca tcacctttaa ct | 692 |

<210> SEQ ID NO 224
<211> LENGTH: 595
<212> TYPE: DNA
<213> ORGANISM: Homo sapiens

<400> SEQUENCE: 224

| | |
|---|---:|
| tgcaaataag gacaagctca gcggctgaaa tctacaaatg gggactacca aaagcccacc | 60 |
| caatccagct cattttgcta tcgttttata acaattaatc tgcattatat ttggatccag | 120 |
| acaaataaag caattataaa tgtatctcac tttagaacag acaaaaaaag gcatgctat | 180 |
| ggaaattgtt taaatctcaa gcaacaatgc tgattaattt ctggtcaata atcgttctat | 240 |
| agttctcctt catgaagcct ggtgaggttc caggaaacag cttgatttgg gaagcctcag | 300 |
| cagaaaagaa agcatctcag aggacacata aaatgtctgg caacccctct tggcggccct | 360 |
| catccagcaa agcttgtgtg gtcttggcaa ctgtcctcag gactctgctt tcaagatgaa | 420 |
| agaggtgtag cttacccgct caatacacca gtacaagat ttagtacgaa aaatgaccca | 480 |
| aagatgacga gactgacaaa atacacccag ggcaattcaa atcccatagc atcattcatc | 540 |
| tgcaagaaat aagatggtct cataggagtg ggttaataag aggatttaat aagga | 595 |

<210> SEQ ID NO 225
<211> LENGTH: 999
<212> TYPE: DNA
<213> ORGANISM: Homo sapiens

<400> SEQUENCE: 225

| | |
|---|---:|
| ggcaaagtac ttccccacat ttagctggat tggtctttgg tttgaagagg ctaatacgtg | 60 |
| aaagatttgt tcacagttgg atgtcccctt ttctgaacca tgaagtaata ttgtgaatgg | 120 |
| agttgaatgc tgacggttag ggtgccggaa agattcaggg tccttcggta ccctcacatg | 180 |
| gcttggcttt ggtagaacaa gaaactaagc tctgatttgg ctttaaatga gagtgctaaa | 240 |
| tttccttttt ctaataaaga acctagctaa acatttatat atactttga acactgaact | 300 |
| ttcttgtcag cagagttaac agctgtaggg ggtagctgac acggctggat cctggtgctg | 360 |
| ttggtaccat ggtacctgaa gtgcacaggc tggtagccac acctgacatt aacaacgtga | 420 |
| gtggtaacct ctctgccgct ggctcacagc tactgtttcc atcagaaatg gctgtcgggc | 480 |
| tcacgtggaa acgaggtaag tgaaagtacg ctagatcctt gttccatcac agctgacgct | 540 |
| ctgtttccca tggcaacacc cagcacggac aagccgccac gccgcataga caaccacaac | 600 |
| cacgtacagc tctccacaag tcagctcgtg gctatccatc atgtccctga acaagcccac | 660 |
| accacccccc cccaagcgac acagcaacga gcaccacccg gacgaaccaa aggacggacc | 720 |
| cccctgcccc aacctctcgc ccatccgcga cagacccgcc aagcaaacac gacaacctaa | 780 |
| caaagcagag ggacagaccc atagcgcccg ctaccggaag cgtacaccac ttcccaacag | 840 |

```
taaggccaaa agagcgacgc ggagcacgtg aacggataag aaaacgagag aaggcacggc      900
cgcatggcaa acacaccagc aagcagcaga cagcacgtgg gcacgacaca ggacagaaag      960
cagcccacct cagaggggac caacgaagag tcgcacgac                             999
```

<210> SEQ ID NO 226
<211> LENGTH: 695
<212> TYPE: DNA
<213> ORGANISM: Homo sapiens
<220> FEATURE:
<221> NAME/KEY: misc_feature
<222> LOCATION: (695)..(695)
<223> OTHER INFORMATION: a or g or c or t/u

<400> SEQUENCE: 226

```
ctgggcccaa catatccatt tttaaaccct ttcccccaaa tacactgcgt cctggttcct       60
gtttagctgt tctgaaatac ggtgtgtaag taagtcagaa cccagctacc agtgattatt      120
gcgagggcaa tggacctca taaataaggt tttctgtgat gtgacgccag tttacataag      180
agaatatcac tccggtggtc ggtttctgac tgtcacgcta agggcaactg taaactggaa      240
taataatgca ctcgcaacca ggtaaactta gatacactag tttgtttaaa attatagatt      300
tactgtacat gacttgtaat atactataat ttgtatttgt aaagagatgg tctatatttt      360
gtaattactg tattgtattt gaactgcagc aatatccatg ggtcctaata attgtagttc      420
cccactaaaa tctagaaatt attagtattt ttactcgggc tatccagaag tagaagaaat      480
agagccaatt ctcatttatt cagcgaaaat cctctgggt taaaatttta agtttgaaag      540
aacttgacac tacagaaatt tttctaaaat attttgagtc actataaacc tatcatcttt      600
ccacaagata taccagatga ctatttgcag tcttttcttt gggcaagagt tccatgattt      660
tgatactgta cctttggatc caccatgggt tgcan                                 695
```

<210> SEQ ID NO 227
<211> LENGTH: 870
<212> TYPE: DNA
<213> ORGANISM: Homo sapiens

<400> SEQUENCE: 227

```
ggaaaagaaa tactgtttta gagaaataac attttcaaca aaacatccct ggagtcagat       60
tttgagttgg ggtgggctaa tcagggagtc ggggctctct gcgtgatgtc agttctatgg      120
ctaactggtt tttctaaacc agccagctgc ctatcaaaac agtacaactt ttctaggaaa      180
tgcaattggc aaagacactt acgatgctga gaagtacaca aggtgaaact gctccagttt      240
ttctcatagc agggtcagca ggaaagcaag tggtgcccct ggtcccatct cacacaggtg      300
agactgcacc gagaggtaac gtggccctca cagcccacca cgcctggcct tcgcccaatt      360
ctgaaacttc gtaggataga gctggaaagt gccacatggt gaagcgagat ccagctgtct      420
gggtggatgt cggagtccat aggctgagca gagatggttc ttagtgaggt tctcgctgcc      480
agttgacggt gaaatcatag ctgccattta cattttgtga gattatgaaa aacataagac      540
taaagaaact aaatgtgtta ttcctgtgga cacaaaaatg tgtgttttc agatggggag      600 gggaccaaaa aggaaaaaca tttcatctta aaactttcct aagacaaagg aaaacaaaaa      660
accatgctct acaacttcaa atttttctta caaagaaaaa tttaatattc gatgagcagg      720
ttgaaccagg cttaaagcag acatactagg aaatggtgca gcctgtaaga atgccagttt      780
gtaagtactg actttggaaa agatcatcgc tctatcagac acttagggtc ctggtctggc      840
```
cattttggcc tgatgtgatg ccaaaagacc                                      870

<210> SEQ ID NO 228
<211> LENGTH: 368
<212> TYPE: DNA
<213> ORGANISM: Homo sapiens

<400> SEQUENCE: 228
ttttatcgtg tggaaagatg ataggtttat agtgactcaa aatatttag aaaaatttct      60 gtagtgtcaa gttctttcaa acttaaaatt ttaacccag aggattttcg ctgaataaat     120
gagaattggc tctatttctt ctacttctgg atagcccgag taaaaatact aataatttct     180
agattttagt ggggaactac aattattagg acccatggat attgctgcag ttcaaataca     240
atacagtaat tacaaaatat agaccatctc tttacaaata caattatag tatattacaa      300 gtcatgtaca gtaaatctat tttaaacaaa ctagtgtatc aagtttacc tggttgcgag      360 tgcattat                                                              368

<210> SEQ ID NO 229
<211> LENGTH: 412
<212> TYPE: DNA
<213> ORGANISM: Homo sapiens

<400> SEQUENCE: 229
cttacaaaga aaatttaat attcgatgag aggttgaacc aggcttaaag cagacatact       60
aggaaatggt gcagcctgta agaatgccag tttgtaagta ctgactttgg aaaagatcat     120
cgcctctatc agacacttag ggtcctggtc tggcaatttt ggcctgatgt gatgccacaa     180
gacccaacag agagagacac agagtccagg ataatgttga cagtggtgta gccctttagg     240
agaaatggcg ctccctgcgg ctggtattag gttaccattg gcaccgaaga gaccaggagg     300
ataagaatat ccataatttc agagctgccc tggcacagta cctgccccgt cggaggctct     360
cactggcaaa tgacagctct gtgcaaggag cactcccaag tataaaaatt at             412

<210> SEQ ID NO 230
<211> LENGTH: 610
<212> TYPE: DNA
<213> ORGANISM: Homo sapiens

<400> SEQUENCE: 230
ccgcgtccgg tcagatggta caagtttgtc tctataatta agacttttcc accatcacaa      60
actttaaaca caaagtctaa aatcttgggc agcatagaaa ataggttcta gctaagcagg     120
agttttgtcc tctaccaaga cctttcctga aaatcactta tcaagacagt ttcctgtaag     180
aaaaagccat atcccagctg attttccttc ctggggccaa aatctgctat tattcggcct     240
gaaagccttg atgactctgt gtgtgtgtgt gtgtgtgtgt gtgtgtgtgt gtgtgtgtgt     300
gtatggatgc ttgtgtgtgt gtatggggaa tatgtgatta atgtgtgttg gctgctgttg     360
tctctgattt ggctactgtt gtttctgatt taaatctaag taaatgttta attaaatgta     420
tagaatgctg tctctaatgt gaccctctct ccttattaaa tcctcttatt aacccactcc     480
tatgagacca tcttatttct tgcagatgaa tgatgctatg ggatttgaat tgccctgggt     540
gtattttgtc agtctcgtca tctttgggtc attttcgta ctaaatcttg tacttggtgt      600
attgagcggg                                                            610

<210> SEQ ID NO 231
<211> LENGTH: 236

```
<212> TYPE: DNA
<213> ORGANISM: Homo sapiens
<220> FEATURE:
<221> NAME/KEY: misc_feature
<222> LOCATION: (195)..(195)
<223> OTHER INFORMATION: a or g or c or t/u

<400> SEQUENCE: 231
aatgcaaaat gttcttcaga ataaaactgt gtaataattt ttatacttgg gatgtgctcc      60
ttgcacagag ctgtcatttg ccagtgagag cctcgacagg caggtactgt gccagggcag     120
ctctgaaatt atggatattc ttatcctcct ggttccttct gtgctcaatg gtaacctaat     180
accagccgca ggacncgcca tttctcctaa agggctacac cactgtcaac attatc         236

<210> SEQ ID NO 232
<211> LENGTH: 427
<212> TYPE: DNA
<213> ORGANISM: Homo sapiens

<400> SEQUENCE: 232
tcagcgaaaa tcctctgggg ttaaaatttt aagtttgaaa gaacttgaca ctacagaaat      60
ttttctaaaa tattttgagt cactataaac ctatcatctt tccacaagat ataccagatg     120
actatttgca gtcttttctt tgggcaagag ttccatgatt ttgatactgt acctttggat     180
ccaccatggg ttgcaactgt cttttggtttt gtttgtttga cttgaaccac cctctggtaa    240
gtaagtaagt gaattacaga gcaggtccag ctggctgctc tgccccttgg gtatccatag     300
ttacggtttt ctctgtggcc cacccagggt gttttttgca tcgctggtgc agaaatgcat     360
aggtggatga gatatagctg ctcttgtcct ctggggactg gtggtgctgc ttaagaaata     420
aggggtg                                                               427

<210> SEQ ID NO 233
<211> LENGTH: 838
<212> TYPE: DNA
<213> ORGANISM: Homo sapiens

<400> SEQUENCE: 233
ttttgtcagt ctcgtcatct ttgggtcatt tttcgtacta aatcttgtac ttggtgtatt      60
gagcgggcac agtggctcac gcctataatc ccagcacttt cggaggccga ggcagctgga     120
ccacccgaga tcaggagttt gagaccagcc tgactaaggc agtgaaaccc tgtctctact     180
aaaaatacaa aaattagcca ggcatggtgg cgcatgcctg taatcccagc tacttgggag     240
gctgaggcag gagaatcact tgaaccaggg aggtggagat tgcagtgagc caagactgca     300
ccattgcatt ccagcctggg tgacaagagc aaaactccat ctcaaaaaaa aaaaaaaaa      360
aaaaaaaaa agactttcct ctcattcaac actttaccag catctactga cagaaaatgg     420
acaattgaat ttcctccaat atatatacct ctgatatgtc tgctttgtaa agagtagtg      480
taattgctta caacattgaa aaggttgtta tggggtcct ggggtagcca ggatatcggc      540
atgatttgtc accatattca gaataaaact gtactgcaat agtgagttaa ttccatatct     600
tggccaacag agaattttg gccagtggct actaaggcac acggaagtcc agtctaaaag     660
ggacagggga ggactctttg tagatagttc ttatgattaa aaaataactt cctatgtgtt     720
gtagtgatga tttaagctga cagaatgcta aagacacccc ttatgattac ctggtagcaa     780
agtaccttcc ccacatttaa cctggatttg ccctttggg tttgaaagag gctaaata       838

<210> SEQ ID NO 234
```

```
<211> LENGTH: 904
<212> TYPE: DNA
<213> ORGANISM: Homo sapiens

<400> SEQUENCE: 234
ggtgggattc ggcacgaggg caagacttcc ccacatttag ctggatttgt ctttggtttg      60
aagaggctaa tacgtgaaag atttgttcac agttggatgt cccctttct gaaccatgaa     120
gtaatatttg tgatatggag ttcgaatggc tgaggtctag gtgtgccgag aaagattcag    180
ggtccttcgg taccctcaca tggcttggct ttggtagaac aagaaactaa gctctgattt    240
ggctttaaat gagagtgcta aatttccttt ttctaataaa gaacctagct aaacatttat    300
atatactttt gaacactgaa ctttcttgtt gcagagttaa cagctgttgg gggtagctga    360
cagctggatc ctggtgctgt tggtaccatg gtacctgaag tgcacaggct ggtagccaca    420
cctgacatta acaagtgagt ggtaacctct ctgccgctgg ctcacagcta ctgtttccat    480
agaaatggct gtcgggatca gtggaaacga ggtaagtgaa agttttcgct gatccttgtt    540
tccatcaagc tgacgtctgt ttccctggca acagcagtgg acagcagcca ggcgctagca    600
acagattcag tagagctctc acttgtcagc tgtggctatc atctgttcct gaccaagttc    660
ttttttttt ttttaataat gtacagaaag acctctgagg acccaggagg cacctctggc    720
cacatgtgcc ctcctggatg ctcgttttgc agatggagag ctgtgtgctg agttgacttc    780
tctgtccgca gttccccctc cacctgtgct ctgggttgtt gatgtgccag ttaaaacagg    840
gaggctgctt cagggtatta gtgttgccaa ggggaggctg ttgaaatctg gttgatccca    900
aatc                                                                  904

<210> SEQ ID NO 235
<211> LENGTH: 935
<212> TYPE: DNA
<213> ORGANISM: Homo sapiens

<400> SEQUENCE: 235
caaagtactt ccccacattt agctggattt gtctttggtt tgaagaggct aatacgtgaa      60
agatttgttc acagttggat gtccccttt ctgaaccatg aagtaatatt gtgaatggag    120
ttgaatgctg aggttagggt gccggaaaga ttcagggtcc ttcggtaccc tcacatggct    180
tggcttggt agaacaagaa actaagctct gatttggctt taaatgagag tgctaaattt    240
ccttttcta ataaagaacc tagctaaaca tttatatata cttttgaaca ctgaactttc    300
ttgttgcaga gttaacagct gttggggta gctgacagct ggatcctggt gctgttggta    360
ccatggtacc tgaagtgcac aggctggtag ccacacctga cattaacaag tgagtggtaa    420
cctctctgcc gctggctcac agctactgtt tccatagaaa tggctgtcgg gatcagtgga    480
aacgaggtaa gtgaaagttt tcgctgatcc ttgtttccat caagctgacg tctgtttccc    540
tggcaacagc agtggacagc agccaggcgc tagcaacaga ttcagtagag ctctcacttg    600
tcagctgtgg ctatcatctg ttcctgacca agttcttttt tttttttta ataatgtaca    660
gaaagacctc tgaggaccca gggagcacct ctggccacat gtgccctcct gaatgctcgt    720
tttgcaaatg gagagctgtg tgctgagttg acttctctgt ccgcaggtcc cctccaact    780
gtgctcctgg gttgtgatgt gcagggttaa accagggaag ctgttgaagg gtattagtgt    840
tgccagggaa aggctgttga attctggttg atcccaaatc cctaggggga agagaaatcc    900
cttacgagtg gttttcatg gccaggaacc ctata                                935
```

<210> SEQ ID NO 236
<211> LENGTH: 382
<212> TYPE: DNA
<213> ORGANISM: Homo sapiens

<400> SEQUENCE: 236

```
tcagcgaaaa tcctctgggg ttaaaatttt aagtttgaaa gaacttgaca ctacagaaat      60
ttttctaaaa tattttgagt cactataaac ctatcatctt tccacaagat ataccagatg     120
actatttgca gtcttttctt tgggcaagag ttccatgatt ttgatactgt acctttggat     180
ccaccatggg ttgcaactgt ctttggtttt gtttgtttga cttgaaccac cctctggtaa     240
gtaagtaagt gaattacaga gcaggtccag ctggctgctc tgccccttgg gtatccatag     300
ttacggtttt ctctgtggcc cacccagggt gttttttgca tcgctggtgc agaaatgcat     360
aggtggatga gatatagctg ct                                               382
```

<210> SEQ ID NO 237
<211> LENGTH: 461
<212> TYPE: DNA
<213> ORGANISM: Homo sapiens

<400> SEQUENCE: 237

```
gtatatcttg tggaaagatg ataggtttat agtgactcaa atatttag aaaaatttct       60
gtagtgtcaa gttctttcaa acttaaaatt ttaaccccag aggattttcg ctgaataaat     120
gagaattggc tctatttctt ctacttctgg atagcccgag taaaaatact aataatttct     180
agattttagt ggggaactac aattattagg acccatggat atagctgcag ttcaaataca     240
atacagtaat tacaaaatat agaccatctc tttacaaata caaattatag tatattacaa     300
gtcatgtaca gtaaatctat aattttaaac aaactagtgt atctaagttt accaggttgc     360
gagtgcatta ttattccagt ttacagttgc ccttagcgtg acagtcagaa accgaccatc     420
ggagtgatat tctcttatgt aaacaggcgt cacatcacag a                         461
```

<210> SEQ ID NO 238
<211> LENGTH: 557
<212> TYPE: DNA
<213> ORGANISM: Homo sapiens

<400> SEQUENCE: 238

```
tttttttttt tgtggaaaga tgataggttt atagtgactc aaaatatttt agaaaaattt      60
ctgtagtgtc aagttctttc aaacttaaaa ttttaacccc agaggatttt cgctgaataa     120
atgagaattg gctctatttc ttctacttct ggatagcccg agtaaaaata ctaataattt     180
ctagattttta gtggggaact acaattatta ggacccatgg atattgctgc agttcaaata     240
caatacagta attacaaaat atagaccatc tctttacaaa tacaaattat agtatattac     300
aagtcatgta cagtaaatct ataattttaa acaaactagt gtatctaagt ttacctggtt     360
gcgagtgcat tattattcca gtttacagtt gcccttagcg tgacagtcag aaaccgacca     420
tcggagtgat attctcttat gtaaactggc gtcacatcac agaaaacctt atttatgagg     480
tcccattgcc ctcgcaataa tcactggtag ctgggttctg acttacttac acaccgtatt     540
tcagaacagc taaacag                                                    557
```

<210> SEQ ID NO 239
<211> LENGTH: 481
<212> TYPE: DNA
<213> ORGANISM: Homo sapiens

<400> SEQUENCE: 239

```
tttggtatat cttgtggaaa gatgataggt ttatagtgac tcaaaatatt ttagaaaaat    60
ttctgtagtg tcaagttctt tcaaacttaa aattttaacc ccagaggatt ttcgctgaat   120
aaatgagaat tggctctatt tcttctactt ctggatagcc cgagtaaaaa tactaataat   180
ttctagattt tagtggggaa ctacaattat taggacccat ggatattgct gcagttcaaa   240
tacaatacag taattacaaa atatagacca tctctttaca atacaaatt atagtatatt    300
acaagtcatg tacagtaaat ctataatttt aaacaaacta gtgtatctaa gtttacctgg   360
ttgcgagtgc attattattc cagtttacag ttgcccttag cgtgacagtc agaaaccgac   420
catcggagtg atattctctt atgtaaactg gcgtcacatc acagaaaacc ttatttatga   480
g                                                                  481
```

<210> SEQ ID NO 240
<211> LENGTH: 466
<212> TYPE: DNA
<213> ORGANISM: Homo sapiens

<400> SEQUENCE: 240

```
tttttttgtg gaaagatgat aggtttatag tgactcaaaa tatttttagaa aaatttctgt   60
agtgtcaagt tctttcaaac ttaaaatttt aaccccagag gattttcgct gaataaatga   120
gaattggctc tatttcttct acttctggat agcccgagta aaaatactaa taatttctag   180
attttagtgg ggaactacaa ttattaggac ccatggatat tgctgcagtt caaatacaat   240
acagtaatta caaatatag accatctctt tacaaataca aattatagta tattacaagt   300
catgtacagt aaatctataa ttttaaacaa actagtgtat ctaagtttac tggttgcga   360
gtgcattatt attccagttt acagttgccc ttagcgtgac agtcagaaac cgaccatcgg   420
agtgatattc tcttatgtaa actggcgtca catcacagaa aacctt                   466
```

<210> SEQ ID NO 241
<211> LENGTH: 353
<212> TYPE: DNA
<213> ORGANISM: Homo sapiens

<400> SEQUENCE: 241

```
cggccgccaa cttttttgaa tgagtgaagt gccaggtacc atgagaaaac cctagctggt    60
aaagatcaaa cctgagttag ttctaaattc acatacggat ttttttttgca tgacgaaatc   120
tattctcttt ttcctgacaa cttctccacc tagatgtttg gaaagttgc catgagagat    180
aacaaccaga tcaataggaa caataacttc cagacgtttc cccaggcggt gctgctgctc   240
ttcaggtgac tgcaactggc ttgggcggtg ctcctgggca gggggtccg ctaggcgtgg    300
gtccagaggg acggaggaca caggttatta aagcagtgtg cctttctcag ttg           353
```

<210> SEQ ID NO 242
<211> LENGTH: 526
<212> TYPE: DNA
<213> ORGANISM: Homo sapiens

<400> SEQUENCE: 242

```
taaataacta acaccatttt gttatgaaga ccttacaaac ctcttcttaa gacattctta    60
ctctgatcca ggcaaaaaca cttcaaggtt tgtaaatgac tctttcctga cataaatcct   120
ttttttatta aaatgcaaaa tgttcttcag aataaaactg tgtaataatt tttatacttg   180
ggagtgctcc ttgcacagag ctgtcatttg ccagtgagag cctccgacgg ggcaggtact   240
```

```
gtgccagggc agctctgaaa ttatggatat tcttatcctc ctggttcctt cggtgccaat    300
ggtaacctaa taccagccgc agggagcgcc atttctccta aagggctaca ccactgtcaa    360
cattatcctg gactctgtgt ctctctctgt tgggtcttgt ggcatcacat caggccaaaa    420
ttgccagacc aggaccctaa gtgtctgata gaggcgatga tcttttccaa agtcagtact    480
tacaaactgg cattcttaca ggctgcacca tttcctagta tgtctg                   526
```

<210> SEQ ID NO 243
<211> LENGTH: 750
<212> TYPE: DNA
<213> ORGANISM: Homo sapiens

<400> SEQUENCE: 243

```
acttttctag gaaatgcaat tggcaaagac acttacgatg ctgagaagta cacaaggtga     60
aactgctcca gttttttctca tagcagggtc agcaggaaag caagtggtgc ccctggtccc   120
atctcacaca ggtgagactg caccgagagg taacgtggcc ctcacagccc accacgcctg    180
gccttcgccc aattctgaaa cttcgtagga tagagctgga aagtgccaca tggtgaagcg    240
agatccagct gtctgggtgg atgtcggagt ccataggctg agcagagatg gttcttagtg    300
aggttctcgc tgccagttga cggtgaaatc atagctgcca tttacatttt gtgagattat    360
gaaaaacata agactaaaga aactaaatgt gttattcctg tggacacaaa aatgtgtgtt    420
tttcagatgg ggaggggacc aaaaaggaaa aacatttcat cttaaaactt tcctaagaca    480
aaggaaaaca aaaaccatg ctctacaact tcaaattttt cttacaaaga aaaatttaat    540
attcgatgag aggttgaacc aggcttaaag cagacatact aggaaatggt gcagcctgta    600
agaatgccag tttgtaagta ctgactttgg aaaagatcat cgcctctatc agacacttag    660
ggtcctggtc tggcaatttt tggcctgatgt gatgccacaa gacccaacag agagagacac    720
agagtccagg ataatgttga cagtggtgta                                      750
```

<210> SEQ ID NO 244
<211> LENGTH: 432
<212> TYPE: DNA
<213> ORGANISM: Homo sapiens

<400> SEQUENCE: 244

```
ttttttttt tttttttaga agaaatagag ccaattctca tttattcagc gaaaatcctc      60
tggggttaaa attttaagtt tgaaagaact tgacactaca gaaattttc taaaatattt    120 tgagtcacta taaacctatc atctttccac aagatatacc agatgactat ttgcagtctt    180
ttctttgggc aagagttcca tgattttgat actgtacctt tggatccacc atgggttgca    240
actgtctttg gttttgtttg tttgacttga accacccctct ggtaagtaag tgaattacag    300
agcaggtcca gctggctgct ctgccccttg ggtatccata gttacggttt tctctgtggc    360
ccacccaggg tgttttttgc atcgctggtg cagaaatgca caggtggatg agatatagct    420
gctcttgtcc tc                                                        432
```

<210> SEQ ID NO 245
<211> LENGTH: 502
<212> TYPE: DNA
<213> ORGANISM: Homo sapiens

<400> SEQUENCE: 245

```
ttatcttgtg gaaagatgat aggtttatag tgactcaaaa tattttagaa aaatttctgt     60
```

```
agtgtcaagt tctttcaaac ttaaaatttt aaccccagag gattttcgct gaataaatga      120
gaattggctc tatttcttct acttctggat agcccgagta aaaatactaa taatttctag      180
attttagtgg ggaactacaa ttattaggac ccatggatat tgctgcagtt caaatacaat      240
acagtaatta caaatatag accatctctt tacaaataca aattatagta tattacaagt      300
catgtacagt aaatctataa ttttaaacaa actagtgtat ctaagtttac ctggttgcga      360
gtgcattatt attccagttt acagttgccc ttagcgtgac agtcagaaac cgaccatcgg      420
agtgatattc tcttatgtaa actggcgtca catcacagaa aaccttattt atgaggtccc      480
attgccctcg caataatcac tg                                              502

<210> SEQ ID NO 246
<211> LENGTH: 356
<212> TYPE: DNA
<213> ORGANISM: Homo sapiens

<400> SEQUENCE: 246
tttttcttgt ggaaagatga taggtttata gtgactcaaa atattttaga aaaatttctg      60
tagtgtcaag ttctttcaaa cttaaaattt aaccccagta ggattttcgc tgaataaatg      120
agaattggct ctatttcttc tacttctgga tagcccgagt aaaaatacta ataatttcta      180
gattttagtg gggaactaca attattagga cccatggata ttgctgcagt tcaaatacaa      240
tacagtaatt acaaaatata gaccatctct ttacaaatac aaattatagt atattacaag      300
tcatgtacag taaatctata attttaaaca actagtgtat ctaagtttta cctggt         356

<210> SEQ ID NO 247
<211> LENGTH: 442
<212> TYPE: DNA
<213> ORGANISM: Homo sapiens

<400> SEQUENCE: 247
atcttgtgga agatgatag gtttatagtg actcaaaata ttttagaaaa atttctgtag      60
tgtcaagttc tttcaaactt aaaattttaa ccccagagga ttttcgctga taaatgaga      120 attggctcta tttcttctac ttctggatag cccgagtaaa aatactaata atttctagat      180
tttagtgggg aacctacaat tattaggacc catggatatt gctgcagttc aaatacaata      240
cagtaattac aaaatataga ccatctcttt acaaatacaa attatagtat attacaagtc      300
atgtacagta aatctataat tttaaacaaa ctagtgtatc taagtttacc tggttgcgag      360
tgcattatta ttccagttta cagttgccct tagcgtgaca gtcagaaacc gaccatcgga      420
gtgatattct cttatgtaaa ct                                              442

<210> SEQ ID NO 248
<211> LENGTH: 552
<212> TYPE: DNA
<213> ORGANISM: Homo sapiens

<400> SEQUENCE: 248
ttttcttcaa ataattacaa gctcagcggc tgaaatctac aaatggggac taccaaaagc      60
ccacccaatc cagctcattt tgctatcgtt ttataacaat taatctgcat tatatttgga      120
tccagacaaa taaagcaatt ataaatgtat ctcactttag aacagacaaa aaagggcat      180 gctatggaaa ttgtttaaat ctcaagcaac aatgctgatt aatttctggt caataatcgt      240
tctatagttc tccttcatga agcctggtga ggttccaggg aaacagcttg atttgggaag      300
cctcagcaga aagaaagca tctcagagga cacataaaat gtctggcaac ccctcttggc      360
```

```
ggccctcatc cagcaaagct tgtgtggtct tggcaactgt cctcaggact ctgctttcaa    420
gatgaaagag gtgtagctta cccgctcaat acaccaagta caagatttag tacgaaaaat    480
gacccaaaga tgacgagact gacaaaatac acccagggca attcaaatcc catagcatca    540
ttcatctgca ag                                                        552

<210> SEQ ID NO 249
<211> LENGTH: 491
<212> TYPE: DNA
<213> ORGANISM: Homo sapiens

<400> SEQUENCE: 249
tttgtaaata acaaacacca ctttgttatg aagaccttac aaacctcttc ttaagacatt     60
cttactctga tccaggcaaa acacttcaa ggtttgtaaa tgactctttc ctgacataaa     120 tccttttta ttaaaatgca aaatgttctt cagaataaaa ctgtgtaata atttttatac     180 tgggagtgc tccttgcaca gagctgtcat tgccagtga gagcctccga cggggcaggt     240
actgtgccag ggcagctctg aaattatgga tattcttatc ctcctggttc cttcggtgcc    300
aatggtaacc taataccagc cgcagggagc gccatttctc ctaaagggct acaccactgt    360
caacattatc ctggactctg tgtctctctc tgttgggtct tgtggcatca catcaggcca    420
aaattgccag accaggaccc taagtgtctg atagaggcga tgatcttttc caaagtcagt    480
acttacaaac t                                                         491

<210> SEQ ID NO 250
<211> LENGTH: 401
<212> TYPE: DNA
<213> ORGANISM: Homo sapiens

<400> SEQUENCE: 250
tttttttttg gtccaaaatt tttaatagta tacagacaac ctgttaattt ttttttttt     60 ttttttgta aataacaaac accactttgt tatgaagacc ttacaaacct cttcttaaga    120
cattcttact ctgatccagg caaaacact tcaaggtttg taaatgactc tttcctgaca    180
taaatccttt tttattaaaa tgcaaaatgt tcttcagaat aaaactgtgt aataattttt    240
atacttggga gtgctccttg cacagagctg tcatttgcca gtgagagcct ccgacggggc    300
aggtactgtg ccagggcagc tctgaaatta tggatattct tatcctcctg gttccttcgg    360
tgccaatggt aacctaatac cagccgcagg gagcgccatt t                       401

<210> SEQ ID NO 251
<211> LENGTH: 387
<212> TYPE: DNA
<213> ORGANISM: Homo sapiens

<400> SEQUENCE: 251
tcgacagcta ccagtgatta ttgcgagggc aatgggacct cataaataag gttttctgtg     60
atgtgacgcc atttacataa gagaatatca ctccgatggt cggtttctga ctgtcacgct    120
aagggcaact gtaaactgga ataataatgc actcgcaacc aggtaaactt agatacacta    180
gtttgtttaa aattatagat ttactgtaca tgacttgtaa tatactataa tttgtatttg    240
taaagagatg gtctatattt tgtaattact gtattgtatt tgaactgcag caatatccat    300
gggtcctaat aattgtagtt ccccactaaa atctagaaat tattagtatt tttactcggg    360
ctatccagaa gtagaagaaa tagagcc                                        387
```

<210> SEQ ID NO 252
<211> LENGTH: 474
<212> TYPE: DNA
<213> ORGANISM: Homo sapiens

<400> SEQUENCE: 252

```
gaatatgtga ttaatgtgtg ttggctgctg ttgtctctga tttggctact gttgtttctg      60
atttaaatct aagtaaatgt ttaattaaat gtatagaatg ctgtctctaa tgtgaccctc     120
tctccttatt aaatcctctt attaacccac tcctatgaga ccatcttatt tcttgcagat     180
gaatgatgct atgggatttg aattgccctg ggtgtatttt gtcagtctcg tcatctttgg     240
gtcatttttc gtactaaatc ttgtacttgg tgtattgagc gggtaagcta cacctctttc     300
atcttgaaag cagagtcctg aggacagttg ccaagaccac acaagctttg ctggatgagg     360
gccgccaaga ggggttgcca gacattttat gtgtcctctg agatgctttc ttttctgctg     420
aggcttccca aatcaagctg tttcctggaa cctcaccagg cttcatgaag gaga           474
```

<210> SEQ ID NO 253
<211> LENGTH: 594
<212> TYPE: DNA
<213> ORGANISM: Homo sapiens

<400> SEQUENCE: 253

```
tttgtaaata acaaacacca ctttgttatg aagaccttac aaacctcttc ttaagacatt      60
cttactctga tccaggcaaa acacttcaa ggtttgtaaa tgactctttc ctgacataaa      120
tccttttta ttaaaatgca aatgttctt cagaataaaa ctgtgtaata atttttatac      180
ttgggagtgc tccttgcaca gagctgtcat ttgccagtga gagcctccga cggggcaggt     240
actgtgccag ggcagctctg aaattatgga tattcttatc ctcctggttc cttcggtgcc     300
aatggtaacc taataccagc cgcagggagc gccatttctc ctaaagggct acaccactgt     360
caacattatc ctggactctg tgtctctctc tgttgggtct tgtggcatca catcaggcca     420
aaattgccag accaggaccc taagtgtctg atagaggcga tgatcttttc caaagtcagt     480
acttacaaac tggcattctt acaggctgca ccatttccta gtatgtctgc tttaagcctg     540
gttcaacctc tcatcgaata ttaaatttt ctttgtaaga aaaaaaaaa aaaa             594
```

<210> SEQ ID NO 254
<211> LENGTH: 548
<212> TYPE: DNA
<213> ORGANISM: Homo sapiens

<400> SEQUENCE: 254

```
tttgtaaata acaaacacca ctttgttatg aagaccttac aaacctcttc ttaagacatt      60
cttactctga tccaggcaaa acacttcaa ggtttgtaaa tgactctttc ctgacataaa      120
tccttttta ttaaaatgca aatgttctt cagaataaaa ctgtgtaata atttttatac      180
ttgggagtgc tccttgcaca gagctgtcat ttgccagtga gagcctccga cagggcaggt     240
actgtgccag ggcagctctg aaattatgga tattcttatc ctcctggttc cttcggtgcc     300
aatggtaacc taataccagc cgcagggagc gccatttctc ctaaagggct acaccactgt     360
caacattatc ctggactctg tgtctctctc tgttgggtct tgtggcatca catcaggcca     420
aaattgccag accaggaccc taagtgtctg atagaggcga tgatcttttc caaagtcagt     480
acttacaaac tggcattctt acaggctgca ccatttccta gtatgtctgc tttaagcctg     540
gttcaacc                                                              548
```

-continued

<210> SEQ ID NO 255
<211> LENGTH: 456
<212> TYPE: DNA
<213> ORGANISM: Homo sapiens
<220> FEATURE:
<221> NAME/KEY: misc_feature
<222> LOCATION: (57)..(57)
<223> OTHER INFORMATION: a or g or c or t/u
<220> FEATURE:
<221> NAME/KEY: misc_feature
<222> LOCATION: (324)..(324)
<223> OTHER INFORMATION: a or g or c or t/u
<220> FEATURE:
<221> NAME/KEY: misc_feature
<222> LOCATION: (396)..(396)
<223> OTHER INFORMATION: a or g or c or t/u

<400> SEQUENCE: 255

```
ggagaaagga gggaaaccag gagcagccgg catgggcagt ggcagaattg gccctgntag    60
agagcagagc tgatgccatc cttttggcaa atagctgaca ttttatggtg tggtgctggg   120
tgagcccect gtgagggttg aacagatgtg gacaggactt gggtccaggc actagagtgg   180
tgcagcctgt aagaatgcca gtttgtaagt actgactttg gaaagatca tcgcctctat    240
cagacactta gggtcctggt ctggcaattt tggcctgatg tgatgccaca agacccaaca   300
gagagagaca cagagtccag gatnaatgtt gacagtggtg tagcctttag gaagaaatgg   360
cgctccctgc ggctggtatt aggttaccat tggcanccga aggaacccag gaggattaag   420
aatttcccta atttcagaac ttgccctggc acagta                             456
```

<210> SEQ ID NO 256
<211> LENGTH: 434
<212> TYPE: DNA
<213> ORGANISM: Homo sapiens
<220> FEATURE:
<221> NAME/KEY: misc_feature
<222> LOCATION: (194)..(194)
<223> OTHER INFORMATION: a or g or c or t/u
<220> FEATURE:
<221> NAME/KEY: misc_feature
<222> LOCATION: (351)..(351)
<223> OTHER INFORMATION: a or g or c or t/u
<220> FEATURE:
<221> NAME/KEY: misc_feature
<222> LOCATION: (401)..(401)
<223> OTHER INFORMATION: a or g or c or t/u
<220> FEATURE:
<221> NAME/KEY: misc_feature
<222> LOCATION: (426)..(426)
<223> OTHER INFORMATION: a or g or c or t/u

<400> SEQUENCE: 256

```
ggtccaaaat ttttaatagt atacagacaa cctgttaatt tttttttttt ttttttttgt    60
aaataacaaa caccactttg ttatgaagac cttacaaacc tcttcttaag acattcttac   120
tctgatccag gcaaaaacac ttcaaggttt gtaaatcgac tctttcctga cataaatcct   180
tttttattaa aatngcaaaa ttgttcttca gaataaaact gtgtaataat ttttatactt   240
gggagtgctc cttgcacaga gctgtcattt gccagtgaga gcctccgacg gggcaggtac   300
tgtgccaggg cagctctgaa attatggaaa ttcttatccc cctggttcct ncggtggcca   360
atgggtaacc taataccagc ccgcgggaag cgccaatttc ncccaaaagg gggtaaacca   420
ctggtnaaac atta                                                     434
```

<210> SEQ ID NO 257

```
<211> LENGTH: 199
<212> TYPE: DNA
<213> ORGANISM: Homo sapiens
<220> FEATURE:
<221> NAME/KEY: misc_feature
<222> LOCATION: (187)..(187)
<223> OTHER INFORMATION: a or g or c or t/u
<220> FEATURE:
<221> NAME/KEY: misc_feature
<222> LOCATION: (195)..(195)
<223> OTHER INFORMATION: a or g or c or t/u

<400> SEQUENCE: 257
tttttctttt gtaaataaca aacaccactt tgttatgaag accttacaaa cctcttctta      60
agacattctt actctgatcc aggcaaaaac acttcaaggt ttgtaaatga ctctttcctg     120
acataaatcc ttttttatta aaatgcaaaa tgttcttcag aataaaactg tgtaataatt     180
tttatangtg ggggngctc                                                  199

<210> SEQ ID NO 258
<211> LENGTH: 459
<212> TYPE: DNA
<213> ORGANISM: Homo sapiens
<220> FEATURE:
<221> NAME/KEY: misc_feature
<222> LOCATION: (405)..(405)
<223> OTHER INFORMATION: a or g or c or t/u
<220> FEATURE:
<221> NAME/KEY: misc_feature
<222> LOCATION: (456)..(456)
<223> OTHER INFORMATION: a or g or c or t/u

<400> SEQUENCE: 258
acaaagaaaa atttaatatt cgatgagagg ttgaaccagg cttaaagcag acatactagg      60
aaatggtgca gcctgtaaga atgccagttt gtaagtactg actttggaaa agatcatcgc     120
ctctatcaga cacttagggt cctggtctgg caattttggc ctgatgtgat gccacaagac     180
ccaacagaga gagacacaga gtccaggata atgttgacag tggtgtagcc ctttaggaga     240
aatggcgctc cctgcggctg gtattaggtt accattggca ccgaagaacc aggaggataa     300
gaatatccat aatttcagag cttgccctgg cacagtacct gccccgtcgg aggctctcac     360
tgggcaaatg gacagctctg tgcaaggagc actcccaagt ataanaatta ttacacagtt     420
ttattctgaa gaacattttg cattttaata aaaaangga                            459

<210> SEQ ID NO 259
<211> LENGTH: 443
<212> TYPE: DNA
<213> ORGANISM: Homo sapiens

<400> SEQUENCE: 259
tttttttttt ttttgggcca aaatttttaa tagtatacag acaacctgtt aatttttttt      60
tttttttttt ttgtaaataa caaacaccac tttgttatga agaccttaca aacctctttt     120
taagacattc ttactctgat ccaggcaaaa acacttcaag gtttgtaaat gacttttttcc    180 tgacataaat ccttttttat taaaatgcaa aatgttcttc agaataaaac tgtgtaataa     240
ttttatatct tgggagtgct ccttgcacag agctgtcatt tgccagtgag agcctccgac     300
ggggcaggta ctgtgccagg gcagctctga aattatggat attcttatcc tcctggttcc     360
ttcggtgcca atggtaacct aataccagcc gcagggagcg ccatttctcc taaagggcta     420
caccactgtc aacattatcc tgg                                             443
```

```
<210> SEQ ID NO 260
<211> LENGTH: 442
<212> TYPE: DNA
<213> ORGANISM: Homo sapiens

<400> SEQUENCE: 260 ttttttttg gtccaaaatt tttaatagta tacagacaac ctgttaattt tttttttttt      60
tttttttgta aataacaaac accactttgt tatgaagacc ttacaaacct cttcttaaga    120
cattcttact ctgatccagg caaaaacact tcaaggtttg taaatgactc tttcctgaca    180
taaatccttt tttattaaaa tgcaaaatgt tcttcagaat aaaactgtgt aataattttt    240
atacttggga gtgctccttg cacagagctg tcatttgcca gtgagagcct ccgacgggc     300 aggtactgtg ccagggcagc tctgaaatta tggatattct tatcctcctg gttccttcgg    360
tgccaatggt aacctaatac cagccgcagg gagcgccatt tctcctaaag ggctacacca    420
ctgtcaacat tatcctggac tc                                              442

<210> SEQ ID NO 261
<211> LENGTH: 471
<212> TYPE: DNA
<213> ORGANISM: Homo sapiens

<400> SEQUENCE: 261
tttgtggaaa gatgataggt ttatagtgac tcaaaatatt ttagaaaaat ttctgtagtg     60
tcaagttctt tcaaacttaa aattttaacc ccagaggatt ttcgctgaat aaaatgagaa    120
ttggctctat ttcttctact tctggatagc ccgagtaaaa atactaataa tttctagatt    180
ttagtgggga actacaatta ttaggaccca tggatattgc tgcagttcaa atacaataca    240
gtaattacaa aatatagacc atctctttac aaatacaaat tatagtatat tacaagtcat    300
gtacagtaaa tctataattt taaacaaact agtgtatcta agtttacctg gttgcgagtg    360
cattattatt ccagtttaca gttgccctta gcgtgacagt cagaaaccga ccatcggagt    420
gatattctct tatgtaaact ggcgtcacat cacagaaaac cttatttatg a             471

<210> SEQ ID NO 262
<211> LENGTH: 7635
<212> TYPE: DNA
<213> ORGANISM: Homo sapiens

<400> SEQUENCE: 262
gggcgagcgc ctccgtcccc ggatgtgagc tccggctgcc cgcggtcccg agccagcggc     60 gcgcgggcg cggcggcggg caccgggcac cgcggcgggc gggcagacgg gcgggcatgg    120
ggggagcgcc gagcggcccc ggcggccggg ccggcatcac cgcggcgtct ctccgctaga    180
ggaggggaca agccagttct cctttgcagc aaaaaattac atgtatatat tattaagata    240
atatatacat tggatttat tttttttaaaa agtttatttt gctccatttt tgaaaaagag    300
agagcttggg tggcgagcgg tttttttta aaatcaatta tccttatttt ctgttatttg    360
tccccgtccc tccccacccc cctgctgaag cgagaataag ggcagggacc gcggctccta    420
cctcttggtg atcccttcc ccattccgcc cccgccccaa cgcccagcac agtgccctgc    480
acacagtagt cgctcaataa atgttcgtgg atgatgatga tgatgatgat gaaaaaaatg    540
cagcatcaac ggcagcagca agcggaccac gcgaacgagg caaactatgc aagaggcacc    600
agacttcctc tttctggtga aggaccaact tctcagccga atagctccaa gcaaactgtc    660
ctgtcttggc aagctgcaat cgatgctgct agacaggcca aggctgccca aactatgagc    720
```

```
acctctgcac ccccacctgt aggatctctc tcccaaagaa aacgtcagca atacgccaag    780
agcaaaaaac agggtaactc gtccaacagc cgacctgccc gcgcccttt ctgtttatca    840
ctcaataacc ccatccgaag agcctgcatt agtatagtgg aatggaaacc atttgacata    900
tttatattat tggctatttt tgccaattgt gtggccttag ctatttacat cccattccct    960
gaagatgatt ctaattcaac aaatcataac ttggaaaaag tagaatatgc cttcctgatt   1020
atttttacag tcgagacatt tttgaagatt atagcgtatg gattattgct acatcctaat   1080
gcttatgtta ggaatggatg gaatttactg gattttgtta tagtaatagt aggattgttt   1140
agtgtaattt tggaacaatt aaccaaagaa acagaaggcg ggaaccactc aagcggcaaa   1200
tctggaggct ttgatgtcaa agccctccgt gcctttcgag tgttgcgacc acttcgacta   1260
gtgtcaggag tgcccagttt acaagttgtc ctgaactcca ttataaaagc catggttccc   1320
ctccttcaca tagcccttt ggtattattt gtaatcataa tctatgctat tataggattg   1380
gaacttttta ttggaaaaat gcacaaaaca tgttttttg ctgactcaga tatcgtagct   1440
gaagaggacc cagctccatg tgcgttctca gggaatggac gccagtgtac tgccaatggc   1500
acggaatgta ggagtggctg ggttggcccg aacggaggca tcaccaactt tgataacttt   1560
gcctttgcca tgcttactgt gtttcagtgc atcaccatgg agggctggac agacgtgctc   1620
tactggatga atgatgctat gggatttgaa ttgccctggg tgtatttgt cagtctcgtc   1680
atctttgggt cattttcgt actaaatctt gtacttggtg tattgagcgg agaattctca   1740
aaggaaagag agaaggcaaa agcacgggga gatttccaga agctccggga gaagcagcag   1800
ctggaggagg atctaaaggg ctacttggat tggatcaccc aagctgagga catcgatccg   1860
gagaatgagg aagaaggagg agaggaaggc aaacgaaata ctagcatgcc caccagcgag   1920
actgagtctg tgaacacaga gaacgtcagc ggtgaaggcg agaaccgagg ctgctgtgga   1980
agtctctgtc aagccatctc aaaatccaaa ctcagccgac gctggcgtcg ctggaaccga   2040
ttcaatcgca gaagatgtag ggccgccgtg aagtctgtca cgttttactg gctggttatc   2100
gtcctggtgt ttctgaacac cttaaccatt tcctctgagc actacaatca gccagattgg   2160
ttgacacaga ttcaagatat tgccaacaaa gtcctcttgg ctctgttcac ctgcgagatg   2220
ctggtaaaaa tgtacagctt gggcctccaa gcatatttcg tctctctttt caaccggttt   2280
gattgcttcg tggtgtgtgg tggaatcact gagacgatct tggtggaact ggaaatcatg   2340
tctcccctgg ggatctctgt gtttcggtgt gtgcgcctct aagaatcttc aaagtgacc    2400
aggcactgga cttccctgtg caacttagtg gcatccttat taaactccat gaagtccagt   2460
gcttcgctgt tgcttctgct ttttctcttc attatcatct tttccttgct tgggatgcag   2520
ctgtttggcg gcaagtttaa ttttgatgaa acgcaaacca agcggagcac ctttgacaat   2580
ttccctcaag cacttctcac agtgttccag atcctgacag gcgaagactg gaatgctgtg   2640
atgtacgatg gcatcatggc ttacggggggc ccatcctctt caggaatgat cgtctgcatc   2700
tacttcatca tcctcttcat ttgtggtaac tatattctac tgaatgtctt cttggccatc   2760
gctgtagaca atttggctga tgctgaaagt ctgaacactg ctcagaaaga agaagcggaa   2820
gaaaaggaga ggaaaagat tgccagaaaa gagagcctag aaaataaaaa gaacaacaaa   2880
ccagaagtca accagatagc caacagtgac aacaaggtta caattgatga ctatagagaa   2940
gaggatgaag acaaggaccc ctatccgcct tgcgatgtgc cagtagggga agaggaagag   3000
gaagaggagg aggatgaacc tgaggttcct gccggaccc gtcctcgaag gatctcggag   3060
ttgaacatga aggaaaaaat tgcccccatc cctgaaggga gcgctttctt cattcttagc   3120
```

```
aagaccaacc cgatccgcgt aggctgccac aagctcatca accaccacat cttcaccaac    3180
ctcatccttg tcttcatcat gctgagcagt gctgccctgg ccgcagagga ccccatccgc    3240
agccactcct tccggaacac gatactgggt tactttgact atgccttcac agccatcttt    3300
actgttgaga tcctgttgaa gatgacaact tttggagctt tcctccacaa aggggccttc    3360
tgcaggaact acttcaattt gctggatatg ctggtggttg gggtgtctct ggtgtcattt    3420
gggattcaat ccagtgccat ctccgttgtg aagattctga gggtcttaag ggtcctgcgt    3480
cccctcaggg ccatcaacag agcaaaagga cttaagcacg tggtccagtg cgtcttcgtg    3540
gccatccgga ccatcggcaa catcatgatc gtcaccaccc tcctgcagtt catgtttgcc    3600
tgtatcgggg tccagttgtt caaggggaag ttctatcgct gtacggatga agccaaaagt    3660
aaccctgaag aatgcagggg acttttcatc ctctacaagg atggggatgt tgacagtcct    3720
gtggtccgtg aacggatctg gcaaaacagt gatttcaact tcgacaacgt cctctctgct    3780
atgatggcgc tcttcacagt ctccacgttt gagggctggc ctgcgttgct gtataaagcc    3840
atcgactcga atggagagaa catcggccca atctacaacc accgcgtgga gatctccatc    3900
ttcttcatca tctacatcat cattgtagct tccttcatga tgaacatctt tgtgggcttt    3960
gtcatcgtta catttcagga acaaggagaa aaagagtata agaactgtga gctggacaaa    4020
aatcagcgtc agtgtgttga atacgccttg aaagcacgtc ccttgcggag atacatcccc    4080
aaaaacccct accagtacaa gttctggtac gtggtgaact cttcgccttt cgaatacatg    4140
atgtttgtcc tcatcatgct caacacactc tgcttggcca tgcagcacta cgagcagtcc    4200
aagatgttca atgatgccat ggacattctg aacatggtct tcaccggggt gttcaccgtc    4260
gagatggttt tgaaagtcat cgcatttaag cctaagggg atttagtga cgcctggaac    4320 acgtttgact ccctcatcgt aatcggcagc attatagacg tggccctcag cgaagcagac    4380
ccaactgaaa gtgaaaatgt ccctgtccca actgctacac ctgggaactc tgaagagagc    4440
aatagaatct ccatcacctt tttccgtctt ttccgagtga tgcgattggt gaagcttctc    4500
agcagggggg aaggcatccg gacattgctg tggacttttta ttaagttctt tcaggcgctc    4560
ccgtatgtgg ccctcctcat agccatgctg ttcttcatct atgcggtcat ggcatgcag    4620 atgtttggga agttgccat gagagataac aaccagatca ataggaacaa taacttccag    4680
acgtttcccc aggcggtgct gctgctcttc aggtgtgcaa caggtgaggc ctggcaggag    4740
atcatgctgg cctgtctccc agggaagctc tgtgaccctg agtcagatta caaccccggg    4800
gaggagcata catgtgggag caactttgcc attgtctatt tcatcagttt ttacatgctc    4860
tgtgcatttc tgatcatcaa tctgtttgtg gctgtcatca tggataattt cgactatctg    4920
acccgggact ggtctatttt ggggcctcac catttagatg aattcaaaag aatatggtca    4980
gaatatgacc ctgaggcaaa gggaaggata aaacaccttg atgtggtcac tctgcttcga    5040
cgcatccagc ctcccctggg gtttgggaag ttatgtccac acagggtagc gtgcaagaga    5100
ttagttgcca tgaacatgcc tctcaacagt gacgggacag tcatgtttaa tgcaaccctg    5160
tttgctttgg ttcgaacggc tcttaagatc aagaccgaag ggaacctgga gcaagctaat    5220
gaagaacttc gggctgtgat aaagaaaatt tggaagaaaa ccagcatgaa attacttgac    5280
caagttgtcc ctccagctgg tgatgatgag gtaaccgtgg ggaagttcta tgccactttc    5340
ctgatacagg actactttag gaaattcaag aaacggaaag aacaaggact ggtgggaaag    5400 tacccctgcga agaacaccac aattgcccta caggcgggat taaggacact gcatgacatt    5460
```

```
gggccagaaa tccggcgtgc tatatcgtgt gatttgcaag atgacgagcc tgaggaaaca    5520
aaacgagaag aagaagatga tgtgttcaaa agaaatggtg ccctgcttgg aaaccatgtc    5580
aatcatgtta atagtgatag gagagattcc cttcagcaga ccaataccac ccaccgtccc    5640
ctgcatgtcc aaaggccttc aattccacct gcaagtgata ctgagaaacc gctgtttcct    5700
ccagcaggaa attcggtgtg tcataaccat cataaccata attccatagg aaagcaagtt    5760
cccacctcaa caaatgccaa tctcaataat gccaatatgt ccaaagctgc ccatggaaag    5820
cggcccagca ttgggaacct tgagcatgtg tctgaaaatg gcatcattc ttcccacaag     5880 catgaccggg agcctcagag aaggtccagt gtgaaaagaa cccgctatta tgaaacttac    5940
attaggtccg actcaggaga tgaacagctc ccaactattt gccgggaaga cccagagata    6000
catggctatt tcagggaccc ccactgcttg ggggagcagg agtatttcag tagtgaggaa    6060
tgctacgagg atgacagctc gcccacctgg agcaggcaaa actatggcta ctacagcaga    6120
tacccaggca gaaacatcga ctctgagagg ccccgaggct accatcatcc ccaaggattc    6180
ttggaggacg atgactcgcc cgtttgctat gattcacgga gatctccaag gagacgccta    6240
ctacctccca ccccagcatc ccaccggaga tcctccttca actttgagtg cctgcgccgg    6300
cagagcagcc aggaagaggt cccgtcgtct cccatcttcc cccatcgcac ggccctgcct    6360
ctgcatctaa tgcagcaaca gatcatggca gttgccggcc tagattcaag taaagcccag    6420
aagtactcac cgagtcactc gaccggtcg tgggccaccc ctccagcaac cctccctac     6480 cgggactgga caccgtgcta cacccccctg atccaagtgg agcagtcaga ggccctggac    6540
caggtgaacg gcagcctgcc gtccctgcac cgcagctcct ggtacacaga cgagcccgac    6600
atctcctacc ggactttcac accagccagc ctgactgtcc ccagcagctt ccggaacaaa    6660
aacagcgaca gcagaggag tgcggacagc ttggtggagg cagtcctgat atccgaaggc     6720
ttgggacgct atgcaaggga cccaaaattt gtgtcagcaa caaaacacga aatcgctgat    6780
gcctgtgacc tcaccatcga cgagatggag agtgcagcca gcaccctgct taatgggaac    6840
gtgcgtcccc gagccaacgg ggatgtgggc cccctctcac accggcagga ctatgagcta    6900
caggactttg gtcctggcta cagcgacgaa gagcccgacc ctgggaggga tgaggaggac    6960
ctggcggatg aaatgatatg catcaccacc ttgtagcccc cagcgagggg cagactggct    7020
ctggcctcag gtggggcgca ggagagccag gggaaaagtg cctcatagtt aggaaagttt    7080
aggcactagt tgggagtaat attcaattaa ttagacttt gtataagaga tgtcatgcct     7140
caagaaagcc ataaacctgg taggaacagg tcccaagcgg ttgagcctgg cagagtacca    7200
tgcgctcggc cccagctgca ggaaacagca ggccccgccc tctcacagag gatgggtgag    7260
gaggccagac ctgccctgcc ccattgtcca gatgggcact gctgtggagt ctgcttctcc    7320
catgtaccag ggcaccaggc ccacccaact gaaggcatgg cggcggggtg caggggaaag    7380
ttaaaggtga tgacgatcat cacacctgtg tcgttacctc agccatcggt ctagcatatc    7440
agtcactggg cccaacatat ccattttaa accctttccc ccaaatacac tgcgtcctgg     7500
ttcctgttta gctgttctga aatacggtgt gtaagtaagt cagaacccag ctaccagtga    7560
ttattgcgag ggcaatggga cctcataaat aaggttttct gtgatgtgac gccagtttac    7620
ataagagaat atcac                                                     7635
```

<210> SEQ ID NO 263
<211> LENGTH: 637
<212> TYPE: DNA
<213> ORGANISM: Homo sapiens

<400> SEQUENCE: 263

```
tttttttttt cttacaaaga aaaatttaat attcgatgag aggttgaacc aggcttaaag      60
cagacatact aggaaatggt gcagcctgta agaatgccag tttgtaagta ctgactttgg     120
aaaagatcat cgcctctatc agacacttag ggtcctggtc tggcaatttt ggcctgatgt     180
gatgccacaa gacccaacag agagagacac agagtccagg ataatgttga cagtggtgta     240
gcccttaggg agaaatggcg ctccctgcgg ctggtattag gttaccattg gcaccgaagg     300
aaccaggagg ataagaatat ccataatttc agagctgccc tggcacagta cctgccccgt     360
cggaggctct cactggcaaa tgacagctct gtgcaaggag cactcccaag tataaaaatt     420
attacacagt tttattctga agaacatttt gcattttaat aaaaaaggat ttatgtcagg     480
aaagagtcat ttacaaacct tgaagtgttt ttgcctggat cagagtaaga atgtcttaag     540
aagaggtttg taaggtcttc ataacaaagt ggtgtttgtt atttacaaaa aaaaaaaaaa     600
aaaaaaatta acaggttgtc tgtatactat taaaaat                              637
```

<210> SEQ ID NO 264
<211> LENGTH: 7193
<212> TYPE: DNA
<213> ORGANISM: Homo sapiens

<400> SEQUENCE: 264

```
agaataaggg cagggaccgc ggctcctatc tcttggtgat ccccttcccc attccgcccc      60
cgcctcaacg cccagcacag tgccctgcac acagtagtcg ctcaataaat gttcgtggat     120
gatgatgatg atgatgatga aaaaaatgca gcatcaacgg cagcagcaag cggaccacgc     180
gaacgaggca aactatgcaa gaggcaccag acttcctctt tctggtgaag gaccaacttc     240
tcagccgaat agctccaagc aaactgtcct gtcttggcaa gctgcaatcg atgctgctag     300
acaggccaag gctgcccaaa ctatgagcac ctctgcaccc ccacctgtag gatctctctc     360
ccaaagaaaa cgtcagcaat acgccaagag caaaaaacag ggtaactcgt ccaacagccg     420
acctgcccgc gcccttttct gtttatcact caataacccc atccgaagag cctgcattag     480
tatagtggaa tggaaaccat tgacatatt tatattattg gctattttg ccaattgtgt     540
ggccttagct atttacatcc cattccctga agatgattct aattcaacaa atcataactt     600
ggaaaaagta gaatatgcct tcctgattat ttttacagtc gagacatttt tgaagattat     660
agcgtatgga ttattgctac atcctaatgc ttatgttagg aatggatgga atttactgga     720
ttttgttata gtaatagtag gattgtttag tgtaattttg gaacaattaa ccaaagaaac     780
agaaggcggg aaccactcaa gcggcaaatc tggaggcttt gatgtcaaag ccctccgtgc     840
ctttcgagtg ttgcgaccac ttcgactagt gtcaggggtg cccagtttac aagttgtcct     900
gaactccatt ataaaagcca tggttcccct ccttcacata gcccttttgg tattatttgt     960
aatcataatc tatgctatta taggattgga acttttttatt ggaaaaatgc acaaaacatg    1020
ttttttttgct gactcagata tcgtagctga agaggaccca gctccatgtg cgttctcagg    1080
gaatggacgc cagtgtactg ccaatggcac ggaatgtagg agtggctggg ttggcccgaa    1140
cggaggcatc accaactttg ataactttgc ctttgccatg cttactgtgt tcagtgcat     1200
caccatggag ggctggacag acgtgctcta ctgggtaaat gatgcgatag gatgggaatg    1260
gccatgggtg tattttgtta gtctgatcat ccttggctca ttttttcgtcc ttaacctggt    1320
tcttggtgtc cttagtggag aattctcaaa ggaaagagag aaggcaaaag cacggggaga    1380
```

```
tttccagaag ctccgggaga agcagcagct ggaggaggat ctaaagggct acttggattg    1440
gatcacccaa gctgaggaca tcgatccgga gaatgaggaa gaaggaggag aggaaggcaa    1500
acgaaatact agcatgccca ccagcgagac tgagtctgtg aacacagaga acgtcagcgg    1560
tgaaggcgag aaccgaggct gctgtggaag tctctggtgc tggtggagac ggagaggcgc    1620
ggccaaggcg gggccctctg ggtgtcggcg gtggggtcaa gccatctcaa aatccaaact    1680
cagccgacgc tggcgtcgct ggaaccgatt caatcgcaga agatgtaggg ccgccgtgaa    1740
gtctgtcacg ttttactggc tggttatcgt cctggtgttt ctgaacacct taaccatttc    1800
ctctgagcac tacaatcagc cagattggtt gacacagatt caagatattg ccaacaaagt    1860
cctcttggct ctgttcacct gcgagatgct ggtaaaaatg tacagcttgg gcctccaagc    1920
atatttcgtc tctcttttca accggtttga ttgcttcgtg gtgtgtggtg gaatcactga    1980
gacgatcctg gtggaactgg aaatcatgtc tcccctgggg atctctgtgt ttcggtgtgt    2040
gcgcctctta agaatcttca aagtgaccag gcactggact tccctgagca acttagtggc    2100
atccttatta aactccatga agtccatcgc ttcgctgttg cttctgcttt ttctcttcat    2160
tatcatcttt tccttgcttg ggatgcagct gtttggcggc aagtttaatt ttgatgaaac    2220
gcaaaccaag cggagcacct ttgacaattt ccctcaagca cttctcacag tgttccagat    2280
cctgacaggc gaagactgga atgctgtgat gtacgatggc atcatggctt acggggggccc    2340
atcctcttca ggaatgatcg tctgcatcta cttcatcatc ctcttcattt gtggtaacta    2400
tattctactg aatgtcttct tggccatcgc tgtagacaat ttggctgatg ctgaaagtct    2460
gaacactgct cagaaagaag aagcggaaga aaggagagg aaaaagattg ccagaaaaga    2520
gagcctagaa aataaaaaga caacaaaccc agaagtcaac cagatagcca acagtgacaa    2580
caaggttaca attgatgact atagagaaga ggatgaagac aaggacccct atccgccttg    2640
cgatgtgcca gtaggggaag aggaagagga agaggaggag gatgaacctg aggttcctgc    2700
cggacccgt cctcgaagga tctcggagtt gaacatgaag gaaaaaattg cccccatccc    2760
tgaagggagc gctttcttca ttcttagcaa gaccaacccg atccgcgtag ctgccacaa    2820
gctcatcaac caccacatct tcaccaacct catccttgtc ttcatcatgc tgagcagcgc    2880
tgccctggcc gcagaggacc ccatccgcag ccactccttc cggaacacga tactgggtta    2940
ctttgactat gccttcacag ccatctttac tgttgagatc ctgttgaaga tgacaacttt    3000
tggagctttc tcccacaaag gggccttctg caggaactac ttcaatttgc tggatatgct    3060
ggtggttggg gtgtctctgg tgtcatttgg gattcaatcc agtgccatct ccgttgtgaa    3120
gattctgagg gtcttaaggg tcctgcgtcc cctcagggcc atcaacagag caaaaggact    3180
taagcacgtg gtccagtgcg tcttcgtggc catccgacc atcggcaaca tcatgatcgt    3240
cactacccte ctgcagttca tgtttgcctg tatcgggtc cagttgttca aggggaagtt    3300
ctatcgctgt acggatgaag ccaaaagtaa ccctgaagaa tgcagggac ttttcatcct    3360
ctacaaggat ggggatgttg acagtcctgt ggtccgtgaa cggatctggc aaaacagtga    3420
tttcaacttc gacaacgtcc tctctgctat gatggcgctc ttcacagtct ccacgtttga    3480
gggctggcct gcgttgctgt ataaagccat cgactcgaat ggagagaaca tcggcccaat    3540
ctacaaccac cgcgtggaga tctccatctt cttcatcatc tacatcatca ttgtagcttt    3600
cttcatgatg aacatctttg tgggcttttg catcgttaca tttcaggaac aaggagaaaa    3660
agagtataag aactgtgagc tggacaaaaa tcagcgtcag tgtgttgaat acgccttgaa    3720
agcacgtccc ttgcggagat acatccccaa aaacccctac cagtacaagt tctggtacgt    3780
```

```
ggtgaactct tcgcctttcg aatacatgat gtttgtcctc atcatgctca acacactctg    3840
cttggccatg cagcactacg agcagtccaa gatgttcaat gatgccatgg acattctgaa    3900
catggtcttc accggggtgt tcaccgtcga gatggttttg aaagtcatcg catttaagcc    3960 taagggtat tttagtgacg cctggaacac gtttgactcc ctcatcgtaa tcggcagcat    4020
tatagacgtg gccctcagcg aagcggaccc aactgaaagt gaaaatgtcc ctgtcccaac    4080
tgctacacct gggaactctg aagagagcaa tagaatctcc atcaccttttt tccgtctttt    4140 ccgagtgatg cgattggtga agcttctcag caggggggaa ggcatccgga cattgctgtg    4200 gactttatt aagtcctttc aggcgctccc gtatgtggcc ctcctcatag ccatgctgtt    4260
cttcatctat gcggtcattg gcatgcagat gtttgggaaa gttgccatga gagataacaa    4320
ccagatcaat aggaacaata acttccagac gtttccccag gcggtgctgc tgctcttcag    4380
gtgtgcaaca ggtgaggcct ggcaggagat catgctggcc tgtctcccag ggaagctctg    4440
tgaccctgag tcagattaca accccgggga ggagtataca tgtgggagca actttgccat    4500
tgtctatttc atcagtttttt acatgctctg tgcatttctg atcatcaatc tgtttgtggc    4560
tgtcatcatg gataatttcg actatctgac ccgggactgg tctattttgg ggcctcacca    4620
tttagatgaa ttcaaaagaa tatggtcaga atatgaccct gaggcaaagg gaaggataaa    4680
acaccttgat gtggtcactc tgcttcgacg catccagcct ccctggggt ttgggaagtt    4740 atgtccacac agggtagcgt gcaagagatt agttgccatg aacatgcctc tcaacagtga    4800
cgggacagtc atgtttaatg caaccctgtt tgctttggtt cgaacggctc ttaagatcaa    4860
gaccgaaggg aacctggagc aagctaatga agaacttcgg gctgtgataa agaaaatttg    4920
gaagaaaacc agcatgaaat tacttgacca agttgtccct ccagctggtg atgatgaggt    4980
aaccgtgggg aagttctatg ccactttcct gatacaggac tactttagga aattcaagaa    5040
acggaaagaa caaggactgg tgggaaagta ccctgcgaag aacaccacaa ttgccctaca    5100
ggcgggatta aggacactgc atgacattgg gccagaaatc cggcgtgcta tatcgtgtga    5160
tttgcaagat gacgagcctg aggaaacaaa acgagaagaa gaagatgatg tgttcaaaag    5220
aaatggtgcc ctgcttggaa accatgtcaa tcatgttaat agtgatagga gagattccct    5280
tcagcagacc aataccaccc accgtcccct gcatgtccaa aggccttcaa ttccacctgc    5340
aagtgatact gagaaaccgc tgtttcctcc agcaggaaat tcggtgtgtc ataaccatca    5400
taaccataat tccataggaa agcaagttcc cacctcaaca aatgccaatc tcaataatgc    5460
caatatgtcc aaagctgccc atggaaagcg gcccagcatt gggaaccttg agcatgtgtc    5520
tgaaaatggg catcattctt cccacaagca tgaccgggag cctcagagaa ggtccagtgt    5580
gaaaagaacc cgctattatg aaacttacat taggtccgac tcaggagatg aacagctccc    5640
aactatttgc cgggaagacc cagagataca tggctatttc agggaccccc actgcttggg    5700
ggagcaggag tatttcagta gtgaggaatg ctacgaggat gacagctcgc ccacctggag    5760
caggcaaaac tatggctact acagcagata cccaggcaga aacatcgact ctgagaggcc    5820
ccgaggctac catcatcccc aaggattctt ggaggacgat gactcgcccg tttgctatga    5880
ttcacggaga tctccaagga gacgcctact acctcccacc ccagcatccc accggagatc    5940
ctccttcaac tttgagtgcc tgcgccggca gagcagccag gaagaggtcc gtcgtctcc    6000 catcttcccc catcgcacgg ccctgcctct gcatctaatg cagcaacaga tcatggcagt    6060
tgccggccta gattcaagta aagcccagaa gtactcaccg agtcactcga cccggtcgtg    6120
```

```
ggccacccct ccagcaaccc ctccctaccg ggactggaca ccgtgctaca ccccctgat    6180 ccaagtggag cagtcagagg ccctggacca ggtgaacggc agcctgccgt ccctgcaccg    6240
cagctcctgg tacacagacg agcccgacat ctcctaccgg actttcacac cagccagcct    6300
gactgtcccc agcagcttcc ggaacaaaaa cagcgacaag cagaggagtg cggacagctt    6360
ggtggaggca gtcctgatat ccgaaggctt gggacgctat gcaagggacc caaaatttgt    6420
gtcagcaaca aaacacgaaa tcgctgatgc ctgtgacctc accatcgacg agatggagag    6480
tgcagccagc accctgctta atgggaacgt gcgtccccga gccaacgggg atgtgggccc    6540
cctctcacac cggcaggact atgagctaca ggactttggt cctggctaca gcgacgaaga    6600
gccagaccct gggagggatg aggaggacct ggcggatgaa atgatatgca tcaccacctt    6660
gtagcccccc gcgaggggca gactggctct ggcctcaggt ggggcgcagg agagccaggg    6720
gaaaagtgcc tcatagttag gaaagtttag gcactagttg ggagtaatat tcaattaatt    6780
agacttttgt ataagagatg tcatgcctca agaaagccat aaacctggta ggaacaggtc    6840
ccaagcggtt gagcctggca gagtaccatg cgctcggccc cagctgcagg aaacagcagg    6900
ccccgccctc tcacagagga tgggtgagga ggccagacct gccctgcccc attgtccaga    6960
tgggcactgc tgtggagtct gcttctccca tgtaccaggg caccaggccc acccaactga    7020
aggcatggcg gcggggtgca ggggaaagtt aaaggtgatg acgatcatca cacctcgtgt    7080
cgttacctca gccatcggtc tagcatatca gtcactgggc ccaacatatc cattttaaaa    7140
ccctttcccc caaatacact gcgtcctggt tcctgtttag ctgttctgaa ata           7193

<210> SEQ ID NO 265
<211> LENGTH: 243
<212> TYPE: DNA
<213> ORGANISM: Homo sapiens

<400> SEQUENCE: 265
gtactgtgcc ggggcagctc tgaaattatg gatattctta tcctcctggt tccttcggtg     60
ccaatggtaa cctaatacca gccgcaggga gcgccatttc tcctaaaggg ctacaccact    120
gtcaacatta tcctggactc tgtgtctctc tctgttgggt cttgtggcat cacatcaggc    180
caaaattgcc agaccaggac cctaagtgtc tgatagaggc gatgatcttt tcaaagtcag    240
tac                                                                  243

<210> SEQ ID NO 266
<211> LENGTH: 341
<212> TYPE: DNA
<213> ORGANISM: Homo sapiens
<220> FEATURE:
<221> NAME/KEY: misc_feature
<222> LOCATION: (9)..(9)
<223> OTHER INFORMATION: a or g or c or t/u

<400> SEQUENCE: 266
tgcagcaant ggcacggaat gtaggagtgg gtgggtggga ccgaacggag gcatcaccaa     60
ctttgataac ttggcctatg ccatgcttac ggtgtttcag tgcatcacca tggagggctg    120
gacagatgtg ctctactggg taaatgatgc gataggatgg gaatggccat gggcgtattt    180
tgttagtctg atcatccttg gctcattttt cgtccttaac ctggttcttg gtgtccttag    240
tggagaattc tcaaaggaaa gagagaaggc aaaagcacgg ggagatttcc agaagctccg    300
ggagaagcag cagctggagg aggatctaaa gggctacttg g                        341
```

<210> SEQ ID NO 267
<211> LENGTH: 406
<212> TYPE: DNA
<213> ORGANISM: Homo sapiens
<220> FEATURE:
<221> NAME/KEY: misc_feature
<222> LOCATION: (332)..(332)
<223> OTHER INFORMATION: a or g or c or t/u

<400> SEQUENCE: 267

```
atgactacgg gggaagttca ttctgacctt ccagactagc tagtactata tgaaatccga    60
gagacggaat gaacacggac tgatgggaaa gtaccctgcg aagaacacca caattgccct   120
acaggcgtga ttaaggacac tgcatgatag ttgctccaga atgccggcgt gctatatcgt   180
gtgatttgca agatgacgag cgtgaggaaa caaaacgaga agaagaagat gatgtgttca   240
aaagaaatgg tgccctgctt ggaaaccatg tcaatcatgt aatagtgat aggagagatt   300 cccttcagca gaccaatacc acccaccgtc cnctgcatgt ccaaaggcct tcaattccac   360
ctgcaagtga tactgagaaa ccgctgttcc tccagcagga aattcg                  406
```

<210> SEQ ID NO 268
<211> LENGTH: 236
<212> TYPE: DNA
<213> ORGANISM: Homo sapiens

<400> SEQUENCE: 268

```
tacatctccg ctatctgtgc cgtgtaacac ggtgtccagt ctcgttaggg aggggctgct    60
ggaggggtgg cccacgaccg ggtcgagtga ctcggtgagc acttctgtgc tttacttgaa   120
tctaggccgg caactgccat gatctgttgc tgcattagat gcagaggcag tgccgcgcga   180
tggtgaagat gggagacgac gggacctctt gctggctgct ctgccggcgc aggcac       236
```

<210> SEQ ID NO 269
<211> LENGTH: 586
<212> TYPE: DNA
<213> ORGANISM: Homo sapiens

<400> SEQUENCE: 269

```
tgtcgtgact ggcgatacct ggcgttagtg tgtacatggt gttcataatt gctgctgcat    60
aacattttgt gagaattaat gtgacaatgt atgtgcagtg cttagcacat agcaagtgct   120
catgaatggt agccaccaag atggctgttg tcatttagt ttgcagcagt tccacttgtc    180
atcattgagt tcccagggag tcccctcttc tttgggaaca gacttgctct ctgtagctcc   240
attgcggtaa aaacagatga ggttaatccc tgtcccaatc attttggaga tggcgtcgtt   300
tgtattccaa ttccacagcc cagttcttgt ctttgtcttc cttttattta agcagcagcc   360
acacagaatt agcccttttc aaaaataaat aagattatca tcctgttttg cgtccctggg   420
gtaacagact ctaacatttc tttctctttc tcttctttca gattgtctag tgtaattttg   480
gaacaattaa ccaaagaaac agaaggcggg aaccactcac gcggcaaatc tggaggcttt   540
gatgtcaaag ccctccgtgc ctttcgagtg ttgcgaccac ttcgaa                  586
```

<210> SEQ ID NO 270
<211> LENGTH: 549
<212> TYPE: DNA
<213> ORGANISM: Homo sapiens

<400> SEQUENCE: 270

```
agttcccacc tcaacaaatg ccaatctcaa taatgccaat atgtccaaag ctgcccatgg    60
```

| | |
|---|---|
| aaagcggccc agcattggga accttgagca tgtgtctgaa atgggcatc attcttccca | 120 |
| caagcatgac cgggagcctc agagaaggtc cagtgtgaaa aggtccgact caggagatga | 180 |
| acagctccca actatttgcc gggaagaccc agagatacat ggctatttca ggacccccca | 240 |
| ctgcttgggg gagcaggagt atttcagtag tgaggaatgc tacgaggatg acagctcgcc | 300 |
| cacctggagc aggcaaaact atggctacta cagcagatac ccaggcagaa acatcgactc | 360 |
| tgagaggccc cgaggctacc atcatcccca aggattcttg gaggacgatg actcgcccgt | 420 |
| ttgctatgat tcacggagat ctccaaggag acgcctacta cctcccaccc cagcatgtga | 480 |
| ggccagattt tttgtttttg ggtggaacct cccggggaac agtgtacctt tcccccaacc | 540 |
| cccgctctg | 549 |

<210> SEQ ID NO 271
<211> LENGTH: 595
<212> TYPE: DNA
<213> ORGANISM: Homo sapiens

<400> SEQUENCE: 271

| | |
|---|---|
| attcggcacg agcctccttc aactttgagt gctctgcccc ttgggtatcc atagttacgg | 60 |
| ttttctctgt ggcccaccca gggtgttttt tgcatcgctg gtgcagaaat gcacaggtgg | 120 |
| atgagatata gctgctcttg tcctctgggg actggtggtg ctgcttaaga ataaggggt | 180 |
| gctggggaca gaggagcaac gtggtgatct ataggattgg agtgtcgggg tctgtacaaa | 240 |
| tcgtattgtt gccttttaca aaactgctgt actgtatgtt ctctttgagg gcttttatat | 300 |
| gcaattgact gagggctgaa gttttcatta gaatgcactc acactctgac tgtacgtcct | 360 |
| gatgaaaacc cacttttgga taattagaac cgtcaaggct tcattttctg tcaacagaat | 420 |
| taggccgact gtcaggttac cttggcaggg attccctgca atcaaaaaga tagatgatag | 480 |
| gtagcaattt tggtccaaaa ttttaatag tatacagaca acctgttaat tttttttttt | 540 |
| tttttttttg taaataacaa acaccacttt gttatgaaga ccttacaaac ctctt | 595 |

<210> SEQ ID NO 272
<211> LENGTH: 209
<212> TYPE: DNA
<213> ORGANISM: Homo sapiens

<400> SEQUENCE: 272

| | |
|---|---|
| ggaaaactca agtccagagc aatactacgt aaaattcaga agtgagaaca tacaaaggca | 60 |
| acacacaggc tgacgaagaa acagaaagaa gatactgacc tgagtttgga ttttgagatg | 120 |
| gcttgactga agaaagaca aaagtgtta agattctggt tccgagggct tgagcacaca | 180 |
| ctcccccatca tttcagctgg agatttcat | 209 |

<210> SEQ ID NO 273
<211> LENGTH: 687
<212> TYPE: DNA
<213> ORGANISM: Homo sapiens
<220> FEATURE:
<221> NAME/KEY: misc_feature
<222> LOCATION: (632)..(632)
<223> OTHER INFORMATION: a or g or c or t/u

<400> SEQUENCE: 273

| | |
|---|---|
| tttttttttt ttttttttat tctgaagaac attttgcatt ttaataaaaa aggatttatg | 60 |
| tcaggaaaga gtcatttaca aaccttgaag tgttttgcc tggatcagag taagaatgtc | 120 |
| ttaagaagag gtttgtaagg tcttcataac aaagtggtgt ttgttattta caaaaaaaaa | 180 |

```
aaaaaaaaat taacaggttg tctgtatact attaaaaatt ttggaccaaa attgctacct       240
atcatctatc ttttgattg cagggaatcc ctgccaaggt aacttgacag tcggcctaat        300
tctgttgaca gaaatgaag ccttgacggt tctaattatc caaagtggg ttttcatcag         360 gacgtacagt cagagtgtga gtgcattcta atgaaaactt cttcagccct cattcaattg       420
catacaaaag ccctcaaaga gaacatacag tacagcagtt ttgtaaaagg caacaatacg       480
atttgtacag accccgacac tccaatccta tagatcacca cgttgctcct ctgtccccag       540
caccccttat ttcttaagca gcaccaccag tccccagagg acaagagcag ctatatctca       600
tccacctgtg catttctgca ccagcgatgc anaaaacacc ctggggtggg ccacagagaa       660
aaccgtaact atggataccc aaggggc                                           687

<210> SEQ ID NO 274
<211> LENGTH: 573
<212> TYPE: DNA
<213> ORGANISM: Homo sapiens

<400> SEQUENCE: 274
taaataacaa acaccacttt gttatgaaga ccttacaaac ctcttcttaa gacattctta       60
ctctgatcca ggcaaaaaca cttcaaggtt tgtaaatgac tctttcctga cataaatcct      120 ttttattaa aatgcaaaat gttcttcaga ataaaactgt gtaataattt ttatacttgg       180
gagtgctcct tgcacagagc tgtcatttgc cagtgagagc ctccgacggg gcaggtactg      240
tgccagggca gctctgaaat tatggatatt cttatcctcc tggttccttc ggtgccaatg      300
gtaacctaat accagccgca gggagcgcca tttctcctaa agggctacac cactgtcaac      360
attatcctgg actctgtgtc tctctctgtt gggtcttgtg gcatcacatc aggccaaaat      420
tgccagacca ggaccctaag tgtctgatag aggcgatgat cttttccaaa gtcagtactt      480
acaaactggc attcttacag gctgcaccat ttcctagtat gtctgcttta agcctggttc      540
aacctctcat cgaatattaa attttctttt gta                                   573

<210> SEQ ID NO 275
<211> LENGTH: 453
<212> TYPE: DNA
<213> ORGANISM: Homo sapiens

<400> SEQUENCE: 275 ttttttttt ttttcttgg ggaaagatga taggtttata gtgactcaaa atatttaaa          60 aaaatttctg tagggtcaag ttcttttcaaa cttaaaattt taaccccaga ggattttcgc    120
tgaataaatg aaaattggct ctatttcttc aacttcggga tagcccgagt aaaaatacta     180
ataatttcta aattttaggg gggaactaca attattagga cccatggata ttgctgcagt     240
tcaaatacaa tacagtaatt acaaaatata gaccatctct ttacaaatac aaattatagt     300
atattacaag tcatgtacag taaatctata atttttaaaca aactagtgta tctaagttta    360
cctggttgcg agtgcattat tattccagtt tacagttgcc cttagcgtga cagtcagaaa     420
ccgaccatcg gagtgatatt ctcttatgta aac                                   453

<210> SEQ ID NO 276
<211> LENGTH: 415
<212> TYPE: DNA
<213> ORGANISM: Homo sapiens
<220> FEATURE:
<221> NAME/KEY: misc_feature
<222> LOCATION: (311)..(311)
```

<223> OTHER INFORMATION: a or g or c or t/u

<400> SEQUENCE: 276

| tgattacttg tagcaaagta cttccccaca tttagctgga tttgtctttg gtttgaagag | 60 |
| gctaatacgt gaaagatttg ttcacagttg gatgtcccct tttctgaacc atgaagtaat | 120 |
| attgtgaatg gagttgaatg ctgaggttag ggtgccggaa agattcaggg tccttcggta | 180 |
| ccctcacatg gcttggcttt ggtagaacaa gaaactaagc tctgatttgg ctttaaatga | 240 |
| gagtgctaaa tttccttttt ctaataaaga acctagctaa acatttatat atacttttga | 300 |
| acactgaact ntcttgttgc agagttaaca gctgttgggg gtagctgaca gctggatcct | 360 |
| ggtgctgttg gtaccatggt acctgaagtg cacaggctgg tagccacacc tgaca | 415 |

<210> SEQ ID NO 277
<211> LENGTH: 646
<212> TYPE: DNA
<213> ORGANISM: Homo sapiens
<220> FEATURE:
<221> NAME/KEY: misc_feature
<222> LOCATION: (43)..(43)
<223> OTHER INFORMATION: a or g or c or t/u
<220> FEATURE:
<221> NAME/KEY: misc_feature
<222> LOCATION: (573)..(573)
<223> OTHER INFORMATION: a or g or c or t/u

<400> SEQUENCE: 277

| tttttttttt tttttcttac aaagaaaaat ttaatattcg atngagaggt tgaaccaggc | 60 |
| ttaaagcaga catactagga aatggtgcag cctgtaagaa tgccagtttg taagtactga | 120 |
| ctttggaaaa gatcatcgcc tctatcagac acttagggtc ctggtctggc aattttggcc | 180 |
| tgatgtgatg ccacaagacc caacagagag agacacagag tccaggataa tgttgacagt | 240 |
| ggtgtagccc tttaggagaa atggcgctcc ctgcggctgg tattaggtta ccattggcac | 300 |
| cgaaggaacc aggaggataa gaatatccat aatttcagag ctgccctggc acagtacctg | 360 |
| ccccgtcgga ggctctcact ggcaaatgac agctctgtgc aaggagcact cccaagtata | 420 |
| aaaattatta cacagtttta ttctgaagaa catttttgcat tttaataaaa aaggatttat | 480 |
| gtcaggaaag agtcatttac aaaccttgaa gtgttttgc ctggatcaga gtaagaatgt | 540 |
| cttaagaaga ggtttgtaag gtcttcataa canagtggtg tttgttattt acaaaaaaaa | 600 |
| aaaaaaaaaa aataaaaaaa aaaaaaaaaa cctcgtgccg aattct | 646 |

<210> SEQ ID NO 278
<211> LENGTH: 668
<212> TYPE: DNA
<213> ORGANISM: Homo sapiens

<400> SEQUENCE: 278

| tttttttttt tttttgtaa ataacaaaca ccactttggt tatgaagacc ttacaaacct | 60 |
| cttcttaaga cattcttact ctgatccagg caaaaacact tcaaggtttg taaatgactc | 120 |
| tttcctgaca taaatccttt tttattaaaa tgcaaaatgt tcttcagaat aaaactgtgt | 180 |
| aataatttt atactggga gtgctccttg cacagagctg tcatttgcca gtgagagcct | 240 |
| ccgacagggc aggtactgtg ccagggcagc tctgaaatta tggatattct tatcctcctg | 300 |
| gttccttcgg tgccaatggt aacctaatac cagccgcagg gagcgccatt tctcctaaag | 360 |
| ggctacacca ctgtcaacat tatcctggac tctgtgtctc tctctgttgg gtcttgtggc | 420 |
| atcacatcag gccaaaattg ccagaccagg accctaagtg tctgatagag gcgatgatct | 480 |

```
tttccaaagt cagtacttac aaactggcat tcttacaggc tgcaccattt cctagtatgt    540
ctgctttaag cctggttcaa cctctcatcg aatattaaat ttttctttgt aagaaaaatt    600
tgaagttgta gagcatggtt ttttgttttc ccttgtctta ggaaagtttt aagatgaaat    660
gttttttcc                                                             668

<210> SEQ ID NO 279
<211> LENGTH: 496
<212> TYPE: DNA
<213> ORGANISM: Homo sapiens

<400> SEQUENCE: 279
agtacacaag gtgaaactgc tccagttttt ctcatagcag ggtcagcagg aaagcaagtg     60
gtgcccctgg tcccatctca cacaggtgag actgcaccga gaggtaacgt ggccctcaca    120
gcccaccacg cctggccttc gcccaattct gaaacttcgt aggatagagc tggaaagtgc    180
cacatggtga agcgagatcc agctgtctgg gtggatgtcg gagtccatag gctgagcaga    240
gatggttctt agtgaggttc tcgctgccag ttgacggtga atcatagct gccatttaca     300 ttttgtgaga ttatgaaaaa cataagacta aagaaactaa atgtgttatt cctgtggaca    360
caaaaatgtg tgttttttcag atggggaggg gaccaaaaag gaaaaacatt tcatcttaaa    420
acttccctaa gacaaaggaa aacaaaaaac catgctctac aacttcaaat ttttcttaca    480
aagaaaaatt taatat                                                    496

<210> SEQ ID NO 280
<211> LENGTH: 701
<212> TYPE: DNA
<213> ORGANISM: Homo sapiens

<400> SEQUENCE: 280
agctgaggaa acaaaacgag agaagaagat gatgtgttca aaagaaatgg tgccctgctt     60
ggaaaccatg tcaatcatgt taatagtgat aggagagatt cccttcagca gaccaatacc    120
acccaccgtc ccctgcatgt ccaaaggcct tcaattccac ctgcaagtga tactgagaaa    180
ccgctgtttc ctccagcagg aaattcggtg tgtcataacc atcataacca taattccata    240
ggaaagcaag ttcccacctc aacaaatgcc aatctcaata atgccaatat gtccaaagct    300
gcccatggaa agcggcccag catagggaac cttgagcatg tgtctgaaaa tgggcatcat    360
tcttcccaca agcatgaccg ggagcctcag agaaggtcca gtgtgaaaag gtccgactca    420
ggagatgaac agctcccaac tattggccgg gaagacccag agatacatgg ctatttcagg    480
cacccccacg gcttggggga gcaggagtat ttcagtagtg aggaatgcta cgaggatgac    540
agctcgccca cctggagcag gcaaaactat ggctactaca gcagataccc aggcagaaac    600
atcgactctg agaggcgcga ggctacatca tcccaagatt ctggaggaga tgactcgccg    660
tttgtatgat cacgagatct caagagagct atactcccac c                        701

<210> SEQ ID NO 281
<211> LENGTH: 515
<212> TYPE: DNA
<213> ORGANISM: Homo sapiens

<400> SEQUENCE: 281
tcttgtggaa agatgatagg tttatagtga ctcaaaatat tttagaaaaa tttctgtagg     60
gtcaagttct ttcaaactta aaattttaac cccagaggat tttcgctgaa taaatgaaaa    120
```

```
ttggctctat ttcttctact tctggatagc ccgagtaaaa atactaataa tttctagatt     180
ttagtgggga actacaatta ttaggaccca tggatattgc tgcagttcaa atacaataca     240
gtaattacaa aatatagacc atctctttac aaatccaaat tatagtatat tacaagtcat     300
gtaccgtaaa tctattttaa acaaactagg gtatctaagt ttacctggtt gcaagtgcat     360
tattattcca gtttacagtt gcccttagcg tgacagtcag aaaccgacca tcggagtgat     420
attctcttat gtaaactggc gtcacatcac agaaaacctt atttatttgg gggaaagggt     480
ttaaaaatgg atatgttggg cccagtgact gatac                                515
```

<210> SEQ ID NO 282
<211> LENGTH: 258
<212> TYPE: DNA
<213> ORGANISM: Homo sapiens

<400> SEQUENCE: 282

```
ggaaaagatc atcgcctcta tcagacactt agggtcctgg tctggcaatt ttggcctgat      60
gtgatgccac aagacccaac agagagagac acagagtcca ggataatgtt gacagtggtg     120
tagcccttta ggagaaatgg cgctccctgc ggctggtatt aggttaccat tggcaccgaa     180
ggaaccagga ggataagaat atccataatt tcagagctgc cctggcacgg tacctgcccc     240
gtcggaggct ctcactgg                                                    258
```

<210> SEQ ID NO 283
<211> LENGTH: 510
<212> TYPE: DNA
<213> ORGANISM: Homo sapiens

<400> SEQUENCE: 283

```
gatgcgtgat ggctgatcta gaggtatccc atggactctc atcgcagctc ctggtacaca      60
gacgagcccg acatctccta ccggactttc acaccagcca gcctgactgt ccccagcagc     120
ttccggaaca aaaacagcga caagcagagg agtgcggaca gcttggtgga ggcagtcctg     180
atatccgaag gcttgggacg ctatgcaagg gacccaaaat ttgtgtcagc aacaaaacac     240
gagatcgctg atgcctgtga cctcaccatc gacgagatgg agagtgcagc cagcaccctg     300
cttaatggga acgtgcgtcc ccgagccaac ggggatgtgg gccccctctc acaccggcag     360
gactatgagc tacaggactt tggtcctggc tacagcgacg aagggccaga ccctgggagg     420
gatgaggagg acctggcgga tgaaatgata tgcatcacca ccttgtagcc cccagcgagg     480
ggcagactgg ctctggcctc aggtggggcg                                      510
```

<210> SEQ ID NO 284
<211> LENGTH: 405
<212> TYPE: DNA
<213> ORGANISM: Homo sapiens
<220> FEATURE:
<221> NAME/KEY: misc_feature
<222> LOCATION: (75)..(75)
<223> OTHER INFORMATION: a or g or c or t/u
<220> FEATURE:
<221> NAME/KEY: misc_feature
<222> LOCATION: (142)..(142)
<223> OTHER INFORMATION: a or g or c or t/u

<400> SEQUENCE: 284

```
cgctcgttcg ctgtgccagg acaaagtcct gtagctcata gtcctgccgt gtgagagggg      60
gccacatccc cgttnctcgg gacgcacgac ccattaagca gggtgctggc tgcccccctcc    120 atctcgtcga tggagaggtc ancaggcatc agcgatttcg tgttttgtgt gcgtgacaca    180
```

```
aattttgggt cccttgcata cgcgtcccac agccttacgg agtatcagcg actgctctcc    240
accaatgctg cccgcgactc ctactgcttg tccgctgttt ttggttccgg aagctgctgg    300
ggacagtcag gctggctggt gtgaaagtcc ggtaggagat gtcgggctcg tctgtgtacc    360
aggagctgcg gtgcagggac ggcaggctgc cgttcacctg gtccg                   405
```

<210> SEQ ID NO 285
<211> LENGTH: 892
<212> TYPE: DNA
<213> ORGANISM: Homo sapiens
<220> FEATURE:
<221> NAME/KEY: misc_feature
<222> LOCATION: (27)..(27)
<223> OTHER INFORMATION: a or g or c or t/u
<220> FEATURE:
<221> NAME/KEY: misc_feature
<222> LOCATION: (35)..(35)
<223> OTHER INFORMATION: a or g or c or t/u
<220> FEATURE:
<221> NAME/KEY: misc_feature
<222> LOCATION: (42)..(42)
<223> OTHER INFORMATION: a or g or c or t/u
<220> FEATURE:
<221> NAME/KEY: misc_feature
<222> LOCATION: (49)..(49)
<223> OTHER INFORMATION: a or g or c or t/u
<220> FEATURE:
<221> NAME/KEY: misc_feature
<222> LOCATION: (831)..(831)
<223> OTHER INFORMATION: a or g or c or t/u
<220> FEATURE:
<221> NAME/KEY: misc_feature
<222> LOCATION: (835)..(835)
<223> OTHER INFORMATION: a or g or c or t/u

<400> SEQUENCE: 285

```
gagtttcgag cttctctttt cctaagngaa aaaanaaaga ancacaagna aaccaaataa     60
ccatgttact ctgtataaaa atgctaatca gggaattctg aatcaataat gctccaatga    120
aggacagaat ttaattagaa acaacactaa ccacaagagc ctagcacaac ccaaactcag    180
agcttcctgg taatctcaat gcgatggatt cattacacag accatcttat taaaattctc    240
atctgagagc taatcagcat tgaatgcatc atttatttta tgacaccaaa attaactgca    300
gtgattcttt aagcatgggg acacgtgact cccactctca gccccgaggg atgacagcca    360
agagcctggc ttctgcccaa gattccatcc gttttggtct gcagtgcatg gtcaaccatg    420
atccacaaag cagcaacccg ggggctgtag ctgccgtgat gcggggtaa gcctggcagg     480 ctgcaactgt tgcagggctc ccaacacagc ccctggacaa acgcgtcagg ggaaaatagg    540
gttacctggc aatcttttc ctctcctttt cttccgcttc ttctttctga gcagtgttca     600
gactttcagc atcagccaaa gtgtctacag cgatggccaa gaagacattc agtagaatat    660
ctaattacaa cttttttaagg gcacaacaca ctactaaatg caactacgtg cggccaacaa    720
tggcaacgcc acacacctct gcatcccggg aagctgggta gtaggtgacg tccccaagtg    780
ttatactcac acagcaaacc tagagtacca gagccctgct tttcaaacaa nacanaacaa    840
acaaacaacc caaagtaaaa cctggtaagg gacgtcttca gaagtaaatt ac            892
```

<210> SEQ ID NO 286
<211> LENGTH: 425
<212> TYPE: DNA
<213> ORGANISM: Homo sapiens

<400> SEQUENCE: 286

```
ctggctttcc catagcacgc tcggcaggaa agcaagtgat gcccctggct cccatctcac    60
acaggtgaca ctgcaccgag aggtaacgtg gccctcacag cccaccacgc ctggccttcg   120
cccaattctg aaacttcgta ggatagagct ggaaagtggc acatggtgaa gcgagatcca   180
gctgtctggg tggatgtcgg agctccatag gctgagcaga gatggttctt agtgaggttc   240
tcgctgccag ttgacggtga aatcatagct gccatttaca ttttgtgaga ttatgaaaaa   300
cataagacta aagaaactaa atgtgttatt cctgtggaca caaaaatgtg tgttttcag    360 atggggaggg gaccaaaaag gaaaaacatt tcatcttaaa actttcctaa gacaaaggaa   420
aacaa                                                               425
```

<210> SEQ ID NO 287  
<211> LENGTH: 441  
<212> TYPE: DNA  
<213> ORGANISM: Homo sapiens  
<220> FEATURE:  
<221> NAME/KEY: misc_feature  
<222> LOCATION: (10)..(10)  
<223> OTHER INFORMATION: a or g or c or t/u
<400> SEQUENCE: 287

```
ctcagcatgn atgaaacagg atgaggttgg tgaagatgtg gtggttgatg agcttgtggc    60
agcctacgcg gatcgggttg gtcttgctaa gaatgaagaa agcgctccct tcagggatgg   120
gggcaatttt ttccttcatg ttcaactccg agatccttcg aggacggggt ccggcaggaa   180
cctcaggttc atcctcctcc tcttcctctt cctcttcccc tacgggcaca tcgcaaggcg   240 gatagggtc cttgtcttca tcctcttctc tatagtcatc aattgtaacc ttgttgtcac    300
tgttggctat ctggttgact tctggtttgt tgttctttt attttctagg ctctcttttc    360
tggcaatctt tttcctctcc ttttcttccg cttcttcttt ctgagcagtg ttcagacttt   420
cagcatcagc caaatggtct a                                             441
```

<210> SEQ ID NO 288  
<211> LENGTH: 165  
<212> TYPE: DNA  
<213> ORGANISM: Homo sapiens
<400> SEQUENCE: 288

```
tcaaagtcga aggaggatct ccgcgtggga tgctggggtg ggaggtagta ggcgtctcct    60
tggagatctc cgtgaatcat agcaaacggg cgagtcatcg tcctacaaga atcctagtgg   120
atgatggtag cctcggggcc tctcagagtc gatgtttctg cctgg                   165
```

<210> SEQ ID NO 289  
<211> LENGTH: 330  
<212> TYPE: DNA  
<213> ORGANISM: Homo sapiens
<400> SEQUENCE: 289

```
ctcgcccgtt tgctatgagt cacggagatc tccaaggaga cgcctactac ctcccacccc    60
agcatcccac cggagatcct ccttcaactt tgagtgcctg cgccggcaga gcagccagga   120
agaggtcccg tcgtctccca tcttccccca tcgcacggcc ctgcctctgc atctaatgca   180
gcaacagatc atggcagttg ccggcctaga ttcaagtaaa gcccagaagt actcaccgag   240
tcactcgacc cggccgtggg ccaccccctcc agcaacccct ccctaccggg actggacacc   300
gtgctacacc ccccagatga cgccgatgta                                    330
```

```
<210> SEQ ID NO 290
<211> LENGTH: 401
<212> TYPE: DNA
<213> ORGANISM: Homo sapiens

<400> SEQUENCE: 290
ccaggcagaa acatcgactc tgagaggccc cgaggctacc atcatcccca aggattcttg      60
gaggacgatg actcgcccgt ttgctatgat tcacggagat ctccaaggag acgcctacta    120
cctcccaccc cagcatccca ccggagatcc tccttcaact tgagtgcct gcgccggcag     180 agcagccagg aagaggtccc gtcgtctccc atcttccccc atcgcacggc cctgcctctg    240
catctaatgc agcaacagat catggcagtt gccggcctag attcaagtaa agcccagaag    300
tactcaccga gtcactcgac ccggtcgtgg gccacccctc cagcaacccc tccctaccgg    360
gactggacac cgtgctacac cccccagatg acgccgatgt a                        401

<210> SEQ ID NO 291
<211> LENGTH: 431
<212> TYPE: DNA
<213> ORGANISM: Homo sapiens
<220> FEATURE:
<221> NAME/KEY: misc_feature
<222> LOCATION: (321)..(321)
<223> OTHER INFORMATION: a or g or c or t/u
<220> FEATURE:
<221> NAME/KEY: misc_feature
<222> LOCATION: (354)..(355)
<223> OTHER INFORMATION: a or g or c or t/u
<220> FEATURE:
<221> NAME/KEY: misc_feature
<222> LOCATION: (373)..(373)
<223> OTHER INFORMATION: a or g or c or t/u
<220> FEATURE:
<221> NAME/KEY: misc_feature
<222> LOCATION: (401)..(401)
<223> OTHER INFORMATION: a or g or c or t/u

<400> SEQUENCE: 291
tacatcggcg tcatctgggg ggtgtagcac ggtgtccagt cccggtaggg aggggttgct      60
ggaggggtgg cccacgaccg ggtcgagtga ctcggtgagt acttctgggc tttacttgaa    120
tctaggccgg caactgccat gatctgttgc tgcattagat gcagaggcag ggccgtgcga    180
tgggggaaga tgggagacga cgggacctct tcctggctgc tctgccggcg caggcactca    240
aagttgaagg aggatctccg gtgggatgct ggggtggag gtagtaggcg tctccttgga    300
gatctccgtg aatcatagca nacgggcgag tcatcgtcct ccaagaatcc ttgnngatga    360
tggtagcctc ggngcctctc agagtcgatg tttctgcctg ngtatctgct cgggcgagcc    420
ggtaccgagc t                                                          431

<210> SEQ ID NO 292
<211> LENGTH: 330
<212> TYPE: DNA
<213> ORGANISM: Homo sapiens

<400> SEQUENCE: 292
tacatcggcg tcatctgggg ggtgtagcac ggtgtccagt cccggtaggg aggggttgct      60
ggaggggtgg cccacgaccg ggtcgagtga ctcggtgagt acttctgggc tttacttgaa    120
tctaggccgg caactgccat gatctgttgc tgcattagat gcagaggcag ggccgtgcga    180
tgggggaaga tgggagacga cgggacctct tcctggctgc tctgccggcg caggcactca    240
aagttgaagg aggatctccg gtgggatgct ggggtggag gtagtaggcg tctccttgga    300
```
gatctccgtg aatcatagca aacgggcgag                                        330

<210> SEQ ID NO 293
<211> LENGTH: 183
<212> TYPE: DNA
<213> ORGANISM: Homo sapiens
<220> FEATURE:
<221> NAME/KEY: misc_feature
<222> LOCATION: (42)..(42)
<223> OTHER INFORMATION: a or g or c or t/u
<220> FEATURE:
<221> NAME/KEY: misc_feature
<222> LOCATION: (70)..(70)
<223> OTHER INFORMATION: a or g or c or t/u
<220> FEATURE:
<221> NAME/KEY: misc_feature
<222> LOCATION: (133)..(133)
<223> OTHER INFORMATION: a or g or c or t/u

<400> SEQUENCE: 293
gcggacagct tggtggaggc agtcctgata tccgaagcct tnggacgcta tgcaagggac       60
ccaaaatttn tttcagcaac aaaacacgaa atcgctgatg cctgtaacct caccatcgac      120
gagatggaga gtncagccag caccctgctt aatgggaacg tgcgtccccg agccaacggg      180
gat                                                                    183

<210> SEQ ID NO 294
<211> LENGTH: 132
<212> TYPE: DNA
<213> ORGANISM: Homo sapiens

<400> SEQUENCE: 294
aagaaatagg aggataagaa tatcatattt cagagctgcc ctggcacagt acctgccccg       60
tcggaggctc tcactggcaa atgacagctc tgtgcaagga gcactcccaa gtataaaaat      120
tattacacag tt                                                          132

<210> SEQ ID NO 295
<211> LENGTH: 358
<212> TYPE: DNA
<213> ORGANISM: Homo sapiens

<400> SEQUENCE: 295
ccattggtac gagagaaatt aggaggataa gattatctat tattctgagc tgccctggca       60
cagtacctgc cccgtcggag gctctcactg gcaaatgaca gctctgtgca aggagcactc      120
ccaagtataa aaattattac atagttttat tctgaagaac attttgcatt ttaataaaaa      180
aggatttatg tcaggaaaga gtcatttaca taccttgaat tgttttttgcc tggatcagag     240 taagaatgtc ttaagaagag gtttgtaagg tcttcataac aaagtggtgt tgttatttta      300 caaaaaaaa aaaaaaaaa atttttatac cgggtttgtc tgtatacaaa tttctctg          358

<210> SEQ ID NO 296
<211> LENGTH: 289
<212> TYPE: DNA
<213> ORGANISM: Homo sapiens

<400> SEQUENCE: 296
tccagagtag aagaaatcag ccaagtatca tttattcagc gaaaatcctc tggggattaa       60
aattttaagt ttgaaagaac ttgcactac agaaattttt ctaaatatt ttgagtcact        120 ataaacctat catctttcca caagatatac cagatgacta tttgcagtct ttctttggg       180 caagagttcc atgattttga tactgtacct ttggatccac catgggttgc aactgtcttt      240

<210> SEQ ID NO 297
<211> LENGTH: 889
<212> TYPE: DNA
<213> ORGANISM: Homo sapiens

<400> SEQUENCE: 297

```
gggattccccc cggctgggtg gggagagcga gctgggtgcc cccatagatt cccctgcccg        60
aacctcatga gccgaccctc ggctccatgg agcccggaaa ttatgccacc ttggatggag       120
ccaaggatat cgaaggcttg ttgggagcgg agggggggcg gaatctggtc gcccactccc       180
tctctgacca gccacccagc gcgctacgct tgatgcctgt gtcaatatgc ccccttgatc       240
tgccaggctc ggggagcggc caaaagcaat gcccaccta tgctctgggg gtgcccaggg       300
gactgtcccc ggctccgtgc cttatggtta ctgtggggcg gggtacatac tcctgcagag       360
ttgtcccgga gctcgttgaa accttgtgcc gaggagagcc accctggcgg tacccggaa       420
gactccccag ggcgggaaga gtaccccagc ggcccaatga gttgtgcttc tatcgggata       480
tccgggacct accaggccta tgtgcaggta ctggacgtgt cctgtgctgc agactctggg       540
tgtccgtgga gcaccggaca ttggctcgct gtggcctgtg gccggtacca gtcttgggct       600
ctcggtgtgt ggctggacac gccggttgtg ttcgcgggag accgcaccca ccaggttcct       660
ttgggagggc cgcttttgcag actccggggg aggcccctct gaggcggggc cttttcgggg       720
gggcgaagaa agctttccga cgcaggcgct tgcggagctg gcgggacatc gggacacttc       780
acccagcgaa gcgcggcttg ggcccctct gggcgcggtc tcggttgaca ccggcgaaga       840
gtttcgggag aggcccatat cttctgggga gggcgttgcg tcgcccccg                    889
```

<210> SEQ ID NO 298
<211> LENGTH: 1356
<212> TYPE: DNA
<213> ORGANISM: Homo sapiens

<400> SEQUENCE: 298

```
ggattccccc ggcctgggtg gggagagcga gctgggtgcc cctagattc cccgcccccg         60
cacctcatga gccgaccctc ggctccatgg agcccggcaa ttatgccacc ttggatggag       120
ccaaggatat cgaaggcttg ctgggagcgg agggggggcg gaatctggtc gcccactccc       180
ctctgaccag ccacccagcg gcgcctacgc tgatgcctgc tgtcaactat gccccccttgg      240
atctgccagg ctcggcggag ccgccaaagc aatgccaccc atgccctggg gtgccccagg       300
ggacgtcccc agctcccgtg ccttatggtt actttggagg cgggtactac tcctgccgag       360
tgtcccggag ctcgctgaaa ccctgtgccc aggcagccac cctggccgcg tacccgcgg        420
agactcccac ggccggggaa gagtacccca gccgcccccac tgagtttgcc ttctatccgg      480
gatatccggg aacctaccag cctatggcca gttacctgga cgtgtctgtg gtgcagactc       540
tgggtgctcc tggagaaccg cgacatgact ccctgttgcc tgtggacagt taccagtctt       600
gggctctcgc tggtggctgg aacagccaga tgtgttgcca gggagaacag aacccaccag       660
gtcccttttg gaaggcagca tttgcagact ccagcgggca gcaccctcct gacgcctgcg       720
cctttcgtcg cggccgcaag aaacgcattc cgtacagcaa ggggcagttg cgggagctgg       780
agcgggagta tgcggctaac aagttcatca ccaaggacaa gaggcgcaag atctcggcag       840
ccaccagcct ctcggagcgc cagattacca tctggtttca gaaccgccgg gtcaaagaga       900
```

| | |
|---|---|
| agaaggttct cgccaaggtg aagaacagcg ctacccctta agagatctcc ttgcctgggt | 960 |
| gggaggagcg aaagtggggg tgtcctgggg agaccaggaa cctgccaagc ccaggctggg | 1020 |
| gccaaggact ctgctgagag gcccctagag acaacaccct tcccaggcca ctggctgctg | 1080 |
| gactgttcct caggagcggc ctgggtaccc agtatgtgca gggagacgga accccatgtg | 1140 |
| acagcccact ccaccagggt tcccaaagaa cctggcccag tcataatcat tcatcctgac | 1200 |
| agtggcaata atcacgataa ccagtactag ctgccatgat cgttagcctc atattttcta | 1260 |
| tctagagctc tgtagagcac tttagaaacc gctttcatga attgagctaa ttatgaataa | 1320 |
| atttggaaaa aaaaaaaaaa aaaaaaaaaa aaaaaa | 1356 |

<210> SEQ ID NO 299
<211> LENGTH: 727
<212> TYPE: DNA
<213> ORGANISM: Homo sapiens

<400> SEQUENCE: 299

| | |
|---|---|
| attccccgg cctgggtggg gagagcgagc tgggtgcccc ctagattccc cgcccccgca | 60 |
| cctcatgagc cgaccctcgg ctccatggag cccggcaatt atgccacctt ggatggagcc | 120 |
| aaggatatcg aaggcttgct gggagcggga gggggcgga atctggtcgc ccactcccct | 180 |
| ctgaccagcc acccagcggc gcctacgctg atgcctgctg tcaactatgc ccccttggat | 240 |
| ctgccaggct cggcggagcc gccaaagcaa tgccacccat gccctggggt gccccagggg | 300 |
| acgtccccag ctcccgtgcc ttatggttac tttggaggcg ggtactactc ctgccgagtg | 360 |
| tcccggagct cgctgaaacc ctgtgcccag gcagccaccc tggccgcgta ccccgcggag | 420 |
| actcccacgg ccggggaaga gtaccccagc cgccccactg agtttgcctt ctatccggga | 480 |
| tatccgggaa cctaccagcc tatggccagt tacctggacg tgtctgtggt gcagactctg | 540 |
| ggtgctcctg gagaaccgcg acatgactcc ctgttgcctg tggacagtta ccagtcctgg | 600 |
| gctctcgctg gtggctggaa cagccagatg tgttgccagg gagaacagaa cccaccaggt | 660 |
| ccccttttgg aaggcagcat ttgcagactc cagcgggcag caccctcctg acgcctgcgc | 720 |
| cttttcgt | 727 |

<210> SEQ ID NO 300
<211> LENGTH: 793
<212> TYPE: DNA
<213> ORGANISM: Homo sapiens

<400> SEQUENCE: 300

| | |
|---|---|
| gcaggcgact tgcgagctgg gagcgattta aaacgctttg gattcccccg gcctgggtgg | 60 |
| ggagagcgag ctgggtgccc cctagattcc ccgcccccgc acctcatgag ccgaccctcg | 120 |
| gctccatgga gcccggcaat tatgccacct tggatggagc caaggatatc gaaggcttgc | 180 |
| tgggagcggg agggggcgg aatctggtcg cccactcccc tctgaccagc cacccagcgg | 240 |
| cgcctacgct gatgcctgct gtcaactatc ccccttgga tctgccaggc tcggcggagc | 300 |
| cgccaaagca atgccaccca tgccctgggg tgcccagggg acgtcccca gctcccgtgc | 360 |
| cttatggtta ctttgaggc gggtactact cctgccgagt gtcccggagc tcgctgaaac | 420 |
| cctgtgccca ggcagccacc ctggccgcgt accccgcgga gactcccacg gccggggaag | 480 |
| agtaccccag ccgccccact gagtttgcct tctatccggg atatccggga acctaccagc | 540 |
| ctatggccag ttacctggac gtgtctgtgg tgcagactct gggtgctcct ggagaaccgc | 600 |
| gacatgactc cctgttgcct gtggacagtt accagtcttg ggctctcgct ggtggctgga | 660 |

| | |
|---|---|
| acagccagat gtgttgccag ggagaacaga agccaccagg tcccttttgg aaggcagcat | 720 |
| ctgcagactc cagcgggcag gacctcctga cgcctgcggc ctttcgtcgc gagcgcaaga | 780 |
| aacgcattcc gta | 793 |

<210> SEQ ID NO 301
<211> LENGTH: 759
<212> TYPE: DNA
<213> ORGANISM: Homo sapiens

<400> SEQUENCE: 301

| | |
|---|---|
| ggatttaaaa cgctttggat tcccccggcc tgggtgggga gagcgagctg ggtgcccct | 60 |
| agattccccg cccccgcacc tcatgagccg accctcggct ccatggagcc cggcaattat | 120 |
| gccaccttgg atggagccaa ggatatcgaa ggcttgctgg gagcgggagg ggggcggaat | 180 |
| ctggtcgccc actcccctct gaccagccac ccagcggcgc ctacgctgat gcctgctgtc | 240 |
| aactatgccc ccttggatct gccaggctcg gcggagccgc caaagcaatg ccacccatgc | 300 |
| cctggggtgc cccagggacg tccccagctc ccgtgcctta tggttacttt ggaggcgggt | 360 |
| actactcctg ccgagtgtcc cggagctcgc tgaaaccctg tgcccaggca gccaccctgg | 420 |
| ccgcgtaccc cgcggagact cccacggccg gggaagagta ccccagccgc cccactgagt | 480 |
| ttgccttcta tccgggatat ccgggaacct accagcctat ggccagttac ctggacgtgt | 540 |
| ctgtggtgca gactctgggt gctcctggag aaccgcgaca tgactccctg ttgcctgtgg | 600 |
| acagttacca gtcttgggct ctcgctggtg ggctggaaca gccagatgtg ttgccagcgc | 660 |
| agaacagaac ccaccaggtc ccttttggaa ggcagcattt gcagactcca gcgggcagaa | 720 |
| ccctcctgac gcctgcgcct ttcgttcgcg ggcgaaaaa | 759 |

<210> SEQ ID NO 302
<211> LENGTH: 614
<212> TYPE: DNA
<213> ORGANISM: Homo sapiens

<400> SEQUENCE: 302

| | |
|---|---|
| aagaaacgca ttccgtacag caaggggcag ttgcgggagc tggagcggga gtatgcggct | 60 |
| aacaagttca tcaccaagga caagaggcgc aagatctcgg cagccaccag cctctcggag | 120 |
| cgccagatta ccatctggtt tcagaaccgc cgggtcaaag agaagaaggt tctcgccaag | 180 |
| gtgaagaaca gcgctacccc ttaagagatc tccttgcctg ggtgggagga gcgaaagtgg | 240 |
| gggtgtcctg gggagaccag gaacctgcca agcccaggct ggggcaagg actctgctga | 300 |
| gaggccccta gagacaacac ccttcccagg ccactggctg ctggactgtt cctcaggagc | 360 |
| ggcctgggta cccagtatgt gcaggagac ggaaccccat gtgacagccc actccaccag | 420 |
| ggttcccaaa gaacctggcc cagtcataat cattcatcct gacagtggca ataatcacga | 480 |
| taaccagtac tagctgccat gatcgttagc ctcatatttt ctatctagag ctctgtagag | 540 |
| cactttagaa accgctttca tgaattgagc taattatgaa taaatttgga aggcgaaaaa | 600 |
| aaaaacctcg tgcc | 614 |

<210> SEQ ID NO 303
<211> LENGTH: 318
<212> TYPE: DNA
<213> ORGANISM: Homo sapiens

<400> SEQUENCE: 303

```
attcggcacg aggttttttt tttcgccttc caaatttatt cataattagc tcaattcatg      60
aaagcggttt ctaaagtgct ctacagagct ctagatagaa aatatgaggc taacgatcat     120
ggcagctagt actggttatc gtgattattg ccactgtcag gatgaatgat tatgactggg     180
ccaggttctt tgggaaccct ggtggagtgg gctgtcacat ggggttccgt ctccctgcac     240
atactgggta cccaggccgc tcctgaggaa cagtccagca accagtggcc tgggaagggt     300
gttgtctcta ggggcctc                                                   318
```

<210> SEQ ID NO 304  
<211> LENGTH: 1483  
<212> TYPE: DNA  
<213> ORGANISM: Homo sapiens
<400> SEQUENCE: 304

```
gggtggggag agcgagctgg gtgcccccta gattccccgc ccccgcacct catgagccga      60
ccctcggctc catggagccc ggcaattatg ccaccttgga tggagccaag gatatcgaag     120
gcttgctggg agcgggaggg gggcggaatc tggtcgccca ctcccctctg accagccacc     180
cagcggcgcc tacgctgatg cctgctgtca actatgcccc cttggatctg ccaggctcgg     240
cggagccgcc aaagcaatgc cacccatgcc ctggggtgcc caggggacg tccccagctc      300 ccgtgcctta tggttacttt ggaggcgggt actactcctg ccgagtgtcc cggagctcgc     360
tgaaaccctg tgccaggcag ccaccctggc cgcgtaaccc gacggagact ctcacgtgcg     420
gggaagagta cccctagcgc cccacatgag tttgccttct atccgggata tccgggaccg     480
taccagccta tggcagttac ctggacgtgt ctgtggtgcc gactctgggt gctcctggag     540
aaccgcggac atgactcctt gtttgctgtg cgacgctcac cagtctgggc tcctcgtcgg     600
tggtcgcact cccactttt gccgggcgac atccccgggg gcccttccg gaacagcgac       660 cttgcgagcc cccggggaca caccccgta agcggcctat catcgctgat aaacctcatc      720
agagggcacc gaaagccgcg actctaaccc ccccactacg actcacgacc gcacaggtac     780
tcgaaccgcc caatatctgg ttctaaccca tggcgcatct cagccgctag agagccaacc     840
aaacgcgcca cgcgcaacca cactacacca cggcacccct ttcatctcac tcccacgccg     900
atcactcttc accctccaga atcattcccc tcgcacatcc tacctatctc atgcctccca     960
gttcacccca ttccctcccc taatctcacc cacacattca cgcacgttct cactacgctt    1020
cgctccgacc cacatcctca cccccacatt cataccactt caccatcacg ccccccccct    1080
ctcatcgact cctgtctcat tctcaaccac agtactacca gctccaacac accactcacc    1140
ccaagctatc catcacctac acgctttcac ccctcaccgc tcccaagtaa ttcagatcac    1200
tcaaacacaa tctgctacat actcatccct ccccactcc cagtacagtc caaccaccga    1260
ccaactacct ccgcgccacc cgcgccgccc cacctcaccg gccccaaccg cccgcacagg    1320
gcacgcaccc cccggcaacc gcgcgatccg gccgtacaca ctcttgggcg gcacgcagct    1380
gaggacattc cgcgggagcg ccccaccgtg ggctacgtgg gtcgcgaccc ggcggggcgc    1440
gtgcggcgtc gcccgcccgc ccgccgactg cgacccagtc gag                     1483
```

<210> SEQ ID NO 305  
<211> LENGTH: 758  
<212> TYPE: DNA  
<213> ORGANISM: Homo sapiens  
<220> FEATURE:  
<221> NAME/KEY: misc_feature  
<222> LOCATION: (561)..(561)  
<223> OTHER INFORMATION: a or g or c or t/u
<220> FEATURE:
<221> NAME/KEY: misc_feature
<222> LOCATION: (656)..(656)
<223> OTHER INFORMATION: a or g or c or t/u

<400> SEQUENCE: 305

| | | | | | |
|---|---|---|---|---|---|
| ggggctttgg | attccccgg | cctgggtggg | gagagcgagc | tgggtgcccc | ctagattccc | 60 |
| cgcccccgca | cctcatgagc | cgaccctcgg | ctccatggag | cccggcaatt | atgccacctt | 120 |
| ggatggagcc | aaggatatcg | aaggcttgct | gggagcggga | gggggcgga | atctggtcgc | 180 |
| ccactcccct | ctgaccagcc | acccagcggc | gcctacgctg | atgcctgctg | tcaactatgc | 240 |
| cccttggat | ctgccaggct | cggcggagcc | gccaaagcaa | tgccacccat | gccctggggt | 300 |
| gccccagggg | acgtccccag | ctcccgtgcc | ttatggttac | tttggaggcg | ggtactactc | 360 |
| ctgccgagtg | tcccggagct | cgctgaaacc | ctgtgcccag | gcagccaccc | tggccgcgta | 420 |
| ccccgcggag | actcccacgg | ccggggaaga | gtaccccagc | cgccccactg | agtttgcctt | 480 |
| ctatccggga | tatccgggaa | cctaccagcc | tatggccagt | tacctggacg | tgtctgtggt | 540 |
| gcagactctg | ggtgctcctg | nagaaccgcg | acatgactcc | ctgttgcctg | tggacagtta | 600 |
| ccagtcttgg | gctctcgctg | gtggcctgga | acagcccaga | tgtgtttgcc | cagggnagaa | 660 |
| cacgaacccc | acccggttcc | ccctttttggg | aaagggcagc | cattttggcc | agccttccaa | 720 |
| gcggggccaa | ccaccccctc | ccctggacag | gccctggt | | | 758 |

<210> SEQ ID NO 306
<211> LENGTH: 476
<212> TYPE: DNA
<213> ORGANISM: Homo sapiens

<400> SEQUENCE: 306

| | | | | | |
|---|---|---|---|---|---|
| gcggccgcaa | gaaacgcatt | ccgtacagca | aggggcagtt | gcgggactgg | agcgggagta | 60 |
| tgcggctaac | aagttcatca | ccaaggacaa | gaggcgcaag | atctcggcag | ccaccagcct | 120 |
| ctcggagcgc | cagattacca | tctggtttca | gaaccgccgg | gtcaaagaga | agaaggttct | 180 |
| cgccaaggtg | aagaacagcg | ctaccccttta | agagatctcc | ttgcctgggt | gggaggagcg | 240 |
| aaaagtggggg | tgtcctgggg | agaccaggaa | cctgccaagc | ccaggctggg | gccaaggact | 300 |
| ctgctgagag | gccctagag | acaacaccct | tcccaggcca | ctggctgctg | gactgttcct | 360 |
| caggagcggc | ctgggtaccc | agtatgtgca | gggagacgga | accccatgtg | acagcccatt | 420 |
| ccaccagggt | tcccaaagaa | cctggcccag | tcataatcat | tcatcctgac | agtggc | 476 |

<210> SEQ ID NO 307
<211> LENGTH: 552
<212> TYPE: DNA
<213> ORGANISM: Homo sapiens

<400> SEQUENCE: 307

| | | | | | |
|---|---|---|---|---|---|
| agcggccgca | agaaacgcat | tccgtacagc | aaggggcagt | gcgggagct | ggagcgggag | 60 |
| tatgcggcta | acaagttcat | caccaaggac | aagaggcgca | agatctcggc | agccaccagc | 120 |
| ctctcggagc | gccagattac | catctggttt | cagaaccgcc | gggtcaaaga | gaagaaggtt | 180 |
| ctcgccaagg | tgaagaacag | cgctacccct | taagagatct | ccttgcctgg | gtgggaggag | 240 |
| cgaaagtggg | ggtgtcctgg | ggagaccagg | aacctgccaa | gcccaggctg | ggccaagga | 300 |
| ctctgctgag | aggcccctag | agacaacacc | cttcccaggc | cactggctgc | tggactgttc | 360 |
| ctcaggagcg | gcctgggtac | ccagtatgtg | cagggagacg | gaaccccatg | tgacagccca | 420 |

```
ctccaccagg gttcccaaag aacctggccc agtcataatc attcatcctg acagtggcaa      480
taatcacgat aaccagtact agctgccatg atcgttagcc tcatattttc tatctagagc      540
tctgtagagc ac                                                          552
```

<210> SEQ ID NO 308
<211> LENGTH: 447
<212> TYPE: DNA
<213> ORGANISM: Homo sapiens

<400> SEQUENCE: 308

```
gcggccgcaa gaaacgcatt ccgtacagca aggggcagtt gcgggactgg agcgtgagta       60
tgcggctaac aagttcatca ccaaggacaa gaggcgcaag atctcggcag ccaccagcct      120
ctcggagcgc cagattacca tctggtttca gaaccgccgg gtcaaagaga agaaggttct      180
cgccaaggtg aagaacagcg ctaccccttta agagatctcc ttgcctgggt gggaggagcg      240
aaagtggggg tgtcctgggg agaccaggaa cctgccaagc ccaggctggg gccaaggact      300
ctgctgagag gccctagag acaacaccct tcccaggcca ctggctgctg gactgttcct      360
caggagcggc tgggtaccc agtatgtgca gggagacgga accccatgtg acagcccact      420 ccaccaggt tcccaagaa cctggcc                                            447
```

<210> SEQ ID NO 309
<211> LENGTH: 418
<212> TYPE: DNA
<213> ORGANISM: Homo sapiens

<400> SEQUENCE: 309

```
tttttttttt ttttttttc gccttccaaa tttattcata attagctcaa ttcatgaaag       60
cggtttctaa agtgctctac aaagctctaa ataaaaaata tgaggctaac gatcatggca      120
gctagtactg gttatcggga ttattgccac tgtcaggatg aatgattatg actgggccag      180
gttctttggg aaccctggtg gagtgggctg tcacatgggg ttccgtctcc ctgcacatac      240
tgggtaccca ggccgttcct gaggaacagt ccaccaccca gtggcctggg aagggtgttg      300
tctctagggg cctctcaaca aagtccttgg ccccagcctg gcttggcag gttcctggtc      360 tccccaggac accccactt tcgctcctcc cacccaggca aggagatctc ttaaggggg       418
```

<210> SEQ ID NO 310
<211> LENGTH: 405
<212> TYPE: DNA
<213> ORGANISM: Homo sapiens
<220> FEATURE:
<221> NAME/KEY: misc_feature
<222> LOCATION: (6)..(6)
<223> OTHER INFORMATION: a or g or c or t/u
<220> FEATURE:
<221> NAME/KEY: misc_feature
<222> LOCATION: (380)..(380)
<223> OTHER INFORMATION: a or g or c or t/u

<400> SEQUENCE: 310

```
gacgcnaggt atgcggctaa caagttcatc accaaggaca gaggcgcaa gatctcggca       60 gccaccagcc tctcggagcg ccagattacc atctggtttc agaaccgccg gtcaaagag      120 aagaaggttc tcgccaaggt gaagaacagc gctacccctt aagagatctc cttgcctggg      180
tgggaggagc gaaagtgggg gtgtcctggg gagaccagga acctgccaag cccaggctgg      240
ggccaaggac tctgctgaga ggcccctaga gacaacaccc ttcccaggcc actggctgct      300
ggactgttcc tcaggagcgg cctgggtacc catgtatgtg cagggagacg gaaccccatg      360
```

```
tgacagccca ctccaccagn gttcctaaag aaccctggcc agtca            405
```

<210> SEQ ID NO 311
<211> LENGTH: 369
<212> TYPE: DNA
<213> ORGANISM: Homo sapiens
<220> FEATURE:
<221> NAME/KEY: misc_feature
<222> LOCATION: (301)..(301)
<223> OTHER INFORMATION: a or g or c or t/u
<220> FEATURE:
<221> NAME/KEY: misc_feature
<222> LOCATION: (318)..(318)
<223> OTHER INFORMATION: a or g or c or t/u

<400> SEQUENCE: 311

```
gcaggcgact tgcgagctgg gagcggttta aaacgctttg gattccccg gcctgggtgg    60
ggagagcgag ctgggtgccc cctagattcc ccgccccgc acctcatgag ccgaccctcg   120
gtccatggac acggcaatta tgccaccttg gatggagcca aggatatcga aggcttgctg   180
ggagcgggag gggggcggaa tctggtcgcc cactcccctc tgaccagcca cccagcggcg   240
cctacgctga tgcctgctgt caactatgcc cccttggatc tgccaggctc ggcggactct   300
naaagcatat gccacccnat gccctggggt gccccagggg aacgtcccca gctcccgtgc   360
cttatggtt                                                          369
```

<210> SEQ ID NO 312
<211> LENGTH: 374
<212> TYPE: DNA
<213> ORGANISM: Homo sapiens

<400> SEQUENCE: 312

```
gcggccgcaa gaaacgcatt ccgtacagca aggggcagtt gcgggagctg gagcgggagt    60
atgcggctaa caagttcatc accaaggaca agaggcgcaa gatctcggca gccaccagcc   120
tctcggagcg ccagattacc atctggtttc agaaccgccg ggtcaaagag aagaaggttc   180
tcgccaaggt gaagaacagc gctaccccctt aagagatctc cttgcctggg tgggaggagc   240
gaaagtgggg gtgtcctggg gagaccagga acctgccaag cccaggctgg ggccaaggac   300
tctgctgaga ggcccctaga cacaacaccc ttcccaggcc actggctgct ggactgttcc   360
tcaggagcgg cctg                                                    374
```

<210> SEQ ID NO 313
<211> LENGTH: 337
<212> TYPE: DNA
<213> ORGANISM: Homo sapiens

<400> SEQUENCE: 313

```
gtcgacgaac agcgctaccc cttaagagat ctccttgcct gggtgggagg agcgaaagtg    60
ggggtgtcct ggggagaccg gaactgcca gcccaggct ggggcaagga ctctgctgag   120
aggcccctag acaacaccc cttcccaggc cactgctgct ggactgttcc tcaggagcgg   180
cctgggtacc cagtatgtgc agggagacgg aaccccatgt gacagcccac tccaccaggg   240
ttcccaaaga acctggccca gtcataatca ttcatcctga cagtggcaat aatcacgata   300
accagtactc agctgccatg atcgttagcc tcatatt                           337
```

<210> SEQ ID NO 314
<211> LENGTH: 452
<212> TYPE: DNA

<213> ORGANISM: Homo sapiens

<400> SEQUENCE: 314

| | | | | | |
|---|---|---|---|---|---|
| gcgtcgaccc | cttgaagaga | tctccttgcc | tgggtgggag | gagcgaaagt | gggggtgtcc | 60 |
| tggggagacc | aggaacctgc | caagcccagg | ctggggccaa | ggactctgct | gagaggcccc | 120 |
| tagagacaac | acccttccca | ggccactggc | tgctggactg | ttcctcagga | gcggcctggg | 180 |
| tacccagtat | gtgcagggag | acggaacccc | atgtgacagc | ccactccacc | agggttccca | 240 |
| aagaacctgg | cccagtcata | atcattcatc | ctgacagtgg | caataatcac | gataaccagt | 300 |
| actagctgcc | atgatcgtta | gcctcatatt | ttctatctag | agctctgtag | agcacttgta | 360 |
| gaaaccgctt | tcatgaattg | agctaattat | gaatagattt | ggaagggaa | aaaagtggaa | 420 |
| aaagttttgc | ccaaagtggg | tcgtttacgt | cg | | | 452 |

<210> SEQ ID NO 315
<211> LENGTH: 358
<212> TYPE: DNA
<213> ORGANISM: Homo sapiens

<400> SEQUENCE: 315

| | | | | | |
|---|---|---|---|---|---|
| ctccctggca | acacatctgg | ctgttccagc | accagcgaga | cccaagactg | gtaactgtcc | 60 |
| acaggcaaca | gggagtcatg | tcgcggttct | ccaggagcac | ccagagtctg | caccacagac | 120 |
| acgtccaggt | aactggccat | agctgagtag | gttcccggat | atcccggata | gaaggcaaac | 180 |
| tcagtggggc | ggctggggta | ctcttccccg | gccgtggaga | gtctccgcgg | ggtacggccc | 240 |
| agggtggctg | cctgggcatc | agggtttcag | cgagctccgg | acactcggc | aggagtagta | 300 |
| cccgcctcca | aagtaaccat | aaggcacggg | agctggggac | gtccctgggg | caccccag | 358 |

<210> SEQ ID NO 316
<211> LENGTH: 474
<212> TYPE: DNA
<213> ORGANISM: Homo sapiens

<400> SEQUENCE: 316

| | | | | | |
|---|---|---|---|---|---|
| tttaaaacgc | tttggattcc | cccggcctgg | gtggggagag | cgagctgggt | gccccctaga | 60 |
| ttccccgccc | ccgcacctca | tgagccgacc | ctcggtccat | ggagccggcg | aattatgcca | 120 |
| ccttggatgg | agccaaggat | atcgaaggct | tgctgggagc | gggaggggg | cggaatctgg | 180 |
| tcgcccactc | ccctctgacc | agccacccag | cggcgctacg | tgatgcctgc | tgtcaactat | 240 |
| gcccttggat | ctgccagctc | gcggagccaa | agcaatgcca | cccatgccct | ggggtgcccc | 300 |
| aggtgacgtc | cccagctccc | gtgccttatg | gttactttgg | aggcgggtac | tactcctgcc | 360 |
| gagtgtcccg | gagctcgctg | aaaccctgtg | cccaggcagc | caccctggcc | gcgtaccccg | 420 |
| cgatgactcc | cacggccggg | gaagagtacc | ccagccgccc | cactgagttt | gcct | 474 |

<210> SEQ ID NO 317
<211> LENGTH: 739
<212> TYPE: DNA
<213> ORGANISM: Homo sapiens
<220> FEATURE:
<221> NAME/KEY: misc_feature
<222> LOCATION: (616)..(616)
<223> OTHER INFORMATION: a or g or c or t/u
<220> FEATURE:
<221> NAME/KEY: misc_feature
<222> LOCATION: (678)..(678)
<223> OTHER INFORMATION: a or g or c or t/u
<220> FEATURE:
<221> NAME/KEY: misc_feature

```
<222> LOCATION: (730)..(730)
<223> OTHER INFORMATION: a or g or c or t/u

<400> SEQUENCE: 317
caggcgactt gcgagtctgg gagcgattta aaacgctttg gattccccg gcctgggtgg       60 ggagagcgag ctgggtgccc cctagattcc ccgccccgc acctcatgag ccgaccctcg      120
gctccatgga gcccggcaat tatgccacct tggatggagc caaggatatc gaaggcttgc    180
tgggagcggg aggggggcgg aatctggtcg cccactcccc tctgaccagc acccagcgg     240 cgcctacgct gatgcctgct gtcaactatg cccccttgga tctgccaggc tcggcggagc    300
cgccaaagca atgccaccca tgccctgggg tgccccaggg gacgtcccca gctcccgtgc   360
cttatggtta ctttggaggc gggtactact cctgccgagt gtcccggagc tcgctgaaac    420
cctgtgccca ggcagccacc ctggccgcgt acccgcgga gactcccacg gccggggaag    480
agtaccccag ccgccccact gagtttgcct tctatccggg atatccggga acctaccagc    540
ctatggccag ttaccttgga cgtgtctgtg gtgcagactc tgggtgctcc tggagaaccg   600
cgacatgact ccctgntgcc tgtggacagt taccagtctt gggctctcgc tggtggctgg    660
aacagccaga tgtgttgnca gggagaacag aacccaccag gtccctttg gaaggcagat     720 ttgcagactn cagcgggca                                                  739

<210> SEQ ID NO 318
<211> LENGTH: 924
<212> TYPE: DNA
<213> ORGANISM: Homo sapiens

<400> SEQUENCE: 318
aggcagccac cctggccgcg taccccgcgg agactcccac ggccggggaa gagtacccca       60
gccgccccac tgagtttgcc ttctatccgg gatatccggg aacctaccag cctatggcca    120
gttacctgga cgtgtctgtg gtgcagactc tgggtgctcc tggagaaccg cgacatgact    180
ccctgttgcc tgtggacagt taccagtctt gggctctcgc tggtggctgg aacagccaga    240
tgtgttgcca gggagaacag aacccaccag gtccctttg gaaggcagca tttgcagact     300
ccagcgggca gcaccctcct gacgcctgcg cctttcgtcg cggccgcaag aaacgcattc    360
cgtacagcaa ggggcagttg cgggagctgg agcgggagta tgcggctaac aagttcatca    420
ccaaggacaa gaggcgcaag atctcggcag ccaccagcct ctcggagcgc cagattacca    480
tctggtttca gaaccgccgg gtcaaagaga agaaggttct cgccaaggtg aagaacagcg    540 ctaccccta agagatctcc ttgcctgggt gggaggagcg aaagtggggg tgtcctgggg   600
agaccaggaa cctgccaagc cccaggctgg ggccaaggac tctgctgaga ggcccctaga   660
gacaacaccc ttcccaggcc actggctgct ggactgttcc tcaggagcgg cctgagtacc   720
ccgtatgtgc aggggagacg gaaccccctg tgaccagccc cctccaccc gtggtctccc   780 agataacctg gccccactc ataaatcatt tcttcccggg ccggggcca atcattcccc    840 gaactacccc ggtaccttat acaattagat tggacatgaa tcctctcggg ggcattccct   900
atggcgctga ggcccctcac acct                                          924

<210> SEQ ID NO 319
<211> LENGTH: 566
<212> TYPE: DNA
<213> ORGANISM: Homo sapiens
<220> FEATURE:
<221> NAME/KEY: misc_feature
<222> LOCATION: (421)..(421)
```

```
<223> OTHER INFORMATION: a or g or c or t/u
<220> FEATURE:
<221> NAME/KEY: misc_feature
<222> LOCATION: (541)..(541)
<223> OTHER INFORMATION: a or g or c or t/u

<400> SEQUENCE: 319
gggtgctgtc ctctggagtc tgcaaatgct gccttccaaa agggacctgg tgggttctgt      60
tctccctggc aacacatctg gctgttccag ccaccagcga gagcccaaga ctggtaactg     120
tccacaggca acagggagtc atgtcgcggt tctccaggag cacccagagt ctgcaccaca     180
gacacgtcca ggtaactggc cataggctgg taggttcccg gatatcccgg atagaaggca     240
aactcaatgg ggcggctggg gtactcttcc ccggccgtgg gagtctccgc ggggtacgcg     300
gccagggtgg ctgcctgggc acagggtttc agcgagctcc gggacactcg gcaggagtag     360
tacccgcctc caaagtaacc ataaggcacg ggagctgggg acgtcccctg ggcaccccca     420
nggcatgggt ggcattgctt tggcggctcc gccgagcctg gcagatccaa ggggggcatag    480 ttgacagcag gcatcagcgt aggcgccgct gggtggctgg tcaaaaggga gtggcgacca    540
nattccgccc ccctcccgct tcccag                                          566

<210> SEQ ID NO 320
<211> LENGTH: 526
<212> TYPE: DNA
<213> ORGANISM: Homo sapiens
<220> FEATURE:
<221> NAME/KEY: misc_feature
<222> LOCATION: (472)..(472)
<223> OTHER INFORMATION: a or g or c or t/u
<220> FEATURE:
<221> NAME/KEY: misc_feature
<222> LOCATION: (501)..(501)
<223> OTHER INFORMATION: a or g or c or t/u

<400> SEQUENCE: 320
gggtgctgcc cgctggagtc tgcaaatgct gccttccaaa agggacctgg tgggttctgt      60
tctccctggc aacacatctg gctgttccag ccaccagcga gagcccagga ctggtaactg     120
tccacaggca acagggagtc atgtcgcggt tctccaggag cacccagagt ctgcaccaca     180
gacacgtcca ggtaactggc cataggctgg taggttcccg gatatcccgg atagaaggca     240
aactcagtgg ggcggctggg gtactcttcc ccgccgtggg agtctccgcg gggtacgcgg     300
ccagggtggc tgcctgggca cagggtttca gcgagctccg ggacactcgg caggagtagt     360
acccgcctcc aaagtaacca taaggcacgg gagctgggga cgtcccctgg gcaccccag     420 ggcatgggtg gcattgctt ggcggctccg ccgagcctgg cagatccaag gnggcatagt     480
tgacagcagg catcagcgta ngcgccgctg ggtggctgtc aagagg                   526

<210> SEQ ID NO 321
<211> LENGTH: 471
<212> TYPE: DNA
<213> ORGANISM: Homo sapiens

<400> SEQUENCE: 321
tcgacgttac ctggacgtgt ctgtggtgca gactctgggt gctcctggag aaccgcgaca      60
tgactccctg ttgcctgtgg acagttacca gtcttgggct ctcgctggtg gctggaacag     120
cagatgtgtt gccagggaga acagaaccca ccaggtccct tttggaaggc agcatttgca     180
gactccagcg ggcagcaccc tcctgacgcc tgcgcctttc gtcgcggccg caagaaacgc     240
attccgtaca gcaaggggca gttgcgggac tggagcggga gtatgcggct aacaagttca     300
```

```
tcaccaagga caagaggcgc aagatctcgg cagccaccag cctctcggag cgccagatta    360
ccatctggtt tcagaaccgc cgggtcaaag agaagaaggt tctcgccaag gtgaagaaca    420
gcgctacccc ttaagagatc tccttgcctg ggtgggagga gcgaaagtgt g             471
```

<210> SEQ ID NO 322
<211> LENGTH: 545
<212> TYPE: DNA
<213> ORGANISM: Homo sapiens
<220> FEATURE:
<221> NAME/KEY: misc_feature
<222> LOCATION: (427)..(427)
<223> OTHER INFORMATION: a or g or c or t/u

<400> SEQUENCE: 322

```
gtcaggaggg tgctgcccgc tggagtctgc aaatgctgcc ttccaaaagg gacctggtgg     60
gttctgttct ccctggcaac acatctggct gttccagcca ccagcgagag cccaggactg    120
gtaactgtcc acaggcaaca gggagtcatg tcgcggttct ccaggagcac ccagagtctg    180
caccacagac acgtccaggt aactggccat aggctggtag gttcccggat atcccggata    240
gaaggcaaac tcagtggggc ggctggggta ctcttccccg gccgtgggag tctccgcggg    300
gtacgcggcc agggtggctg cctgggcaca gggtttcagc gagctccggg acactcggca    360
tgagtagacc cgccttccaa gtaaccataa ggcacgggag ctggtaacgt cccctggggc    420
accccanggc catgggtgca ttgctttggc ggctccgccg agccctgcag atccaaggtg    480
ggcatattga cagcaggcat tcacgtatgc gcccccggg tggctgtcat attggggatt     540
gcgac                                                                545
```

<210> SEQ ID NO 323
<211> LENGTH: 438
<212> TYPE: DNA
<213> ORGANISM: Homo sapiens
<220> FEATURE:
<221> NAME/KEY: misc_feature
<222> LOCATION: (366)..(366)
<223> OTHER INFORMATION: a or g or c or t/u
<220> FEATURE:
<221> NAME/KEY: misc_feature
<222> LOCATION: (375)..(375)
<223> OTHER INFORMATION: a or g or c or t/u
<220> FEATURE:
<221> NAME/KEY: misc_feature
<222> LOCATION: (415)..(415)
<223> OTHER INFORMATION: a or g or c or t/u
<220> FEATURE:
<221> NAME/KEY: misc_feature
<222> LOCATION: (419)..(420)
<223> OTHER INFORMATION: a or g or c or t/u

<400> SEQUENCE: 323

```
gcaggcgtca ggagggtgct gcccgctgga gtctgcaaat gctgccttcc aaagggacc      60 tggtgggttc tgttctccct ggcaacacat ctggctgttc cagccaccag cgagagccca    120
agactggtaa ctgtccacag gcaacaggga gtcatgtcgc ggttctccag gagcacccag    180
agtctgcacc acagacacgt ccaggtaact ggccataggc tggtaggttc ccggatatcc    240
cggatagaag gcaaactcag tggggcgact ggggtactct tccccggccgt ggggagtctc    300 cgcggggtac gcggccaggg gtggctgcct gggcaccagg ggtttcagcg agctccggga    360
cactcngcag gaaantagta cccgcctccc aaagtaacca taagcaccgg actgngggnn    420
ggacgtcccc tggggcac                                                  438
```

<210> SEQ ID NO 324
<211> LENGTH: 370
<212> TYPE: DNA
<213> ORGANISM: Homo sapiens

<400> SEQUENCE: 324

| | |
|---|---|
| gcgaccggac gaaaggaggc gtcaggaggg tgctgcccgc tggagtctgc aaatgctgcc | 60 |
| ttccaaaagg gacctggtgg gttctgttct ccctggcaac acatctggct gttccagcac | 120 |
| cagcgagacc caagactggt aactgtccac aggcaacagg gagtcatgtc gcggttctcc | 180 |
| aggagcaccc agagtctgca ccacagacac gtccaggtaa ctggccatag ctaggtaggt | 240 |
| tcccggatat cccggataga aggcaaactc agtggggcga ctggggtact cttccccggc | 300 |
| cgtgggagtc tccgcggggt acgcccatgg gtggctgcct gggcacaggg tttcagcgag | 360 |
| ctccgggaca | 370 |

<210> SEQ ID NO 325
<211> LENGTH: 495
<212> TYPE: DNA
<213> ORGANISM: Homo sapiens

<400> SEQUENCE: 325

| | |
|---|---|
| gcaggcgtca ggagggtgct gcccgctgga gtctgcaaat gctgccttcc aaaagggacc | 60 |
| tggtgggttc tgttctccct ggcaacacat ctggctgttc cagccaccag cgagagccca | 120 |
| agactggtaa ctgtccacag gcaacaggga gtcatgtcgc ggttctccag gagcacccag | 180 |
| agtctgcacc acagacacgt ccaggtaact ggccataggc tggtaggttc ccggatatcc | 240 |
| cggatagaag gcaaactcag tggggcgact ggggtactct tccccggccg tgggagtctc | 300 |
| cgcggggtac gcggccaggg tggctgcctg ggcacagggt tcagcgagc tccgggacac | 360 |
| tcggcaggag tagtacccgc ctccaaagta accataaggc acgggagctg gatgcgtccc | 420 |
| ctagggcacc ccatggcatg ggtggcattg ctttggcggc tccgccgagc ctggcagatc | 480 |
| caaggaggca ctgtt | 495 |

<210> SEQ ID NO 326
<211> LENGTH: 408
<212> TYPE: DNA
<213> ORGANISM: Homo sapiens

<400> SEQUENCE: 326

| | |
|---|---|
| gggtgctgcc cgctggagtc tgcaaatgct gccttccaaa agggacctgg tgggttctgt | 60 |
| tctccctggc aacacatctg ctgttccag ccaccagcga gacccaagac tggtaactgt | 120 |
| ccacaggcaa cagggagtca tgtcgcggtt ctccaggagc acccagagtc tgcaccacag | 180 |
| acacgtccag gtaactggcc ataggctggt aggttcccgg atatcccgga tagaaggcaa | 240 |
| actcagtggg gcggctgggg tactcttccc cggccgtggg agtctccgcg ggtacgcgt | 300 |
| ccagggtggc tgcctgggca cagggtttca gcgagctccg gacactcgg caggagtagt | 360 |
| acccgcctcc aaagtaacca taaggcacgg gagctgggga cgtccctg | 408 |

<210> SEQ ID NO 327
<211> LENGTH: 344
<212> TYPE: DNA
<213> ORGANISM: Homo sapiens

<400> SEQUENCE: 327

| | |
|---|---|
| gggtgctgcc cgctggagtc tgcaaatgct gccttccaaa agggacctgg tgggttctgt | 60 |

```
tctccctggc aacacatctg gctgttccag ccaccagcga gacccaagac tggtaactgt     120
ccacaggcaa cagggagtca tgtcgcggtt ctccaggagc acccagagtc tgcaccacag     180
acacgtccag gtaactggcc ataggtggta ggttcccgga tatcccggat agaaggcaaa     240
ctcagtgggg cggctggggt actcttcccc ggccgtggga gtctccgcgg ggtacgcggc     300
cagggtggct gcctgggcac agggtttcag cgagctccgg gaca                     344

<210> SEQ ID NO 328
<211> LENGTH: 334
<212> TYPE: DNA
<213> ORGANISM: Homo sapiens

<400> SEQUENCE: 328
gggtgctgcc cgctggagtc tgcaaatgct gccttccaaa agggacctgg tgggttctgt      60
tctccctggc aacacatctg gctgttcctg ccaccagcga gagcccaaga ctggtaactg     120
tccacaggca acaggagtc atgtcgcggt tctccaggag cacccagagt ctgcaccaca     180
gacacgtcca ggtaactggc cataggctgg taggttcccg gatatcccgg atagaaggca     240
aactcagtgg ggcggctggg gtactcttcc ccggccgtgg gagtctccgc ggggtacgcg     300
gccagggtgg ctgcctgggc acagggtttc agcg                                334

<210> SEQ ID NO 329
<211> LENGTH: 288
<212> TYPE: DNA
<213> ORGANISM: Homo sapiens
<220> FEATURE:
<221> NAME/KEY: misc_feature
<222> LOCATION: (207)..(207)
<223> OTHER INFORMATION: a or g or c or t/u

<400> SEQUENCE: 329
gggtgctgcc cgctggagtc tgcaaatgct gccttccaaa agggacctgg tgggttctgt      60
tctccctggc aacacatctg gctgttccag ccaccagcga gacccaagac tggtaactgt     120
ccacaggcaa cagggagtca tgtcgcggtt ctccaggagc acccagagtc tgcaccacag     180
acacgtccag gtaactggcc ataggtnggt aggttcccgg atatcccgga tagaaggcaa     240
actcagtggg gcggctgggg tactcttccc cggccgtggg agtctccg                  288

<210> SEQ ID NO 330
<211> LENGTH: 343
<212> TYPE: DNA
<213> ORGANISM: Homo sapiens
<220> FEATURE:
<221> NAME/KEY: misc_feature
<222> LOCATION: (238)..(238)
<223> OTHER INFORMATION: a or g or c or t/u
<220> FEATURE:
<221> NAME/KEY: misc_feature
<222> LOCATION: (300)..(300)
<223> OTHER INFORMATION: a or g or c or t/u
<220> FEATURE:
<221> NAME/KEY: misc_feature
<222> LOCATION: (321)..(321)
<223> OTHER INFORMATION: a or g or c or t/u

<400> SEQUENCE: 330
ctccctggca acacatctgg ctgttccagc accagcgaga gccaagactg gtaactgtcc      60
acaggcaaca gggagtcatg tcgcggttct ccaggagcac ccagagtctg caccacagac     120
acgtccaggt aactggccat aggtcggtag gttcccggat atcccggata gaaggcaaac     180
```

```
tcagtggggc gactggggta ctcttccccg gccgtgggag tctccgcggg gtacggcnac    240
agggtggctg cctgggcaca gggtttcagc gagctccggg acactcggca ggagtagtan    300
ccgcctcaaa gtaaccataa ngcacgggag ctggggacgt ccc                      343

<210> SEQ ID NO 331
<211> LENGTH: 441
<212> TYPE: DNA
<213> ORGANISM: Homo sapiens
<220> FEATURE:
<221> NAME/KEY: misc_feature
<222> LOCATION: (379)..(379)
<223> OTHER INFORMATION: a or g or c or t/u

<400> SEQUENCE: 331
acgaaaggcg caggcgtcag gagggtgctg cccgctggag tctgcaaatg ctgccttcca    60
aaagggacct ggtgggttct gttctccctg gcaacacatc tggctgttcc agccaccagc  120
gagagcccaa gactggtaac tgtccacagg caacagggag tcatgtcgcg gttctccagg  180
agcacccaga gtctgcacca cagacacgtc caggtaactg ccataggct ggtaggttcc   240 cggatatccc ggatagaagg caaactcagt ggggcgactg gggtactctt ccccggcccg  300
gggagtctcc gcggggtacg cggccagggt ggctgcctgg gcacagggtt tcagcgagct  360
ccgggacact cggcggagnt agtacccgcc tccaaagtaa ccataaggca cgggagctgg  420
ggaaccgtcc cctggggcac c                                            441

<210> SEQ ID NO 332
<211> LENGTH: 729
<212> TYPE: DNA
<213> ORGANISM: Homo sapiens

<400> SEQUENCE: 332
gagcgagctg ggtgcccct agattccccg ccccgcacc tcatgagccg accctcggct     60
ccatggagcc cggcaattat gccaccttgg atggagccaa ggatatcgaa ggcttgctgg  120
gagcgggagg ggggcggaat ctggtcgccc actccctct gaccagccac ccagcggcgc   180
ctacgctgat gcctgctgtc aactatgccc ccttggatct gccaggctcg gcggagccgc  240
caaagcaatg ccacccatgc cctggggtgc cccagggacg tccccagctc ccgtgcctta  300
tggttacttt ggaggcgggt actactcctg ccgagtgtcc cggagctcgc tgaaaccctg  360
tgcccaggca gccaccctgg ccgcgtaccc cgcggagact cccacggccg gggaagagta  420
ccccagccgc cccactgagt ttgccttcta tccgggatat ccgggaacct accagcctat  480
ggccagttac ctggacgtgt ctgtggtgca gactctgggt gctcctggag aaccgcgaca  540
tgactccctg ttgcctgtgg acagttacca gtcttgggct ctcgctggtg gctggaacag  600
ccagatgtgt tgccagggag aacagaaccc accaggtccc tttttggaag gcagcatttg  660
cagactccag cggcaggacc tcctgaacgc ctgcgccttt cgtcgcggcg tctaaagtaa  720
tcctcgagg                                                          729

<210> SEQ ID NO 333
<211> LENGTH: 502
<212> TYPE: DNA
<213> ORGANISM: Homo sapiens
<220> FEATURE:
<221> NAME/KEY: misc_feature
<222> LOCATION: (301)..(301)
<223> OTHER INFORMATION: a or g or c or t/u
<220> FEATURE:
<221> NAME/KEY: misc_feature
```

```
<222> LOCATION: (479)..(479)
<223> OTHER INFORMATION: a or g or c or t/u

<400> SEQUENCE: 333
gcggccgcgg cccaccacca actgctcgcc accgaccccca ctactcgcca ccgacccgct      60
gctcggagct tcggttctgc ggggttgtcca gacttcaggc ctgtgcgctc aatcgtggag     120
aatgcgccgg caggcccccc acccccagcc taaggtgcag aaggaccag cacgaacccg      180 ctggctttgc tgcgcggcca ggagatgagt cccaccgggc actgagccca ggtacaggac      240
atcagagaat gaacacagag gcagaggccc tcatgtccct ctcagagtcc cggctctgca      300
nagagcccgt ctgtctccag cttccagaat tccgcactgt gaatctgtct acgtggactg      360
ggaaaacagg gttggcacca ctctgccact ccgtttgtgc ctgggaaggg ctaagtatgc      420
aaggctacaa acatctactt cactgggatc ccaaatgctc aacaaaccat gacctgctnt      480
ggtcagaacc accagaaata tt                                               502

<210> SEQ ID NO 334
<211> LENGTH: 282
<212> TYPE: DNA
<213> ORGANISM: Homo sapiens

<400> SEQUENCE: 334
gcaggcgact tgcgagctgg gagcacttta aaacgctttg gattccccccg gcctgggtgg      60 ggagagcgag ctgggtgccc cctagattcc ccgccccgc acctcatgag ccgaccctcg      120
gctccatgga gcctggcata ttatgccacc ttggtatgga gccaaggata tcgaaggctt      180
gctgggagcg ggaggggggc ggaatctggt cgcccactcc cctctgacca gccacccagc      240
ggcgcctacg ctgatgcctg ctgtcaacta tgcccccttg ga                         282

<210> SEQ ID NO 335
<211> LENGTH: 381
<212> TYPE: DNA
<213> ORGANISM: Homo sapiens
<220> FEATURE:
<221> NAME/KEY: misc_feature
<222> LOCATION: (201)..(201)
<223> OTHER INFORMATION: a or g or c or t/u

<400> SEQUENCE: 335
gcccgctgga gtctgcaaat gctgccttcc aaaagggacc tggtgggttc tgttctccct      60
ggcaacacat ctggctgttc cagccaccag cgagacgcca agactggtaa ctgtccacag     120
gcaacaggga gtcatgtcgc ggttctccag gagcacccag agtctgcacc acagacacgt     180
ccaggtaact ggccataggt nggtaggttc ccggatatcc cggatagaag gcaaactcag     240
tggggcggct ggggtactct tccccggccg tgggagtctc cgcggggtac gcgcacaggg      300
tggctgcctg ggcacagggt ttcagcgagc tccgggacac tcggcaggag tagtacccgc      360
ctccaaagta accataaggc a                                                381

<210> SEQ ID NO 336
<211> LENGTH: 405
<212> TYPE: DNA
<213> ORGANISM: Homo sapiens

<400> SEQUENCE: 336
aactgctcgc caccgacccc actactcgcc accgacccgc tgctcggagc ttcggttctg      60 cggggttgtcc agacttcagg cctgtgcgct caatcgtgga gaatgcgccg gcagccccca     120
```

| | |
|---|---|
| cccccagcct aaggtgcagg aaggaccagc acgaacccgc tggctttgct gcgcggccag | 180 |
| gagatgagtc ccaccgggca ctgagcccag gtacaggaca tcagagaatg aacacagagg | 240 |
| cagaggccct catgtccctc tcagagtccc ggctctgcaa agagcccgtc tgtctccagc | 300 |
| ttccagaatt ccgcactgtg aatctgtcta cgtggactgg gaaaacaggg ttggcaccac | 360 |
| tctgccactc cgtttgtgcc tgggaagggc taagtatgca aggct | 405 |

```
<210> SEQ ID NO 337
<211> LENGTH: 328
<212> TYPE: DNA
<213> ORGANISM: Homo sapiens

<400> SEQUENCE: 337
```

| | |
|---|---|
| gatcccttg cagggaagct ttctctcaga ccccttcca ttacacctct caccctggta | 60 |
| acagcaggaa gactgaggag aggggaacgg gcagattcgt tgtgtggctg tgatgtccgt | 120 |
| ttagcatttt tctcagctga cagctgggta ggtggacaat tgtagaggct gtctcttcct | 180 |
| ccctccttgt ccaccccata gggtgtaccc actggtcttg gaagcaccca tccttaatac | 240 |
| gatgattttt ctgtcgtgtg aaaatgaagc cagcaggctg ccctagtca gtccttcctt | 300 |
| ccagagaaaa agagatttga gaaagtga | 328 |

```
<210> SEQ ID NO 338
<211> LENGTH: 320
<212> TYPE: DNA
<213> ORGANISM: Homo sapiens

<400> SEQUENCE: 338
```

| | |
|---|---|
| ttttttttt tttttttttt cttttcact ttctcaaatc tcttttctc tggaaggaag | 60 |
| gactgactag gggcagcctg ctggcttcat tttcacacga caaaaaaatc atcgtattaa | 120 |
| ggatgggtgc ttccaaaacc agtgggtaca ccctatgggg gggacaagga gggaggaaga | 180 |
| gacagcctct acaattgtcc acctacccag ctgtcagctg agaaaaatgc taaacggaca | 240 |
| tcacagccac acaacgaatc tgcccgttcc cctctcctca gtcttcctgc tgttaccagg | 300 |
| gtgagaggtg taatggaagg | 320 |

```
<210> SEQ ID NO 339
<211> LENGTH: 321
<212> TYPE: DNA
<213> ORGANISM: Homo sapiens

<400> SEQUENCE: 339
```

| | |
|---|---|
| ttttttttt tttttttttt cttttcact ttcccaaatc tcttttctc tggaaggaag | 60 |
| gactgactag gggcagcctg ctggcttcat tttcacacga cagaaaaatc atcgtattaa | 120 |
| ggatgggtgc ttccaagacc agtgggtaca ccctatgggg tggacacagg agggaggaag | 180 |
| agacagcctc tacaattgtc cacctaccca gctgtcagct gagaaaaatg ctaaacggac | 240 |
| atcacagcca cacaacgaat ctgcccgttc ccctctcctc agtcttcctg ctgttaccag | 300 |
| ggtgagaggt gtaatggaag g | 321 |

```
<210> SEQ ID NO 340
<211> LENGTH: 354
<212> TYPE: DNA
<213> ORGANISM: Homo sapiens

<400> SEQUENCE: 340
```

| | |
|---|---|
| gcggccgcgg cccaccacca actgctcgcc accgacccca ctactcgcca ccgacccgct | 60 |

```
gctcggagct tcggttctgc gggttgtcca gacttcaggc ctgtgcgctc aatcttggag    120
aatgcgccgg caggcccccc accccccagcc taaggtgcag gaaggaccag cacgaacccg    180
ctggctttgc tgcgcggcca ggagatgagt cccaccgggc actgagccca ggtacaggac    240
atcagagaat gaacacagag gcagaggccc tcatgtccct ctcagagtcc cggctctgca    300
aagagcccgt ctgtctccag cttccagaat ccgcactgt gaatctgtct acgt            354
```

<210> SEQ ID NO 341
<211> LENGTH: 448
<212> TYPE: DNA
<213> ORGANISM: Homo sapiens

<400> SEQUENCE: 341

```
cacgcgtcga tcccagtgaa gtagatgttt gtagccttgc atacttagtc cttcccaggc     60
acaaacggag tggcagagtg gtgccaaccc tgttttccca gtccacgtag acagattcac    120
agtgcggaat tctggaagct ggagacagac gggctctttg cagagccggg actctgagag    180
ggacatgagg gcctctgcct ctgtgttcat tctctgatgt cctgtacctg gctcagtgc     240 ccggtgggac tcatctcctg gccgcgcagc aaagccagcg ggttcgtgct ggtccttcct    300
gcaccttagg ctgggggtgg ggggcctgcc ggcgcattct ccacgattga gcgcacaggc    360
ctgaagtctg gacaacccgc agaaccgaag ctccgagcag cgggtcggtg gcgagtagtg    420
gggtcggtgg cgagcagttg gtggtggg                                        448
```

<210> SEQ ID NO 342
<211> LENGTH: 223
<212> TYPE: DNA
<213> ORGANISM: Homo sapiens

<400> SEQUENCE: 342

```
tcgacctcgc caaggtgaag aacaacgcta ccccttaaga gatctccttg cctgggtggg     60
aggagcgaaa gtgggggtgt cctggggaga ccaggaacct gccaagccca ggctggggcc    120
aaggactctg ctgagaggcc cctagagaca acacccttcc caggccactg gctgctggac    180
tgttcctcag gagcggcctg ggtacccagt atgtgcaggg aga                       223
```

<210> SEQ ID NO 343
<211> LENGTH: 157
<212> TYPE: DNA
<213> ORGANISM: Homo sapiens

<400> SEQUENCE: 343

```
ttttttactg gttatcgtgg ttattgccac tgtcaggatg aatgattatg actgggccag     60
gttctttggg aaccctggtg gagtgggctg tcacatgggg ttccgtctcc ctgcacatac    120
tgggtaccca ggccgctcct gaggaacagt ccagcag                              157
```

<210> SEQ ID NO 344
<211> LENGTH: 344
<212> TYPE: DNA
<213> ORGANISM: Homo sapiens

<400> SEQUENCE: 344

```
ggcccaccac caactgctcg ccaccgaccc cactactcgc caccgacccg ctgctcggag     60
cttcggttct gcgggttgtc cagacttcag gcctgtgcgc tcaatcgtgg agaatgcgcc    120
ggcaggcccc ccacccccag cctaaggtgc aggaaggacc agcacgaacc cgctggcttt    180
```

```
gctgcgcggc aggagatga gtcccaccgg gcactgagcc caggtacagg acatcagaga    240
atgaacacag aggcagaggc cctcatgtcc ctctcagagt cccggctctg caaagagccc    300
gtctgtctcc agcttccaga attccgcact gtgaacctcg tgcc                    344

<210> SEQ ID NO 345
<211> LENGTH: 344
<212> TYPE: DNA
<213> ORGANISM: Homo sapiens

<400> SEQUENCE: 345
ggcacgaggt tcacagtgcg gaattctgga agctggagac agacgggctc tttgcagagc     60
cgggactctg agagggacat gagggcctct gcctctgtgt tcattctctg atgtcctgta    120
cctgggctca gtgcccggtg ggactcatct cctggccgcg cagcaaagcc agcgggttcg    180
tgctggtcct tcctgcacct taggctgggg gtgggggggcc tgccggcgca ttctccacga    240
ttgagcgcac aggcctgaag tctggacaac ccgcagaacc gaagctccga gcagcgggtc    300
ggtggcgagt agtggggtcg gtggcgagca gttggtggtg ggcc                    344

<210> SEQ ID NO 346
<211> LENGTH: 305
<212> TYPE: DNA
<213> ORGANISM: Homo sapiens

<400> SEQUENCE: 346
gctgctcgga gcttcggttc tgcgggttgt ccagacttca ggcctgtgcg ctcaatcgtg     60
gagaatgcgc cggcagcccc cacccccagc ctaaggtgca ggaaggacca gcacgaaccc    120
gctggctttg ctgcgcggcc aggagatgag tcccaccggc actgagccag gtacaggaca    180
tcagagaatg aacacagagg cagaggcctc atgtccctct cagagtcccg gctctgcaaa    240
gagccgtact gtctccagct tccagaattc cgcactgtga atctgtctac gtggactggg    300
aaaac                                                                305

<210> SEQ ID NO 347
<211> LENGTH: 687
<212> TYPE: DNA
<213> ORGANISM: Homo sapiens

<400> SEQUENCE: 347
cacgaggatt ttctatctag agctctgtag agcactttag aaaccgcttt catgaattga     60
gctaattatg aataaatttg gaaggcgatc cctttgcagg gaagctttct ctcagacccc    120
cttccattac acctctcacc ctggtaacag caggaagact gaggagaggg gaacgggcag    180
attcgttgtg tggctgtgat gtccgtttag cattttctc agctgacagc tgggtaggtg    240
gacaattgta gaggctgtct cttcctccct ccttgtccac cccatagggt gtacccactg    300
gtcttggaaa cacccatcct taatacgatg attttctgt cgtgtgaaaa tgaagccagc    360
aggctgcccc tagtcagtcc ttccttccag agaaaagag atttgagaaa gtgcctgggt    420
aattcaccat taatttcctc ccccaaactc tctgagtctt cccttaatat ttctggtggt    480
tctgaccaaa gcaggtcatg gtttgttgag catttgggat cccagtgaag tagatgtttg    540
tagccttgca tacttagccc ttcccaggca caaacggagt ggcagagtgg tgccaaccct    600
gttttcccag tccacgtaga cagattcaca gtgcggaatt ctggaagctg gagacagacg    660
ggctctttgc agagccggga ctctgag                                        687
```

<210> SEQ ID NO 348
<211> LENGTH: 687
<212> TYPE: DNA
<213> ORGANISM: Homo sapiens
<220> FEATURE:
<221> NAME/KEY: misc_feature
<222> LOCATION: (17)..(17)
<223> OTHER INFORMATION: a or g or c or t/u
<220> FEATURE:
<221> NAME/KEY: misc_feature
<222> LOCATION: (42)..(42)
<223> OTHER INFORMATION: a or g or c or t/u

<400> SEQUENCE: 348

| | | | | | |
|---|---|---|---|---|---|
| cacgaggatt | ttctatncta | gagctctggt | agagcacttt | anaaaccgct | ttcatgaatt | 60 |
| gagctaatta | tgaataaatt | tggaaggcga | tcccttttgca | gggaagcttt | ctctcagacc | 120 |
| cccttccatt | acacctctca | ccctggtaac | agcaggaaga | ctgaggagag | gggaacgggc | 180 |
| agattcgttg | tgtggctgtg | atgtccgttt | agcattttc | tcagctgaca | gctgggtagg | 240 |
| tggacaattg | tagaggctgt | ctcttcctcc | ctccttgtcc | accccatagg | gtgtacccac | 300 |
| tggtcttgga | aacacccatc | cttaatacga | tgattttct | gtcgtgtgaa | aatgaagcca | 360 |
| gcaggctgcc | cctagtcagt | ccttccttcc | agagaaaaag | agattgagaa | agtgcctggg | 420 |
| taattcacca | ttaatttcct | cccccaaact | ctctgagtct | tcccttaata | tttctggtgg | 480 |
| ttctgaccaa | agcaggtcat | ggtttgttga | gcatttggga | tcccagtgaa | gtagatgttt | 540 |
| gtagccttgc | atacttagcc | cttccaggc | acaaacggag | tggcagagtg | gtgccaaccc | 600 |
| tgttttccca | gtccacgtag | acagattcac | agtgcggaat | tctggaagct | ggagacagac | 660 |
| gggctctttg | cagagccggg | actctga | | | | 687 |

<210> SEQ ID NO 349
<211> LENGTH: 473
<212> TYPE: DNA
<213> ORGANISM: Homo sapiens

<400> SEQUENCE: 349

| | | | | | |
|---|---|---|---|---|---|
| cacgagggaa | gccagcaggc | tgcccctagt | cagtccttcc | ttccagagaa | aaagagattt | 60 |
| gagaaagtgc | ctgggtaatt | caccattaat | ttcctcccc | aaactctctg | agtcttccct | 120 |
| taatatttct | ggtggttctg | accaaagcag | gtcatggttt | gttgagcatt | tgggatccca | 180 |
| gtgaagtaga | tgtttgtagc | cttgcatact | tagcccttcc | caggcacaaa | cggagtggca | 240 |
| gagtggtgcc | aaccctgttt | tcccagtcca | cgtagacaga | ttcacagtgc | ggaattctgg | 300 |
| aagctgagga | cagacgggct | ctttgcagag | ccgggactct | gagagggaca | tgagggcctc | 360 |
| tgcctctgtg | ttcattctct | gatgtcctgt | acctgggctc | agtgcccggt | gggactcatc | 420 |
| tcctgggcgc | gcagcaaagc | cagcgggttc | gtgctggtcc | ttcctgcacc | tta | 473 |

<210> SEQ ID NO 350
<211> LENGTH: 514
<212> TYPE: DNA
<213> ORGANISM: Homo sapiens

<400> SEQUENCE: 350

| | | | | | |
|---|---|---|---|---|---|
| cacgaggcct | ggtaacagca | ggaagactga | ggagagggga | acgggcagat | tcgttgtgtg | 60 |
| gctgtgatgt | ccgtttagca | tttttctcag | ctgacagctg | ggtaggtgga | caattgtaga | 120 |
| ggctgtctct | tcctccctcc | ttgtccaccc | cataggtgt | acccactggt | cttgaaaaca | 180 |
| cccatcctta | atacgatgat | ttttctgtcg | tgtgaaaatg | aagccagcag | gctgccccta | 240 |

```
gtcagtcctt ccttccagag aaaaagagat ttgagaaagt gcctgggtaa ttcaccatta    300
atttcctccc ccaaactctc tgagtcttcc cttaatattt ctggtggttc tgaccaaagc    360
aggtcatggt ttgttgagca tttgggatcc cagtgaagta gatgtttgta gccttgcata    420
cttagccctt cccaggcaca aacggagtgg cagagtggtg ccaaccctgt tttcccagtc    480
cacgtagaca gattcacagt gcggaattct ggaa                               514
```

<210> SEQ ID NO 351
<211> LENGTH: 477
<212> TYPE: DNA
<213> ORGANISM: Homo sapiens

<400> SEQUENCE: 351

```
cacgaggtct tcccttaata tttctggtgg ttctgaccaa agcaggtcat ggtttgttga     60
gcatttggga tcccagtgaa gtagatgttt gtagccttgc atacttagcc cttcccaggc    120
acaaacggag tggcagagtg gtgccaaccc tgttttccca gtccacgtag acagattcac    180
agtgcggaat tctggaagct ggagacagac gggctctttg cagagccggg actctgagag    240
ggacatgagg gcctctgcct ctgtgttcat tctctgatgt cctgtacctg ggctcagtgc    300
ccggtgggac tcatctcctg gccgcgcagc aaagccagcg gttcgtgct ggtccttcct    360 gcaccttagg ctggggtgg ggggcctgcc ggcgcattct ccacgattga gcgcacaggc    420
ctgaagtctg gacaacccgc agaaccgaag ctccgagcag cgggtcggtg gcgagta      477
```

<210> SEQ ID NO 352
<211> LENGTH: 355
<212> TYPE: DNA
<213> ORGANISM: Homo sapiens

<400> SEQUENCE: 352

```
cacgaggatt tctggtggtt ctgaccaaag caggtcatgg tttgttgagc atttgggatc     60
ccagtgaagt agatgtttgt agccttgcat acttagccct tcccaggcac aaacggagtg    120
gcagagtggt gccaaccctg ttttcccagt ccacgtagac agattcacag tgcggaattc    180
tggaagctgg agacagacgg ctctttgca gagccgggac tctgagaggg acatgagggc    240
ctctgcctct gtgttcattc tctgatgtcc tgtacctggg ctcagtgccc ggtgggactc    300
atctcctggc cgcgcagcaa agccagcggg ttcgtgctgg tccttcctgc acctt        355
```

<210> SEQ ID NO 353
<211> LENGTH: 490
<212> TYPE: DNA
<213> ORGANISM: Homo sapiens

<400> SEQUENCE: 353

```
cacgaggaag gcgatcccct tgcagggaag ctttctctca gaccccttc cattacacct      60 ctcaccctgg taacagcagg aagactgagg agagggaac gggcagattc gttgtgtggc    120
tgtgatgtcc gtttagcatt tttctcagct gacagctggg taggtggaca attgtagagg    180
ctgtctcttc ctccctcctt gtccacccca tagggtgtac ccactggtct tggaaacacc    240
catccttaat acgatgattt ttctgtcgtg tgaaaatgaa gccagcaggc tgcccctagt    300
cagtccttcc ttccagagaa aaagagattt gagaaagtgc ctgggtaatt caccattaat    360
ttcctccccc aaactctctg agtcttccct taatatttct ggtggttctg accaaagcag    420
gtcatggttt gttgagcatt tgggatccca gtgaagtaga tgtttgtagc cttgcatact    480
tagcccttcc                                                         490
```

<210> SEQ ID NO 354
<211> LENGTH: 403
<212> TYPE: DNA
<213> ORGANISM: Homo sapiens

<400> SEQUENCE: 354

```
cacgaggtgg attcccccgg cctgggtggg gagagcgagc tgggtgcccc ctagattccc      60
cgccccgca cctcatgagc cgaccctcgg ctccatggag cccggcaatt atgccacctt     120
ggatggagcc aaggatatcg aaggcttgct gggagcggga gggggcgga atctggtcgc     180
ccactcccct ctgagcagcc acccagcggc gcctacgctg atgcctgctg tcaactatgc     240
ccccttggat ctgccaggct cggcggagcc gccaaagcaa tgccacccat gccctggggt     300
gccccagggg acgtccccag ctcccgtgcc ttatggttac tttggaggcg ggtactactc     360
ctgccgagtg tcgcggagct cgctgaaacc ctgtgcccag gca                       403
```

<210> SEQ ID NO 355
<211> LENGTH: 562
<212> TYPE: DNA
<213> ORGANISM: Homo sapiens
<220> FEATURE:
<221> NAME/KEY: misc_feature
<222> LOCATION: (533)..(533)
<223> OTHER INFORMATION: a or g or c or t/u

<400> SEQUENCE: 355

```
cacgaggatt ttctatctag agctctgtag agcactttag aaaccgcttt catgaattga      60
gctaattatg aataaatttg gaaggcgatc cctttgcagg gaagctttct ctcagacccc     120
cttccattac acctctcacc ctggtaacag caggaagact gaggagaggg gaacgggcag     180
attcgttgtg tggctgtgat gtccgtttag cattttctc agctgacagc tgggtaggtg     240
gacaattgta gaggctgtct cttcctccct ccttgtccac cccatagggt gtacccactg     300
gtcttggaaa cacccatcct taatacgatg atttttctgt cgtgtgaaaa tgaagccagc     360
aggctgcccc tagtcagtcc ttccttccag agaaaaagag atttgagaaa gtgcctgggt     420
aattcaccat taatttcctc ccccaaactc tctgagtctt cccttaatat ttctggtggt     480
tctgaccaaa gcaggtcatg gtttgttgag catttgggat cccagtgaag tanatgtttg     540
tagccttgca tacttagccc tt                                              562
```

<210> SEQ ID NO 356
<211> LENGTH: 463
<212> TYPE: DNA
<213> ORGANISM: Homo sapiens

<400> SEQUENCE: 356

```
cattttcaca cgactgtaaa atcatcgtat taaggatggg tgcttccaag accagtgggt      60
acaccctatg gggtggacaa ggagggagga agagacagcc tctacaattg tccacctacc     120
cagctgtcag ctgagaaaaa tgctaaacgg acatcacagc cacacaacga atctgcccgt     180
tcccctctcc tcagtcttcc tgctgttacc agggtgagag gtgtaatgga aggggtctg     240
agagaaagct tccctgcaaa gggatcgcct tccaaattta ttcataatta gctcaattca     300
tgaaagcggt ttctaaagtg ctctacagag ctctagatag aaaatatgag gctaacgatc     360
atggcagcta gtactggtta tcgtgattat tgccactgtc aggatgaatg attatgactg     420
ggccaggttc tttgggaacc ctggtggagt gggctgtcac atg                       463
```

<210> SEQ ID NO 357
<211> LENGTH: 198
<212> TYPE: DNA
<213> ORGANISM: Homo sapiens

<400> SEQUENCE: 357

```
tgcagctagt actggttatc gtgattattg ccactgtcag gatgaatgat tatgactggg      60
ccaggttctt tgggaaccct ggtggagtgg gctgtcacat ggggttccgt ctccctgcac     120
atactgggta cccaggccgc tcctgaggaa cagtccagca cagggtttca gcgagctccg     180
ggacactcgg cctcgtgc                                                   198
```

<210> SEQ ID NO 358
<211> LENGTH: 320
<212> TYPE: DNA
<213> ORGANISM: Homo sapiens

<400> SEQUENCE: 358

```
tttttttttt ttttttttt cttttcact ttctcaaatc tcttttctc tggaaggaag         60
gactgactag gggcagcctg ctggcttcat tttcacacca caaaaaaatc atcgtattaa     120
ggatgggtgc ttccaaaacc agtgggtaca ccctatgggg tggacaagga gggaggaaaa     180
aacagcctct acaattgtcc acctacccag ctgtcagctg aaaaaaatgc taaacggaca     240
tcacagccac acaacgaatc tgcccgttcc cctctcctca gtcttcctgc tgttaccagg     300
gtgaaaggtg taatggaagg                                                 320
```

<210> SEQ ID NO 359
<211> LENGTH: 421
<212> TYPE: DNA
<213> ORGANISM: Homo sapiens

<400> SEQUENCE: 359

```
accgacccca ctacttgcca ccgacccgct gctcggagct tcggttctgc gggttgtcca      60
gacttcaggc ctgtgcgctc aatcgtggag aatgcgccgg caggcccccc accccagcc     120
taaggtgcag gaaggaccag cacgaacccg ctggcttgc tgcgcggcca ggagatgagt      180
cccaccgggc actgagccca ggtacaggac atcagagaat gaacacagag gcagaggccc     240
tcatgtccct ctcagagtcc cggctctgca aagagcccgt ctgtctccag cttccagaat     300
tccgcactgt gaatctgtct acgtggactg ggaaaacagg gttggcacca ctctgccact     360
ccgtttgtgc ctgggaaggg ctaagtatgc aaggctacaa acatctactt cactgggatc     420
c                                                                     421
```

<210> SEQ ID NO 360
<211> LENGTH: 272
<212> TYPE: DNA
<213> ORGANISM: Homo sapiens

<400> SEQUENCE: 360

```
tttttttttt tttttccctg caaagggatc gccttccaaa tttattcata attagctcaa      60
ttcatgaaag cggtttctaa agtgctctac agagctctag atagaaaata tgaggctaac     120
gatcatggca gctagtactg gttatcgtga ttattgccac tgtcaggatg aatgattatg     180
actgggccag gttctttggg aaccctggtg gagtgggctg tcacatgggg ttccgtctcc     240
ctgcacatac tgggtaccca ggccgctcct ga                                   272
```

```
<210> SEQ ID NO 361
<211> LENGTH: 679
<212> TYPE: DNA
<213> ORGANISM: Homo sapiens

<400> SEQUENCE: 361
cacgaggcga cttgcgagct gggagcgatt taaaacgctt tggattcccc ggcctgggtg      60
gggagagcga gctgggtgcc ccctagattc cccgccccg cacctcatga gccgaccctc     120
ggctccatgg agcccggcaa ttatgccacc ttggatggag ccaaggatat cgaaggcttg     180
ctgggagcgg agggggggcg gaatctggtc gcccactccc ctctgaccag ccacccagcg     240
gcgcctacgc tgatgcctgc tgtcaactat gccccttgg atctgccagg ctcggcggag      300
ccgccaaagc aatgccaccc atgccctggg gtgcccagg ggacgtcccc agctcccgtg      360
ccttatggtt actttggagg cgggtactac tcctgccgag tgtcccggag ctcgctgaaa     420
ccctgtgccc aggcagccac cctggccgcg taccccgcgg agactcccac ggccggggaa     480
gagtacccca gccgcccac tgagtttgcc ttctatccgg gatatccggg aacctaccag      540
cctatggcca gttacctgga cgtgtctgtg gtgcagactc tgggtgctcc tggagaacgc     600
gacatgactc cctgttgcct gtggacagtt accagtcttg ggctctcgct ggtggctgga     660
acagccagat gtgttgcca                                                  679

<210> SEQ ID NO 362
<211> LENGTH: 393
<212> TYPE: DNA
<213> ORGANISM: Homo sapiens

<400> SEQUENCE: 362
gcggccgcgg cccaccacca actgctcgcc attcgacccc actactcgcc accgacccgc      60
tgctcggagc ttcggttctg cgggttgtcc agacttcagg cctgtgcgct caatcgtgga     120
gaatgcgccg gcaggccccc cacccccagc ctaaggtgca ggaaggacca gcacgaaccc     180
gctggctttg ctgcgcggcc aggagatgag tcccaccggg cactgagccc aggtacagga     240
catcagagaa tgaacacaga ggcagaggcc ctcatgtccc ctcagagtc ccggctctgc      300 aaagagcccg tctgtctcca gcttccagaa ttccgcactg tgaatctgtc tacgtggact     360
gggaaaacag ggttggcacc actctgccac tcc                                  393

<210> SEQ ID NO 363
<211> LENGTH: 504
<212> TYPE: DNA
<213> ORGANISM: Homo sapiens
<220> FEATURE:
<221> NAME/KEY: misc_feature
<222> LOCATION: (479)..(479)
<223> OTHER INFORMATION: a or g or c or t/u

<400> SEQUENCE: 363
gcggccgcgg cccaccacca actgctcgcc accgacccca ctactcgcca ccgacccgct      60
gctcggagct tcggttctgc gggttgtcca gacttcaggc ctgtgcgctc aatcgtggag     120
aatgcgccgg caggccccc accccagcc taaggtgcag gaaggaccag cacgaacccg      180
ctggctttgc tgcgcggcca ggagatgagt cccaccgggc actgagccca ggtacaggac     240
atcagagaat gaacacagag gcagaggccc tcatgtccct ctcagagtcc ggctctgca      300 aagagcccgt ctgtctccag cttccagaat tccgcactgt gaatctgtct acgtggactg     360
ggaaaacagg gttggcacca ctctgccact ccgtttgtgc ctgggaaggg ctaagtatgc     420
```

```
aaggctacaa acatctactt cactgggatc ccaaatgctc aacaaaccat gacctgctnt    480
ggtcagaacc accagaaata ttaa                                           504

<210> SEQ ID NO 364
<211> LENGTH: 451
<212> TYPE: DNA
<213> ORGANISM: Homo sapiens

<400> SEQUENCE: 364
gcggccgcgg cccaccacca actgctcgcc accgacccca ctactcgcca ccgacccgct     60
gctcggagct tcggttctgc gggttgtcca gacttcaggc ctgtgcgctc aatcgtggag    120
aatgcgccgg caggcccccc accccagcc taaggtgcag aaggaccag cacgaacccg     180 ctggctttgc tgcgcggcca ggagatgagt cccaccgggc actgagccca ggtacaggac    240
atcagagaat gaacacagag gcagaggccc tcatgtccct ctcagagtcc cggctctgca    300
aagagcccgt ctgtctccag cttccagaat tccgcactgt gaatctgtct acgtggactg    360
ggaaaacagg gttggcacca ctctgccact ccgtttgtgc ctgggaaggg ctaagtatgc    420
aaggctacaa acatctactt cactgggatc c                                   451

<210> SEQ ID NO 365
<211> LENGTH: 219
<212> TYPE: DNA
<213> ORGANISM: Homo sapiens

<400> SEQUENCE: 365
tcctccctct aagaaaggcg caagcgtcaa gagggtgctg cccgctggtt tctgcaaatg     60
ctgccttcca aaaaggacct ggtgggttct gttctccctg gcaacacatc tggctgttcc    120
agccaccagc gagagcccaa gactggtaac tgtccacagg caacagggag tcatgtcgcg    180
gttctccagg agcacccaga gtctgcacca cagacacgt                           219

<210> SEQ ID NO 366
<211> LENGTH: 699
<212> TYPE: DNA
<213> ORGANISM: Homo sapiens

<400> SEQUENCE: 366
ttaatacgat gattttctg tcgtgtgaaa atgaagccag caggctgccc ctagtcagtc      60
cttccttcca gagaaaaaga gatttgagaa agtgcctggg taattcacca ttaatttcct    120
cccccaaact ctctgagtct tcccttaata tttctggtgg ttctgaccaa agcaggtcat    180
ggtttgttga gcatttggga tcccagtgaa gtagatgttt gtagccttgc atacttagcc    240
cttcccaggc acaaacggag tggcagagtg gtgccaaccc tgttttccca gtccacgtag    300
acagattcac agtgcggaat tctggaagct ggagacagac gggctctttg cagagccggg    360
actctgagag ggacatgagg gcctctgcct ctgtgttcat tctctgatgt cctgtacctg    420
ggctcagtgc ccggtgggac tcatctcctg gccgcgcagc aaagccagcg ggttcgtgct    480
ggtccttcct gcaccttagg ctgggggtgg ggggcctgcc ggcgcattct ccacgattga    540
gcgcacaggc ctgaagtctg gacaacccgc agaaccgaag ctccgagcag cgggtcggtg    600
gcgagtagtg ggggtcggtg gcgaacaagt ggtggtgggc cggggccgca taactcgagg    660
actttcctcc cggagcagtc cctaaaaaacc cggggggcgc                         699

<210> SEQ ID NO 367
<211> LENGTH: 575
```

```
<212> TYPE: DNA
<213> ORGANISM: Homo sapiens

<400> SEQUENCE: 367
gacgaggaca attgtagagg ctgtctcttc ctccctcctt gtcaccccat agggtgtacc     60
actggtcttg gaagcaccca tccttaatac gatgattttt ctgtcgtgtg aaaatgaagc    120
cagcaggctg ccactagtca gtccttcctt ccagagaaaa agagatttga gaaagtgcct    180
gggtaattca ccattaattt cctcccccaa actctctgag tcttcccttta atatttctgg    240 tggttctgac caaagcaggt catggtttgt tgagcatttg ggatcccagt gaagtagatg    300
tttgtagcct tgcatactta gcccttccca ggcacaaacg gagtggcaga gtggtgccaa    360
ccctgttttc ccagtccacg tagacagatt cacagtgcgg aattctggaa gctggagaca    420
gacgggctct ttgcagagcc gggactctga gagggacatg agggcctctg cctctgtgtt    480
cattctctga tgtcctgtac ctgggctcag tgcccggtgg gactcatctc ctggccgcgc    540
agcaaagcca gcgggttcgt gctggtcctt cctgc                              575

<210> SEQ ID NO 368
<211> LENGTH: 684
<212> TYPE: DNA
<213> ORGANISM: Homo sapiens

<400> SEQUENCE: 368
cacgaggcga cttgcgagct gggagcgatt taaaacgctt tggattcccc cggcctgggt     60
ggggagagcg agctgggtgc cccctagatt ccccgccccc gcacctcatg agccgaccct    120
cggctccatg gagcccggca attatgccac cttggatgga gccaaggata tcgaaggctt    180
gctgggagcg ggaggggggc ggaatctggt cgcccactcc cctctgacca gccacccagc    240
ggcgcctacg ctgatgcctg ctgtcaacta tgccccttg gatctgccag gctcggcgga    300
gccgccaaag caatgccacc catgccctgg ggtgccccag gggacgtccc cagctcccgt    360
gccttatggt tactttggag gcgggtacta ctcctgccga gtgtcccgga gctcgctgaa    420
accctgtgcc caggcagcca ccctggccgt gtacccgcg gagactccca cggccgggga    480
agagtaccca gccgccccac tgagtttgcc ttctatccgg gatatccggg aacctaccag    540
cctatggcca gttacctgga cgtgtctgtg gtgcagactc tgggtgctcc tggagaacgc    600
gacatgactc cctgttgcct gtggacagtt accaatcttg ggctctcgct ggtggctgga    660
acagccagat gtgttgccag ggag                                          684

<210> SEQ ID NO 369
<211> LENGTH: 855
<212> TYPE: DNA
<213> ORGANISM: Homo sapiens

<400> SEQUENCE: 369
atggagcccg gcaattatgc caccttggat ggagccaagg atatcgaagg cttgctggga     60
gcgggagggg ggcggaatct ggtcgcccac tcccctctga ccagccaccc agcggcgcct    120
acgctgatgc ctgctgtcaa ctatgccccc ttggatctgc caggctcggc ggagccgcca    180
aagcaatgcc acccatgccc tggggtgccc caggggacgt ccccagctcc cgtgccttat    240
ggttactttg gaggcgggta ctactcctgc cgagtgtccc ggagctcgct gaaaccctgt    300
gcccaggcag ccaccctggc cgcgtacccc gcggagactc ccacggccgg ggaagagtac    360
cccagccgcc ccactgagtt tgccttctat ccgggatatc cgggaaccta ccagcctatg    420
```

```
gccagttacc tggacgtgtc tgtggtgcag actctgggtg ctcctggaga accgcgacat    480
gactccctgt tgcctgtgga cagttaccag tcttgggctc tcgctggtgg ctggaacagc    540
cagatgtgtt gccagggaga acagaaccca ccaggtccct tttggaaggc agcatttgca    600
gactccagcg ggcagcaccc tcctgacgcc tgcgcctttc gtcgcggccg caagaaacgc    660
attccgtaca gcaaggggca gttgcgggag ctggagcggg agtatgcggc taacaagttc    720
atcaccaagg acaagaggcg caagatctcg gcagccacca gcctctcgga gcgcagatt    780 accatctggt ttcagaaccg ccgggtcaaa gagaagaagg ttctcgccaa ggtgaagaac    840
agcgctaccc cttag                                                    855
```

<210> SEQ ID NO 370
<211> LENGTH: 1356
<212> TYPE: DNA
<213> ORGANISM: Homo sapiens

<400> SEQUENCE: 370

```
ggattccccc ggcctgggtg gggagagcga gctgggtgcc ccctagattc cccgccccg     60 cacctcatga gccgaccctc ggctccatgg agcccggcaa ttatgccacc ttggatggag    120
ccaaggatat cgaaggcttg ctgggagcgg aggggggcg gaatctggtc gcccactccc    180
ctctgaccag ccacccagcg gcgcctacgc tgatgcctgc tgtcaactat gccccttgg    240 atctgccagg ctcggcggag ccgccaaagc aatgccaccc atgccctggg gtgccccagg    300
ggacgtcccc agctcccgtg ccttatggtt actttggagg cgggtactac tcctgccgag    360
tgtcccggag ctcgctgaaa ccctgtgccc aggcagccac cctggccgcg taccccgcgg    420
agactcccac ggccggggaa gagtacccca gccgcccac tgagtttgcc ttctatccgg    480
gatatccggg aacctaccag cctatggcca gttacctgga cgtgtctgtg gtgcagactc    540
tgggtgctcc tggagaaccg cgacatgact ccctgttgcc tgtggacagt taccagtctt    600
gggctctcgc tggtggctgg aacagccaga tgtgttgcca gggagaacag aacccaccag    660 gtccctttg gaaggcagca tttgcagact ccagcgggca gcaccctcct gacgcctgcg    720
cctttcgtcg cggccgcaag aaacgcattc cgtacagcaa ggggcagttg cgggagctgg    780
agcgggagta tgcggctaac aagttcatca ccaaggacaa gaggcgcaag atctcggcag    840
ccaccagcct ctcggagcgc agattacca tctggtttca gaaccgccgg gtcaaagaga    900
agaaggttct cgccaaggtg aagaacagcg ctaccccta gagatctcc ttgcctgggt    960 gggaggagcg aaagtggggg tgtcctgggg agaccaggaa cctgccaagc ccaggctggg    1020
gccaaggact ctgctgagag gcccctagag acaacaccct tcccaggcca ctggctgctg    1080
gactgttcct caggagcggc ctgggtaccc agtatgtgca gggagacgga acccatgtg    1140 acagcccact ccaccagggt tcccaaagaa cctggcccag tcataatcat tcatcctgac    1200
agtggcaata atcacgataa ccagtactag ctgccatgat cgttagcctc atattttcta    1260
tctagagctc tgtagagcac tttagaaacc gctttcatga attgagctaa ttatgaataa    1320
atttggaaaa aaaaaaaaaa aaaaaaaaaa aaaaaa                              1356
```

<210> SEQ ID NO 371
<211> LENGTH: 1026
<212> TYPE: DNA
<213> ORGANISM: Homo sapiens

<400> SEQUENCE: 371

```
cgggtgcccc ctagattccc cgcccccgca cctcatgagc cgaccctcgg ctccatggag     60
```

```
cccggcaatt atgccacctt ggatggagcc aaggatatcg aaggcttgct gggagcggga    120 gggggggcgga atctggtcgc ccactcccct ctgaccagcc acccagcggc gcctacgctg    180
atgcctgctg tcaactatgc ccccttggat ctgccaggct cggcggagcc gccaaagcaa    240
tgccacccat gccctggggt gccccagggg acgtccccag ctcccgtgcc ttatggttac    300
tttggaggcg ggtactactc ctgccgagtg tcccggagct cgctgaaacc ctgtgcccag    360
gcagccaccc tggccgcgta ccccgcgag actcccacgg ccggggaaga gtaccccagc    420
cgccccactg agtttgcctt ctatccggga tatccgggaa cctaccacgc tatggccagt    480
tacctggacg tgtctgtggt gcagactctg ggtgctcctg gagaaccgcg acatgactcc    540
ctgttgcctg tggacagtta ccagtcttgg gctctcgctg gtggctggaa cagccagatg    600
tgttgccagg gagaacagaa cccaccaggt ccctttttgga aggcagcatt tgcagactcc    660
agcgggcagc accctcctga cgcctccgcc tttcgtcgcg gccgcaagaa acgcattccg    720
tacagcaagg gcagttgcg gggagctgag cgggagtatg cggctaacaa gttcatcacc    780
aaggacaaga ggcgcaagat ctcggcagcc accagcctct cggagcgcca gattaccatc    840
tggtttcaga accgccggt caaagagaag aaggttctcg ccaaggtgaa gaacagcgct    900
accccttaag agatctcctt gcctgggtgg gaggagcgaa agtgggggtg tcctggggag    960
accaggaacc tgccaagccc aggctggggc caaggactct gctgagaggc cctagagac   1020 aacacc                                                              1026

<210> SEQ ID NO 372
<211> LENGTH: 1316
<212> TYPE: DNA
<213> ORGANISM: Homo sapiens

<400> SEQUENCE: 372
tcctaatacg actcactata gggctcgagc ggccgcccgg gcaggtcgaa tgcaggcgac     60
ttgcgagctg ggagcgattt aaaacgcttt ggattccccc ggcctgggtg gggagagcga    120
gctgggtgcc ccctagattc cccgcccccg cacctcatga gccgaccctc ggctccatgg    180
agcccggcaa ttatgccacc ttggatggag ccaaggatat cgaaggcttg ctgggagcgg    240
gaggggggcg gaatctggtc gcccactccc ctctgaccag ccacccagcg gcgcctacgc    300
tgatgcctgc tgtcaactat gccccttgg atctgccagg ctcggcggag ccgccaaagc    360
aatgccaccc atgccctggg gtgccccagg gacgtcccc agctcccgtg ccttatggtt    420
actttggagg cgggtactac tcctgccgag tgtcccggag ctcgctgaaa ccctgtgccc    480
aggcagccac cctggccgcg tacccgcgg agactcccac ggccggggaa gagtacccca    540
gtcgccccac tgagtttgcc ttctatccgg gatatccggg aacctaccac gctatggcca    600
gttacctgga cgtgtctgtg gtgcagactc tgggtgctcc tggagaaccg cgacatgact    660
ccctgttgcc tgtggacagt taccagtctt gggctctcgc tggtggctgg aacagccaga    720
tgtgttgcca gggagaacag aacccaccag gtcccttttg aaggcagca tttgcagact    780 ccagcgggca gcaccctcct gacgcctgcg cctttcgtcg cggccgcaag aaacgcattc    840
cgtacagcaa gggcagttg cgggagctgg agcgggagta tgcggctaac aagttcatca    900
ccaaggacaa gaggcgcaag atctcggcag ccaccagcct ctcggagcgc cagattacca    960
tctggtttca gaaccgccgg gtcaaagaga agaaggttct cgccaaggtg aagaacagcg   1020 ctaccccctta agagatctcc ttgcctgggt gggaggagcg aaagtggggg tgtcctgggg   1080
```

| | |
|---|---|
| agaccagaaa cctgccaagc ccaggctggg gccaaggact ctgctgagag gcccctagag | 1140 |
| acaacaccct tcccaggcca ctggctgctg gactgttcct caggagcggc ctgggtaccc | 1200 |
| agtatgtgca gggagacgga accccatgtg acaggcccac tccaccaggg ttcccaaaga | 1260 |
| acctggccca gtcataatca ttcatcctca cagtggcaat aatcacgata accagt | 1316 |

<210> SEQ ID NO 373
<211> LENGTH: 506
<212> TYPE: DNA
<213> ORGANISM: Homo sapiens

<400> SEQUENCE: 373

| | |
|---|---|
| attttctgt cgtgtgaaaa tgaagccagc aggctgcccc tagtcagtcc ttccttccag | 60 |
| agaaaaagag atttgagaaa gtgcctgggt aattcaccat taatttcctc ccccaaactc | 120 |
| tctgagtctt cccttaatat ttctggtggt tctgaccaaa gcaggtcatg gtttgttgag | 180 |
| catttgggat cccagtgaag tagatgtttg tagccttgca tacttagccc ttcccaggca | 240 |
| caaacggagt ggcagagtgg tgccaaccct gttttcccag tccacgtaga cagattcaca | 300 |
| gtgcggaatt ctggaagctg gagacagacg ggctctttgc agagccggga ctctgagagg | 360 |
| gacatgaggg cctctgcctc tgtgttcatt ctctgatgtc ctgtacctgg gctcagtgcc | 420 |
| cggtgggact catctcctgg ctgcgcagca aagccagcgg gttcgtgctg gtccttcctg | 480 |
| caccttaggc tggggtggg gggcct | 506 |

<210> SEQ ID NO 374
<211> LENGTH: 597
<212> TYPE: DNA
<213> ORGANISM: Homo sapiens

<400> SEQUENCE: 374

| | |
|---|---|
| attttctgt cgtgtgaaaa tgaagccagc aggctgcccc tagtcagtcc ttccttccag | 60 |
| agaaaaagag atttgagaaa gtgcctgggt aattcaccat taatttcctc ccccaaactc | 120 |
| tctgagtctt cccttaatat ttctggtggt tctgaccaaa gcaggtcatg gtttgttgag | 180 |
| catttgggat cccagtgaag tagatgtttg tagccttgca tacttagccc ttcccaggca | 240 |
| caaacggagt ggcagagtgg tgccaaccct gttttcccag tccacgtaga cagattcaca | 300 |
| gtgcggaatt ctggaagctg gagacagacg ggctctttgc agagccggga ctctgagagg | 360 |
| gacatgaggg cctctgcctc tgtgttcatt ctctgatgtc ctgtacctgg gctcagtgcc | 420 |
| cggtgggact catctcctgg ctgcgcagca aagccagcgg gttcgtgctg gtccttcctg | 480 |
| caccttaggc tggggtggg gggggcctgc cggcgcattc tccacgattg agcgcacagg | 540 |
| cctgaagtct ggacaacccg cagaaccgaa gctccgagca gcgggtcggt ggcgagt | 597 |

<210> SEQ ID NO 375
<211> LENGTH: 300
<212> TYPE: DNA
<213> ORGANISM: Homo sapiens

<400> SEQUENCE: 375

| | |
|---|---|
| atttaaaacg ctttggattc tttcgtcctg cgtggggaga gcgagctggg tgcccctag | 60 |
| attccccgcc cccgcacctc atgagccgac cctcggctcc atggagcccg gcacttatgc | 120 |
| caccttggat ggagccaagg atatcgaagg cttgctggga gcgggagggg ggcggaatct | 180 |
| ggtcgcccac tcccctctga ccagccaccc agcggcgcct acgctgatgc ctgctgtcaa | 240 |
| ttatgccccc ttgcatctgc caggctcggc ggagccgcca aagcaatgcc acccatgccc | 300 |

<210> SEQ ID NO 376
<211> LENGTH: 508
<212> TYPE: DNA
<213> ORGANISM: Homo sapiens

<400> SEQUENCE: 376

```
atttttctgt cgtgtgaaaa tgaagccagc aggctgcccc tagtcagtcc ttccttccag      60
agaaaaagag atttgagaaa gtgcctgggt aattcaccat taatttcctc ccccaaactc     120
tctgagtctt cccttaatat ttctggtggt tctgaccaaa gcaggtcatg gtttgttgag     180
catttgggat cccagtgaag tagatgtttg tagccttgca tacttagccc ttcccaggca     240
caaacggagt ggcagagtgg tgccaaccct gttttcccag tccacgtaga cagattcaca     300
gtgcggaatt ctggaagctg agacagacg ggctctttgc agagccggga ctctgagagg      360
gacatgaggg cctctgcctc tgtgttcatt ctctgatgtc ctgtacctgg gctcagtgcc     420
cggtgggact catctcctgg ctgcgcagca aagccagcgg ttcgtgctg gtccttcctg      480
caccttaggc tgggggtggg gggcctgc                                        508
```

<210> SEQ ID NO 377
<211> LENGTH: 284
<212> TYPE: DNA
<213> ORGANISM: Homo sapiens
<220> FEATURE:
<221> NAME/KEY: misc_feature
<222> LOCATION: (227)..(227)
<223> OTHER INFORMATION: a or g or c or t/u
<220> FEATURE:
<221> NAME/KEY: misc_feature
<222> LOCATION: (269)..(269)
<223> OTHER INFORMATION: a or g or c or t/u

<400> SEQUENCE: 377

```
aggccgcacc cagtcttaag gtgcagtgaa ggacagcacg aacccgctgt gctttgctgc      60
gcggcaggag atgagtccca ccgggcactg agcccaggta caggacatca gagaatgaac     120
acagaggcag aggccctcat gtccctctca gagtcccggc tctgcaaaga gcccgtctgt     180
ctccagcttc cagaattccg cactgtgaat ctgtctacgt ggactgngaa aacagggttg     240
gcaccactct gccactccgt ttgtgcctng gggcgggcag aggg                      284
```

<210> SEQ ID NO 378
<211> LENGTH: 651
<212> TYPE: DNA
<213> ORGANISM: Homo sapiens

<400> SEQUENCE: 378

```
aaaaacgctt tggattcccc cggcctgggt ggggagagcg agctgggtgc ccctagatt       60
ccccgccccc gcacctcatg agccgaccct cggctccatg gagcccggca attatgccac     120
cttggatgga gccaaggata tcgaaggctt gctgggagcg ggaggggggc ggaatctggt     180
cgcccactcc cctctgacca gccacccagc ggcgcctacg ctgatgcctg ctgtcaacta     240
tgccccttg gatctgccag gctcggcgga gccgccaaag caatgccacc catgccctgg      300
ggtgccccag gggacgtccc cagctcccgt gccttatggt tactttggag gcgggtacta     360
ctcctgccga gtgtcccgga gctcgctgaa accctgtgcc caggcagcca cctggccgc      420
gtaccccgcg gagactccca cggccgggga agagtacccc agccgcccca ctgagtttgc     480
cttctatccg ggatatccgg gaacctacca gcctatggc agttacctgg acgtgtctgt      540
```

```
ggtgcagact ctgggtgctc ctggagaacc gcgacatgac tccctgttgc ctgtggacag    600
ttaccagtct tgggctctcg ctggtggctg aacagccag atgtgttgcc a              651
```

<210> SEQ ID NO 379
<211> LENGTH: 498
<212> TYPE: DNA
<213> ORGANISM: Homo sapiens

<400> SEQUENCE: 379

```
gcagactctg gtgctcctg gagaaccgcg acgtgactcc ctgttgcctg tggacagtta    60
ccactcttgg gctctcgctg gtggctgaa cagccagatg tgttgccagg agaacagaa     120 cccaccaggt cccttttgga aggcagcatt tgcagactcc agcgggcagc accctcctga   180
cgcctgcgcc tttcgtcgcg gccgcaagaa acgcattccg tacagcaagg ggcagttgcg   240
ggagctggag cgggagtatg cggctaacaa gttcatcacc aaggacaaga ggcgcaagat   300
ctcggcagcc accagcctct cggagcgcca gattaccatc tggtttcaga accgccgggt   360
caaagagaag aaggttctcg ccaaggtgaa gaacagcgct accccttaag agatctcctt   420
gcctgggtgg gaggatctaa agtgggggtg tcctggggag accaggaacc tgccaagccc   480
aggctggggc caaggact                                                 498
```

<210> SEQ ID NO 380
<211> LENGTH: 233
<212> TYPE: DNA
<213> ORGANISM: Homo sapiens

<400> SEQUENCE: 380

```
acgctgcact gcgtttcaaa gagaagaagg ttctcgccaa ggtgaagaac agcgctaccc    60
cttaagagat ctccttgctt gggtgggagg agcgaaagtg ggggtgtcct ggggagacca   120
ggaacctgcc atcaccaggc tgggcccaag gactctgctg agaggcccct agagacaaca   180 ccctttcccag gccattgctt gctggactgt gcctcaggag cggcctgggt acc         233
```

<210> SEQ ID NO 381
<211> LENGTH: 539
<212> TYPE: DNA
<213> ORGANISM: Homo sapiens

<400> SEQUENCE: 381

```
gagttttcca atttccaaag aaaaatttag gtttcctgca gccgtgacat atgtgtgtgc    60
actgggatgg gttaatgtgt gtgtgtgtgt gtgtatgcgc atgtattggg agtggggca   120 gaaacgtgtt tccagaattt gcctgtagaa tctaaaagag tggccaagag tctggaaatg   180
catgaagact ggacgtatgt gatggtgggc aaaggcctga ctgtgtgtgg tgtgtgggta   240
tgtttgcaga ttcgcgggtg tgagagcagt gatgggtgag ggtggccttc aggagccaag   300
gctgatcggt ggtgagagaa caagccgaa gccaggtgc tgtcctggta tgctttggag    360
gaacaggatt gcacgtgcgc ctgtagggtg acctgtgtgc acctgtgaga tgacttagct   420
tggggcttgc aaggcctggg tctgcatggg tgggtatctg accatgcctt ttcctccctc   480
cctttcacgc cgcgcagact ccagcgggca gcaccctcct gacgcctgcg cctttcgtc   539
```

<210> SEQ ID NO 382
<211> LENGTH: 240
<212> TYPE: DNA
<213> ORGANISM: Homo sapiens

<400> SEQUENCE: 382

```
ccggcctggg tggggagagc gagctgggtg cccctagat tccccgcccc cgcacctcat    60
gagccgaccc tcggctccat ggagcccggc aattatgcca ccttggatgg agccaaggat   120
atcgaaggct tgctgggagc gggagggggg cggaatctgg tcgcccactc ccctctgacc   180
agccacccag cggcgcctac gcttgatgcc tgcttgtcaa ctatgccccc ttggatctgc   240
```

<210> SEQ ID NO 383
<211> LENGTH: 469
<212> TYPE: DNA
<213> ORGANISM: Homo sapiens

<400> SEQUENCE: 383

```
accgcgggtc aaatttattc ataattagct caatcatgaa agcggttcta aagtgctcta    60
cagagctcta gatagaaaat atgaggctaa cgatcatggc agctagtact ggttatcgtg   120
attatggcca ctgtcaggat gaatgataat gactgggcca ggtcctttgg aaaccctggt   180
ggagtgggct gtcacatggg gtcccgtctc cctgcacata ctgggtaccc aggccgctcc   240
tgaggaacag tccagcagcc agtggcctgg aagggtgtg gtctctaggg gcctctcagc    300
agagtccttg gccccagcct gggcttggca ggtccctggt ctccccagga caccccacct   360
ttcgctcctc ccacccaggc aaggagatct cttaaggggt agcgctgttc ttcaccttgg   420
cgagaacctt cttctctttg aaccggcggt gcggcgtggg gtaccgagc                469
```

<210> SEQ ID NO 384
<211> LENGTH: 472
<212> TYPE: DNA
<213> ORGANISM: Homo sapiens

<400> SEQUENCE: 384

```
attttctgt cgtgtgaaaa tgaagccagc aggctgcccc tagtcagtcc ttccttccag    60
agaaaaagag atttgagaaa gtgcctgggt aattcaccat taatttcctc ccccaaactc   120
tctgagtctt cccttaatat ttctggtggt tctgaccaaa gcaagtcatg gtttgttgag   180
catttgggat cccagtgaag tagatgtttg tagccttgca tacttagccc ttcccaggca   240
caaacggagt ggcagagtgg tgccaaccct gttttcccag tccacgtaga cagattcaca   300
gtgcggaatt ctggaagctg agacagacg ggctctttgc agagccggga ctctgagagg    360
gacatgaagg cctctgcctc tgtgttcatt ctctgatgtc ctgtacctgg gctcagtgcc   420
cggtgggact catctcctgg ctgcgcagca aagccagcgg ttcgtgctg gt            472
```

<210> SEQ ID NO 385
<211> LENGTH: 450
<212> TYPE: DNA
<213> ORGANISM: Homo sapiens

<400> SEQUENCE: 385

```
ccaacgagaa gaaggttctc gcaaggtgaa gaacagcgct acccttaag agatctcctt     60 gcgtgggtgg gaggagcgaa agtgggggtg tcctggggag accaggaacc tgccagccca   120
ggctgaggcc aaggactctg ctgagaggcc cctagagaca acaccttcc caggccactg    180 gatgctgaac tgtccctcag gagcggcctg ggtacccagt atgtgcaggg agacggaacc   240
ccatgtgaca gcccactcca ccagggttcc caaagaacct ggcccagtc ataatcattc    300 atcctgacag tggcaataat cacgataacc agtactagct gccatgatcg taagcctcat   360
atttgctatc tagagctctg tagagcactt tagaaaccgc tttcatgaat tgagctaatt   420
```

```
atgactcaat ttgaaccggc gtccggcgtg                                     450
```

<210> SEQ ID NO 386
<211> LENGTH: 472
<212> TYPE: DNA
<213> ORGANISM: Homo sapiens

<400> SEQUENCE: 386

```
acgcgcaccg cggtcaagag aagaaggttc tcgcaaggtg aagaacagcg ctacccctta     60
agagatctcc ttgcgtgggt gggaggagcg aaagtgggg tgtcctgggg agaccaggaa    120
cctgccaagc ccaggctgtg gccaaggact ctgctgagag gccctatga dacaacaccc     180
ttcccaggcc actggctgct gggactgttc ctcaggagcg gcctgggtac ccgagtaatg    240
tgcaggggag acggaacccc catgtgacagc ccactccacc agggttccca aaagaaccct   300
ggcccagtca taatcattca tcctgacagt ggcaataatc acgataacca gtactagctg    360
ccatgatcgt aagcctcata tttgctatct agagctctgt agagcccttt agaaaccgct    420
ttcatgaatg gagctaaatt atgaatacat ttgaaccggc gatccgacgt ga             472
```

<210> SEQ ID NO 387
<211> LENGTH: 320
<212> TYPE: DNA
<213> ORGANISM: Homo sapiens

<400> SEQUENCE: 387

```
ctagaggatc ccggaagcaa ctgcaacagg ttcccaaaga accgggccag tcataatcat     60
tcatcctgac agggcaataa tcacgataac cagtactagc tgccatgatc gttagcctca    120
tattttctat ctagagctct gtagagcact ttagaaaccg ctttcatgaa tggagctaat    180
tatgaataaa tttggaaggc gatcccttgg caggaagct ttctctcaga cccccttcca     240
ttacacctct caccctggta acagcaggaa gactgaggag aggggaacgg gcagattcgt    300
ggtgttgcag tgtgcttccg                                                320
```

<210> SEQ ID NO 388
<211> LENGTH: 459
<212> TYPE: DNA
<213> ORGANISM: Homo sapiens
<220> FEATURE:
<221> NAME/KEY: misc_feature
<222> LOCATION: (393)..(393)
<223> OTHER INFORMATION: a or g or c or t/u
<220> FEATURE:
<221> NAME/KEY: misc_feature
<222> LOCATION: (439)..(440)
<223> OTHER INFORMATION: a or g or c or t/u
<220> FEATURE:
<221> NAME/KEY: misc_feature
<222> LOCATION: (443)..(443)
<223> OTHER INFORMATION: a or g or c or t/u
<220> FEATURE:
<221> NAME/KEY: misc_feature
<222> LOCATION: (459)..(459)
<223> OTHER INFORMATION: a or g or c or t/u

<400> SEQUENCE: 388

```
gagcgaatgc aggcgacttg cgagctggga gcgatttaaa acgctttgga ttccccggc      60
ctgggtgggg agagcgagct gggtgccccc tagattcccc gccccgcac ctcatgagcc    120
gaccctcggc tccatggagc ccggcaatta tgccaccttg gatggagcca aggatatcga    180
agacttgctg ggagcgggag gggggcgaa tctggtcgcc cactcccctc tgaccagcca     240
cccagcggcg cctacgctga tgcctgctgt caactatgcc cccttggatc tgccaggctc    300
```

```
ggcggagccg ccaaagcaat gccacccatg ccctggggtg ccccagggga cgtcccagc    360 tcccgtgcct tatggttact ttggaggcgg gtnctactcc tgccgagtgt cccggagctc    420
gctgaaaccc tgtgcccann canccaccct ggccgcgtn                          459
```

<210> SEQ ID NO 389
<211> LENGTH: 156
<212> TYPE: DNA
<213> ORGANISM: Homo sapiens

<400> SEQUENCE: 389

```
ctctgcctct gtgttcattc tctgatgtcc tgtacctgtg ctcagtgccc ggtgggactc     60
atctcctggc tgcgcagcaa agccagcggg ttcgtgctgg tccttcctgc accttcggct    120
gggggtgggg ggcctgccgg cgcattctcc acgatt                             156
```

<210> SEQ ID NO 390
<211> LENGTH: 467
<212> TYPE: DNA
<213> ORGANISM: Homo sapiens
<220> FEATURE:
<221> NAME/KEY: misc_feature
<222> LOCATION: (233)..(233)
<223> OTHER INFORMATION: a or g or c or t/u

<400> SEQUENCE: 390

```
acgctgcacc gccggtccaa gagaagaagg ttctcgccaa ggtgaagaac agcgctaccc     60
ctttaagaga tctccttgct ggggtgggag gagcgaaagt gggggtgtct ggggagacca    120
ggaacctgcc agccccaggc tgggcccaag gactctgctg agaggcccct agagacaaca    180
cccttcccag gccactgtct gctggactgt tcctcaggag cggcctgggt acncagtatg    240
tgcagggaga cggaacccca tgtgacagcc cactccacca gggttcccaa agaacctggc    300
ccagtcataa tcattcatcc tgacagtggc aataatcacg ataaccagta ctagctgcca    360
tgatcgttag cctcatattt tctatctaga gctctgtaga gcactttaga aaccgctttc    420
atgaattgag ctacttatga atcactttga accggcggtg cggcgtg                 467
```

<210> SEQ ID NO 391
<211> LENGTH: 666
<212> TYPE: DNA
<213> ORGANISM: Homo sapiens
<220> FEATURE:
<221> NAME/KEY: misc_feature
<222> LOCATION: (594)..(594)
<223> OTHER INFORMATION: a or g or c or t/u

<400> SEQUENCE: 391

```
gggggagagc gagctgggtg cccctagat tccccgcccc cgcacctcat gagccgaccc      60
tcggctccat ggagcccggc aattatgcca ccttggatgg agccaaggat atcgaaggct    120
tgctgggagc gggagggggg cggaatctgg tcgcccactc ccctctgacc agccacccag    180
cggcgcctac gctgacgcct gctgtcaact atgccccctt ggatctgcca ggctcggcgg    240
agccgccaaa gcaatgccac ccatgccctg gggtgcccca ggggacgtcc ccagctcccg    300
tgccttatgg ttactttgga ggcgggtact actcctgccg agtgtcccgg agctcgctga    360
aaccctgtgc ccaggcagcc acccctggccg cgtaccccgc ggagactccc acggccgggg    420
aagagtaccc cagccgcccc actgagtttg ccttctatcc gggatatccg ggaacctacc    480
agcctatggc cagttacctg gacgtgtctg tggtgcagac tctgggtgct cctggagaac    540
```

| | |
|---|---|
| cgcgacatga ctccctgttg cctgtggaca gttaccagtc ttgggctctc gctngtggct | 600 |
| ggaacagcca gatgtgttgc cagggagaac agaacccacc aggtcccttt tggaaggcag | 660 |
| catttg | 666 |

<210> SEQ ID NO 392
<211> LENGTH: 664
<212> TYPE: DNA
<213> ORGANISM: Homo sapiens

<400> SEQUENCE: 392

| | |
|---|---|
| gctgagttct gaagcttctg agttctgcag cctcacctct gagaaaacct cttttccacc | 60 |
| aataccatga agctctgcgt gactgtcctg tctctcctca tgctagtagc tgccttctgc | 120 |
| tctctagcgc tctcagcacc aatgggctca gaccctccca ccgcctgctg ctttctttac | 180 |
| accgcgagga agcttcctcg caactttgtg gtagattact atgagaccag cagcctctgc | 240 |
| tcccagccag ctgtggtatt ccaaaccaaa agaagcaagc aagtctgtgc tgatcccagt | 300 |
| gaatcctggg tccaggagta cgtgtatgac ctggaactga actgagctgc tcagagacag | 360 |
| gaagtcttca gggaaggtca cctgagcccg gatgcttctc catgagacac atctcctcca | 420 |
| tactcaggac tcctctccgc agttcctgtc ccttctctta atttaatctt ttttatgtgc | 480 |
| cgtgttattg tattaggtgt catttccatt atttatatta gtttagccaa aggataagtg | 540 |
| tcccctatgg ggatggtcca ctgtcactgt ttctctgctg ttgcaaatac atggataaca | 600 |
| catttgattc tgtgtgtttt cataataaaa ctttaaaata aaatgcaaaa aaaaaaaaa | 660 |
| aaaa | 664 |

<210> SEQ ID NO 393
<211> LENGTH: 1308
<212> TYPE: DNA
<213> ORGANISM: Homo sapiens

<400> SEQUENCE: 393

| | |
|---|---|
| gccacgtgct gctgggtctc agtcctccac ttcccgtgtc ctctggaagt tgtcaggagc | 60 |
| aatgttgcgc ttgtacgtgt tggtaatggg agtttctgcc ttcacccttc agcctgcggc | 120 |
| acacacaggg gctgccagaa gctgccggtt tcgtgggagg cattacaagc gggagttcag | 180 |
| gctggaaggg gagcctgtag ccctgaggtg cccccaggtg ccctactggt tgtgggcctc | 240 |
| tgtcagcccc cgcatcaacc tgacatggca taaaaatgac tctgctagga cggtcccagg | 300 |
| agaagaagag acacggatgt gggcccagga cggtgctctg tggcttctgc agccttgca | 360 |
| ggaggactct ggcacctacg tctgcactac tagaaatgct tcttactgtg acaaaatgtc | 420 |
| cattgagctc agagtttttg agaatacaga tgctttcctg ccgttcatct catacccgca | 480 |
| aattttaacc ttgtcaacct ctggggtatt agtatgccct gacctgagtg aattcacccg | 540 |
| tgacaaaact gacgtgaaga ttcaatggta caaggattct cttcttttgg ataaagacaa | 600 |
| tgagaaattt ctaagtgtga gggggaccac tcacttactc gtacacgatg tggccctgga | 660 |
| agatgctggc tattaccgct gtgtcctgac atttgcccat gaaggccagc aatacaacat | 720 |
| cactaggagt attgagctac gcatcaagaa aaaaaaagaa gagaccattc ctgtgatcat | 780 |
| ttcccccctc aagaccatat cagcttctct ggggtcaaga ctgacaatcc cgtgtaaggt | 840 |
| gtttctggga accggcacac ccttaaccac catgctgtgg tggacggcca atgacaccca | 900 |
| catagagagc gcctacccgg gaggccgcgt gaccgagggg ccacgccagg aatattcaga | 960 |
| aaataatgag aactacattg aagtgccatt gattttttgat cctgtcacaa gagaggattt | 1020 |

```
gcacatggat tttaaatgtg ttgtccataa taccctgagt tttcagacac tacgcaccac   1080
agtcaaggaa gcctcctcca cgttctcctg gggcattgtg ctggcccac tttcactggc    1140 cttcttggtt ttgggggggaa tatggatgca cagacggtgc aaacacagaa ctggaaaagc  1200
agatggtctg actgtgctat ggcctcatca tcaagacttt caatcctatc ccaagtgaaa   1260
taaatggaat gaaataattc aaacacaaaa aaaaaaaaa aaaaaaa                  1308
```

<210> SEQ ID NO 394
<211> LENGTH: 2110
<212> TYPE: DNA
<213> ORGANISM: Homo sapiens

<400> SEQUENCE: 394

```
ggatccaagc tattgtcctg cccatggctt cccatctcag gacgctctct ggccgctatc    60
atcccagcag tggagttcag cccactactc tgaaccagcc gcaggtggct gctatgggac   120
tgaagccatg aatggtgccg gcctggccc cgccgcagcc gccccggtcc cagtcccggt    180
cccggtcccg gactggcggc agttctgcga gctgcatgcg caggcggccg ccgtggactt   240
tgcgcacaag ttctgccgtt tcctgcggga caacccagct tacgacacgc ccgacgccgg   300
cgcctccttc tcccgccact tcgccgccaa cttcctggac gtcttcggcg aggaggtgcg   360
ccgcgtgctg gtggctgggc cgacgactcg gggcgcggcc gtgagcgcag aggccatgga   420
gccggagctc gcggacacct ctgcactcaa ggcggcgtcc tacggccact cgcggagctc   480
ggaggacgtg tccacgcacg cggccaccaa ggcccgcgtt cgcaagggct tctcgctgcg   540
caacatgagc ctgtgcgtgg tggacggcgt gcgcgacatg tggcaccggc gcgcctcgcc   600
cgagcccgac gcggcagctg ccccgcgcac cgccgagccc cgcgacaagt ggacgcggcg   660
cctgaggctg tcgcggacgc tggctgccaa ggtggagctg gtggacattc aacgcgaggg   720
ggcgctgcgc ttcatggtgg ccgacgacgg ggccgcgggc tccgggggct cggctcagtg   780
gcagaagtgc cgcctgctcc tgcgcagggc tgtggccgag gaacgcttcc gcctggagtt   840
cttcgtgccg cccaaaagcct ccaggcccaa ggtcagcatc ccactgtcag ccatcattga   900
ggtccgcacc accatgcccc tggaaatgcc agagaaggat aacacattcg tcctcaaggt   960
agagaatgga gccgaataca tcttggagac catcgactct ctgcagaagc actcgtgggt  1020
agctgacatc cagggctgcg tggaccccgg tgacagtgag gaagacaccg agctctcctg  1080
tacccgagga ggctgtctgg ccagccgcgt ggcctcctgc agctgtgagc tcctgactga  1140
tgcagtcgac ctgccccgcc ccccagagac gacagccgtg ggtgcagtgg tgacagcccc  1200
ccacagccga ggtcgagatg ccgtcagaga atccctgatc cacgtcccgc tagagacctt  1260
tctgcagacc ctggaatccc cggcggcag cggcagtgac agcaataaca caggggaaca  1320
gggtgcagag acggatcccg aggctgaacc cgagctggag ctatccgact acccatggtt  1380
ccacgggaca ctgtccgggg tcaaggctgc tcaactggtt ctggcagggg gccccggaa   1440 ccacggcctc ttcgtgatcc gccaaagtga gactcggcct ggggagtacg tgctgacctt  1500
caacttccag ggcaaggcca agcacctgcg cctgtccctg aacggccacg gccagtgtca  1560
cgtacagcat ctgtggttcc agtctgtgct tgacatgctc cgccacttcc acacacaccc  1620
catcccactg gagtcagggg gctcggccga catcaccctt cgcagctatg tgcgggccca  1680
ggacccccca ccagagccgg gccccacgcc cctgccgcg cccgcgtccc ggcctgctg    1740 gagcgactcg cccggccagc actacttctc cagcctcgcc gcggccgcct gccgcctgc   1800
```

```
ctcgccctcc gacgccgccg gcgcctcctc gtcttccgcc tcgtcgtcct ctgccgcgtc      1860
ggggcccgcc cccccgcgcc ccgtcgaggg ccagctcagc gcgcggagcc gcagcaacag      1920
cgccgagcgc ctgctggagg ccgtggccgc caccgccgcc gaggagcccc cggaggccgc      1980
gcccggccgc gcgcgcgccg tggagaacca gtactccttc tactagcccg cggcgccgcc      2040
cgggtgggac acgccaagct cttcagtgaa gacacgatgt tattaaaagc ctgttttagg      2100
gactgcaaaa                                                             2110
```

<210> SEQ ID NO 395
<211> LENGTH: 496
<212> TYPE: DNA
<213> ORGANISM: Homo sapiens

<400> SEQUENCE: 395

```
gattccagca cgggcttcgc agactgcagg acacagaggc acgcgtgcac atcatgtctt       60
ctaaggaatt tgaacactgt tgagaagact gtgtacaaga gagatgtgcc atgtcagcct      120
tgcaagggac agcgtgaaaa ctacccatct ccggtcacca agttgcagga ggccaggagc      180
caggagggga aaccgctcag tttgcaaaac gtcgcttcca caagcctgat ggctgaaact      240
gctcactgta ccctgaaacc agctttacct acagcttctg agataaactg ctgcaactct      300
ggacccacg atgcctatca cagtggctca tcaatggaac ctgccggctc ccaaccgttc      360
ctagggccca tgaactctct gaaaagagga acagaaatat ttctccttt tgtaaaatct      420
ttaaccttcc ctttgttctt catgtacacg ctgaactgca attcttcttc ccaaataaaa      480
cattaaattt aaaaaa                                                      496
```

<210> SEQ ID NO 396
<211> LENGTH: 824
<212> TYPE: DNA
<213> ORGANISM: Homo sapiens

<400> SEQUENCE: 396

```
ggccccggag ggagagtaac ccggcccatc catccgtcgc ccggttcttg gggaactact       60
ttcaggggct tcttgccgtc ccctcatcag ctctgtgcga accctctgtc ggcagccatt      120
gaggagaccc tgcccctgg accctgacca catatagatt gaggccgagg agtggctgcc      180
ctgtcccttt tatgacagcc cgcagaagcc ccggggtgag gcatggagga ggcaggcgac      240
agctgacagg gaccctgttg gcctccagca tgtccagcca gcgggcagg atttctctgc      300
ttctggctgg cagccaggaa ctgagtatga caatgttgta ctaaagaaag gcccaaagtg      360
acagaggcag cagagggatg gtccaccgcc ccttggcttc tgctggtgac tcctcctggc      420
cactgcatca gaagaacctc ctctgcccct tctggagccc gaggcctggc ctgtcttcgt      480
tggggctgat aaattgcctc tcccagggcc tgctgggtga gtcaccatcc caaagcagga      540
agggtgccct ggagagaacc accctcctcc tactctttt ccacttcctc ctctttcttt      600
ccccagctga ggaggaacct ggggcattta gggcagagga caaaaggatg tcagcaattg      660
cttgggctgc ttggctatgc aagcctcctg cctgctgatg gccacttcag ggacagcctg      720
ggcccaggca cccaggggga tggcggcagc ttcctgcacc tttcagattt cttggtggca      780
ttaaagcatt ttcagaacaa aaaaaaaaaa aaaaaaaaaa aaaa                       824
```

<210> SEQ ID NO 397
<211> LENGTH: 2429
<212> TYPE: DNA
<213> ORGANISM: Homo sapiens

<400> SEQUENCE: 397

```
ggcgggcctg gacggccgcg tgctgtactg gccacgcggc cgcgtctggg gtggctcctc    60
atccctcaat gccatggtct acgtccgtgg gcacgccgag gactacgagc gctggcagcg   120
ccagggcgcc cgcggctggg actacgcgca ctgcctgccc tacttccgca aggcgcaggg   180
ccacgagctg ggcgccagcc ggtaccgggg cgccgatggc ccgctgcggg tgtcccgggg   240
caagaccaac caccgctgc actgcgcatt cctggaggcc acgcagcagg ccggctaccc    300
gctcaccgag gacatgaatg gcttccagca ggagggcttc ggctggatgg acatgaccat   360
ccatgaaggc aaacggtgga gcgcggcctg tgcctacctg cacccagcac tgagccgcac   420
caacctcaag gccgaggccg agacgcttgt gagcagggtg ctatttgagg cacccgtgc    480
agtgggcgtg gagtatgtta agaatggcca gagccacagg gcttatgcca gcaaggaggt   540
gattctgagt ggaggtgcca tcaactctcc acagctgctc atgctctctg gcatcgggaa   600
tgctgatgac ctcaagaaac tgggcatccc tgtggtgtgc cacctacctg ggttggcca    660
gaacctgcaa gaccacctgg agatctacat tcagcaggca tgcacccgcc ctatcaccct   720
ccattcagca cagaagcccc tgcggaaggt ctgcattggt ctggagtggc tctggaaatt   780
cacaggggag ggagccactg cccatctgga aacaggtggg ttcatccgca gccagcctgg   840
ggtccccac ccggacatcc agttccattt cctgccatcc caagtgattg accacgggcg    900
ggtccccacc cagcaggagg cttaccaggt acatgtgggg cccatgcggg gcacgagtgt   960
gggctggctc aaactgagaa gtgccaatcc ccaagaccac cctgtgatcc agcccaacta  1020
cttgtcaaca gaaactgata ttgaggattt ccgtctgtgt gtgaagctca ccagagaaat  1080
ttttgcacag gaagccctgg ctccgttccg agggaaagag ctccagccag gaagccacat  1140
tcagtcagat aaagagatag atgcctttgt gcgggcaaaa gccgacagcg cctaccaccc  1200
ctcgtgcacc tgtaagatgg gccagccctc cgatcccact gccgtggtgg atccgcagac  1260
aagggtcctc ggggtggaaa acctcaggt cgtcgatgcc tccatcatgc ctagcatggt  1320
cagcggcaac ctgaacgccc ccacaatcat gatcgcagag aaggcagctg acattatcaa  1380
ggggcagcct gcactctggg acaaagatgt ccctgtctac aagcccagga cgctggccac  1440
ccagcgctaa gacagttgct gctggaggat gaccagggaa gccccctgat aagccaagag  1500
ggccagcaca gcccttgctc ccaggctcct gcctgaaact atctagcaca ctaggaccca  1560
ggtggtaccc tactcagtgg ctgagaattg gataaagtct tkgggaaatg agacaagtac  1620
tgggcagtga atccagctcc ttttccccag cctttccctg tgggccattt ggggaaggcc  1680
agcattycag cctgagatgt tcctccctgc ctcctggggg ggcaraaggg vtaggwtggt  1740
taactcctgc cgcatccttc cctgcctcct ggagggacag aagggagga tggttaactc   1800
ctgccgcatc cttttcttg tgttcacgtg gcattctcta acccagggca gtggttcctt   1860
cccaggccat gcacagaggc tgggtgcctg ccagacccac ggagggttcg cgaaggaagg  1920
ggcatcctcc ttcttgagct gcaagcttta gctgaggcag taagtcacac agtagttagt  1980
tcagcctggg ctggcacata agtcccagt gtccctgttg agaggggaaa gttgcctgct  2040
ggttgaaaaa ctggcttttc ctttctcgct gcctaattc actctcagag tgaggcaggt  2100
aactggggct ccactgggtc actctgagag ggttgtggct ctggttctta ttaaaccagg  2160
gccaggtgca gggctcacac ctgtaatccc agcactttgg gaaggtcact tgagctcagg  2220
agttcaagac cagcctgggc aacatagtga gaccttgtct ctggaaaaca attagctggg  2280
```

| | |
|---|---|
| catggtggta cacacctgta gtcccagcta cttgggaggc tgaggcggga ggatggcttt | 2340 |
| agcccaggag gttgaggctc ctgtgaaccc tgatggcacc actgcactcc agcctgggtg | 2400 |
| acagggtgag accctgtctc aaaaaaaaa | 2429 |

<210> SEQ ID NO 398
<211> LENGTH: 626
<212> TYPE: DNA
<213> ORGANISM: Homo sapiens
<220> FEATURE:
<221> NAME/KEY: misc_feature
<222> LOCATION: (10)..(10)
<223> OTHER INFORMATION: a or g or c or t/u
<220> FEATURE:
<221> NAME/KEY: misc_feature
<222> LOCATION: (39)..(39)
<223> OTHER INFORMATION: a or g or c or t/u
<220> FEATURE:
<221> NAME/KEY: misc_feature
<222> LOCATION: (77)..(77)
<223> OTHER INFORMATION: a or g or c or t/u
<220> FEATURE:
<221> NAME/KEY: misc_feature
<222> LOCATION: (83)..(83)
<223> OTHER INFORMATION: a or g or c or t/u
<220> FEATURE:
<221> NAME/KEY: misc_feature
<222> LOCATION: (102)..(102)
<223> OTHER INFORMATION: a or g or c or t/u
<220> FEATURE:
<221> NAME/KEY: misc_feature
<222> LOCATION: (121)..(121)
<223> OTHER INFORMATION: a or g or c or t/u

<400> SEQUENCE: 398

| | |
|---|---|
| ccgccgttgn caaagggccc agaatatggg ccatggacna tctccatgcc tggggaaatt | 60 |
| ccctcgggtc ttttggntaa ccnccttata gaaaggtaat gncatggagt ctctacaggg | 120 |
| ngcacaaggt ggactaattg atacgaagag ccctgtaaat atgtgggcag cggcagattt | 180 |
| tgaccatttg gaccgaactg tatttgacac agcgcaatat ctggaactgg ttggtcaaaa | 240 |
| acctgcttgt cttgttaaat ttcctctgtc caaggacatg gaatctctct ctaattttac | 300 |
| ttcaaatttc cctttccttc atttctctaa aaacgttaaa taagaaagaa gattgtaaag | 360 |
| ccagcatttg aagcctaagt attgaaagtc tttgacaatt tctgaaatca gacttgacat | 420 |
| cttccccccg ccttgcaaat ttcttgaaga aataagaagc tacatgtaag catcatcatg | 480 |
| tttattaaat tacaatgaga actctcactc aatcttgacc agagcagact cttaacttgg | 540 |
| aagcagagtc cctctaaagg taactcttgt ggtcactcaa tattgtattg gcatttgcat | 600 |
| attaaataga catttcagta gcattt | 626 |

<210> SEQ ID NO 399
<211> LENGTH: 691
<212> TYPE: DNA
<213> ORGANISM: Homo sapiens

<400> SEQUENCE: 399

| | |
|---|---|
| tggcccgcgg tcgcggtggg atcctagccc tgtctcctct cctgggaagg agtgagggtg | 60 |
| ggacgtgact tagacaccta caaatctatt taccaaagag gagcccggga ctgagggaaa | 120 |
| aggccaaaga gtgtgagtgc atgcggactg ggggttcagg ggaagaggac gaggaggagg | 180 |
| aagatgaggt cgatttcctg atttaaaaaa tcgtccaagc cccgtggtcc agcttaaggt | 240 |
| cctcggttac atgcgccgct cagagcaggt cactttctgc cttccacgtc ctccttcaag | 300 |
| gaagcccat gtgggtagct ttcaatatcg caggttctta ctcctctgcc tctataagct | 360 |

```
caaacccacc aacgatcggg caagtaaacc ccctccctcg ccgacttcgg aactggcgag      420
agttcagcgc agatgggcct gtggggaggg ggcaagatag atgaggggga gcggcatggt      480
gcggggtgac cccttggaga gaggaaaaag gccacaagag gggctgccac cgccactaac      540
ggagatggcc ctggtagaga cctttggggg tctggaacct ctggactccc catgctctaa      600
ctcccacact ctgctatcag aaacttaaac ttgaggattt tctctgtttt tcactcgcaa      660
taaattcaga gcaaacaaaa aaaaaaaaaa a                                     691

<210> SEQ ID NO 400
<211> LENGTH: 1824
<212> TYPE: DNA
<213> ORGANISM: Homo sapiens

<400> SEQUENCE: 400
caataggccg gcttttgaac tgcttcgcag gggacttgga acagctggac cagctcttgc       60
ccatcttttc agagcagttc ctggtcctgt ccttaatggt gatcgccgtc ctgttgattg      120
tcagtgtgct gtctccatat atcctgttaa tgggagccat aatcatggtt atttgcttca      180
tttattatat gatgttcaag aaggccatcg gtgtgttcaa gagactggag aactatagcc      240
ggtctccttt attctcccac atcctcaatt ctctgcaagg cctgagctcc atccatgtct      300
atggaaaaac tgaagacttc atcagccagt ttaagaggct gactgatgcg cagaataact      360
acctgctgtt gtttctatct tccacacgat ggatggcatt gaggctggag atcatgacca      420
accttgtgac cttggctgtt gccctgttcg tggcttttgg catttcctcc acccctact       480 cctttaaagt catggctgtc aacatcgtgc tgcagctggc gtccagcttc caggccactg      540
cccggattgg cttggagaca gaggcacagt tcacggctgt agagaggata ctgcagtaca      600
tgaagatgtg tgtctcggaa gctccttac acatggaagg cacaagttgt ccccagggt       660 ggccacagca tggggaaatc atatttcagg attatcacat gaaatacaga gacaacacac      720
ccaccgtgct tcacggcatc aacctgacca tccgcggcca cgaagtggtg ggcatcgtgg      780
gaaggacggg ctctgtaggt ttttactgag cacctactat gtgcctggga accgaaaggg      840
aagtcctcct tgggcatggc tctcttccgc ctggtggagc ccatggcagg ccggattctc      900
attgacggcg tggacatttg cagcatcggc ctggaggact gcggtccaa gctctcagtg       960 atccctcaag atccagtgct gctctcagga accatcagat tcaacctaga tcccttgac      1020 cgtcacactg accagcagat ctgggatgcc ttggagagga cattcctgac caaggccatc     1080
tcaaagttcc ccaaaaagct gcatacagat gtggtgaaa acggtggaaa cttctctgtg     1140
ggggagaggc agctgctctg cattgccagg gctgtgcttc gcaactccaa gatcatcctt     1200
atcgatgaag ccacagcctc cattgacatg gagacagaca ccctgatcca cgcacaatc     1260 cgtgaagcct tccagggctg caccgtgctc gtcattgccc accgtgtcac cactgtgctg     1320
aactgtgacc acatcctggt tatgggcaat gggaaggtgg tagaatttga tcggccggag     1380
gtactgcgga agaagcctgg gtcattgttc gcagccctca tggccacagc cacttcttca     1440
ctgagataag gagatgtgga gacttcatgg aggctggcag ctgagctcag aggttcacac     1500
aggtgcagct tcgaggccca cagtctgcga ccttcttgtt tggagatgag aacttctcct     1560
ggaagcaggg gtaaatgtag gggggtggg gattgctgga tggaaaccct ggaataggct     1620
acttgatggc tctcaagacc ttagaacccc agaaccatct aagacatggg attcagtgat     1680
catgtggttc tccttttaac ttacatgctg aataatttta taataaggta aaagcttata     1740
```
gttttctgat ctgtgttaga agtgttgcaa atgctgtact gactttgtaa aatataaaac   1800
taaggaaaac tcaaaaaaaa aaaa   1824

<210> SEQ ID NO 401
<211> LENGTH: 3621
<212> TYPE: DNA
<213> ORGANISM: Homo sapiens

<400> SEQUENCE: 401
cccacagggg gaccggccct gtgacccctc accggggccg tgggcccgag ccccggactt     60
ccctaagccg gcaatgaccg cctgcgcccg ccgagcgggt gggcttccgg accccgggct    120
ctgcggtccc gcgtggtggg ctccgtccct gccccgcctc ccccgggccc tgccccggct    180
cccgctcctg ctgctcctgc ttctgctgca gcccccccgcc ctctccgccg tgttcacggt    240
gggggtcctg ggcccctggg cttgcgaccc catcttctct cgggctcgcc cggacctggc    300
cgcccgcctg gccgccgccc gcctgaaccg cgaccccggc ctggcaggcg gtccccgctt    360
cgaggtagcg ctgctgcccg agccttgccg gacgccgggc tcgctggggg ccgtgtcctc    420
cgcgctggcc cgcgtgtcgg gcctcgtggg tccggtgaac cctgcggcct gccggccagc    480
cgagctgctc gccgaagaag ccgggatcgc gctggtgccc tggggctgcc cctggacgca    540
ggcggagggc accacggccc ctgccgtgac ccccgccgcg gatgccctct acgccctgct    600
tcgcgcattc ggctgggcgc gcgtggccct ggtcaccgcc cccaggacc tgtgggtgga    660 ggcgggacgc tcactgtcca cggcactcag ggcccggggg ctgcctgtcg cctccgtgac    720
ttccatggag cccttggacc tgtctggagc cggggaggcc ctgaggaagg ttcgggacgg    780
gcccagggtc acagcagtga tcatggtgat gcactcggtg ctgctgggtg gcgaggagca    840
gcgctacctc ctggaggccg cagaggagct gggcctgacc gatggctccc tggtcttcct    900
gcccttcgac acgatccact acgccttgtc cccaggcccg gaggccttgg ccgcactcgc    960
caacagctcc cagcttcgca gggcccacga tgccgtgctc accctcacgc gccactgtcc   1020
ctctgaaggc agcgtgctgg acagcctgcg cagggctcaa gagcgccgcg agctgccctc   1080
tgacctcaat ctgcagcagg tctccccact ctttggcacc atctatgacg cggtcttctt   1140
gctggcaagg ggcgtggcag aagcgcgggc tgccgcaggt ggcagatggg tgtccggagc   1200
agctgtggcc cgccacatcc gggatgcgca ggtccctggc ttctgcgggg acctaggagg   1260
agacgaggag cccccattcg tgctgctaga cacggacgcg gcgggagacc ggcttttttgc   1320 cacatacatg ctggatcctg cccggggctc cttcctctcc gccggtaccc ggatgcactt   1380
cccgcgtggg ggatcagcac ccggacctga ccctcgtgc tggttcgatc caaacaacat   1440
ctgcggtgga ggactggagc cgggcctcgt ctttcttggc ttcctcctgg tggttgggat   1500
ggggctggct ggggccttcc tggcccatta tgtgaggcac cggctacttc acatgcaaat   1560
ggtctccggc cccaacaaga tcatcctgac cgtggacgac atcacctttc tccacccaca   1620
tgggggcacc tctcgaaagg tggcccaggg gagtcgatca agtctgggtg cccgcagcat   1680
gtcagacatt cgcagcggcc ccagccaaca cttggacagc cccaacattg gtgtctatga   1740
gggagacagg gtttggctga agaaattccc aggggatcag cacatagcta tccgcccagc   1800
aaccaagacg gccttctcca agctccagga gctccggcat gagaacgtgg ccctctacct   1860
ggggcttttc ctggctcggg gagcagaagg ccctgcggcc ctctgggagg caacctggc   1920 tgtggtctca gagcactgca cgcggggctc tcttcaggac ctcctcgctc agagagaaat   1980
aaagctggac tggatgttca gtcctccct cctgctggac cttatcaagg gaataaggta   2040

```
tctgcaccat cgaggcgtgg ctcatgggcg gctgaagtca cggaactgca tagtggatgg    2100
cagattcgta ctcaagatca ctgaccacgg ccacgggaga ctgctggaag cacagaaggt    2160
gctaccggag cctcccagag cggaggacca gctgtggaca gccccggagc tgcttaggga    2220
cccagccctg gagcgccggg gaacgctggc cggcgacgtc tttagcttgg ccatcatcat    2280
gcaagaagta gtgtgccgca gtgcccctta tgccatgctg gagctcactc ccgaggaagt    2340
ggtgcagagg gtgcggagcc ccctccact gtgtcggccc ttggtgtcca tggaccaggc    2400
acctgtcgag tgtatcctcc tgatgaagca gtgctgggca gagcagccgg aacttcggcc    2460
ctccatggac cacaccttcg acctgttcaa gaacatcaac aagggccgga gacgaacat    2520 cattgactcg atgcttcgga tgctggagca gtactctagt aacctggagg atctgatccg    2580
ggagcgcacg gaggagctgg agctggaaaa gcagaagaca gaccggctgc ttacacagat    2640
gctgcctccg tctgtggctg aggccttgaa gacggggaca ccagtggagc ccgagtactt    2700
tgagcaagtg acactgtact ttagtgacat tgtgggcttc accaccatct ctgccatgag    2760
tgagcccatt gaggttgtgg acctgctcaa cgatctctac acactctttg atgccatcat    2820
tggttcccac gatgtctaca aggtgggaga aatagggggac gcctatatgg tggcctcggg    2880
gctgccccag cggaatgggc agcgacacgc ggcagagatc gccaacatgt cactggacat    2940
cctcagtgcc gtgggcactt ccgcatgcg ccatatgcct gaggttcccg tgcgcatccg    3000
cataggcctg cactcgggtc catgcgtggc aggcgtggtg ggcctcacca tgccgcggta    3060
ctgcctgttt ggggacacgg tcaacaccgc ctcgcgcatg gagtccaccg gctgccctta    3120
ccgcatccac gtgaacttga gcactgtggg gattctccgt gctctggact cgggctacca    3180
ggtggagctg cgaggccgca cggagctgaa gggcaagggc gccgaggaca cttctggct    3240 agtgggcaga cgcggcttca acaagcccat ccccaaaccg cctgacctgc aaccggggtc    3300
cagcaaccac ggcatcagcc tgcaggagat cccaccgag cggcgacgga agctggagaa    3360
ggcgcggccg ggccagttct cttgagaagt gaggcccggc cccggacagg gtctgggccc    3420 tgctcccctgt cccatctgca gtggacccca ggcaccccc tttgaggagg tggggtgaac    3480
tgctccttgg cagggatttg tgacactgca ttgctgggct gtgttcctcg ggctcttctg    3540
gaccttgcac cgtggatacc aggccatgtg ccatggtatt gggtcctgg agggtgggt    3600 gaaataaagg catactgtct t                                             3621

<210> SEQ ID NO 402
<211> LENGTH: 1284
<212> TYPE: DNA
<213> ORGANISM: Homo sapiens

<400> SEQUENCE: 402
ctttcacaga aagaaagtaa caggcataat tcctgttgat gaggctggga ttgttttaa       60 gaggagagat aataacttca tattttaaa gtgccagtag cctaatatgt gaaacagatc     120
agaatctgtt gtgtagtaag tctgctttgt tgaagaattt attatgggag taaagataag     180
aaggaaagag atcaccatca gaaacaagtc agccttttca tgcttttttg agcattttg      240 gagatgattc cacttctcaa gttattatca tttgtgcatc tcttcaatgc tattgttaaa     300
tgctttagaa ttgaatatt ttgatccttt aattaaagta agccaaacgt ctaggcaaaa      360
acagccaatc attaaacttt aatagtaatt caaatataga tttctcatac agttttccat     420
gtctgtagaa atcaaagttg taatgttaag cagagggaaa tgcgtgtgat ttactaatac     480
```

| | |
|---|---|
| acttcaacgt tctactttg aaaggatact catgtgggtg gggcagagaa catagaaaaa | 540 |
| gatatgatgg aaaacctgtc cattttctac ctgttaacct tcatcatttt gtgcaggccc | 600 |
| tggaagcaaa gagaggaagg gaccgactgc atttatcttt gaacacttga gcatcagtag | 660 |
| tactactgag tggccagggg tcttgtctgt caaagcaaat gataagttca ctcaggccat | 720 |
| tattgactgc tgaactctct tccttcccaa ctcttccttg aaagagaaaa aaatactttg | 780 |
| ccttcttgct ctccttatca aatgtttttg tacaaatagt gtaagcctgt ttaagcaaac | 840 |
| caattaaaat aggcactgat tattttgatc tgtttgtaac aaatgaatgt aagtactatt | 900 |
| tacatggtgt gcctaggagg agctgaaatc attggcactt taatccatat tgtaaagatc | 960 |
| agtatcaaaa gcatagtgtt cttcacctct cctcctcagc atccatctct atatacttga | 1020 |
| ttaaatggaa aagtctcttt tatcacctct atgtaaagtt ttatgggtag ttatcgtcag | 1080 |
| tgtatttaaa tatatcttct agtatgtttt aaaggctggt cttcaatact gtggagacaa | 1140 |
| aaaataaaag agcgtatgaa aagtacgtta gacttttgct ggcattcaag tcatggctag | 1200 |
| tctgtgtatt taataaatgt gtgttattta tgtcgtgttt gtcaatggaa aataaagttg | 1260 |
| aatattctga aaaaaaaaaa aaaa | 1284 |

<210> SEQ ID NO 403
<211> LENGTH: 547
<212> TYPE: DNA
<213> ORGANISM: Homo sapiens
<220> FEATURE:
<221> NAME/KEY: misc_feature
<222> LOCATION: (5)..(5)
<223> OTHER INFORMATION: a or g or c or t/u
<220> FEATURE:
<221> NAME/KEY: misc_feature
<222> LOCATION: (10)..(10)
<223> OTHER INFORMATION: a or g or c or t/u
<220> FEATURE:
<221> NAME/KEY: misc_feature
<222> LOCATION: (42)..(42)
<223> OTHER INFORMATION: a or g or c or t/u
<220> FEATURE:
<221> NAME/KEY: misc_feature
<222> LOCATION: (49)..(49)
<223> OTHER INFORMATION: a or g or c or t/u
<220> FEATURE:
<221> NAME/KEY: misc_feature
<222> LOCATION: (80)..(80)
<223> OTHER INFORMATION: a or g or c or t/u
<220> FEATURE:
<221> NAME/KEY: misc_feature
<222> LOCATION: (115)..(115)
<223> OTHER INFORMATION: a or g or c or t/u

<400> SEQUENCE: 403

| | |
|---|---|
| cctanaagtn ccattttggc aaggataaac tcccatgaca anctcccant actgcatgtg | 60 |
| aatgaataag aaacaagaan tgaccacacc aaagcctccc tggctggtgt tacangggat | 120 |
| caggtccaca gtggtgcaga ttcaaccacc acccagggag tgcttgcaga ctctgcatag | 180 |
| atgttgctgc atgcgtccca tgtgcctgtc agaatggcag tgtttaattc tcttgaaaga | 240 |
| aagttatttg ctcactatcc ccagcctcaa ggagccaagg aagagtcatt cacatggaag | 300 |
| gtccgggact ggtcagccac tctgactttt ctaccacatt aaattctcca ttacatctca | 360 |
| ctattggtaa tggcttaagt gtaaagagcc atgatgtgta tattaagcta tgtgccacat | 420 |
| atttattttt agactctcca cagcattcat gtcaatatgg gattaatgcc taaactttgt | 480 |
| aaatattgta cagtttgtaa atcaatgaat aaaggttttg agtgtaaaaa aaaaaaaaa | 540 |
| aaaaaaa | 547 |

<210> SEQ ID NO 404
<211> LENGTH: 784
<212> TYPE: DNA
<213> ORGANISM: Homo sapiens

<400> SEQUENCE: 404

```
ggcacgaggg caaagagtag tcagtccctt cttggctctg ctgacactcg agcccacatt      60
ccatcacctg ctcccaatca tgcaggtctc cactgctgcc cttgccgtcc tcctctgcac     120
catggctctc tgcaaccagg tcctctctgc accacttgct gctgacacgc cgaccgcctg     180
ctgcttcagc tacacctccc ggcagattcc acagaatttc atagctgact actttgagac     240
gagcagccag tgctccaagc ccagtgtcat cttcctaacc aagagaggcc ggcaggtctg     300
tgctgacccc agtgaggagt gggtccagaa atacgtcagt gacctggagc cgagtgcctg     360
aggggtccag aagcttcgag gcccagcgac ctcagtgggc ccagtgggga ggagcaggag     420
cctgagcctt gggaacatgc gtgtgacctc cacagctacc tcttctatgg actggttatt     480
gccaaacagc cacactgtgg gactcttctt aacttaaatt ttaatttatt tatactattt     540
agttttata atttattttt gatttcacag tgtgtttgtg attgtttgct ctgagagttc     600
cccctgtccc ctccaccttc cctcacagtg tgtctggtga caaccgagtg gctgtcatcg     660
gcctgtgtag gcagtcatgg caccaaagcc accagactga caaatgtgta tcagatgctt     720
ttgttcaggg ctgtgatcgg cctggggaaa taataaagat gttcttttaa acggtaaaaa     780
aaaa                                                                  784
```

<210> SEQ ID NO 405
<211> LENGTH: 1216
<212> TYPE: DNA
<213> ORGANISM: Homo sapiens

<400> SEQUENCE: 405

```
agaaaactat tttctaaata ttaacactga aaatgttttg ttagcttttc cttctttctc      60
tccagaagaa acatggatag atgatagctg tttcattgtt tgtttttgtc aagcatattc     120
actttcctcc ttgtcctctg attctgagca aagggcctca gactctgaac ttccctcaag     180
tgccgttgtt atgtgaactc ttccattcag attccagaga ggttctcatg ctcccccccc     240
ctccttattt gtagcaatcg tagcaactaa ttccactaag tacaagggag ttttttacac     300
tcctccattt ttatagcatc tgcattttt tttttgtta ggtacatgta tacacctgcc     360
tgagtataaa tactctctct acctaataat aacatcaacc aacatctttt ccaaattagg     420
gccacagaac agcaacattt gtctgacagt agtataaaga ataatgatag ctctatcctt     480
aagaagtatt tcctttcctt tttatatagt cccgttaggg tttaaaacca tattgatcaa     540
ctagaaagaa aaatatgaaa agagaaaaat attttaattt aaaaattgta atacattgat     600
ttataaaatg ccttctctga tacttttgaa acagatgtga aaaacagaaa aagaaaaaat     660
tgtctgaaat gtttattttg caaaacagtg caatagaatc tagttatgcc ttcatcactg     720
ttgacagtaa atactgacag ccccttgcag tgtgttagtt ttagatcact ctgttttagt     780
tgagagaaat gttttatatc atggttttta tatgaataca aattatttct caaagattta     840
tagcacacac tattctcagg aattctgtat tacatgaatg ctgcttatat attttcatat     900
tctaacttgt cttttcaagc aaataactaa tatatatgtg catgcagtct gccttgacaa     960
gttgttccaa gctgaagagc tttcactgta caatgtgtgg aaaatcacca tagatcatgg    1020
```

```
ctgaaatagt tgtaattgt ctgagtctgt gcacgtactt ttagataaaa tgctgctgag      1080
tgactgcatg atgagataca acttctgaat gctgcacatt cttccaaaat gatccttagc      1140
acaatctatt gtatgatgga atgaatagaa aactttttca ctcaataaat tattatttga      1200
tatggtaaaa aaaaaa                                                     1216

<210> SEQ ID NO 406
<211> LENGTH: 993
<212> TYPE: DNA
<213> ORGANISM: Homo sapiens

<400> SEQUENCE: 406
cccaaggttg ttatatcttc atgtcctcat ttcttaggga ggtaccttca gaaccaatag        60 tgaccctaa cttctctggt ggtcggttcc atgaaaggca aggagtgtg agagaggagt         120 ggatggtcaa cctcccactg ccatggtaac atgggtgctg gctgatggga gcagaaaata       180
atttagtgaa agtctgtggg ggcagtcaca agatgtctga aaaactggc gagccagctg        240 ctgaaaacag ggacaaggaa gcctccgtgg ctggagccca atcacactg cagacccaga        300 caccgtgacc accaccatgg actccagaga gagcagctta tagtactcaa tcagctgcca       360
ctaccaccat ccagaacacc agatgttgta gccatggctg cagcaggaat ggatgtccca       420
ctgtccctgc tcctcggtgt gacttgctcc caagttcagg gcaggtccat ctgattggct       480
gagtctggaa tgtctgcctg tgcctcagct gtgagggagg cagggaaagt aagcctttc       540 agcttctgtc gtgggaggtg ggctctgcct cctaccaaga atcaaagggt ggaggatctt       600
caaacacagg aaaagaaccc ggatcctggc accccaaat tttcagagtc catttcagag        660
cataagaaat tgagggtcca agatcattca tgtaagaagt ttagaggggg aagaaaagaa       720
tgataaacga aagaacagc aatagtaaag gatcttttct ttgtttcagt aagatgaaga       780
ggcctgagca gtttcgtgga ggggaagaaa caggaaaacc tcttcaaaag acaaaaagct      840
ggcactgcat tctctctctg tagcaggaca gaactgtcta aagacaagac ccctttggcc       900
aaaataaagg aacctgaaac attaaaaaaa aaaaaaaaaa aaaaaaaaaa aaaaaaaaa       960 aaaaaaaaaa aaaaaaaaaa aaaaaacctc ggg                                    993

<210> SEQ ID NO 407
<211> LENGTH: 2214
<212> TYPE: DNA
<213> ORGANISM: Homo sapiens

<400> SEQUENCE: 407
aaatttaatt aattataaac tcagtctctt ggttgcacca gccacatttc agatgctcaa        60
tagccacatg tggctagtgg gtaccatatt ggacagggca gctatagaat atttccatca       120
ttgcagaaag ttctattgga tagtaccata atctttttat agtaacttgg aaatactatt       180
tgatattaga tgttagacca caaaagaag aaaaatgtta ggactatttc agatataaaa       240
aggaactgaa ttgtgacata attagcatct tacattccat acagttgaat accttatgct       300
gtgacaacca tagttaatca tttcagtgct gttcaacata catacctatc agcagtgtgt       360
ttagaccagg gtctgcaaa cttttctgtga atggacaaag agtaaatact ttagtaaatg       420
tcttaggctt tgtggcctac atgatctttg ttgcaagtac tcaactctgc cattatagag       480
ttaaagcagc catacacaat atataaacaa aatgggcata gttgtatttc agtaaaactt       540
tatttacaaa gacaggcggt aggccagatt tggcttgcat gctgtagagc tgtggtctaa       600 atttttattca tagactttct ttgcaaatac agtgtgagta ttgttccatt tacagtatta       660
```

```
ttattttta gatacctggt ttttagattc ttgcctggta actttttact gaaaatacaa      720
gaatttcgta ctgcatttgc atctccgaga ttagggagca cctgtcagga tatgttgttc      780
tatcagggtt acttctgttg actacctctt agattttgat acagttatat tgttgagttt      840
cattttcata tattcttgta gtgtctgctt gcctgtgact tctggtaaaa taaaataagc      900
ctttgaaaat attttagcat ggtatttaac attttctaaa tattatggca ttttgacata      960
ttttagtcag cgaagacatc tgccccttttg gtgtttctac ttgcttatga ttgagatttt     1020
acaagccctt caaactccgt tttaaaggaa tttattgtaa acattaact ttaataaatt       1080 agtgttttca cagatcagat cattatactt ggaacttcta atcatgcaa tttctgaata       1140 aggacataag gctagattca ttttttcttaa tagagaaaaa ggaaatttct gatttatcac     1200
ttttctagtt gataagtagg attcaaaacg tttgatatgt aagtatttat ataagactaa     1260
tgtaatttaa agttctgtat tattgtgatt aatcatacag aaattcagga actgatcaga     1320
agtgagattc ttttccacat ctggttaatg tagtgagttg acaccctgtg ggtggtaaag     1380
cattataaac atttcatctt gaaccatgat ttatacacat ctgtgttata agggaggctt     1440
gagtacatat accaatgaag agatattcag catttgtcta tttgataagg aattaaatgt     1500
cctagtgatt ataaagtaaa accacagacc aatttgcaaa tgatcttcaa tgttaagcac     1560
ttgctctaag attaaaattc ctttttctttt taaggtaag ggtgtgtacg tatggcagtg      1620
atgtctatgt tgagattaac ttatgtattg aggaaaattt gaagtttatt ttttcgatga     1680
ataaggctgt caaatgattt agtatagatt aatgacatct tttttagaaa tattaaagtg     1740
agtattcctc attatgtcat catttctgat aattagagtg ctaatttgaa tgttagataa     1800
tgtttccaca tctataccta tttctttcta gggcacttct gaccctgggg cttggggatg     1860
gcctttaggc cacagtagtg tctgtgttaa gttcactaaa tgtgtattta atgagaaaca     1920
ttcctatgta aaaatgtgtg tatgtgaacg tatgcataca ttttttattgt gcacctgtac    1980 attgtgaaga agtagtttgg aaatttgtaa agcacaaacc ataaagagt gtggagttat      2040 taaatgatgt agcacaaatg taatgtttag cttataaaag gtcctttcta ttttctatgg     2100
caaagacttt gacacttgaa aaataaaacc aatatttgat ttattttttgt aagtatttag    2160 gatattattt taaataaatg attgtccatt atcaataaaa aaaaaaaaaa aaaa           2214
```

<210> SEQ ID NO 408
<211> LENGTH: 1182
<212> TYPE: DNA
<213> ORGANISM: Homo sapiens

<400> SEQUENCE: 408

```
gtcctgagca gccaacacac cagcccagac agctgcaagt caccatggac gctgaaggcc       60
tggcgctgct gctgccgccc gtcaccctgg cagccctggt ggacagctgg ctccgagagg      120
actgcccagg gctcaactac gcagccttgg tcagcggggc aggcccctcg caggcggcgc      180
tgtgggccaa atcccctggg gtactggcag ggcagccttt cttcgatgcc atatttaccc      240
aactcaactg ccaagtctcc tggttcctcc ccgagggatc gaagctggtg ccggtggcca      300
gagtggccga ggtccggggc cctgcccact gcctgctgct gggggaacgg gtggccctca      360
acacgctggc ccgctgcagt ggcattgcca gtgctgccgc cgctgcagtg gaggccgcca      420
ggggggccgg ctggactggg cacgtggcag gcacgaggaa gaccacgcca ggcttccggc      480
tggtggagaa gtatgggctc ctggtgggcg gggccgcctc gcaccgctac gacctgggag      540
```

| | |
|---|---|
| ggctggtgat gttgaaggat aaccatgtgg tgcccccgg tggcgtggag aaggcggtgc | 600 |
| gggcggccag acaggcggct gacttcgctc tgaaggtgga agtggaatgc agcagcctgc | 660 |
| aggaggtcgt ccaggcagct gaggctggcg ccgaccttgt cctgctggac aacttcaagc | 720 |
| cagaggagct gcaccccacg gccaccgcgc tgaaggccca gttcccgagt gtggctgtgg | 780 |
| aagccagtgg gggcatcacc ctggacaacc tcccccagtt ctgcgggccg cacatagacg | 840 |
| tcatctccat ggggatgctg acccaggcgg tcccagccct tgatttctcc ctcaagctgt | 900 |
| ttgccaaaga ggtggctcca gtgcccaaaa tccactagtc ctaaaccgga agaggatgac | 960 |
| accggccatg ggttaacgtg ctcctcagg accctctggg tcacacatct ttagggtcag | 1020 |
| tgaacaatgg ggcacatttg gcactagctt gagcccaact ctggctctgc cacctgctgc | 1080 |
| tcctgtgacc tgtcagggct gacttcacct ctgctcatct cagtttccta atctgtaaaa | 1140 |
| tgggtctaat aaaggatcaa ccaaaaaaaa aaaaaaaaa aa | 1182 |

<210> SEQ ID NO 409
<211> LENGTH: 2630
<212> TYPE: DNA
<213> ORGANISM: Homo sapiens

<400> SEQUENCE: 409

| | |
|---|---|
| cggggcatgc tgcttccctt caccttccac catgattgta agtttcctga ggcctcccca | 60 |
| ggtgtgcttc tgtacagcct gtggaatgtt accaaagacg ttggaagagg tggctatggg | 120 |
| acatcacctg ggagaagtgg aagcaaatgg acactgttca gaagtccata tacagaaaca | 180 |
| tacttggaaa aatatagaaa cctggttttg ctagatggga agcttgcagc tggggccaag | 240 |
| acatcaagag tagagcagca ggacatttca aagaagatt aactcaaaga ttagagatgg | 300 |
| aagaacttgc aaagagaaag tctgtaccgg aagaaatctg gaaatctaga ggccagttta | 360 |
| agaatcagca gctaaacaag gagaataatc tagggcaaga gatagctacc tgcacaaaaa | 420 |
| ttcctaccag aaaagagac atagaatcta atgaatttgt gaaaattttt actgtaagat | 480 |
| caatacttgt tgcagaacag atagatccta tggaagagaa ttgtcataaa tatggtacat | 540 |
| gttgaaagat gctcaaacaa aactcagatt taattataca aagaaagtat gatgaaaaa | 600 |
| aaaaaacctt gtaaatatag tgaatgtggg agaaccttca gaggccacat cactcttgtt | 660 |
| cagcatcaaa taactcattg tggagagaga ccctgtaaat gtactgagtg tagaaaggga | 720 |
| tttaatcaga gttcccactt aagaataat cagagaaaaa ctctttcagg agaaaagccc | 780 |
| tacaaatgca gtgagtgtgg gaaggccttc agttattgct tagttcttaa tcaacaccag | 840 |
| agaattcaca gtggagagaa accttatgag ggtactgaat gtggcaagac attcattcag | 900 |
| tcgtacatac cttactcagc atcaaagaat tcacacactg gtgagaagcc ctatacatgt | 960 |
| cttgaatgtg gaaggctttt tagtcagaac acacatctta ctctacatca gagaatccat | 1020 |
| actggagaga aaccttatga atgcaatgaa tgtggtaggt cctttagtca gactgcacat | 1080 |
| cttactcaac atcaaagaat gtatacagga gaaaaactct atgaatgtaa tgaatgtgag | 1140 |
| aaagccttcc atgatcactc agctcttatt caacatcata ttgtccatac tgcagagaaa | 1200 |
| ccctatgata tcatgactgg gaaaactttc agttactgtt cagacctcat tcaacatcag | 1260 |
| agaatgcaca ctggagagaa accatacaaa tgcaatgaat gtgggaatgc ctttagtgat | 1320 |
| tgttcatccc ttattcagca tcaaagaact cacactggag aagagcctta tgaatgtaag | 1380 |
| caatgtggaa aagcctttag cagaagcaca taccttactc aacatcagag aagtcacgca | 1440 |
| ggagagaaac agtataaatg caatgaatgt gagaaaactt tcagcctgag ttcattcctt | 1500 |

```
acacagcata tgagggttca gactggagaa aaaccctaca aatataatga atatggaaaa    1560
gcttttagtg actgctcagg acattttcag agaactcaca ctggagagaa gccctgtgaa    1620
tgtaatgact gtgggaaacc tttcagtttc tgttcagccc taattcaaca taagagaatt    1680
cataccagaa agaagccctg actgtacctt cataccagta aatgcactga ctgtggaaaa    1740
gccttcagtg attggttagc acttgttcaa catcagataa ctcaacactg gagaaaaacc    1800
gtataaatgt actgaatgtg aaaagcctt cagttggagt acagacctca aaaatcacca    1860
gaaaactcat actagtgaaa aatcctataa atgtaatgaa tgtagaaagg cctttagtta    1920
ctgctctggt cttattcaat gtcaggtcat tcatactata gaaaaaccct atgaatacgg    1980
taaatgtggc aaagccttta ggcagaggac agaccttaaa aaacatcaga aaatgcatac    2040
cgaagagaaa ccctatgaat gtaatgaatg tgggaaagcc tttagccaga gcacatatct    2100
tacaaaacac caaaaaattc atagtgaaga gaaatcaaat atacatactg agtgtgggga    2160
aaccattaga caaaactctt cttttacaa caataaaacc tcacactgga gagttctctg    2220
aatgccttaa gaatttggtt aatatggaga cccttcccag ggaaacagaa ggaggatcgt    2280
gaaaaccgtt gactacttga atgatcacat ggtttagtgg agagagcatg attctgggtt    2340
ttaaaagtca tggatctcaa tctcagctcc tattactaac tagatctttt actttggggt    2400
aagtcacttc atatctttag gccttaattt cctcatctga aaactggaag gcctgacttg    2460
acttgttgag cttaagatcc tcaattatta tatttactag gaattcaagt ttctatagat    2520
gtggttcaga attgtgactt atttattgta catcaggtgt gattcacaag tgagcttgta    2580
gtagttatta aggagtcaat aaagatatga tataaaaaaa aaaaaaaaa                2630

<210> SEQ ID NO 410
<211> LENGTH: 551
<212> TYPE: DNA
<213> ORGANISM: Homo sapiens

<400> SEQUENCE: 410
catttcatct tcattggata gtgttacata gtaatatatt tatgttttct tttaatcatt     60
tcataacttg gaaaatacta acatagtcaa aactctaggg taggtgatac atgagtttct    120
gtagtaatct ggttggagac atgttgtaat tctgtatata tatgtacatt tatcccatgc    180
atgttatgcc taaactaaga cggatacccc tgaattaaga ggtgctgtta tacattgacc    240
aggcttaaga atatctcttt aaagtgtgtc gacatttaat tgaccttgg aagttcattc    300 tgttaatcat actcaaagtg ctaaagctat ggttgactgc tctggtgttt ttatattcat    360
tcgtgcttta gcatataaat tcttcagcat aattgctact tatttagcaa gagtttcctt    420
tatttgaaaa tgtgagttgt gcttgtattt ttgtgtcttt ctttctttct ttcttttttt    480
aaactttgct tcaggctggg tagtggtaga ggtttgaatt aaaatgtttt cctgtcagta    540 aaaaaaaaa a                                                           551

<210> SEQ ID NO 411
<211> LENGTH: 2390
<212> TYPE: DNA
<213> ORGANISM: Homo sapiens

<400> SEQUENCE: 411
gagcgagccc agcagcttgc ccttgacagg tgggggctgg ctggggcctt aatgtgaaaa     60
gacagtggca ggcagctgga gtagagcgag cccagcagcc ctaaaaggct gccttcatgg    120
```

```
ccatctagcc ccagttcagg gcagcatcca tagcccacaa gccagcgtgg gtggggcggg      180
ggtggtccca cagctgggtt ccacctgaag agcctccgtg cctcggagca ggagaggcag      240
gctatggctg tcaccctccc tcctgcctgt gtcccagtga aactgacct gagtcccctt       300
ccaaacccag acccacctcc tgccccaggc ccactgaagc atgttccatt tctaaaaagc      360
ccagagttca gtgtgtccca aggaaaaccc aaagtggagg tgctcaggtc caggggagtc      420
cagtgggcag gacccttggc aggcaagccc ctcccttcac tcccaggacc taccttctgc      480
tagtaaagga ctggcttcat tctaattatg gcccacagac tgccccggag acctggagga      540
cagcagtgct ggcactgggg tgtccatggg cccgtctgcc ggctctgcct gtgctgcaag      600
tgttggccgt gggtccagcc aacaactccc tacgtcctgt gtggggccct gcccaagtgg      660
atgaggcatt ccttgaggag tatcattttc cctgacaatc cccatcacct ttaggggttc      720
cctgcttggc tcctttccag ctgaaaaact agacctgtgc cattgggaa gctggacaaa       780
gtctagggg cccgcctggt agagggtccc gggaagctgg atctgtcagc ctcggccctg       840
aggcccctgt taactcaaga ctgtgagctg cctctaggtg gtcacgtctg ggagctagct      900
tgtatggctt ctgaccagta tcaggatttc tgttctgaga gcagcgtggg cagcaaggca      960
gggcagccca gaggtggcag cggcaggcaa tctggtcact aggtctttgt gatgccaaaa     1020
ataaaagagg gtggggtggg tgctttctgt tcctctgatt ggatggagtc cgccagcagg     1080
catgggcta cattccagtg cctgactata ggaggcact cctgattcca tggagcagcc       1140
cggactttga gaatgggctc tggtttgcgg ggggcaggcg taccagactg caagacccc      1200
cagtacctca ccgtgccaaa taggaagagg tggccttggt gtagccaaat ggatcttttt     1260
aacagtgtgc ctttggggag ggacccatgt ccatggcttc gttgagggcc atccatatgc     1320
cagctggggg ccagcccaca gtggccatat tggctgcagc aggaatggtg cccacctcgg     1380
cgaattgaag ggctaagagt cccagatagc taggccagag ctggaagcag acagtaaggg     1440
gaagagctgc tcccacagga gagggagaga ttccagctca ctgcgcagcc tgggaggagg     1500
cgtggatcct ggcacgctga gcctcaggca ccagcctccc tgtgctcgac agcaaagtct     1560
tgactccttc ctgctgagca ctgtgctacc ttcactgctc caaagccaga ctaacagctc     1620
tccaagccct tgggggtgact cggcttccag gagctgttgg agaaatgagg atgtctgtcc     1680
ctgtctgcct gggcaggcca gattcctccc cagcagccgg gtctctccag accctgattc     1740
ggtgcctttc tgtttaccag ctacttcaat cccaaagttt gaatctgcag ataccttact     1800
cccagccact ttgccttctt actgtgttgt gtgttttcc tggtgcttca agagcgtgtg      1860
cagggcaagt gccgtcactg ggaactgcac cagatgctca gacttggttg tcttatgttt     1920
accaataaat aaaagtagac tttttctatt tttatttgct gctatttgtg tgtgtgtttg     1980
tgtttgtgta gctaggtatc tggcacttct gacgatgcat tgttgctttt ttcccgaagg     2040
tcccgcagga actgtggcaa tggtgtgtgt gtgaaatggt gtgttaaccg cgttttgttt     2100
gctcctgtat tgaataggaa gcagtggcca gtctgtcttc cttagagatg ttagcatatt     2160
tttatatgta tatattttgt accaaaaaag agtgttcctt gttttggtta cactcgaaat     2220
tctgacctag ctggagaggg ctctgggccg agagctttca ctaaggggag acttcagggg     2280
aggatcaagc tttgaaccaa agccaatcac tggcttgatt tgtgtttttt aattaaaaaa     2340
aaaatcattc atgtatgcca cttctaaaaa aaaaaaaaaa aaaaaaaaaa                2390
```

<210> SEQ ID NO 412
<211> LENGTH: 1303

<212> TYPE: DNA
<213> ORGANISM: Homo sapiens

<400> SEQUENCE: 412

| | | | | | |
|---|---|---|---|---|---|
| ggcacgaggc | tgagaccggt | gcgccgcgcg | ctagtggccg | ctcttccgcg | ggctagcggg | 60 |
| cggtgggggc | gccagcagcg | cggaaggcgg | gcacgcgggc | catggctccc | tgggcggagg | 120 |
| ccgagcactc | ggcgctgaac | ccgctgcgcg | cggtgtggct | cacgctgacc | gccgccttcc | 180 |
| tgctgaccct | actgctgcag | ctcctgccgc | ccggcctgct | cccgggctgc | gcgatcttcc | 240 |
| aggacctgat | ccgctatggg | aaaaccaagt | gtggggagcc | gtcgcgcccc | gccgcctgcc | 300 |
| gagcctttga | tgtccccaag | agatattttt | cccacttta | tatcatctca | gtgctgtgga | 360 |
| atggcttcct | gctttggtgc | cttactcaat | ctctgttcct | gggagcacct | tttccaagct | 420 |
| ggcttcatgg | tttgctcaga | attctcgggg | cggcacagtt | ccagggaggg | gagctggcac | 480 |
| tgtctgcatt | cttagtgcta | gtatttctgt | ggctgcacag | cttacgaaga | ctcttcgagt | 540 |
| gcctctacgt | cagtgtcttc | tccaatgtca | tgattcacgt | cgtgcagtac | tgtttttggac | 600 |
| ttgtctatta | tgtccttgtt | ggcctaactg | tgctgagcca | agtgccaatg | gatggcagga | 660 |
| atgcctacat | aacagggaaa | aatctattga | tgcaagcacg | gtggttccat | attcttggga | 720 |
| tgatgatgtt | catctggtca | tctgcccatc | agtataagtg | ccatgttatt | ctcggcaatc | 780 |
| tcaggaaaaa | taaagcagga | gtggtcattc | actgtaacca | caggatccca | tttggagact | 840 |
| ggtttgaata | tgtttcttcc | cctaactact | tagcagagct | gatgatctac | gtttccatgg | 900 |
| ccgtcacctt | tgggttccac | aacttaactt | ggtggctagt | ggtgacaaat | gtcttcttta | 960 |
| atcaggccct | gtctgccttt | ctcagccacc | aattctacaa | aagcaaattt | gtctcttacc | 1020 |
| cgaagcatag | gaaagctttc | ctaccatttt | tgttttaagt | taacctcagt | catgaagaat | 1080 |
| gcaaaccagg | tgatggtttc | aatgcctaag | gacagtgaag | tctggagccc | aaagtacagt | 1140 |
| ttcagcaaag | ctgtttgaaa | ctctccattc | catttctata | ccccacaagt | tttcactgaa | 1200 |
| tgagcatggc | agtgccactc | aagaaaatga | atctccaaag | tatcttcaaa | gaataaatac | 1260 |
| taatggcaga | aaaaaaaaaa | aaaaaaaaaa | aaaaaaaaaa | aaa | | 1303 |

PREDICTING BREAST CANCER TREATMENT OUTCOME

RELATED APPLICATIONS

This application claims benefit of priority from U.S. Provisional Patent Application 60/504,087, filed Sep. 19, 2003, and is a continuation-in-part of U.S. patent application Ser. No. 10/727,100, filed Dec. 2, 2003, now U.S. Pat. No. 7,504,214. Both applications are hereby incorporated by reference in their entireties as if fully set forth.

FIELD OF THE INVENTION

The invention relates to the identification and use of gene expression profiles, or patterns, with clinical relevance to the treatment of breast cancer using tamoxifen (nolvadex) and other "antiestrogen" agents against breast cancer, including other "selective estrogen receptor modulators" ("SERM"s), "selective estrogen receptor downregulators" ("SERD"s), and aromatase inhibitors ("AI"s). In particular, the invention provides the identities of gene sequences the expression of which are correlated with patient survival and breast cancer recurrence in women treated with tamoxifen or other "antiestrogen" agents against breast cancer. The gene expression profiles, whether embodied in nucleic acid expression, protein expression, or other expression formats, may be used to select subjects afflicted with breast cancer who will likely respond positively to treatment with tamoxifen or another "antiestrogen" agent against breast cancer as well as those who will likely be non-responsive and thus candidates for other treatments. The invention also provides the identities of three sets of sequences from three genes with expression patterns that are strongly predictive of responsiveness to tamoxifen and other "antiestrogen" agents against breast cancer.

BACKGROUND OF THE INVENTION

Breast cancer is by far the most common cancer among women. Each year, more than 180,000 and 1 million women in the U.S. and worldwide, respectively, are diagnosed with breast cancer. Breast cancer is the leading cause of death for women between ages 50-55, and is the most common non-preventable malignancy in women in the Western Hemisphere. An estimated 2,167,000 women in the United States are currently living with the disease (National Cancer Institute, Surveillance Epidemiology and End Results (NCI SEER) program, *Cancer Statistics Review* (*CSR*), www-seer.ims.nci.nih.gov/Publications/CSR1973 (1998)). Based on cancer rates from 1995 through 1997, a report from the National Cancer Institute (NCI) estimates that about 1 in 8 women in the United States (approximately 12.8 percent) will develop breast cancer during her lifetime (NCI's Surveillance, Epidemiology, and End Results Program (SEER) publication *SEER Cancer Statistics Review* 1973-1997). Breast cancer is the second most common form of cancer, after skin cancer, among women in the United States. An estimated 250,100 new cases of breast cancer are expected to be diagnosed in the United States in 2001. Of these, 192,200 new cases of more advanced (invasive) breast cancer are expected to occur among women (an increase of 5% over last year), 46,400 new cases of early stage (in situ) breast cancer are expected to occur among women (up 9% from last year), and about 1,500 new cases of breast cancer are expected to be diagnosed in men (Cancer Facts & Figures 2001 American Cancer Society). An estimated 40,600 deaths (40,300 women, 400 men) from breast cancer are expected in 2001. Breast cancer ranks second only to lung cancer among causes of cancer deaths in women. Nearly 86% of women who are diagnosed with breast cancer are likely to still be alive five years later, though 24% of them will die of breast cancer after 10 years, and nearly half (47%) will die of breast cancer after 20 years.

Every woman is at risk for breast cancer. Over 70 percent of breast cancers occur in women who have no identifiable risk factors other than age (U.S. General Accounting Office. Breast Cancer, 1971-1991: Prevention, Treatment and Research. GAO/PEMD-92-12; 1991). Only 5 to 10% of breast cancers are linked to a family history of breast cancer (Henderson I C, Breast Cancer. In: Murphy G P, Lawrence W L, Lenhard R E (eds). *Clinical Oncology*. Atlanta, Ga.: American Cancer Society; 1995:198-219).

Each breast has 15 to 20 sections called lobes. Within each lobe are many smaller lobules. Lobules end in dozens of tiny bulbs that can produce milk. The lobes, lobules, and bulbs are all linked by thin tubes called ducts. These ducts lead to the nipple in the center of a dark area of skin called the areola. Fat surrounds the lobules and ducts. There are no muscles in the breast, but muscles lie under each breast and cover the ribs. Each breast also contains blood vessels and lymph vessels. The lymph vessels carry colorless fluid called lymph, and lead to the lymph nodes. Clusters of lymph nodes are found near the breast in the axilla (under the arm), above the collarbone, and in the chest.

Breast tumors can be either benign or malignant. Benign tumors are not cancerous, they do not spread to other parts of the body, and are not a threat to life. They can usually be removed, and in most cases, do not come back. Malignant tumors are cancerous, and can invade and damage nearby tissues and organs. Malignant tumor cells may metastasize, entering the bloodstream or lymphatic system. When breast cancer cells metastasize outside the breast, they are often found in the lymph nodes under the arm (axillary lymph nodes). If the cancer has reached these nodes, it means that cancer cells may have spread to other lymph nodes or other organs, such as bones, liver, or lungs.

Major and intensive research has been focused on early detection, treatment and prevention. This has included an emphasis on determining the presence of precancerous or cancerous ductal epithelial cells. These cells are analyzed, for example, for cell morphology, for protein markers, for nucleic acid markers, for chromosomal abnormalities, for biochemical markers, and for other characteristic changes that would signal the presence of cancerous or precancerous cells. This has led to various molecular alterations that have been reported in breast cancer, few of which have been well characterized in human clinical breast specimens. Molecular alterations include presence/absence of estrogen and progesterone steroid receptors, HER-2 expression/amplification (Mark H F, et al. HER-2/neu gene amplification in stages I-IV breast cancer detected by fluorescent in situ hybridization. Genet Med; 1(3):98-103 1999), Ki-67 (an antigen that is present in all stages of the cell cycle except G0 and used as a marker for tumor cell proliferation, and prognostic markers (including oncogenes, tumor suppressor genes, and angiogenesis markers) like p53, p27, Cathepsin D, pS2, multi-drug resistance (MDR) gene, and CD31.

Tamoxifen is the antiestrogen agent most frequently prescribed in women with both early stage and metastatic hormone receptor-positive breast cancer (for reviews, see Clarke, R. et al. "Antiestrogen resistance in breast cancer and the role of estrogen receptor signaling." *Oncogene* 22, 7316-39 (2003) and Jordan, C. "Historical perspective on hormonal therapy of advanced breast Cancer." *Clin. Ther.* 24 Suppl A, A3-16 (2002)). In the adjuvant setting, tamoxifen therapy results in a 40-50% reduction in the annual risk of recurrence, leading to a 5.6% improvement in 10 year survival in lymph node negative patients, and a corresponding 10.9% improvement in node-positive patients (Group, E.B.C.T.C. Tamoxifen for early breast cancer. Cochrane Database Syst Rev, CD000486 (2001)). Tamoxifen is thought to act primarily as a competitive inhibitor of estrogen binding to estrogen receptor (ER). The absolute levels of ER expression, as well as that of the progesterone receptor (PR, an indicator of a functional ER pathway), are currently the best predictors of tamoxifen response in the clinical setting (Group, (2001) and Bardou, V. J. et al. "Progesterone receptor status significantly improves outcome prediction over estrogen receptor status alone for adjuvant endocrine therapy in two large breast cancer databases." *J Clin Oncol* 21, 1973-9 (2003)).

However, 25% of ER+/PR+ tumors, 66% of ER+/PR− cases and 55% of ER−/PR+ cases fail to respond, or develop early resistance to tamoxifen, through mechanisms that remain largely unclear (see Clarke et al.; Nicholson, R. I. et al. "The biology of antihormone failure in breast cancer." *Breast Cancer Res Treat* 80 Suppl 1, S29-34; discussion S35 (2003) and Osborne, C. K. et al. "Growth factor receptor cross-talk with estrogen receptor as a mechanism for tamoxifen resistance in breast cancer." *Breast* 12, 362-7 (2003)). Currently, no reliable means exist to allow the identification of these non-responders. In these patients, the use of alternative hormonal therapies, such as the aromatase inhibitors letrozole and anastrozole (Ellis, M. J. et al. "Letrozole is more effective neoadjuvant endocrine therapy than tamoxifen for ErbB-1- and/or ErbB-2-positive, estrogen receptor-positive primary breast cancer: evidence from a phase III randomized trial." *J Clin Oncol* 19, 3808-16 (2001); Buzdar, A. U. "Anastrozole: a new addition to the armamentarium against advanced breast cancer." *Am J Clin Oncol* 21, 161-6 (1998); and Goss, P. E. et al. "A randomized trial of letrozole in postmenopausal women after five years of tamoxifen therapy for early-stage breast cancer." *N Engl J Med* 349, 1793-802 (2003)); chemotherapeutic agents, or inhibitors of other signaling pathways, such as trastuzmab and gefitinib might offer the possibility of improving clinical outcome. Therefore, the ability to accurately predict tamoxifen treatment outcome should significantly advance the management of early stage breast cancer by identifying patients who are unlikely to benefit from TAM so that additional or alternative therapies may be sought.

Citation of documents herein is not intended as an admission that any is pertinent prior art. All statements as to the date or representation as to the contents of documents is based on the information available to the applicant and does not constitute any admission as to the correctness of the dates or contents of the documents.

SUMMARY OF THE INVENTION

The present invention relates to the identification and use of gene expression patterns (or profiles or "signatures") and the expression levels of individual gene sequences which are clinically relevant to breast cancer. In particular, the identities of genes that are correlated with patient survival and breast cancer recurrence (e.g. metastasis of the breast cancer) are provided. The gene expression profiles, whether embodied in nucleic acid expression, protein expression, or other expression formats, may be used to predict survival of subjects afflicted with breast cancer and the likelihood of breast cancer recurrence, including cancer metastasis.

The invention thus provides for the identification and use of gene expression patterns (or profiles or "signatures") and the expression levels of individual gene sequences which correlate with (and thus are able to discriminate between) patients with good or poor survival outcomes. In one embodiment, the invention provides patterns that are able to distinguish patients with estrogen receptor (α isoform) positive (ER+) breast tumors into those with that are responsive, or likely to be responsive, to treatment with tamoxifen (TAM) or another "antiestrogen" agent against breast cancer (such as a "selective estrogen receptor modulator" ("SERM"), "selective estrogen receptor downregulator" ("SERD"), or aromatase inhibitor ("AI")) and those that are non-responsive, or likely to be non-responsive, to such treatment. In an alternative embodiment, the invention may be applied to patients with breast tumors that do not display detectable levels of ER expression (so called "ER−" subjects) but where the patient will nonetheless benefit from application of the invention due to the presence of some low level ER expression. Responsiveness may be viewed in terms of better survival outcomes over time. These patterns are thus able to distinguish patients with ER+ breast tumors into at least two subtypes.

In a first aspect, the present invention provides a non-subjective means for the identification of patients with breast cancer (ER+ or ER−) as likely to have a good or poor survival outcome following treatment with TAM or another "antiestrogen" agent against breast cancer by assaying for the expression patterns disclosed herein. Thus where subjective interpretation may have been previously used to determine the prognosis and/or treatment of breast cancer patients, the present invention provides objective gene expression patterns, which may used alone or in combination with subjective criteria to provide a more accurate assessment of ER+ or ER− breast cancer patient outcomes or expected outcomes, including survival and the recurrence of cancer, following treatment with TAM or another "antiestrogen" agent against breast cancer. The expression patterns of the invention thus provide a means to determine ER+ or ER− breast cancer prognosis. Furthermore, the expression patterns can also be used as a means to assay small, node negative tumors that are not readily assayed by other means.

The gene expression patterns comprise one or more than one gene capable of discriminating between breast cancer outcomes with significant accuracy. The gene sequence(s) are identified as correlated with ER+ breast cancer outcomes such that the levels of their expression are relevant to a determination of the preferred treatment protocols for a patient, whether ER+ or ER−. Thus in one embodiment, the invention provides a method to determine the outcome of a subject afflicted with breast cancer by assaying a cell containing sample from said subject for expression of one or more than one gene disclosed herein as correlated with breast cancer outcomes following treatment with TAM or another "antiestrogen" agent against breast cancer.

The ability to correlate gene expression with breast cancer outcome and responsiveness to TAM is particularly advantageous in light of the possibility that up to 40% of ER+ subjects that undergo TAM treatment are non-responders. Therefore, the ability to identify, with confidence, these non-responders at an early time point permits the consideration and/or application of alternative therapies (such as a different "antiestrogen" agent against breast cancer or other anti-breast cancer treatments) to the non-responders. Stated differently, the ability to identify TAM non-responder subjects permits medical personnel to consider and/or utilize alternative therapies for the treatment of the subjects before time is spent on ineffective TAM therapy. Time spent on an ineffective therapy often permits further cancer growth, and the likelihood of success with alternative therapies diminishes over time given such growth. Therefore, the invention also provides methods to improve the survival outcome of non-responders by use of the methods disclosed herein to identify non-responders for treatment with alternative therapies.

Gene expression patterns of the invention are identified as described below. Generally, a large sampling of the gene expression profile of a sample is obtained through quantifying the expression levels of mRNA corresponding to many genes. This profile is then analyzed to identify genes, the expression of which are positively, or negatively, correlated, with ER+ breast cancer outcome upon treatment with TAM or another "antiestrogen" agent against breast cancer. An expression profile of a subset of human genes may then be identified by the methods of the present invention as correlated with a particular outcome. The use of multiple samples increases the confidence which a gene may be believed to be correlated with a particular survival outcome. Without sufficient confidence, it remains unpredictable whether expression of a particular gene is actually correlated with an outcome and also unpredictable whether expression of a particular gene may be successfully used to identify the outcome for a breast cancer patient. While the invention may be practiced based on the identities of the gene sequences disclosed herein or the actual sequences used independent of identification, the invention may also be practiced with any other sequences the expression of which is correlated with the expression of sequences disclosed herein. Such additional sequences may be identified by any means known in the art, including the methods disclosed herein.

A profile of genes that are highly correlated with one outcome relative to another may be used to assay an sample from a subject afflicted with breast cancer to predict the likely responsiveness (or lack thereof) to TAM or another "antiestrogen" agent against breast cancer in the subject from whom the sample was obtained. Such an assay may be used as part of a method to determine the therapeutic treatment for said subject based upon the breast cancer outcome identified.

As discussed below, the correlated genes may be used singly with significant accuracy or in combination to increase the ability to accurately correlating a molecular expression phenotype with a breast cancer outcome. This correlation is a way to molecularly provide for the determination of survival outcomes as disclosed herein. Additional uses of the correlated gene(s) are in the classification of cells and tissues; determination of diagnosis and/or prognosis; and determination and/or alteration of therapy.

The ability to discriminate is conferred by the identification of expression of the individual genes as relevant and not by the form of the assay used to determine the actual level of expression. An assay may utilize any identifying feature of an identified individual gene as disclosed herein as long as the assay reflects, quantitatively or qualitatively, expression of the gene in the "transcriptome" (the transcribed fraction of genes in a genome) or the "proteome" (the translated fraction of expressed genes in a genome). Additional assays include those based on the detection of polypeptide fragments of the relevant member or members of the proteome. Identifying features include, but are not limited to, unique nucleic acid sequences used to encode (DNA), or express (RNA), said gene or epitopes specific to, or activities of, a protein encoded by said gene. All that is required are the gene sequence(s) necessary to discriminate between breast cancer outcomes and an appropriate cell containing sample for use in an expression assay.

In another embodiment, the invention provides for the identification of the gene expression patterns by analyzing global, or near global, gene expression from single cells or homogenous cell populations which have been dissected away from, or otherwise isolated or purified from, contaminating cells beyond that possible by a simple biopsy. Because the expression of numerous genes fluctuate between cells from different patients as well as between cells from the same patient sample, multiple data from expression of individual genes and gene expression patterns are used as reference data to generate models which in turn permit the identification of individual gene(s), the expression of which are most highly correlated with particular breast cancer outcomes.

In additional embodiments, the invention provides physical and methodological means for detecting the expression of gene(s) identified by the models generated by individual expression patterns. These means may be directed to assaying one or more aspects of the DNA template(s) underlying the expression of the gene(s), of the RNA used as an intermediate to express the gene(s), or of the proteinaceous product expressed by the gene(s).

In further embodiments, the gene(s) identified by a model as capable of discriminating between breast cancer outcomes may be used to identify the cellular state of an unknown sample of cell(s) from the breast. Preferably, the sample is isolated via non-invasive means. The expression of said gene(s) in said unknown sample may be determined and compared to the expression of said gene(s) in reference data of gene expression patterns correlated with breast cancer outcomes. Optionally, the comparison to reference samples may be by comparison to the model(s) constructed based on the reference samples.

One advantage provided by the present invention is that contaminating, non-breast cells (such as infiltrating lymphocytes or other immune system cells) are not present to possibly affect the genes identified or the subsequent analysis of gene expression to identify the survival outcomes of patients with breast cancer. Such contamination is present where a biopsy is used to generate gene expression profiles. However, and as noted herein, the invention includes the identity of genes that may be used with significant accuracy even in the presence of contaminating cells.

In a second aspect, the invention provides a non-subjective means based on the expression of three genes, or combinations thereof, for the identification of patients with breast cancer as likely to have a good or poor survival outcome following treatment with TAM or another "antiestrogen" agent against breast cancer. These three genes are members of the expression patterns disclosed herein which have been found to be strongly predictive of clinical outcome following TAM treatment of ER+ breast cancer.

The present invention thus provides gene sequences identified as differentially expressed in ER+ breast cancer in correlation to TAM responsiveness. The sequences of two of the genes display increased expression in ER+ breast cells that respond to TAM treatment (and thus lack of increased expression in nonresponsive cases). The sequences of the third gene display decreased expression in ER+ breast cells that respond to TAM treatment (and thus lack of decreased expression in nonresponsive cases).

The first set of sequences found to be more highly expressed in TAM responsive, ER+ breast cells are those of interleukin 17 receptor B (IL17RB), which has been mapped to human chromosome 3 at 3p21.1. IL17RB is also referred to as interleukin 17B receptor (IL17BR) and sequences corresponding to it, and thus may be used in the practice of the instant invention, are identified by UniGene Cluster Hs.5470.

The second set of sequences found to be more highly expressed in TAM responsive, ER+ breast cells are those of the calcium channel, voltage-dependent, L type, alpha 1D subunit (CACNA1D), which has been mapped to human chromosome 3 at 3p14.3. Sequences corresponding to CACNA1D, and thus may be used in the practice of the instant invention, are identified by UniGene Cluster Hs.399966.

The set of sequences found to be expressed at lower levels in TAM responsive, ER+ breast cells are those of homeobox B13 (HOXB13), which has been mapped to human chromosome 17 at 17q21.2. Sequences corresponding to HOXB13, and thus may be used in the practice of the instant invention, are identified by UniGene Cluster Hs.66731.

While the invention may be practiced based on the identities of these three gene sequences or the actual sequences used independent of the assigned identity, the invention may also be practiced with any other sequence the expression of which is correlated with the expression of these disclosed sequences. Such additional sequences may be identified by any means known in the art, including the methods disclosed herein.

The identified sequences may thus be used in methods of determining the responsiveness, or non-responsiveness, of a subject's ER+ or ER− breast cancer to TAM treatment, or treatment with another "antiestrogen" agent against breast cancer, via analysis of breast cells in a tissue or cell containing sample from a subject. As non-limiting examples, the lack of increased expression of IL17BR and CACNA1D sequences and/or the lack of decreased expression of HOXB13 sequences may be used as an indicator of nonresponsive cases. The present invention provides an non-empirical means for determining responsiveness to TAM or another SERM in ER+ or ER− patients. This provides advantages over the use of a "wait and see" approach following treatment with TAM or other "antiestrogen" agent against breast cancer. The expression levels of these sequences may also be used as a means to assay small, node negative tumors that are not readily assessed by conventional means.

The expression levels of the identified sequences may be used alone or in combination with other sequences capable of determining responsiveness to treatment with TAM or another "antiestrogen" agent against breast cancer. Preferably, the sequences of the invention are used alone or in combination with each other, such as in the format of a ratio of expression levels that can have improved predictive power over analysis based on expression of sequences corresponding to individual genes. The invention provides for ratios of the expression level of a sequence that is underexpressed to the expression level of a sequence that is overexpressed as a indicator of responsiveness or non-responsiveness.

The present invention provides means for correlating a molecular expression phenotype with a physiological response in a subject with ER+ or ER− breast cancer. This correlation provides a way to molecularly diagnose and/or determine treatment for a breast cancer afflicted subject. Additional uses of the sequences are in the classification of cells and tissues; and determination of diagnosis and/or prognosis. Use of the sequences to identify cells of a sample as responsive, or not, to treatment with TAM or other "antiestrogen" agent against breast cancer may be used to determine the choice, or alteration, of therapy used to treat such cells in the subject, as well as the subject itself, from which the sample originated.

Such methods of the invention may be used to assist the determination of providing tamoxifen or another "antiestrogen" agent against breast cancer as a chemopreventive or chemoprotective agent to a subject at high risk for development of breast cancer. These methods of the invention are an advance over the studies of Fabian et al. (*J Natl Cancer Inst.* 92(15):1217-27, 2000), which proposed a combination of cytomorphology and the Gail risk model to identify high risk patients. The methods may be used in combination with assessments of relative risk of breast cancer such as that discussed by Tan-Chiu et al. (*J Natl Cancer Inst.* 95(4):302-307, 2003). Non-limiting examples include assaying of minimally invasive sampling, such as random (periareolar) fine needle aspirates or ductal lavage samples (such as that described by Fabian et al. and optionally in combination with or as an addition to a mammogram positive for benign or malignant breast cancer), of breast cells for the expression levels of gene sequences as disclosed herein to assist in the determination of administering therapy with an "antiestrogen" agent against breast cancer, such as that which may occur in cases of high risk subjects (like those described by Tan-Chiu et al.). The assays would thus lead to the identification of subjects for who the application of an "antiestrogen" agent against breast cancer would likely be beneficial as a chemopreventive or chemoprotective agent. It is contemplated that such application as enabled by the instant invention could lead to beneficial effects such as those seen with the administration of tamoxifen (see for example, Wickerham D. L., Breast Cancer Res. and Treatment 75 Suppl 1:S7-12, Discussion S33-5, 2000). Other applications of the invention include assaying of advanced breast cancer, including metastatic cancer, to determine the responsiveness, or non-responsiveness, thereof to treatment with an "antiestrogen" agent against breast cancer.

An assay of the invention may utilize a means related to the expression level of the sequences disclosed herein as long as the assay reflects, quantitatively or qualitatively, expression of the sequence. Preferably, however, a quantitative assay means is preferred. The ability to determine responsiveness to TAM or other "antiestrogen" agent against breast cancer and thus outcome of treatment therewith is provided by the recognition of the relevancy of the level of expression of the identified sequences and not by the form of the assay used to determine the actual level of expression. Identifying features of the sequences include, but are not limited to, unique nucleic acid sequences used to encode (DNA), or express (RNA), the disclosed sequences or epitopes specific to, or activities of, proteins encoded by the sequences. Alternative means include detection of nucleic acid amplification as indicative of increased expression levels and nucleic acid inactivation, deletion, or methylation, as indicative of decreased expression levels. Stated differently, the invention may be practiced by assaying one or more aspect of the DNA template(s) underlying the expression of the disclosed sequence(s), of the RNA used as an intermediate to express the sequence(s), or of the proteinaceous product expressed by the sequence(s), as well as proteolytic fragments of such products. As such, the detection of the presence of, amount of, stability of, or degradation (including rate) of, such DNA, RNA and proteinaceous molecules may be used in the practice of the invention.

The practice of the present invention is unaffected by the presence of minor mismatches between the disclosed sequences and those expressed by cells of a subject's sample. A non-limiting example of the existence of such mismatches are seen in cases of sequence polymorphisms between individuals of a species, such as individual human patients within *Homo sapiens*. Knowledge that expression of the disclosed sequences (and sequences that vary due to minor mismatches) is correlated with the presence of non-normal or abnormal breast cells and breast cancer is sufficient for the practice of the invention with an appropriate cell containing sample via an assay for expression.

In one embodiment, the invention provides for the identification of the expression levels of the disclosed sequences by analysis of their expression in a sample containing ER+ or ER− breast cells. In one preferred embodiment, the sample contains single cells or homogenous cell populations which have been dissected away from, or otherwise isolated or purified from, contaminating cells beyond that possible by a simple biopsy. Alternatively, undissected cells within a "section" of tissue may be used. Multiple means for such analysis are available, including detection of expression within an assay for global, or near global, gene expression in a sample (e.g. as part of a gene expression profiling analysis such as on a microarray) or by specific detection, such as quantitative PCR (Q-PCR), or real time quantitative PCR.

Preferably, the sample is isolated via non-invasive or minimally invasive means. The expression of the disclosed sequence(s) in the sample may be determined and compared to the expression of said sequence(s) in reference data of non-normal or cancerous breast cells. Alternatively, the expression level may be compared to expression levels in normal or non-cancerous cells, preferably from the same sample or subject. In embodiments of the invention utilizing Q-PCR, the expression level may be compared to expression levels of reference genes in the same sample or a ratio of expression levels may be used.

When individual breast cells are isolated in the practice of the invention, one benefit is that contaminating, non-breast cells (such as infiltrating lymphocytes or other immune system cells) are not present to possibly affect detection of expression of the disclosed sequence(s). Such contamination is present where a biopsy is used to generate gene expression profiles. However, analysis of differential gene expression and correlation to ER+ breast cancer outcomes with both isolated and non-isolated samples, as described herein, increases the confidence level of the disclosed sequences as capable of having significant predictive power with either type of sample.

While the present invention is described mainly in the context of human breast cancer, it may be practiced in the context of breast cancer of any animal known to be potentially afflicted by breast cancer. Preferred animals for the application of the present invention are mammals, particularly those important to agricultural applications (such as, but not limited to, cattle, sheep, horses, and other "farm animals"), animal models of breast cancer, and animals for human companionship (such as, but not limited to, dogs and cats).

The above aspects and embodiments of the invention may be applied equally with respect to use of more than one "antiestrogen" agent against breast cancer. In the case of a combination of agents, any combination of more than one SERM, SERD, or AI may be used in place of TAM or another "antiestrogen" agent against breast cancer. Aromatase is an enzyme that provides a major source of estrogen in body tissues including the breast, liver, muscle and fat. Without being bound by theory, and solely provided to assist in a better understanding of the invention, AIs are understood to function in a manner comparable to TAM and other "antiestrogen" agents against breast cancer, which are thought to act as antagonists of estrogen receptor in breast tissues and thus as against breast cancer. AIs may be either nonsteroidal or steroidal agents. Examples of the former, which inhibit aromatase via the heme prosthetic group) include, but are not limited to, anastrozole (arimidex), letrozole (femara), and vorozole (rivisor), which have been used or contemplated as treatments for metastatic breast cancer. Examples of steroidal AIs, which inactivate aromatase, include, but are not limited to, exemestane (aromasin), androstenedione, and formestane (lentaron).

Other forms of therapy to reduce estrogen levels include surgical or chemical ovarian ablation. The former is physical removal of the ovaries while the latter is the use of agents to block ovarian production of estrogen. One non-limiting example of the latter are agonists of gonadotropin releasing hormone (GnRH), such as goserelin (zoladex). Of course the instant invention may also be practiced with these therapies in place of treatment with one or more "antiestrogen" agent against breast cancer.

The invention disclosed herein is based in part on the performance of a genome-wide microarray analysis of hormone receptor-positive invasive breast tumors from 60 patients treated with adjuvant tamoxifen alone, leading to the identification of a two-gene expression ratio that is highly predictive of clinical outcome. This expression ratio, which is readily adapted to PCR-based analysis of standard paraffin-embedded clinical specimens, was validated in an independent set of 20 patients as described below.

MODES OF PRACTICING THE INVENTION

Figure 1:
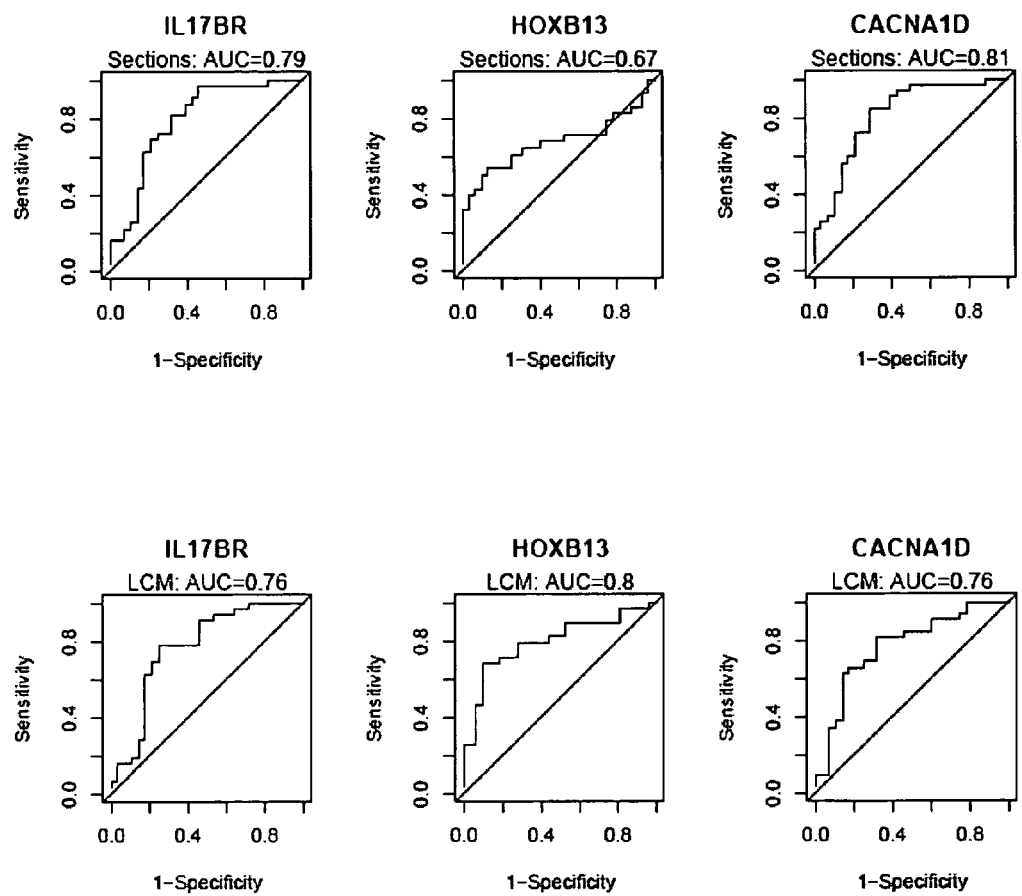
FIG. 1 shows receiver operating characteristic (ROC) analyses of IL17BR, HOXB13, and CACNA1D expression levels as predictors of breast cancer outcomes in whole tissue sections (top 3 graphs) and laser microdissected cells (bottom 3 graphs). AUC refers to area under the curve.

Definitions of terms as used herein:

A gene expression "pattern" or "profile" or "signature" refers to the relative expression of genes correlated with responsiveness to treatment of ER+ breast cancer with TAM or another "antiestrogen" agent against breast cancer. Responsiveness or lack thereof may be expressed as survival outcomes which are correlated with an expression "pattern" or "profile" or "signature" that is able to distinguish between, and predict, said outcomes.

A "selective estrogen receptor modulator" or SERM is an "antiestrogen" agent that in some tissues act like estrogens (agonist) but block estrogen action in other tissues (antagonist). A "selective estrogen receptor downregulators" (or "SERD"s) or "pure" antiestrogens includes agents which block estrogen activity in all tissues. See Howell et al. (Best Bractice & Res. Clin. Endocrinol. Metab. 18(1):47-66, 2004). Preferred SERMs of the invention are those that are antagonists of estrogen in breast tissues and cells, including those of breast cancer. Non-limiting examples of such include TAM, raloxifene, GW5638, and ICI 182,780. The possible mechanisms of action by various SERMs have been reviewed (see for example Jordan et al., 2003, Breast Cancer Res. 5:281-283; Hall et al., 2001, J. Biol. Chem. 276(40): 36869-36872; Dutertre et al. 2000, J. Pharmacol. Exp. Therap. 295(2):431-437; and Wijayaratne et al., 1999, Endocrinology 140(12):5828-5840). Other non-limiting examples of SERMs in the context of the invention include triphenylethylenes, such as tamoxifen, GW5638, TAT-59, clomiphene, toremifene, droloxifene, and idoxifene; benzothiophenes, such as arzoxiphene (LY353381 or LY353381-HCl); benzopyrans, such as EM-800; naphthalenes, such as CP-336,156; and ERA-923.

Non-limiting examples of SERD or "pure" antiestrogens include agents such as ICI 182,780 (fulvestrant or faslodex) or the oral analogue SR16243 and ZK 191703 as well as aromatase inhibitors and chemical ovarian ablation agents as described herein.

Other agents encompassed by SERM as used herein include progesterone receptor inhibitors and related drugs, such as progestomimetics like medroxyprogesterone acetate, megace, and RU-486; and peptide based inhibitors of ER action, such as LH-RH analogs (leuprolide, zoladex, [D-Trp6]LH-RH), somatostatin analogs, and LXXLL motif mimics of ER as well as tibolone and resveratrol. As noted above, preferred SERMs of the invention are those that are antagonist of estrogen in breast tissues and cells, including those of breast cancer. Non-limiting examples of preferred SERMs include the actual or contemplated metabolites (in vivo) of any SERM, such as, but not limited to, 4-hydroxytamoxifen (metabolite of tamoxifen), EM652 (or SCH 57068 where EM-800 is a prodrug of EM-652), and GW7604 (metabolite of GW5638). See Willson et al. (1997, Endocrinology 138(9):3901-3911) and Dauvois et al. (1992, Proc. Nat'l. Acad. Sci., USA 89:4037-4041) for discussions of some specific SERMs.

Other preferred SERMs are those that produce the same relevant gene expression profile as tamoxifen or 4-hydroxytamoxifen. One example of means to identify such SERMs is provided by Levenson et al. (2002, Cancer Res. 62:4419-4426).

A "gene" is a polynucleotide that encodes a discrete product, whether RNA or proteinaceous in nature. It is appreciated that more than one polynucleotide may be capable of encoding a discrete product. The term includes alleles and polymorphisms of a gene that encodes the same product, or a functionally associated (including gain, loss, or modulation of function) analog thereof, based upon chromosomal location and ability to recombine during normal mitosis.

A "sequence" or "gene sequence" as used herein is a nucleic acid molecule or polynucleotide composed of a discrete order of nucleotide bases. The term includes the ordering of bases that encodes a discrete product (i.e. "coding region"), whether RNA or proteinaceous in nature, as well as the ordered bases that precede or follow a "coding region". Non-limiting examples of the latter include 5' and 3' untranslated regions of a gene. It is appreciated that more than one polynucleotide may be capable of encoding a discrete product. It is also appreciated that alleles and polymorphisms of the disclosed sequences may exist and may be used in the practice of the invention to identify the expression level(s) of the disclosed sequences or the allele or polymorphism. Identification of an allele or polymorphism depends in part upon chromosomal location and ability to recombine during mitosis.

The terms "correlate" or "correlation" or equivalents thereof refer to an association between expression of one or more genes and a physiological response of a breast cancer cell and/or a breast cancer patient in comparison to the lack of the response. A gene may be expressed at higher or lower levels and still be correlated with responsiveness, non-responsiveness or breast cancer survival or outcome. The invention provides for the correlation between increases in expression of IL17BR and CACNA1D sequences and responsiveness of ER+ breast cells to TAM or another "antiestrogen" agent against breast cancer. Thus increases are indicative of responsiveness. Conversely, the lack of increases, including unchanged expression levels, are indicators of non-responsiveness. Similarly, the invention provides for the correlation between decreases in expression of HOXB13 sequences and responsiveness of ER+ breast cells to TAM or another SERM. Thus decreases are indicative of responsiveness while the lack of decreases, including unchanged expression levels, are indicators of non-responsiveness. Increases and decreases may be readily expressed in the form of a ratio between expression in a non-normal cell and a normal cell such that a ratio of one (1) indicates no difference while ratios of two (2) and one-half indicate twice as much, and half as much, expression in the non-normal cell versus the normal cell, respectively. Expression levels can be readily determined by quantitative methods as described below.

For example, increases in IL17BR, CACNA1D, or HOXB13 expression can be indicated by ratios of or about 1.1, of or about 1.2, of or about 1.3, of or about 1.4, of or about 1.5, of or about 1.6, of or about 1.7, of or about 1.8, of or about 1.9, of or about 2, of or about 2.5, of or about 3, of or about 3.5, of or about 4, of or about 4.5, of or about 5, of or about 5.5, of or about 6, of or about 6.5, of or about 7, of or about 7.5, of or about 8, of or about 8.5, of or about 9, of or about 9.5, of or about 10, of or about 15, of or about 20, of or about 30, of or about 40, of or about 50, of or about 60, of or about 70, of or about 80, of or about 90, of or about 100, of or about 150, of or about 200, of or about 300, of or about 400, of or about 500, of or about 600, of or about 700, of or about 800, of or about 900, or of or about 1000. A ratio of 2 is a 100% (or a two-fold) increase in expression. Decreases in IL17BR, CACNA1D, or HOXB13 expression can be indicated by ratios of or about 0.9, of or about 0.8, of or about 0.7, of or about 0.6, of or about 0.5, of or about 0.4, of or about 0.3, of or about 0.2, of or about 0.1, of or about 0.05, of or about 0.01, of or about 0.005, of or about 0.001, of or about 0.0005, of or about 0.0001, of or about 0.00005, of or about 0.00001, of or about 0.000005, or of or about 0.000001.

For a given phenotype, a ratio of the expression of a gene sequence expressed at increased levels in correlation with the phenotype to the expression of a gene sequence expressed at decreased levels in correlation with the phenotype may also be used as an indicator of the phenotype. As a non-limiting example, the phenotype of non-responsiveness to tamoxifen treatment of breast cancer is correlated with increased expression of HOXB13 as well as decreased expression of IL17BR and CACNA1D. Therefore, a ratio of the expression levels of HOXB13 to IL17BR (or CACNA1D) may be used as an indicator of non-responsiveness.

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications including labels known in the art, methylation, "caps", substitution of one or more of the naturally occurring nucleotides with an analog, and internucleotide modifications such as uncharged linkages (e.g., phosphorothioates, phosphorodithioates, etc.), as well as unmodified forms of the polynucleotide.

The term "amplify" is used in the broad sense to mean creating an amplification product can be made enzymatically with DNA or RNA polymerases. "Amplification," as used herein, generally refers to the process of producing multiple copies of a desired sequence, particularly those of a sample. "Multiple copies" mean at least 2 copies. A "copy" does not necessarily mean perfect sequence complementarity or identity to the template sequence. Methods for amplifying mRNA are generally known in the art, and include reverse transcription PCR (RT-PCR) and those described in U.S. patent application Ser. No. 10/062,857 (filed on Oct. 25, 2001), as well as U.S. Provisional Patent Application 60/298,847 (filed Jun. 15, 2001) and 60/257,801 (filed Dec. 22, 2000), all of which are hereby incorporated by reference in their entireties as if fully set forth. Another method which may be used is quantitative PCR (or Q-PCR). Alternatively, RNA may be directly labeled as the corresponding cDNA by methods known in the art.

By "corresponding", it is meant that a nucleic acid molecule shares a substantial amount of sequence identity with another nucleic acid molecule. Substantial amount means at least 95%, usually at least 98% and more usually at least 99%, and sequence identity is determined using the BLAST algorithm, as described in Altschul et al. (1990), J. Mol. Biol. 215:403-410 (using the published default setting, i.e. parameters w=4, t=17).

A "microarray" is a linear or two-dimensional or three dimensional (and solid phase) array of preferably discrete regions, each having a defined area, formed on the surface of a solid support such as, but not limited to, glass, plastic, or synthetic membrane. The density of the discrete regions on a microarray is determined by the total numbers of immobilized polynucleotides to be detected on the surface of a single solid phase support, preferably at least about 50/cm$^2$, more preferably at least about 100/cm$^2$, even more preferably at least about 500/cm$^2$, but preferably below about 1,000/cm$^2$. Preferably, the arrays contain less than about 500, about 1000, about 1500, about 2000, about 2500, or about 3000 immobilized polynucleotides in total. As used herein, a DNA microarray is an array of oligonucleotides or polynucleotides placed on a chip or other surfaces used to hybridize to amplified or cloned polynucleotides from a sample. Since the position of each particular group of primers in the array is known, the identities of a sample polynucleotides can be determined based on their binding to a particular position in the microarray. As an alternative to the use of a microarray, an array of any size may be used in the practice of the invention, including an arrangement of one or more position of a two-dimensional or three dimensional arrangement in a solid phase to detect expression of a single gene sequence.

Because the invention relies upon the identification of genes that are over- or underexpressed, one embodiment of the invention involves determining expression by hybridization of mRNA, or an amplified or cloned version thereof, of a sample cell to a polynucleotide that is unique to a particular gene sequence. Preferred polynucleotides of this type contain at least about 16, at least about 18, at least about 20, at least about 22, at least about 24, at least about 26, at least about 28, at least about 30, or at least about 32 consecutive basepairs of a gene sequence that is not found in other gene sequences. The term "about" as used in the previous sentence refers to an increase or decrease of 1 from the stated numerical value. Even more preferred are polynucleotides of at least or about 50, at least or about 100, at least about or 150, at least or about 200, at least or about 250, at least or about 300, at least or about 350, at least or about 400, at least or about 450, or at least or about 500 consecutive bases of a sequence that is not found in other gene sequences. The term "about" as used in the preceding sentence refers to an increase or decrease of 10% from the stated numerical value. Longer polynucleotides may of course contain minor mismatches (e.g. via the presence of mutations) which do not affect hybridization to the nucleic acids of a sample. Such polynucleotides may also be referred to as polynucleotide probes that are capable of hybridizing to sequences of the genes, or unique portions thereof, described herein. Such polynucleotides may be labeled to assist in their detection. Preferably, the sequences are those of mRNA encoded by the genes, the corresponding cDNA to such mRNAs, and/or amplified versions of such sequences. In preferred embodiments of the invention, the polynucleotide probes are immobilized on an array, other solid support devices, or in individual spots that localize the probes.

In another embodiment of the invention, all or part of a disclosed sequence may be amplified and detected by methods such as the polymerase chain reaction (PCR) and variations thereof, such as, but not limited to, quantitative PCR (Q-PCR), reverse transcription PCR (RT-PCR), and real-time PCR (including as a means of measuring the initial amounts of mRNA copies for each sequence in a sample), optionally real-time RT-PCR or real-time Q-PCR. Such methods would utilize one or two primers that are complementary to portions of a disclosed sequence, where the primers are used to prime nucleic acid synthesis. The newly synthesized nucleic acids are optionally labeled and may be detected directly or by hybridization to a polynucleotide of the invention. The newly synthesized nucleic acids may be contacted with polynucleotides (containing sequences) of the invention under conditions which allow for their hybridization. Additional methods to detect the expression of expressed nucleic acids include RNAse protection assays, including liquid phase hybridizations, and in situ hybridization of cells.

Alternatively, and in yet another embodiment of the invention, gene expression may be determined by analysis of expressed protein in a cell sample of interest by use of one or more antibodies specific for one or more epitopes of individual gene products (proteins), or proteolytic fragments thereof, in said cell sample or in a bodily fluid of a subject. The cell sample may be one of breast cancer epithelial cells enriched from the blood of a subject, such as by use of labeled antibodies against cell surface markers followed by fluorescence activated cell sorting (FACS). Such antibodies are preferably labeled to permit their easy detection after binding to the gene product. Detection methodologies suitable for use in the practice of the invention include, but are not limited to, immunohistochemistry of cell containing samples or tissue, enzyme linked immunosorbent assays (ELISAs) including antibody sandwich assays of cell containing tissues or blood samples, mass spectroscopy, and immuno-PCR.

The term "label" refers to a composition capable of producing a detectable signal indicative of the presence of the labeled molecule. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

As used herein, a "breast tissue sample" or "breast cell sample" refers to a sample of breast tissue or fluid isolated from an individual suspected of being afflicted with, or at risk of developing, breast cancer. Such samples are primary isolates (in contrast to cultured cells) and may be collected by any non-invasive or minimally invasive means, including, but not limited to, ductal lavage, fine needle aspiration, needle biopsy, the devices and methods described in U.S. Pat. No. 6,328,709, or any other suitable means recognized in the art. Alternatively, the "sample" may be collected by an invasive method, including, but not limited to, surgical biopsy.

"Expression" and "gene expression" include transcription and/or translation of nucleic acid material.

As used herein, the term "comprising" and its cognates are used in their inclusive sense; that is, equivalent to the term "including" and its corresponding cognates.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in the sequence of a gene disclosed herein interest in comparison to a reference sequence. A sequence mutation includes single nucleotide changes, or alterations of more than one nucleotide in a sequence, due to mechanisms such as substitution, deletion or insertion. Single nucleotide polymorphism (SNP) is also a sequence mutation as used herein. Because the present invention is based on the relative level of gene expression, mutations in non-coding regions of genes as disclosed herein may also be assayed in the practice of the invention.

"Detection" includes any means of detecting, including direct and indirect detection of gene expression and changes therein. For example, "detectably less" products may be observed directly or indirectly, and the term indicates any reduction (including the absence of detectable signal). Similarly, "detectably more" product means any increase, whether observed directly or indirectly.

Increases and decreases in expression of the disclosed sequences are defined in the following terms based upon percent or fold changes over expression in normal cells. Increases may be of 10, 20, 30, 40, 50, 60, 70, 80, 90, 100, 120, 140, 160, 180, or 200% relative to expression levels in normal cells. Alternatively, fold increases may be of 1, 1.5, 2, 2.5, 3, 3.5, 4, 4.5, 5, 5.5, 6, 6.5, 7, 7.5, 8, 8.5, 9, 9.5, or 10 fold over expression levels in normal cells. Decreases may be of 10, 20, 30, 40, 50, 55, 60, 65, 70, 75, 80, 82, 84, 86, 88, 90, 92, 94, 96, 98, 99 or 100% relative to expression levels in normal cells.

Unless defined otherwise all technical and scientific terms used herein have the same meaning as commonly understood to one of ordinary skill in the art to which this invention belongs.

Embodiments of the Invention

In a first aspect, the disclosed invention relates to the identification and use of gene expression patterns (or profiles or "signatures") which discriminate between (or are correlated with) breast cancer survival in a subject treated with tamoxifen (TAM) or another "antiestrogen" agent against breast cancer. Such patterns may be determined by the methods of the invention by use of a number of reference cell or tissue samples, such as those reviewed by a pathologist of ordinary skill in the pathology of breast cancer, which reflect breast cancer cells as opposed to normal or other non-cancerous cells. The outcomes experienced by the subjects from whom the samples may be correlated with expression data to identify patterns that correlate with the outcomes following treatment with TAM or another "antiestrogen" agent against breast cancer. Because the overall gene expression profile differs from person to person, cancer to cancer, and cancer cell to cancer cell, correlations between certain cells and genes expressed or underexpressed may be made as disclosed herein to identify genes that are capable of discriminating between breast cancer outcomes.

The present invention may be practiced with any number of the genes believed, or likely to be, differentially expressed with respect to breast cancer outcomes, particularly in cases of ER+ breast cancer. The identification may be made by using expression profiles of various homogenous breast cancer cell populations, which were isolated by microdissection, such as, but not limited to, laser capture microdissection (LCM) of 100-1000 cells. The expression level of each gene of the expression profile may be correlated with a particular outcome. Alternatively, the expression levels of multiple genes may be clustered to identify correlations with particular outcomes.

Genes with significant correlations to breast cancer survival when the subject is treated with tamoxifen may be used to generate models of gene expressions that would maximally discriminate between outcomes where a subject responds to treatment with tamoxifen or another "antiestrogen" agent against breast cancer and outcomes where the treatment is not successful. Alternatively, genes with significant correlations may be used in combination with genes with lower correlations without significant loss of ability to discriminate between outcomes. Such models may be generated by any appropriate means recognized in the art, including, but not limited to, cluster analysis, supported vector machines, neural networks or other algorithm known in the art. The models are capable of predicting the classification of a unknown sample based upon the expression of the genes used for discrimination in the models. "Leave one out" cross-validation may be used to test the performance of various models and to help identify weights (genes) that are uninformative or detrimental to the predictive ability of the models. Cross-validation may also be used to identify genes that enhance the predictive ability of the models.

The gene(s) identified as correlated with particular breast cancer outcomes relating to tamoxifen treatment by the above models provide the ability to focus gene expression analysis to only those genes that contribute to the ability to identify a subject as likely to have a particular outcome relative to another. The expression of other genes in a breast cancer cell would be relatively unable to provide information concerning, and thus assist in the discrimination of, a breast cancer outcome.

As will be appreciated by those skilled in the art, the models are highly useful with even a small set of reference gene expression data and can become increasingly accurate with the inclusion of more reference data although the incremental increase in accuracy will likely diminish with each additional datum. The preparation of additional reference gene expression data using genes identified and disclosed herein for discriminating between different outcomes in breast cancer following treatment with tamoxifen or another "antiestrogen" agent against breast cancer is routine and may be readily performed by the skilled artisan to permit the generation of models as described above to predict the status of an unknown sample based upon the expression levels of those genes.

To determine the (increased or decreased) expression levels of genes in the practice of the present invention, any method known in the art may be utilized. In one preferred embodiment of the invention, expression based on detection of RNA which hybridizes to the genes identified and disclosed herein is used. This is readily performed by any RNA detection or amplification+detection method known or recognized as equivalent in the art such as, but not limited to, reverse transcription-PCR, the methods disclosed in U.S. patent application Ser. No. 10/062,857 (filed on Oct. 25, 2001) as well as U.S. Provisional Patent Application 60/298,847 (filed Jun. 15, 2001) and 60/257,801 (filed Dec. 22, 2000), and methods to detect the presence, or absence, of RNA stabilizing or destabilizing sequences.

Alternatively, expression based on detection of DNA status may be used. Detection of the DNA of an identified gene as methylated or deleted may be used for genes that have decreased expression in correlation with a particular breast cancer outcome. This may be readily performed by PCR based methods known in the art, including, but not limited to, Q-PCR. Conversely, detection of the DNA of an identified gene as amplified may be used for genes that have increased expression in correlation with a particular breast cancer outcome. This may be readily performed by PCR based, fluorescent in situ hybridization (FISH) and chromosome in situ hybridization (CISH) methods known in the art.

Expression based on detection of a presence, increase, or decrease in protein levels or activity may also be used. Detection may be performed by any immunohistochemistry (IHC) based, blood based (especially for secreted proteins), antibody (including autoantibodies against the protein) based, exfoliate cell (from the cancer) based, mass spectroscopy based, and image (including used of labeled ligand) based method known in the art and recognized as appropriate for the detection of the protein. Antibody and image based methods are additionally useful for the localization of tumors after determination of cancer by use of cells obtained by a non-invasive procedure (such as ductal lavage or fine needle aspiration), where the source of the cancerous cells is not known. A labeled antibody or ligand may be used to localize the carcinoma(s) within a patient or to assist in the enrichment of exfoliated cancer cells from a bodily fluid.

A preferred embodiment using a nucleic acid based assay to determine expression is by immobilization of one or more sequences of the genes identified herein on a solid support, including, but not limited to, a solid substrate as an array or to beads or bead based technology as known in the art. Alternatively, solution based expression assays known in the art may also be used. The immobilized gene(s) may be in the form of polynucleotides that are unique or otherwise specific to the gene(s) such that the polynucleotide would be capable of hybridizing to a DNA or RNA corresponding to the gene(s). These polynucleotides may be the full length of the gene(s) or be short sequences of the genes (up to one nucleotide shorter than the full length sequence known in the art by deletion from the 5' or 3' end of the sequence) that are optionally minimally interrupted (such as by mismatches or inserted non-complementary basepairs) such that hybridization with a DNA or RNA corresponding to the gene(s) is not affected. Preferably, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal.

The immobilized gene(s) may be used to determine the state of nucleic acid samples prepared from sample breast cell(s) for which the outcome of the sample's subject (e.g. patient from whom the sample is obtained) is not known or for confirmation of an outcome that is already assigned to the sample's subject. Without limiting the invention, such a cell may be from a patient with ER+ or ER− breast cancer. The immobilized polynucleotide(s) need only be sufficient to specifically hybridize to the corresponding nucleic acid molecules derived from the sample under suitable conditions. While even a single correlated gene sequence may to able to provide adequate accuracy in discriminating between two breast cancer outcomes, two or more, three or more, four or more, five or more, six or more, seven or more, eight or more, nine or more, ten or more, or eleven or more of the genes identified herein may be used as a subset capable of discriminating may be used in combination to increase the accuracy of the method. The invention specifically contemplates the selection of more than one, two or more, three or more, four or more, five or more, six or more, seven or more, eight or more, nine or more, ten or more, or eleven or more of the genes disclosed in the tables and figures herein for use as a subset in the identification of breast cancer survival outcome.

Of course 1 or more, 2 or more, 3 or more, 4 or more, 5 or more, 6 or more, 7 or more, 8 or more, 9 or more, or all the genes provided in Tables 2 and/or 3 below may be used. "Accession" as used in the context of the Tables herein as well as the present invention refers to the GenBank accession number of a sequence of each gene, the sequences of which are hereby incorporated by reference in their entireties as they are available from GenBank as accessed on the filing date of the present application. P value refers to values assigned as described in the Examples below. The indications of "E-xx" where "xx" is a two digit number refers to alternative notation for exponential figures where "E-xx" is "$10^{-xx}$". Thus in combination with the numbers to the left of "E-xx", the value being represented is the numbers to the left times $10^{-xx}$. "Description" as used in the Tables provides a brief identifier of what the sequence/gene encodes.

Genes with a correlation identified by a p value below or about 0.02, below or about 0.01, below or about 0.005, or below or about 0.001 are preferred for use in the practice of the invention. The present invention includes the use of gene(s) the expression of which identify different breast cancer outcomes after treatment with TAM or another "antiestrogen" agent against breast cancer to permit simultaneous identification of breast cancer survival outcome of a patient based upon assaying a breast cancer sample from said patient.

In a second aspect, the present invention relates to the identification and use of three sets of sequences for the determination of responsiveness of ER+ breast cancer to treatment with TAM or another "antiestrogen" agent against breast cancer. The differential expression of these sequences in breast cancer relative to normal breast cells is used to predict responsiveness to TAM or another "antiestrogen" agent against breast cancer in a subject.

To identify gene expression patterns in ER positive, early stage invasive breast cancers that might predict response to hormonal therapy, microarray gene expression analysis was performed on tumors from 60 women uniformly treated with adjuvant tamoxifen alone. These patients were identified from a total of 103 ER+ early stage cases presenting to Massachusetts General Hospital between 1987 and 1997, from whom tumor specimens were snap frozen and for whom minimal 5 year follow-up was available (see Table 1 for details). Within this cohort, 28 (46%) women developed distant metastasis with a median time to recurrence of 4 years ("tamoxifen non-responders") and 32 (54%) women remained disease-free with median follow-up of 10 years ("tamoxifen responders"). Responders were matched with non-responder cases with respect to TNM staging (see Singletary, S. E. et al. "Revision of the American Joint Committee on Cancer staging system for breast cancer." *J Clin Oncol* 20, 3628-36 (2002)) and tumor grade (see Dalton, L. W. et al. "Histologic grading of breast cancer: linkage of patient outcome with level of pathologist agreement." *Mod Pathol* 13, 730-5. (2000)).

Previous studies linking gene expression profiles to clinical outcome in breast cancer have demonstrated that the potential for distant metastasis and overall survival probability may be predictable through biological characteristics of the primary tumor at the time of diagnosis (see Huang, E. et al. "Gene expression predictors of breast cancer outcomes." *Lancet* 361, 1590-6 (2003); Sorlie, T. et al. "Gene expression patterns of breast carcinomas distinguish tumor subclasses with clinical implications." *Proc Natl Acad Sci USA* 98:10869-74 (2001); Sorlie, T. et al. "Repeated observation of breast tumor subtypes in independent gene expression data sets." *Proc Natl Acad Sci USA* 100, 8418-23 (2003); Sotiriou, C. et al. "Breast cancer classification and prognosis based on gene expression profiles from a population-based study." *Proc Natl Acad Sci USA* 100, 10393-8 (2003); van't Veer, L. J. et al. "Gene expression profiling predicts clinical outcome of breast cancer." Nature 415, 530-6 (2002); and van de Vijver, M. J. et al. "A gene-expression signature as a predictor of survival in breast cancer." *N Engl J Med* 347, 1999-2009 (2002)). In particular, a 70-gene expression signature has proven to be a strong prognostic factor, out-performing all known clinicopathological parameters. However, in those studies patients either received no adjuvant therapy (van't Veer, L. J. et al. Nature 2002) or were treated non-uniformly with hormonal and chemotherapeutic regimens (Huang, E. et al.; Sorlie, T. et al.; Sorlie, T. et al.; Sotiriou, C. et al.; and van de Vijver, M. J. et al. *N Engl J Med* 2002). Patients with ER+ early-stage breast cancer treated with tamoxifen alone, such as the cohort studied here, represent only a subset of the population tested with the 70-gene signature. Of note, 61 of the genes in the 70-gene signature were present on the microarray used as described below, but no significant association with clinical outcome was observed in the defined subset of patients.

In comparison with existing biomarkers, including ESR1, PGR, ERBB2 and EGFR, three sets of gene sequences disclosed herein are significantly more predictive of responsiveness to TAM treatment. Multivariate analysis indicated that these three genes were significant predictors of clinical outcome independent of tumor size, nodal status and tumor grade. ER and progesterone receptor (PR) expression have been the major clinicopathological predictors for response to TAM. However, up to 40% of ER+ tumors fail to respond or develop resistance to TAM. The invention thus provides for the use of the identified biomarkers to allow better patient management by identifying patients who are more likely to benefit from TAM or other endocrine therapy and those who are likely to develop resistance and tumor recurrence.

As noted herein, the sequences(s) identified by the present invention are expressed in correlation with ER+ breast cancer cells. For example, IL17BR, identified by I.M.A.G.E. Consortium Clusters NM_018725 and NM_172234 ("The I.M.A.G.E. Consortium: An Integrated Molecular Analysis of Genomes and their Expression," Lennon et al., 1996, Genomics 33:151-152; see also image.llnl.gov) has been found to be useful in predicting responsiveness to TAM treatment.

In preferred embodiments of the invention, any sequence, or unique portion thereof, of the IL17BR sequences of the cluster, as well as the UniGene *Homo sapiens* cluster Hs.5470, may be used. Similarly, any sequence encoding all or a part of the protein encoded by any IL17BR sequence disclosed herein may be used. Consensus sequences of I.M.A.G.E. Consortium clusters are as follows, with the assigned coding region (ending with a termination codon) underlined and preceded by the 5' untranslated and/or non-coding region and followed by the 3' untranslated and/or non-coding region:

SEQ ID NO:1 (Consensus Sequence for IL17BR, Transcript Variant 1, Identified as NM_018725 or NM_018725.2)

```
agcgcagcgt gcgggtggcc tggatcccgc gcagtggccc ggcgatgtcg ctcgtgctgc taagcctggc cgcgctgtgc aggagcgccg taccccgaga gccgaccgtt caatgtggct ctgaaactgg gccatctcca gagtggatgc tacaacatga tctaatcccc ggagacttga gggacctccg agtagaacct gttacaacta gtgttgcaac agggggactat tcaattttga tgaatgtaag ctgggtactc cgggcagatg ccagcatccg cttgttgaag gccaccaaga tttgtgtgac gggcaaaagc aacttccagt cctacagctg tgtgaggtgc aattacacag aggccttcca gactcagacc agaccctctg gtggtaaatg gacatttttcc tacatcggct
```

-continued

```
tccctgtaga gctgaacaca gtctatttca ttggggccca taatattcct aatgcaaata tgaatgaaga tggcccttcc atgtctgtga atttcacctc accaggctgc ctagaccaca taatgaaata taaaaaaaag tgtgtcaagg ccggaagcct gtgggatccg aacatcactg cttgtaagaa gaatgaggag acagtagaag tgaacttcac aaccactccc ctgggaaaca gatacatggc tcttatccaa cacagcacta tcatcgggtt ttctcaggtg tttgagccac accagaagaa acaaacgcga gcttcagtgg tgattccagt gactggggat agtgaaggtg ctacggtgca gctgactcca tattttccta cttgtggcag cgactgcatc cgacataaag gaacagttgt gctctgccca caaacaggcg tccctttccc tctggataac aacaaaagca agccgggagg ctggctgcct ctcctcctgc tgtctctgct ggtggccaca tgggtgctgg tggcagggat ctatctaatg tggaggcacg aaaggatcaa gaagacttcc ttttctacca ccacactact gccccccatt aaggttcttg tggtttaccc atctgaaata tgtttccatc acacaatttg ttacttcact gaatttcttc aaaaccattg cagaagtgag gtcatccttg aaaagtggca gaaaaagaaa atagcagaga tgggtccagt gcagtggctt gccactcaaa agaaggcagc agacaaagtc gtcttccttc tttccaatga cgtcaacagt gtgtgcgatg gtacctgtgg caagagcgag ggcagtccca gtgagaactc tcaagacctc ttccccttg cctttaacct tttctgcagt gatctaagaa gccagattca tctgcacaaa tacgtggtgg tctactttag agagattgat acaaaagacg attacaatgc tctcagtgtc tgccccaagt accacctcat gaaggatgcc actgctttct gtgcagaact tctccatgtc aagcagcagg tgtcagcagg aaaaagatca caagcctgcc acgatggctg ctgctccttg tagcccaccc atgagaagca agagacctta aaggcttcct atcccaccaa ttacagggaa aaaacgtgtg atgatcctga agcttactat gcagcctaca acagcctta gtaattaaaa cattttatac caataaaatt ttcaaatatt gctaactaat gtagcattaa ctaacgattg gaaactacat ttacaacttc aaagctgttt tatacataga aatcaattac agttttaatt gaaaactata accattttga taatgcaaca ataaagcatc ttcagccaaa catctagtct tccatagacc atgcattgca gtgtacccag aactgtttag ctaatattct atgtttaatt aatgaatact aactctaaga accctcact gattcactca atagcatctt aagtgaaaaa ccttctatta catgcaaaaa atcattgttt ttaagataac aaaagtaggg aataaacaag ctgaacccac tttaaaaaa aaaaaaaaa aaaaaaaaa aaaaaaa
```

SEQ ID NO:2 (Consensus Sequence for IL17BR, Transcript Variant 2, Identified as NM_172234 or NM_172234.1)

```
agcgcagcgt gcgggtggcc tggatcccgc gcagtggccc ggcgatgtcg ctcgtgctgc taagcctggc cgcgctgtgc aggagcgccg taccccgaga gccgaccgtt caatgtggct ctgaaactgg gccatctcca gagtggatgc tacaacatga tctaatcccc ggagacttga gggacctccg agtagaacct gttacaacta gtgttgcaac aggggactat tcaattttga tgaatgtaag ctgggtactc cgggcagatg ccagcatccg cttgttgaag gccaccaaga tttgtgtgac gggcaaaagc aacttccagt cctacagctg tgtgaggtgc aattacacag aggccttcca gactcagacc agaccctctg gtggtaaatg gacattttcc tacatcggct tccctgtaga gctgaacaca gtctatttca ttggggccca taatattcct aatgcaaata tgaatgaaga tggcccttcc atgtctgtga atttcacctc accaggctgc ctagaccaca taatgaaata taaaaaaaag tgtgtcaagg ccggaagcct gtgggatccg aacatcactg
```

-continued cttgtaagaa gaatgaggag acagtagaag tgaacttcac aaccactccc ctgggaaaca gatacatggc tcttatccaa cacagcacta tcatcgggtt ttctcaggtg tttgagccac accagaagaa acaaacgcga gcttcagtgg tgattccagt gactggggat agtgaaggtg ctacggtgca ggtaaagttc agtgagctgc tctggggagg gaagggacat agaagactgt tccatcattc attgctttta aggatgagtt ctctcttgtc aaatgcactt ctgccagcag acaccagtta agtggcgttc atggggctc tttcgctgca gcctccaccg tgctgaggtc aggaggccga cgtggcagtt gtggtccctt ttgcttgtat taatggctgc tgaccttcca aagcactttt tattttcatt ttctgtcaca gacactcagg gatagcagta ccattttact tccgcaagcc tttaactgca agatgaagct gcaaagggtt tgaaatggga aggtttgagt tccaggcagc gtatgaactc tggagagggg ctgccagtcc tctctgggcc gcagcggacc cagctggaac acaggaagtt ggagcagtag gtgctccttc acctctcagt atgtctcttt caactctagt ttttgaggtg gggacacagg aggtccagtg ggacacagcc actccccaaa gagtaaggag cttccatgct tcattccctg gcataaaaag tgctcaaaca caccagaggg ggcaggcacc agccagggta tgatggctac tacccttttc tggagaacca tagacttccc ttactacagg gacttgcatg tcctaaagca ctggctgaag gaagccaaga ggatcactgc tgctcctttt ttctagagga aatgtttgtc tacgtggtaa gatatgacct agccctttta ggtaagcgaa ctggtatgtt agtaacgtgt acaaagttta ggttcagacc ccgggagtct tgggcacgtg ggtctcgggt cactggtttt gactttaggg cttgttaca gatgtgtgac caagggaaa atgtgcatga caacactaga ggtatgggcg aagccagaaa gaagggaagt tttggctgaa gtaggagtct tggtgagatt ttgctctgat gcatggtgtg aactttctga gcctcttgtt tttcctcagc tgactccata ttttcctact tgtggcagcg actgcatccg acataaagga acagttgtgc tctgcccaca acaggcgtc cctttccctc tggataacaa caaaagcaag ccgggaggct ggctgcctct cctcctgctg tctctgctgg tggccacatg ggtgctggtg gcagggatct atctaatgtg gaggcacgaa aggatcaaga agacttcctt ttctaccacc acactactgc cccccattaa ggttcttgtg gtttacccat ctgaaatatg tttccatcac acaatttgtt acttcactga atttcttcaa aaccattgca gaagtgaggt catccttgaa aagtggcaga aaaagaaaat agcagagatg ggtccagtgc agtggcttgc cactcaaaag aaggcagcag acaaagtcgt cttccttctt tccaatgacg tcaacagtgt gtgcgatggt acctgtggca agagcgaggg cagtcccagt gagaactctc aagacctctt ccccccttgcc tttaaccttt tctgcagtga tctaagaagc cagattcatc tgcacaaata cgtggtggtc tactttagag agattgatac aaaagacgat acaatgctc tcagtgtctg ccccaagtac cacctcatga aggatgccac tgctttctgt gcagaacttc tccatgtcaa gcagcaggtg tcagcaggaa aaagatcaca agcctgccac gatggctgct gctccttgta gcccacccat gagaagcaag agaccttaaa ggcttcctat cccaccaatt acagggaaaa aacgtgtgat gatcctgaag cttactatgc agcctacaaa cagccttagt aattaaaaca ttttatacca ataaaatttt caaatattgc taactaatgt agcattaact aacgattgga aactacattt acaacttcaa agctgttta tacatagaaa tcaattacag ttttaattga aaactataac cattttgata atgcaacaat aaagcatctt cagccaaaca tctagtcttc catagaccat gcattgcagt gtacccagaa ctgtttagct aatattctat gtttaattaa tgaatactaa ctctaagaac ccctcactga ttcactcaat agcatcttaa gtgaaaaacc

```
                            -continued
ttctattaca tgcaaaaaat cattgttttt aagataacaa aagtagggaa taaacaagct gaacccactt ttaaaaaaaa aaaaaaaaaa aaaaaaaaaa aaaaa
```

I.M.A.G.E. Consortium Clone ID numbers and the corresponding GenBank accession numbers of sequences identified as belonging to the I.M.A.G.E. Consortium and Uni-Gene clusters, are listed below. Also included are sequences that are not identified as having a Clone ID number but still identified as being those of IL17RB. The sequences include those of the "sense" and complementary strands sequences corresponding to IL17RB. The sequence of each GenBank accession number is presented in the Sequence Listing.

TABLE (I)

| Clone ID numbers | GenBank accession numbers |
| --- | --- |
| 2985728 | AW675096, AW673932, BC000980 |
| 5286745 | BI602183 |
| 5278067 | BI458542 |
| 5182255 | BI823321 |
| 924000 | AA514396 |
| 3566736 | BF110326 |
| 3195409 | BE466508 |
| 3576775 | BF740045 |
| 2772915 | AW299271 |
| 1368826 | AA836217 |
| 1744837 | AI203628 |
| 2285564 | AI627783 |
| 2217709 | AI744263 |
| 2103651 | AI401622 |
| 2419487 | AI826949 |
| 3125592 | BE047352 |
| 2284721 | AI911549 |
| 3643302 | BF194822 |
| 1646910 | AI034244 |
| 1647001 | AI033911 |
| 3323709 | BF064177 |
| 1419779 | AA847767 |
| 2205190 | AI538624 |
| 2295838 | AI913613 |
| 2461335 | AI942234 |
| 2130362 | AI580483 |
| 2385555 | AI831909 |
| 2283817 | AI672344 |
| 2525596 | AW025192 |
| 454687 | AA677205 |
| 1285273 | AA721647 |
| 3134106 | BF115018 |
| 342259 | W61238, W61239 |
| 1651991 | AI032064 |
| 2687714 | AW236941 |
| 3302808 | BG057174 |
| 2544461 | AW058532 |
| 122014 | T98360, T98361 |
| 2139250 | AI470845 |
| 2133899 | AI497731 |
| 121300 | T96629, T96740 |
| 162274 | H25975, H25941 |
| 3446667 | BE539514, BX282554 |
| 156864 | R74038, R74129 |

TABLE (I)-continued

| Clone ID numbers | GenBank accession numbers |
| --- | --- |
| 4611491 | BG433769 |
| 4697316 | BG530489 |
| 429376 | AA007528, AA007529 |
| 5112415 | BI260259 |
| 701357 | AA287951, AA287911 |
| 121909 | T97852, T97745 |
| 268037 | N40294 |
| 1307489 | AA809841 |
| 1357543 | AA832389 |
| 48442 | H14692 |
| 1302619 | AA732635 |
| 1562857 | AA928257 |
| 1731938 | AI184427 |
| 1896025 | AI298577 |
| 2336350 | AI692717 |
| 1520997 | AA910922 |
| 240506 | H90761 |
| 2258560 | AI620122 |
| 1569921 | AI793318, AA962325, AI733290 |
| 6064627 | BQ226353 |
| 299018 | W04890 |
| 5500181 | BM455231 |
| 2484011 | BI492426 |
| 4746376 | BG674622 |
| 233783 | BX111256 |
| 1569921 | BX117618 |
| 450450 | AA682806 |
| 1943085 | AI202376 |
| 2250390 | AI658949 |
| 4526156 | BG403405 |
| 3249181 | BE673417 |
| 2484395 | AW021469 |
| 30515867 | CF455736 |
| 2878155 | AW339874 |
| 4556884 | BG399724 |
| 3254505 | BF475787 |
| 3650593 | BF437145 |
| 233783 | H64601 |
| None (mRNA sequences) | AF212365, AF208110, AF208111, AF250309, AK095091 |
| None | BM983744, CB305764, BM715988, BM670929, BI792416, BI715216, N56060, CB241389, AV660618, BX088671, CB154426, CA434589, CA412162, CA314073, BF921554, BF920093, AV685699, AV650175, BX483104, CD675121, BE081436, AW970151, AW837146, AW368264, D25960, AV709899, BX431018, AL535617, AL525465, BX453536, BX453537, AV728945, AV728939, AV727345 |

In one preferred embodiment, any sequence, or unique portion thereof, of the following IL17BR sequence, identified by AF208111 or AF208111.1, may be used in the practice of the invention.

SEQ ID NO:3 (Sequence for IL17BR):

```
CGGCGATGTCGCTCGTGCTGATAAGCCTGGCCGCGCTGTGCAGGAGCGCCGTACCCCGAG

AGCCGACCGTTCAATGTGGCTCTGAAACTGGGCCATCTCCAGAGTGGATGCTACAACATG

ATCTAATCCCCGGAGACTTGAGGGACCTCCGAGTAGAACCTGTTACAACTAGTGTTGCAA

CAGGGGACTATTCAATTTTGATGAATGTAAGCTGGGTACTCCGGGCAGATGCCAGCATCC

GCTTGTTGAAGGCCACCAAGATTTGTGTGACGGGCAAAAGCAACTTCCAGTCCTACAGCT

GTGTGAGGTGCAATTACACAGAGGCCTTCCAGACTCAGACCAGACCCTCTGGTGGTAAAT
```

-continued

```
GGACATTTTCCTATATCGGCTTCCCTGTAGAGCTGAACACAGTCTATTTCATTGGGGCCC
ATAATATTCCTAATGCAAATATGAATGAAGATGGCCCTTCCATGTCTGTGAATTTCACCT
CACCAGGCTGCCTAGACCACATAATGAAATATAAAAAAAAGTGTGTCAAGGCCGGAAGCC
TGTGGGATCCGAACATCACTGCTTGTAAGAAGAATGAGGAGACAGTAGAAGTGAACTTCA
CAACCACTCCCCTGGGAAACAGATACATGGCTCTTATCCAACACAGCACTATCATCGGGT
TTTCTCAGGTGTTTGAGCCACACCAGAAGAAACAAACGCGAGCTTCAGTGGTGATTCCAG
TGACTGGGGATAGTGAAGGTGCTACGGTGCAGGTAAAGTTCAGTGAGCTGCTCTGGGGAG
GGAAGGGACATAGAAGACTGTTCCATCATTCATTGCTTTTAAGGATGAGTTCTCTCTTGT
CAAATGCACTTCTGCCAGCAGACACCAGTTAAGTGGCGTTCATGGGGGTTCTTTCGCTGC
AGCCTCCACCGTGCTGAGGTCAGGAGGCCGACGTGGCAGTTGTGGTCCCTTTTGCTTGTA
TTAATGGCTGCTGACCTTCCAAAGCACTTTTTATTTTCATTTTCTGTCACAGACACTCAG
GGATAGCAGTACCATTTTACTTCCGCAAGCCTTTAACTGCAAGATGAAGCTGCAAAGGGT
TTGAAATGGGAAGGTTTGAGTTCCAGGCAGCGTATGAACTCTGGAGAGGGGCTGCCAGTC
CTCTCTGGGCCGCAGCGGACCCAGCTGGAACACAGGAAGTTGGAGCAGTAGGTGCTCCTT
CACCTCTCAGTATGTCTCTTTCAACTCTAGTTTTTGAAGTGGGGACACAGGAAGTCCAGT
GGGGACACAGCCACTCCCCPAAGAATAAGGAACTTCCATGCTTCATTCCCTGGCATAAAA
AGTGNTCAAACACACCAGAGGGGGCAGGCACCAGCCAGGGTATGATGGGTACTACCCTTT
TCTGGAGAACCATAGACTTCCCTTACTACAGGGACTTGCATGTCCTAAAGCACTGGCTGA
AGGAAGCCAAGAGGATCACTGCTGCTCCTTTTTTGTAGAGGAAATGTTTGTGTACGTGGT
AAGATATGACCTAGCCCTTTTAGGTAAGCGAACTGGTATGTTAGTAACGTGTACAAAGTT
TAGGTTCAGACCCCGGGAGTCTTGGGCATGTGGGTCTCGGGTCACTGGTTTTGACTTTAG
GGCTTTGTTACAGATGTGTGACCAAGGGGAAAATGTGCATGACAACACTAGAGGTAGGGG
CGAAGCCAGAAAGAAGGGAAGTTTTGGCTGAAGTAGGAGTCTTGGTGAGATTTTGCTGTG
ATGCATGGTGTGAACTTTCTGAGCCTCTTGTTTTTCCTCAGCTGACTCCATATTTTCCTA
CTTGTGGCAGCGACTGCATCCGACATAAAGGAACAGTTGTGCTCTGCCCACAAACAGGCG
TCCCTTTCCCTCTGGATAACAACAAAAGCAAGCCGGGAGGCTGGCTGCCTCTCCTCCTGC
TGTCTCTGCTGGTGGCCACATGGGTGCTGGTGGCAGGGATCTATCTAATGTGGAGGCACG
AAAGGATCAAGAAGACTTCCTTTTCTACCACCACACTACTGCCCCCCATTAAGGTTCTTG
TGGTTTACCCATCTGAAATATGTTTCCATCACACAATTTGTTACTTCACTGAATTTCTTC
AAAACCATTGCAGAAGTGAGGTCATCCTTGAAAAGTGGCAGAAAAAGAAAATAGCAGAGA
TGGGTCCAGTGCAGTGGCTTGCCACTCAAAAGAAGGCAGCAGACAAAGTCGTCTTCCTTC
TTTCCAATGACGTCAACAGTGTGTGCGATGGTACCTGTGGCAAGAGCGAGGGCAGTCCCA
GTGAGAACTCTCAAGACCTCTTCCCCCTTGCCTTTAACCTTTTCTGCAGTGATCTAAGAA
GCCAGATTCATCTGCACAAATACGTGGTGGTCTACTTTAGAGAGATTGATACAAAAGACG
ATTACAATGCTCTCAGTGTCTGCCCCAAGTACCACTTCATGAAGGATGCCACTGCTTTCT
GTGCAGAACTTCTCCATGTCAAGCAGCAGGTGTCAGCAGGAAAAAGATCACAAGCCTGCC
ACGATGGCTGCTGCTCCTTGTAGCCCACCCATGAGAAGCAAGAGACCTTAAAGGCTTCCT
ATCCCACCAATTACAGGGAAAAAACGTGTGATGATCCTGAAGCTTACTATGCAGCCTACA
AACAGCCTTAGTAATTAAAACATTTTATACCAATAAAATTTTCAAATATTACTAACTAAT
GTAGCATTAACTAACGATTGGAAACTACATTTACAACTTCAAAGCTGTTTTATACATAGA
```

-continued

AATCAATTACAGCTTTAATTGAAAACTGTAACCATTTTGATAATGCAACAATAAAGCATC

TTCCAAAAAAAAAAAAAAAAAAAAAAAAAAAAAAAA

In another set of preferred embodiments of the invention, any sequence, or unique portion thereof, of the CACNA1D sequences of the I.M.A.G.E. Consortium cluster NM_000720, as well as the UniGene *Homo sapiens* cluster Hs.399966, may be used. Similarly, any sequence encoding all or a part of the protein encoded by any CACNA1D sequence disclosed herein may be used. The consensus sequence of the I.M.A.G.E. Consortium cluster is as follows, with the assigned coding region (ending with a termination codon) underlined and preceded by the 5' untranslated and/or non-coding region and followed by the 3' untranslated and/or non-coding region:

SEQ ID NO:4 (Consensus Sequence for CACNA1D, Identified as NM_000720 or NM_000720.1)

```
agaataaggg cagggaccgc ggctcctatc tcttggtgat ccccttcccc attccgcccc cgcctcaacg cccagcacag tgccctgcac acagtagtcg ctcaataaat gttcgtggat gatgatgatg atgatgatga aaaaaatgca gcatcaacgg cagcagcaag cggaccacgc gaacgaggca aactatgcaa gaggcaccag acttcctctt tctggtgaag gaccaacttc tcagccgaat agctccaagc aaactgtcct gtcttggcaa gctgcaatcg atgctgctag acaggccaag gctgcccaaa ctatgagcac ctctgcaccc ccacctgtag gatctctctc ccaaagaaaa cgtcagcaat acgccaagag caaaaaacag ggtaactcgt ccaacagccg acctgcccgc gccctttcct gtttatcact caataacccc atccgaagag cctgcattag tatagtggaa tggaaaccat ttgacatatt tatattattg gctatttttg ccaattgtgt ggccttagct atttacatcc cattccctga agatgattct aattcaacaa atcataactt ggaaaaagta gaatatgcct tcctgattat ttttacagtc gagacatttt tgaagattat agcgtatgga ttattgctac atcctaatgc ttatgttagg aatggatgga atttactgga ttttgttata gtaatagtag gattgtttag tgtaattttg gaacaattaa ccaaagaaac agaaggcggg aaccactcaa gcggcaaatc tggaggcttt gatgtcaaag ccctccgtgc ctttcgagtg ttgcgaccac ttcgactagt gtcaggggtg cccagtttac aagttgtcct gaactccatt ataaaagcca tggttcccct ccttcacata gcccttttgg tattatttgt aatcataatc tatgctatta taggattgga acttttttatt ggaaaaatgc acaaaacatg ttttttttgct gactcagata tcgtagctga agaggaccca gctccatgtg cgttctcagg gaatggacgc cagtgtactg ccaatggcac ggaatgtagg agtggctggg ttggcccgaa cggaggcatc accaactttg ataactttgc ctttgccatg cttactgtgt ttcagtgcat caccatggag ggctggacag acgtgctcta ctgggtaaat gatgcgatag gatgggaatg gccatgggtg tattttgtta gtctgatcat ccttggctca tttttcgtcc ttaacctggt tcttggtgtc cttagtggag aattctcaaa ggaaagagag aaggcaaaag cacggggaga tttccagaag ctccgggaga agcagcagct ggaggaggat ctaaagggct acttggattg gatcacccaa gctgaggaca tcgatccgga gaatgaggaa gaaggaggag aggaaggcaa acgaaatact agcatgccca ccagcgagac tgagtctgtg aacacagaga acgtcagcgg tgaaggcgag aaccgaggct gctgtggaag tctctggtgc tggtggagac ggagaggcgc ggccaaggcg gggccctctg ggtgtcggcg gtggggtcaa gccatctcaa aatccaaact cagccgacgc tggcgtcgct ggaaccgatt caatcgcaga agatgtaggg ccgccgtgaa gtctgtcacg ttttactggc tggttatcgt cctggtgttt ctgaacacct taaccatttc ctctgagcac tacaatcagc cagattggtt gacacagatt caagatattg ccaacaaagt cctcttggct ctgttcacct gcgagatgct ggtaaaaatg tacagcttgg gcctccaagc atatttcgtc tctcttttca accggtttga ttgcttcgtg gtgtgtggtg gaatcactga
```

-continued

```
gacgatcctg gtggaactgg aaatcatgtc tccccctgggg atctctgtgt tcggtgtgt
gcgcctctta agaatcttca aagtgaccag gcactggact tccctgagca acttagtggc
atccttatta aactccatga agtccatcgc ttcgctgttg cttctgcttt ttctcttcat
tatcatcttt tccttgcttg ggatgcagct gtttggcggc aagtttaatt ttgatgaaac
gcaaaccaag cggagcacct ttgacaattt ccctcaagca cttctcacag tgttccagat
cctgacaggc gaagactgga atgctgtgat gtacgatggc atcatggctt acggggggccc
atcctcttca ggaatgatcg tctgcatcta cttcatcatc ctcttcattt gtggtaacta
tattctactg aatgtcttct tggccatcgc tgtagacaat ttggctgatg ctgaaagtct
gaacactgct cagaaagaag aagcggaaga aaaggagagg aaaaagattg ccagaaaaga
gagcctagaa aataaaaaga acaacaaacc agaagtcaac cagatagcca acagtgacaa
caaggttaca attgatgact ataggagaaga ggatgaagac aaggacccct atccgccttg
cgatgtgcca gtaggggaag aggaagagga agaggaggag gatgaacctg aggttcctgc
cggaccccgt cctcgaagga tctcggagtt gaacatgaag gaaaaaattg cccccatccc
tgaagggagc gctttcttca ttcttagcaa gaccaacccg atccgcgtag gctgccacaa
gctcatcaac caccacatct tcaccaacct catccttgtc ttcatcatgc tgagcagcgc
tgccctggcc gcagaggacc ccatccgcag ccactccttc cggaacacga tactgggtta
ctttgactat gccttcacag ccatctttac tgttgagatc ctgttgaaga tgacaacttt
tggagctttc ctccacaaag gggccttctg caggaactac ttcaatttgc tggatatgct
ggtggttggg gtgtctctgg tgtcatttgg gattcaatcc agtgccatct ccgttgtgaa
gattctgagg gtcttaaggg tcctgcgtcc cctcagggcc atcaacagag caaaaggact
taagcacgtg gtccagtgcg tcttcgtggc catccggacc atcggcaaca tcatgatcgt
cactaccctc ctgcagttca tgtttgcctg tatcggggtc cagttgttca gggggaagtt
ctatcgctgt acggatgaag ccaaaagtaa ccctgaagaa tgcaggggac ttttcatcct
ctacaaggat ggggatgttg acagtcctgt ggtccgtgaa cggatctggc aaaacagtga
tttcaacttc gacaacgtcc tctctgctat gatggcgctc ttcacagtct ccacgtttga
gggctggcct gcgttgctgt ataaagccat cgactcgaat ggagagaaca tcggcccaat
ctacaaccac cgcgtggaga tctccatctt cttcatcatc tacatcatca ttgtagcttt
cttcatgatg aacatctttg tgggctttgt catcgttaca tttcaggaac aaggagaaaa
agagtataag aactgtgagc tggacaaaaa tcagcgtcag tgtgttgaat acgccttgaa
agcacgtccc ttgcggagat acatccccaa aaaccctac cagtacaagt tctggtacgt
ggtgaactct tcgccttcg aatacatgat gtttgtcctc atcatgctca acacactctg
cttggccatg cagcactacg agcagtccaa gatgttcaat gatgccatgg acattctgaa
catggtcttc accgggtgt tcaccgtcga gatggttttg aaagtcatcg catttaagcc
taagggtat tttagtgacg cctggaacac gtttgactcc ctcatcgtaa tcggcagcat
tatagacgtg gccctcagcg aagcggaccc aactgaaagt gaaaatgtcc ctgtcccaac
tgctacacct ggggaactctg aagagagcaa tagaatctcc atcaccttt tccgtctttt
ccgagtgatg cgattggtga agcttctcag caggggggaa ggcatccgga cattgctgtg
gactttatt aagtccttc aggcgctccc gtatgtggcc ctcctcatag ccatgctgtt
cttcatctat gcggtcattg gcatgcagat gtttgggaaa gttgccatga gagataacaa
ccagatcaat aggaacaata acttccagac gtttcccag gcggtgctgc tgctcttcag
```

-continued

```
gtgtgcaaca ggtgaggcct ggcaggagat catgctggcc tgtctcccag ggaagctctg tgaccctgag tcagattaca accccgggga ggagtataca tgtggagca actttgccat tgtctatttc atcagttttt acatgctctg tgcatttctg atcatcaatc tgtttgtggc tgtcatcatg gataatttcg actatctgac ccgggactgg tctattttgg ggcctcacca tttagatgaa ttcaaaagaa tatggtcaga atatgaccct gaggcaaagg gaaggataaa acaccttgat gtggtcactc tgcttcgacg catccagcct ccctgggt ttgggaagtt atgtccacac agggtagcgt gcaagagatt agttgccatg aacatgcctc tcaacagtga cgggacagtc atgtttaatg caaccctgtt tgctttggtt cgaacggctc ttaagatcaa gaccgaaggg aacctggagc aagctaatga agaacttcgg gctgtgataa agaaaatttg gaagaaaacc agcatgaaat tacttgacca agttgtccct ccagctggtg atgatgaggt aaccgtgggg aagttctatg ccactttcct gatacaggac tactttagga aattcaagaa acggaaagaa caaggactgg tgggaaagta ccctgcgaag aacaccacaa ttgccctaca ggcgggatta aggacactgc atgacattgg gccagaaatc cggcgtgcta tatcgtgtga tttgcaagat gacgagcctg aggaaacaaa acgagaagaa gaagatgatg tgttcaaaag aaatggtgcc ctgcttggaa accatgtcaa tcatgttaat agtgatagga gagattccct tcagcagacc aataccaccc accgtcccct gcatgtccaa aggccttcaa ttccacctgc aagtgatact gagaaaccgc tgtttcctcc agcaggaaat tcggtgtgtc ataaccatca taaccataat tccataggaa agcaagttcc cacctcaaca aatgccaatc tcaataatgc caatatgtcc aaagctgccc atggaaagcg gcccagcatt gggaaccttg agcatgtgtc tgaaaatggg catcattctt cccacaagca tgaccgggag cctcagagaa ggtccagtgt gaaaagaacc cgctattatg aaacttacat taggtccgac tcaggagatg aacagctccc aactatttgc cgggaagacc agagataca tggctatttc agggaccccc actgcttggg ggagcaggag tatttcagta gtgaggaatg ctacgaggat gacagctcgc ccacctggag caggcaaaac tatggctact acagcagata cccaggcaga aacatcgact ctgagaggcc ccgaggctac catcatcccc aaggattctt ggaggacgat gactcgcccg tttgctatga ttcacggaga tctccaagga gacgcctact acctcccacc ccagcatccc accggagatc ctccttcaac tttgagtgcc tgcgccggca gagcagccag gaagaggtcc cgtcgtctcc catcttcccc catcgcacgg ccctgcctct gcatctaatg cagcaacaga tcatggcagt tgccggccta gattcaagta aagcccagaa gtactcaccg agtcactcga cccggtcgtg ggccacccct ccagcaaccc ctccctaccg ggactggaca ccgtgctaca cccccctgat ccaagtggag cagtcagagg ccctggacca ggtgaacggc agcctgccgt ccctgcaccg cagctcctgg tacacagacg agcccgacat ctcctaccgg actttcacac cagccagcct gactgtcccc agcagcttcc ggaacaaaaa cagcgacaag cagaggagtg cggacagctt ggtggaggca gtcctgatat ccgaaggctt gggacgctat gcaagggacc caaaatttgt gtcagcaaca aaacacgaaa tcgctgatgc ctgtgacctc accatcgacg agatggagag tgcagccagc accctgctta atgggaacgt gcgtccccga gccaacgggg atgtgggccc cctctcacac cggcaggact atgagctaca ggactttggt cctggctaca gcgacgaaga gccagaccct ggggagggatg aggaggacct ggcggatgaa atgatatgca tcaccaccctt gtagccccca gcgagggca gactggctct ggcctcaggt ggggcgcagg agagccaggg gaaaagtgcc tcatagttag gaaagtttag gcactagttg ggagtaatat tcaattaatt agacttttgt ataagagatg tcatgcctca agaaagccat aaacctggta ggaacaggtc
```

```
ccaagcggtt gagcctggca gagtaccatg cgctcggccc cagctgcagg aaacagcagg ccccgccctc tcacagagga tgggtgagga ggccagacct gccctgcccc attgtccaga tgggcactgc tgtggagtct gcttctccca tgtaccaggg caccaggccc acccaactga aggcatggcg gcggggtgca ggggaaagtt aaaggtgatg acgatcatca cacctcgtgt cgttacctca gccatcggtc tagcatatca gtcactgggc ccaacatatc cattttaaa cccttttcccc caaatacact gcgtcctggt tcctgtttag ctgttctgaa ata
```

I.M.A.G.E. Consortium Clone ID numbers and the corresponding GenBank accession numbers of sequences identified as belonging to the I.M.A.G.E. Consortium and Uni-Gene clusters, are listed below. Also included are sequences that are not identified as having a Clone ID number but still identified as being those of CACNA1D. The sequences include those of the "sense" and complementary strands sequences corresponding to CACNA1D. The sequence of each GenBank accession number is presented in the Sequence Listing.

TABLE (II)

| Clone ID numbers | GenBank accession numbers |
| --- | --- |
| 5676430 | BM128550 |
| 5197948 | BI755471 |
| 6027638 | BQ549084, BQ549571 |
| 2338956 | AI693324 |
| 36581 | R25307, R46658 |
| 49630 | H29256, H29339 |
| 4798765 | BG716371 |
| 2187310 | AI537488 |
| 838231 | AA458692 |
| 2111614 | AI393327 |
| 2183482 | AI520947 |
| 1851007 | AI248998 |
| 1675503 | AI075844 |
| 2434923 | AI869807 |
| 2434924 | AI869800 |
| 1845827 | AI243110 |
| 2511756 | AI955764 |
| 628568 | AA192669, AA192157 |
| 2019331 | AI361691 |
| 2337381 | AI914244 |
| 2503579 | AW008769 |
| 2503626 | AW008794 |
| 1160989 | AA877582 |
| 1653475 | AI051972 |
| 1627755 | AI017959 |
| 287750 | N79331, N62240 |
| 1867677 | AI240933 |
| 1618303 | AI015031 |
| 1881344 | AI290994 |
| 1408031 | AA861160 |
| 1557035 | AA915941 |
| 956303 | AA493341 |
| 2148234 | AI467998 |
| 1499899 | AA885585 |
| 1647592 | AI033648 |
| 2341185 | AI697633 |
| 981603 | AA523647 |
| 6281678 | BQ710377 |
| 6278348 | BQ706920 |
| 5876024 | BQ016847 |
| 6608849 | CA943595 |
| 5440464 | BM008196 |
| 5209489 | BI769856 |
| 5183025 | BI758971 |
| 880540 | AA468565 |
| 757337 | AA437099 |
| 6608849 | CA867864 |
| 461797 | AA682690 |

TABLE (II)-continued

| Clone ID numbers | GenBank accession numbers |
| --- | --- |
| 434787 | AA701888 |
| 6151588 | BU182632 |
| 6295618 | BQ898429 |
| 6300779 | BQ711800 |
| 434811 | AA703120 |
| 1568025 | AA978315 |
| 3220210 | BE550599 |
| 3214121 | BE502741 |
| 3009312 | AW872382 |
| 2733394 | AW444663 |
| 2872156 | AW341279 |
| 30514550 | CF456750 |
| 2718456 | AW139850 |
| 2543682 | AW029633 |
| 2492730 | AI963788 |
| 2545866 | AI951788 |
| 2272081 | AI680744 |
| 2152336 | AI601252 |
| 2146429 | AI459166 |
| 1274498 | AA885750 |
| 2272081 | BX092736 |
| 287750 | BX114568 |
| 3233645 | BE672659 |
| 289209 | N78509, N73668 |
| 277086 | N46744, N39597 |
| 3272340 | BF439267 |
| 3273859 | BF436153 |
| 3568401 | BF110611 |
| None (mRNA sequences) | M76558, AF088004, M83566 |
| None | CB410657, BQ372430, BQ366601, BQ324528, BQ318830, AL708030, BM509161, N85902, BQ774355, CA774243, CA436347, CA389011, BU679327, BU608029, BU073743, BE175413, AW969248, AI908115, BF754485, BI015409, BG202552, BF883669, BF817590, BF807128, BF806160, BF805244, BF805235, BF805080, T27949, BE836638, BE770685, BE769065, |

In one preferred embodiment, any sequence, or unique portion thereof, of the following CACNA1D sequence, identified by AF088004 or AF088004.1, may be used in the practice of the invention.

SEQ ID NO:5 (Sequence for CACNA1D):

TTTTTTTTTTTTTTTTTTTTCTTACAAAGAAAAATTTAATATTCGATGAGAGGTTGAAC

CAGGCTTAAAGCAGACATACTAGGAAATGGTGCAGCCTGTAAGAATGCCAGTTTGTAAGT

ACTGACTTTGGAAAAGATCATCGCCTCTATCAGACACTTAGGGTCCTGGTCTGGCAATTT

TGGCCTGATGTGATGCCACAAGACCCAACAGAGAGAGACACAGAGTCCAGGATAATGTTG

ACAGTGGTGTAGCCCTTTAGGAGAAATGGCGCTCCCTGCGGCTGGTATTAGGTTACCATT

GGCACCGAAGGAACCAGGAGGATAAGAATATCCATAATTTCAGAGCTGCCCTGGCACAGT

ACCTGCCCCGTCGGAGGCTCTCACTGGCAAATGACAGCTCTGTGCAAGGAGCACTCCCAA

GTATAAAAATTATTACACAGTTTTATTCTGAAGAACATTTTGCATTTTAATAAAAAAGGA

TTTATGTCAGGAAAGAGTCATTTACAAACCTTGAAGTGTTTTTGCCTGGATCAGAGTAAG

AATGTCTTAAGAAGAGGTTTGTAAGGTCTTCATAACAAAGTGGTGTTTGTTATTTACAAA

AAAAAAAAAAAAAAAATTAACAGGTTGTCTGTATACTATTAAAAATTTTGGACCAAAAA

AAAAAAAAAAAAAA

In another set of preferred embodiments of the invention, any sequence, or unique portion thereof, of the HOXB13 sequences of the I.M.A.G.E. Consortium cluster NM_006361, as well as the UniGene *Homo sapiens* cluster Hs.66731, may be used. Similarly, any sequence encoding all or a part of the protein encoded by any HOXB13 sequence disclosed herein may be used. The consensus sequence of the I.M.A.G.E. Consortium cluster is as follows, with the assigned coding region (ending with a termination codon) underlined and preceded by the 5' untranslated and/or non-coding region and followed by the 3' untranslated and/or non-coding region:

SEQ ID NO:6 (Consensus Sequence for HOXB13, Identified as NM_006361 or NM_006361.2)

```
cgaatgcagg cgacttgcga gctgggagcg atttaaaacg ctttggattc ccccggcctg ggtggggaga gcgagctggg tgcccctag attccccgcc cccgcacctc atgagccgac cctcggctcc atggagcccg gcaattatgc caccttggat ggagccaagg atatcgaagg cttgctggga gcgggagggg ggcggaatct ggtcgcccac tccctctga ccagccaccc agcggcgcct acgctgatgc ctgctgtcaa ctatgccccc ttggatctgc caggctcggc ggagccgcca aagcaatgcc acccatgccc tgggtgccc caggggacgt ccccagctcc cgtgccttat ggttactttg gaggcgggta ctactcctgc cgagtgtccc ggagctcgct gaaaccctgt gcccaggcag ccaccctggc cgcgtacccc gcggagactc ccacggccgg ggaagagtac cccagtcgcc ccactgagtt tgccttctat ccgggatatc cgggaaccta ccacgctatg gccagttacc tggacgtgtc tgtggtgcag actctgggtg ctcctggaga accgcgacat gactccctgt tgcctgtgga cagttaccag tcttgggctc tcgctggtgg ctggaacagc cagatgtgtt gccagggaga acagaacccca ccaggtccct tttggaaggc agcatttgca gactccagcg ggcagcaccc tcctgacgcc tgcgcctttc gtcgcggccg caagaaacgc attccgtaca gcaagggggca gttgcgggag ctggagcggg agtatgcggc taacaagttc atcaccaagg acaagaggcg caagatctcg gcagccacca gcctctcgga gcgccagatt accatctggt ttcagaaccg ccgggtcaaa gagaagaagg ttctcgccaa ggtgaagaac agcgctaccc cttaagagat ctccttgcct gggtgggagg agcgaaagtg ggggtgtcct ggggagacca gaaacctgcc aagcccaggc tggggccaag gactctgctg agaggcccct agagacaaca cccttcccag gccactggct gctggactgt tcctcaggag cggcctgggt acccagtatg tgcagggaga cggaaccca tgtgacaggc ccactccacc agggttccca aagaacctgg cccagtcata atcattcatc ctcacagtgg caataatcac gataaccagt
```

I.M.A.G.E. Consortium Clone ID numbers and the corresponding GenBank accession numbers of sequences identified as belonging to the I.M.A.G.E. Consortium and Uni-Gene clusters, are listed below. Also included are sequences that are not identified as having a Clone ID number but still identified as being those of HOXB13. The sequences include those of the "sense" and complementary strands sequences corresponding to HOXB13. The sequence of each GenBank accession number is presented in the Sequence Listing.

TABLE (III)

| Clone ID numbers | GenBank accession numbers |
| --- | --- |
| 4250486 | BF676461, BC007092 |
| 5518335 | BM462617 |
| 4874541 | BG752489 |
| 4806039 | BG778198 |
| 3272315 | CB050884, CB050885 |
| 4356740 | BF965191 |
| 6668163 | BU930208 |
| 1218366 | AA807966 |
| 2437746 | AI884491 |
| 1187697 | AA652388 |
| 3647557 | BF446158 |
| 1207949 | AA657924 |
| 1047774 | AA644637 |
| 3649397 | BF222357 |
| 971664 | AA527613 |
| 996191 | AA533227 |
| 813481 | AA456069, AA455572, BX117624 |
| 6256333 | BQ673782 |
| 2408470 | AI814453 |
| 2114743 | AI417272 |
| 998548 | AA535663 |
| 2116027 | AI400493 |
| 3040843 | AW779219 |
| 1101311 | AA594847 |
| 1752062 | AI150430 |
| 898712 | AA494387 |
| 1218874 | AA662643 |
| 2460189 | AI935940 |
| 986283 | AA532530 |
| 1435135 | AA857572 |
| 1871750 | AI261980 |
| 3915135 | BE888751 |
| 2069668 | AI378797 |

TABLE (III)-continued

| Clone ID numbers | GenBank accession numbers |
| --- | --- |
| 667188 | AA234220, AA236353 |
| 1101561 | AA588193 |
| 1170268 | AI821103, AI821851, AA635855 |
| 2095067 | AI420753 |
| 4432770 | BG180547 |
| 783296 | AA468306, AA468232 |
| 3271646 | CB050115, CB050116 |
| 1219276 | AA661819 |
| 30570598 | CF146837 |
| 30570517 | CF146763 |
| 30568921 | CF144902 |
| 3099071 | CF141511 |
| 3096992 | CF139563 |
| 3096870 | CF139372 |
| 3096623 | CF139319 |
| 3096798 | CF139275 |
| 30572408 | CF122893 |
| 2490082 | AI972423 |
| 2251055 | AI918975 |
| 2419308 | AI826991 |
| 2249105 | AI686312 |
| 2243362 | AI655923 |
| 30570697 | CF146922 |
| 3255712 | BF476369 |
| 3478356 | BF057410 |
| 3287977 | BE645544 |
| 3287746 | BE645408 |
| 3621499 | BE388501 |
| 30571128 | CF147366 |
| 30570954 | CF147143 |
| None (mRNA sequences) | BT007410, BC007092, U57052, U81599 |
| None | CB120119, CB125764, AU098628, CB126130, BI023924, BM767063, BM794275, BQ363211, BM932052, AA357646, AW609525, CB126919, AW609336, AW609244, BF855145, AU126914, CB126449, AW582404, BX641644 |

In one preferred embodiment, any sequence, or unique portion thereof, of the following HOXB13 sequence, identified by BC007092 or BC007092.1, may be used in the practice of the invention.

SEQ ID NO:7 (Sequence for HOXB13):

GGATTCCCCCGGCCTGGGTGGGGAGAGCGAGCTGGGTGCCCCCTAGATTCCCCGCCCCCG

CACCTCATGAGCCGACCCTCGGCTCCATGGAGCCCGGCAATTATGCCACCTTGGATGGAG

CCAAGGATATCGAAGGCTTGCTGGGAGCGGGAGGGGGCGGAATCTGGTCGCCCACTCCC

CTCTGACCAGCCACCCAGCGGCGCCTACGCTGATGCCTGCTGTCAACTATGCCCCCTTGG

ATCTGCCAGGCTCGGCGGAGCCGCCAAAGCAATGCCACCCATGCCCTGGGGTGCCCCAGG

GGACGTCCCCAGCTCCCGTGCCTTATGGTTACTTTGGAGGCGGGTACTACTCCTGCCGAG

TGTCCCGGAGCTCGCTGAAACCCTGTGCCCAGGCAGCCACCCTGGCCGCGTACCCCGCGG

AGACTCCCACGGCCGGGGAAGAGTACCCCAGCCGCCCCACTGAGTTTGCCTTCTATCCGG

GATATCCGGGAACCTACCAGCCTATGGCCAGTTACCTGGACGTGTCTGTGGTGCAGACTC

TGGGTGCTCCTGGAGAACCGCGACATGACTCCCTGTTGCCTGTGGACAGTTACCAGTCTT

GGGCTCTCGCTGGTGGCTGGAACAGCCAGATGTGTTGCCAGGGAGAACAGAACCCACCAG

GTCCCTTTTGGAAGGCAGCATTTGCAGACTCCAGCGGGCAGCACCCTCCTGACGCCTGCG

CCTTTCGTCGCGGCCGCAAGAAACGCATTCCGTACAGCAAGGGGCAGTTGCGGGAGCTGG

AGCGGGAGTATGCGGCTAACAAGTTCATCACCAAGGACAAGAGGCGCAAGATCTCGGCAG

```
                                            -continued
CCACCAGCCTCTCGGAGCGCCAGATTACCATCTGGTTTCAGAACCGCCGGGTCAAAGAGA

AGAAGGTTCTCGCCAAGGTGAAGAACAGCGCTACCCCTTAAGAGATCTCCTTGCCTGGGT

GGGAGGAGCGAAAGTGGGGGTGTCCTGGGGAGACCAGGAACCTGCCAAGCCCAGGCTGGG

GCCAAGGACTCTGCTGAGAGGCCCCTAGAGACAACACCCTTCCCAGGCCACTGGCTGCTG

GACTGTTCCTCAGGAGCGGCCTGGGTACCCAGTATGTGCAGGGAGACGGAACCCCATGTG

ACAGCCCACTCCACCAGGGTTCCCAAAGAACCTGGCCCAGTCATAATCATTCATCCTGAC

AGTGGCAATAATCACGATAACCAGTACTAGCTGCCATGATCGTTAGCCTCATATTTTCTA

TCTAGAGCTCTGTAGAGCACTTTAGAAACCGCTTTCATGAATTGAGCTAATTATGAATAA

ATTTGGAAAAAAAAAAAAAAAAAAAAAAAAAAAAAAA
```

Sequences identified by SEQ ID NO. are provided using conventional representations of a DNA strand starting from the 5' phosphate linked end to the 3' hydroxyl linked end. The assignment of coding regions is generally by comparison to available consensus sequence(s) and therefore may contain inconsistencies relative to other sequences assigned to the same cluster. These have no effect on the practice of the invention because the invention can be practiced by use of shorter segments (or combinations thereof) of sequences unique to each of the three sets described above and not affected by inconsistencies. As non-limiting examples, a segment of IL17BR, CACNA1D, or HOXB13 nucleic acid sequence composed of a 3' untranslated region sequence and/or a sequence from the 3' end of the coding region may be used as a probe for the detection of IL17BR, CACNA1D, or HOXB13 expression, respectively, without being affected by the presence of any inconsistency in the coding regions due to differences between sequences. Similarly, the use of an antibody which specifically recognizes IL17BR, CACNA1D, or HOXB13 protein to detect its expression would not be affected by the presence of any inconsistency in the representation of the coding regions provided above.

As will be appreciated by those skilled in the art, some of the above sequences include 3' poly A (or poly T on the complementary strand) stretches that do not contribute to the uniqueness of the disclosed sequences. The invention may thus be practiced with sequences lacking the 3' poly A (or poly T) stretches. The uniqueness of the disclosed sequences refers to the portions or entireties of the sequences which are found only in IL17BR, CACNA1D, or HOXB13 nucleic acids, including unique sequences found at the 3' untranslated portion of the genes. Preferred unique sequences for the practice of the invention are those which contribute to the consensus sequences for each of the three sets such that the unique sequences will be useful in detecting expression in a variety of individuals rather than being specific for a polymorphism present in some individuals. Alternatively, sequences unique to an individual or a subpopulation may be used. The preferred unique sequences are preferably of the lengths of polynucleotides of the invention as discussed herein.

To determine the (increased or decreased) expression levels of the above described sequences in the practice of the present invention, any method known in the art may be utilized. In one preferred embodiment of the invention, expression based on detection of RNA which hybridizes to polynucleotides containing the above described sequences is used. This is readily performed by any RNA detection or amplification+detection method known or recognized as equivalent in the art such as, but not limited to, reverse transcription-PCR (optionally real-time PCR), the methods disclosed in U.S. patent application Ser. No. 10/062,857 entitled "Nucleic Acid Amplification" filed on Oct. 25, 2001 as well as U.S. Provisional Patent Application 60/298,847 (filed Jun. 15, 2001) and 60/257,801 (filed Dec. 22, 2000), the methods disclosed in U.S. Pat. No. 6,291,170, and quantitative PCR. Methods to identify increased RNA stability (resulting in an observation of increased expression) or decreased RNA stability (resulting in an observation of decreased expression) may also be used. These methods include the detection of sequences that increase or decrease the stability of mRNAs containing the IL17BR, CACNA1D, or HOXB13 sequences disclosed herein. These methods also include the detection of increased mRNA degradation.

In particularly preferred embodiments of the invention, polynucleotides having sequences present in the 3' untranslated and/or non-coding regions of the above disclosed sequences are used to detect expression or non-expression of IL17BR, CACNA1D, or HOXB13 sequences in breast cells in the practice of the invention. Such polynucleotides may optionally contain sequences found in the 3' portions of the coding regions of the above disclosed sequences. Polynucleotides containing a combination of sequences from the coding and 3' non-coding regions preferably have the sequences arranged contiguously, with no intervening heterologous sequence(s).

Alternatively, the invention may be practiced with polynucleotides having sequences present in the 5' untranslated and/or non-coding regions of IL17BR, CACNA1D, or HOXB13 sequences in breast cells to detect their levels of expression. Such polynucleotides may optionally contain sequences found in the 5' portions of the coding regions. Polynucleotides containing a combination of sequences from the coding and 5' non-coding regions preferably have the sequences arranged contiguously, with no intervening heterologous sequence(s). The invention may also be practiced with sequences present in the coding regions of IL17BR, CACNA1D, or HOXB13.

Preferred polynucleotides contain sequences from 3' or 5' untranslated and/or non-coding regions of at least about 16, at least about 18, at least about 20, at least about 22, at least about 24, at least about 26, at least about 28, at least about 30, at least about 32, at least about 34, at least about 36, at least about 38, at least about 40, at least about 42, at least about 44, or at least about 46 consecutive nucleotides. The term "about" as used in the previous sentence refers to an increase or decrease of 1 from the stated numerical value. Even more preferred are polynucleotides containing sequences of at least or about 50, at least or about 100, at least about or 150, at least or about 200, at least or about 250, at least or about 300, at least or about 350, or at least or about 400 consecutive nucleotides. The term "about" as used in the preceding sentence refers to an increase or decrease of 10% from the stated numerical value.

Sequences from the 3' or 5' end of the above described coding regions as found in polynucleotides of the invention are of the same lengths as those described above, except that they would naturally be limited by the length of the coding region. The 3' end of a coding region may include sequences up the 3' half of the coding region. Conversely, the 5' end of a coding region may include sequences up the 5' half of the coding region. Of course the above described sequences, or the coding regions and polynucleotides containing portions thereof, may be used in their entireties.

Polynucleotides combining the sequences from a 3' untranslated and/or non-coding region and the associated 3' end of the coding region are preferably at least or about 100, at least or about 150, at least or about 200, at least or about 250, at least or about 300, at least or about 350, or at least or about 400 consecutive nucleotides. Preferably, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal.

In another embodiment of the invention, polynucleotides containing deletions of nucleotides from the 5' and/or 3' end of the above disclosed sequences may be used. The deletions are preferably of 1-5, 5-10, 10-15, 15-20, 20-25, 25-30, 30-35, 35-40, 40-45, 45-50, 50-60, 60-70, 70-80, 80-90, 90-100, 100-125, 125-150, 150-175, or 175-200 nucleotides from the 5' and/or 3' end, although the extent of the deletions would naturally be limited by the length of the disclosed sequences and the need to be able to use the polynucleotides for the detection of expression levels.

Other polynucleotides of the invention from the 3' end of the above disclosed sequences include those of primers and optional probes for quantitative PCR. Preferably, the primers and probes are those which amplify a region less than about 350, less than about 300, less than about 250, less than about 200, less than about 150, less than about 100, or less than about 50 nucleotides from the from the polyadenylation signal or polyadenylation site of a gene or expressed sequence.

In yet another embodiment of the invention, polynucleotides containing portions of the above disclosed sequences including the 3' end may be used in the practice of the invention. Such polynucleotides would contain at least or about 50, at least or about 100, at least about or 150, at least or about 200, at least or about 250, at least or about 300, at least or about 350, or at least or about 400 consecutive nucleotides from the 3' end of the disclosed sequences.

The invention thus also includes polynucleotides used to detect IL17BR, CACNA1D, or HOXB13 expression in breast cells. The polynucleotides may comprise a shorter polynucleotide consisting of sequences found in the above provided SEQ ID NOS in combination with heterologous sequences not naturally found in combination with IL17BR, CACNA1D, or HOXB13 sequences.

As non-limiting examples, a polynucleotide comprising one of the following sequences may be used in the practice of the invention.

```
SEQ ID NO: 8:
CAATTACAGGGAAAAAACGTGTGATGATCCTGAAGCTTACTATGCAGCCTACAAACAGCC

SEQ ID NO: 9:
GCTCTCACTGGCAAATGACAGCTCTGTGCAAGGAGCACTCCCAAGTATAAAAATTATTAC

SEQ ID NO: 10:
GATCGTTAGCCTCATATTTTCTATCTAGAGCTCTGTAGAGCACTTTAGAAACCGCTTTCA
```

Stated differently, the invention may be practiced with a polynucleotide consisting of the sequence of SEQ ID NOS: 8, 9 or 10 in combination with one or more heterologous sequences that are not normally found with SEQ ID NOS:8, 9 or 10. Alternatively, the invention may also be practiced with a polynucleotide consisting of the sequence of SEQ ID NOS:8, 9 or 10 in combination with one or more naturally occurring sequences that are normally found with SEQ ID NOS:8, 9 or 10.

Polynucleotides with sequences comprising SEQ ID NOS:8 or 9, either naturally occurring or synthetic, may be used to detect nucleic acids which are over expressed in breast cancer cells that are responsive, and those which are not over expressed in breast cancer cells that are non-responsive, to treatment with TAM or another "antiestrogen" agent against breast cancer. Polynucleotides with sequences comprising SEQ ID NO:10, either naturally occurring or synthetic, may be used to detect nucleic acids which are under expressed in breast cancer cells that are responsive, and those which are not under expressed in breast cancer cells that are non-responsive, to treatment with TAM or another "antiestrogen" agent against breast cancer.

Additional sequences that may be used in polynucleotides as described above for SEQ ID NOS:8 and 9 are the following, wherein SEQ ID NOs:33 is complementary to a portion of IL17BR sequences disclosed herein:

```
SEQ ID NO: 11:
TGCCTAATTTCACTCTCAGAGTGAGGCAGGTAACTGGGGCTCCACTGGGTCACTCTGAGA

SEQ ID NO: 12:
TTGGAAGCAGAGTCCCTCTAAAGGTAACTCTTGTGGTCACTCAATATTGTATTGGCATTT

SEQ ID NO: 13:
ACGTTAGACTTTTGCTGGCATTCAAGTCATGGCTAGTCTGTGTATTTAATAAATGTGTGT
```

SEQ ID NO: 14:
CTGGTCAGCCACTCTGACTTTTCTACCACATTAAATTCTCCATTACATCTCACTATTGGT

SEQ ID NO: 15:
TACAACTTCTGAATGCTGCACATTCTTCCAAAATGATCCTTAGCACAATCTATTGTATGA

SEQ ID NO: 16:
GGGATGGCCTTTAGGCCACAGTAGTGTCTGTGTTAAGTTCACTAAATGTGTATTTAATGA

SEQ ID NO: 17:
CTCAAAGTGCTAAAGCTATGGTTGACTGCTCTGGTGTTTTTATATTCATTCGTGCTTTAG

SEQ ID NO: 32:
CTGAAGCTTACTATGCAGCCTACAA

SEQ ID NO: 33:
TCCAATCGTTAGTTAATGCTACATTAGTT

SEQ ID NO: 34:
CAGCCTTAGTAATTAAAAC

Additional sequences that may be used in polynucleotides as described above for SEQ ID NO:10 are the following, wherein SEQ ID NOs:36 is complementary to a portion of IL17BR sequences disclosed herein:

Additionally, polynucleotides containing other sequences, particularly unique sequences, present in naturally occurring nucleic acid molecules comprising SEQ ID NOS:8-37 may be used in the practice of the invention.

SEQ ID NO: 18:
CTATGGGGATGGTCCACTGTCACTGTTTCTCTGCTGTTGCAAATACATGGATAACACATT

SEQ ID NO: 19:
ACTGGAAAAGCAGATGGTCTGACTGTGCTATGGCCTCATCATCAAGACTTTCAATCCTAT

SEQ ID NO: 20:
ACGCCAAGCTCTTCAGTGAAGACACGATGTTATTAAAAGCCTGTTTTAGGGACTGCAAAA

SEQ ID NO: 21:
TTTTTGTAAAATCTTTAACCTTCCCTTTGTTCTTCATGTACACGCTGAACTGCAATTCTT

SEQ ID NO: 22:
AACCTGGGGCATTTAGGGCAGAGGACAAAAGGATGTCAGCAATTGCTTGGGCTGCTTGGC

SEQ ID NO: 23:
CTGGAACCTCTGGACTCCCCATGCTCTAACTCCCACACTCTGCTATCAGAAACTTAAACT

SEQ ID NO: 24:
AACCCCAGAACCATCTAAGACATGGGATTCAGTGATCATGTGGTTCTCCTTTTAACTTAC

SEQ ID NO: 25:
GGCCATGTGCCATGGTATTTGGGTCCTGGGAGGGTGGGTGAAATAAAGGCATACTGTCTT

SEQ ID NO: 26:
GTGTAGGCAGTCATGGCACCAAAGCCACCAGACTGACAAATGTGTATCAGATGCTTTTGT

SEQ ID NO: 27:
GAAAACCTCTTCAAAAGACAAAAAGCTGGCACTGCATTCTCTCTCTGTAGCAGGACAGAA

SEQ ID NO: 28:
CACATCTTTAGGGTCAGTGAACAATGGGGCACATTTGGCACTAGCTTGAGCCCAACTCTG

SEQ ID NO: 29:
GCCTTAATTTCCTCATCTGAAAACTGGAAGGCCTGACTTGACTTGTTGAGCTTAAGATCC

SEQ ID NO: 30:
CTTCAGGGGAGGATCAAGCTTTGAACCAAAGCCAATCACTGGCTTGATTTGTGTTTTTTA

SEQ ID NO: 31:
ACAAGTTTTCACTGAATGAGCATGGCAGTGCCACTCAAGAAAATGAATCTCCAAAGTATC

SEQ ID NO: 35:
GCCATGATCGTTAGCCTCATATT

SEQ ID NO: 36:
CAATTCATGAAAGCGGTTTCTAAAG

SEQ ID NO: 37:
TCTATCTAGAGCTCTGTAGAGC

Other polynucleotides for use in the practice of the invention include those that have sufficient homology to those described above to detect expression by use of hybridization techniques. Such polynucleotides preferably have about or 95%, about or 96%, about or 97%, about or 98%, or about or 99% identity with IL17BR, CACNA1D, or HOXB13 sequences as described herein. Identity is determined using the BLAST algorithm, as described above. The other polynucleotides for use in the practice of the invention may also be described on the basis of the ability to hybridize to polynucleotides of the invention under stringent conditions of about 30% v/v to about 50% formamide and from about 0.01M to about 0.15M salt for hybridization and from about 0.01M to about 0.15M salt for wash conditions at about 55 to about 65° C. or higher, or conditions equivalent thereto.

In a further embodiment of the invention, a population of single stranded nucleic acid molecules comprising one or both strands of a human IL17BR or CACNA1D sequence is provided as a probe such that at least a portion of said population may be hybridized to one or both strands of a nucleic acid molecule quantitatively amplified from RNA of a breast cancer cell. The population may be only the antisense strand of a human IL17BR or CACNA1D sequence such that a sense strand of a molecule from, or amplified from, a breast cancer cell may be hybridized to a portion of said population. The population preferably comprises a sufficiently excess amount of said one or both strands of a human IL17BR or CACNA1D sequence in comparison to the amount of expressed (or amplified) nucleic acid molecules containing a complementary IL17BR or CACNA1D sequence from a normal breast cell. This condition of excess permits the increased amount of nucleic acid expression in a breast cancer cell to be readily detectable as an increase.

Alternatively, the population of single stranded molecules is equal to or in excess of all of one or both strands of the nucleic acid molecules amplified from a breast cancer cell such that the population is sufficient to hybridize to all of one or both strands. Preferred cells are those of a breast cancer patient that is ER+ or for whom treatment with tamoxifen or one or more other "antiestrogen" agent against breast cancer is contemplated. The single stranded molecules may of course be the denatured form of any IL17BR and/or CACNA1D sequence containing double stranded nucleic acid molecule or polynucleotide as described herein.

The population may also be described as being hybridized to IL17BR or CACNA1D sequence containing nucleic acid molecules at a level of at least twice as much as that by nucleic acid molecules of a normal breast cell. As in the embodiments described above, the nucleic acid molecules may be those quantitatively amplified from a breast cancer cell such that they reflect the amount of expression in said cell.

The population is preferably immobilized on a solid support, optionally in the form of a location on a microarray. A portion of the population is preferably hybridized to nucleic acid molecules quantitatively amplified from a non-normal or abnormal breast cell by RNA amplification. The amplified RNA may be that derived from a breast cancer cell, as long as the amplification used was quantitative with respect to IL17BR or CACNA1D containing sequences.

In another embodiment of the invention, expression based on detection of DNA status may be used. Detection of the HOXB13 DNA as methylated, deleted or otherwise inactivated, may be used as an indication of decreased expression as found in non-normal breast cells. This may be readily performed by PCR based methods known in the art. The status of the promoter regions of HOXB13 may also be assayed as an indication of decreased expression of HOXB13 sequences. A non-limiting example is the methylation status of sequences found in the promoter region.

Conversely, detection of the DNA of a sequence as amplified may be used for as an indication of increased expression as found in non-normal breast cells. This may be readily performed by PCR based, fluorescent in situ hybridization (FISH) and chromosome in situ hybridization (CISH) methods known in the art.

A preferred embodiment using a nucleic acid based assay to determine expression is by immobilization of one or more of the sequences identified herein on a solid support, including, but not limited to, a solid substrate as an array or to beads or bead based technology as known in the art. Alternatively, solution based expression assays known in the art may also be used. The immobilized sequence(s) may be in the form of polynucleotides as described herein such that the polynucleotide would be capable of hybridizing to a DNA or RNA corresponding to the sequence(s).

The immobilized polynucleotide(s) may be used to determine the state of nucleic acid samples prepared from sample breast cancer cell(s), optionally as part of a method to detect ER status in said cell(s). Without limiting the invention, such a cell may be from a patient suspected of being afflicted with, or at risk of developing, breast cancer. The immobilized polynucleotide(s) need only be sufficient to specifically hybridize to the corresponding nucleic acid molecules derived from the sample (and to the exclusion of detectable or significant hybridization to other nucleic acid molecules).

In yet another embodiment of the invention, a ratio of the expression levels of two of the disclosed genes may be used to predict response to treatment with TAM or another SERM. Preferably, the ratio is that of two genes with opposing patterns of expression, such as an underexpressed gene to an overexpressed gene, in correlation to the same phenotype. Non-limiting examples include the ratio of HOXB13 over IL17BR or the ratio of HOXB13 over CACNA1D. This aspect of the invention is based in part on the observation that such a ratio has a stronger correlation with TAM treatment outcome than the expression level of either gene alone. For example, the ratio of HOXB13 over IL17BR has an observed classification accuracy of 77%.

As a non-limiting example, the Ct values from Q-PCR based detection of gene expression levels may be used to derive a ratio to predict the response to treatment with one or more "antiestrogen" agent against breast cancer.

Additional Embodiments of the Invention

In embodiments where only one or a few genes are to be analyzed, the nucleic acid derived from the sample breast cancer cell(s) may be preferentially amplified by use of appropriate primers such that only the genes to be analyzed are amplified to reduce contaminating background signals from other genes expressed in the breast cell. Alternatively, and where multiple genes are to be analyzed or where very few cells (or one cell) is used, the nucleic acid from the sample may be globally amplified before hybridization to the immobilized polynucleotides. Of course RNA, or the cDNA counterpart thereof may be directly labeled and used, without amplification, by methods known in the art.

Sequence expression based on detection of a presence, increase, or decrease in protein levels or activity may also be used. Detection may be performed by any immunohistochemistry (IHC) based, bodily fluid based (where a IL17BR, CACNA1D, and/or HOXB13 polypeptide is found in a bodily fluid, such as but not limited to blood), antibody (including autoantibodies against the protein where present) based, ex foliate cell (from the cancer) based, mass spectroscopy based, and image (including used of labeled ligand where available) based method known in the art and recognized as appropriate for the detection of the protein. Antibody and image based methods are additionally useful for the localization of tumors after determination of cancer by use of cells obtained by a non-invasive procedure (such as ductal lavage or fine needle aspiration), where the source of the cancerous cells is not known. A labeled antibody or ligand may be used to localize the carcinoma(s) within a patient.

Antibodies for use in such methods of detection include polyclonal antibodies, optionally isolated from naturally occurring sources where available, and monoclonal antibodies, including those prepared by use of IL17BR, CACNA1D, and/or HOXB13 polypeptides as antigens. Such antibodies, as well as fragments thereof (including but not limited to $F_{ab}$ fragments) function to detect or diagnose non-normal or cancerous breast cells by virtue of their ability to specifically bind IL17BR, CACNA1D, or HOXB13 polypeptides to the exclusion of other polypeptides to produce a detectable signal. Recombinant, synthetic, and hybrid antibodies with the same ability may also be used in the practice of the invention. Antibodies may be readily generated by immunization with a IL17BR, CACNA1D, or HOXB13 polypeptide, and polyclonal sera may also be used in the practice of the invention.

Antibody based detection methods are well known in the art and include sandwich and ELISA assays as well as Western blot and flow cytometry based assays as non-limiting examples. Samples for analysis in such methods include any that contain IL17BR, CACNA1D, or HOXB13 polypeptides. Non-limiting examples include those containing breast cells and cell contents as well as bodily fluids (including blood, serum, saliva, lymphatic fluid, as well as mucosal and other cellular secretions as non-limiting examples) that contain the polypeptides.

The above assay embodiments may be used in a number of different ways to identify or detect the response to treatment with TAM or another "antiestrogen" agent against breast cancer based on gene expression in a breast cancer cell sample from a patient. In some cases, this would reflect a secondary screen for the patient, who may have already undergone mammography or physical exam as a primary screen. If positive from the primary screen, the subsequent needle biopsy, ductal lavage, fine needle aspiration, or other analogous minimally invasive method may provide the sample for use in the assay embodiments before, simultaneous with, or after assaying for ER status. The present invention is particularly useful in combination with non-invasive protocols, such as ductal lavage or fine needle aspiration, to prepare a breast cell sample.

The present invention provides a more objective set of criteria, in the form of gene expression profiles of a discrete set of genes, to discriminate (or delineate) between breast cancer outcomes. In particularly preferred embodiments of the invention, the assays are used to discriminate between good and poor outcomes after treatment with tamoxifen or another "antiestrogen" agent against breast cancer. Comparisons that discriminate between outcomes after about 10, about 20, about 30, about 40, about 50, about 60, about 70, about 80, about 90, about 100, or about 150 months may be performed.

While good and poor survival outcomes may be defined relatively in comparison to each other, a "good" outcome may be viewed as a better than 50% survival rate after about 60 months post surgical intervention to remove breast cancer tumor(s). A "good" outcome may also be a better than about 60%, about 70%, about 80% or about 90% survival rate after about 60 months post surgical intervention. A "poor" outcome may be viewed as a 50% or less survival rate after about 60 months post surgical intervention to remove breast cancer tumor(s). A "poor" outcome may also be about a 70% or less survival rate after about 40 months, or about a 80% or less survival rate after about 20 months, post surgical intervention.

In another embodiment of the invention based on the expression of a few genes, the isolation and analysis of a breast cancer cell sample may be performed as follows:
(1) Ductal lavage or other non-invasive procedure is performed on a patient to obtain a sample.
(2) Sample is prepared and coated onto a microscope slide. Note that ductal lavage results in clusters of cells that are cytologically examined as stated above.
(3) Pathologist or image analysis software scans the sample for the presence of atypical cells.
(4) If atypical cells are observed, those cells are harvested (e.g. by microdissection such as LCM).
(5) RNA is extracted from the harvested cells.
(6) RNA is assayed, directly or after conversion to cDNA or amplification therefrom, for the expression of IL17BR, CACNA1D, and/or HOXB13 sequences.

With use of the present invention, skilled physicians may prescribe or withhold treatment with TAM or another "antiestrogen" agent against breast cancer based on prognosis determined via practice of the instant invention.

The above discussion is also applicable where a palpable lesion is detected followed by fine needle aspiration or needle biopsy of cells from the breast. The cells are plated and reviewed by a pathologist or automated imaging system which selects cells for analysis as described above.

The present invention may also be used, however, with solid tissue biopsies, including those stored as an FFPE specimen. For example, a solid biopsy may be collected and prepared for visualization followed by determination of expression of one or more genes identified herein to determine the breast cancer outcome. As another non-limiting example, a solid biopsy may be collected and prepared for visualization followed by determination of HOXB13, IL17BR and/or CACNA1D expression. One preferred means is by use of in situ hybridization with polynucleotide or protein identifying probe(s) for assaying expression of said gene(s).

In an alternative method, the solid tissue biopsy may be used to extract molecules followed by analysis for expression of one or more gene(s). This provides the possibility of leaving out the need for visualization and collection of only cancer cells or cells suspected of being cancerous. This method may of course be modified such that only cells that have been positively selected are collected and used to extract molecules for analysis. This would require visualization and selection as a prerequisite to gene expression analysis. In the case of an FFPE sample, cells may be obtained followed by RNA extraction, amplification and detection as described herein.

In a further alternative to all of the above, the sequence(s) identified herein may be used as part of a simple PCR or array based assay simply to determine the response to treatment with TAM or another "antiestrogen" agent against breast cancer by use of a sample from a non-invasive or minimally invasive sampling procedure. The detection of sequence expression from samples may be by use of a single microarray able to assay expression of the disclosed sequences as well as other sequences, including sequences known not to vary in expression levels between normal and non-normal breast cells, for convenience and improved accuracy.

Other uses of the present invention include providing the ability to identify breast cancer cell samples as having different responses to treatment with TAM or another "anti-estrogen" agent against breast cancer for further research or study. This provides an advance based on objective genetic/molecular criteria.

The genes identified herein also may be used to generate a model capable of predicting the breast cancer survival and recurrence outcomes of an ER+ breast cell sample based on the expression of the identified genes in the sample. Such a model may be generated by any of the algorithms described herein or otherwise known in the art as well as those recognized as equivalent in the art using gene(s) (and subsets thereof) disclosed herein for the identification of breast cancer outcomes. The model provides a means for comparing expression profiles of gene(s) of the subset from the sample against the profiles of reference data used to build the model. The model can compare the sample profile against each of the reference profiles or against a model defining delineations made based upon the reference profiles. Additionally, relative values from the sample profile may be used in comparison with the model or reference profiles.

In a preferred embodiment of the invention, breast cell samples identified as normal and cancerous from the same subject may be analyzed, optionally by use of a single microarray, for their expression profiles of the genes used to generate the model. This provides an advantageous means of identifying survival and recurrence outcomes based on relative differences from the expression profile of the normal sample. These differences can then be used in comparison to differences between normal and individual cancerous reference data which was also used to generate the model.

Articles of Manufacture

The materials and methods of the present invention are ideally suited for preparation of kits produced in accordance with well known procedures. The invention thus provides kits comprising agents (like the polynucleotides and/or antibodies described herein as non-limiting examples) for the detection of expression of the disclosed sequences. Such kits, optionally comprising the agent with an identifying description or label or instructions relating to their use in the methods of the present invention, are provided. Such a kit may comprise containers, each with one or more of the various reagents (typically in concentrated form) utilized in the methods, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more primer complexes of the present invention (e.g., appropriate length poly(T) or random primers linked to a promoter reactive with the RNA polymerase). A set of instructions will also typically be included.

The methods provided by the present invention may also be automated in whole or in part. All aspects of the present invention may also be practiced such that they consist essentially of a subset of the disclosed genes to the exclusion of material irrelevant to the identification of breast cancer survival outcomes via a cell containing sample.

Having now generally described the invention, the same will be more readily understood through reference to the following examples which are provided by way of illustration, and are not intended to be limiting of the present invention, unless specified.

EXAMPLES

Example 1

General Methods

Patient and Tumor Selection Criteria and Study Design

Patient inclusion criteria for this study were: Women diagnosed at the Massachusetts General Hospital (MGH) between 1987 and 2000 with ER positive breast cancer, treatment with standard breast surgery (modified radical mastectomy or lumpectomy) and radiation followed by five years of systemic adjuvant tamoxifen; no patient received chemotherapy prior to recurrence. Clinical and follow-up data were derived from the MGH tumor registry. There were no missing registry data and all available medical records were reviewed as a second tier of data confirmation.

All tumor specimens collected at the time of initial diagnosis were obtained from frozen and formalin fixed paraffin-embedded (FFPE) tissue repositories at the Massachusetts General Hospital. Tumor samples with greater than 20% tumor cells were selected with a median of greater than 75% for all samples. Each sample was evaluated for the following features: tumor type (ductal vs. lobular), tumor size, and Nottingham combined histological grade. Estrogen and progesterone receptor expression were determined by biochemical hormone binding analysis and/or by immunohistochemical staining as described (Long, A. A. et al. "High-specificity in-situ hybridization. Methods and application." *Diagn Mol Pathol* 1, 45-57 (1992)); receptor positivity was defined as greater than 3 fmol/mg tumor tissue (Long et al.) and greater than 1% nuclear staining for the biochemical and immunohistochemical assays, respectively.

Study design is as follows: A training set of 60 frozen breast cancer specimens was selected to identify gene expression signatures predictive of outcome or response, in the setting of adjuvant tamoxifen therapy. Tumors from responders were matched to the non-responders with respect to TNM staging and tumor grade. Differential gene expression identified in the training set was validated in an independent group of 20 invasive breast tumors with formalin fixed paraffin-embedded (FFPE) tissue samples.

LCM, RNA Isolation and Amplification

With each frozen tumor sample within the 60-case cohort, RNA was isolated from both a whole tissue section of 8 μm in thickness and a highly enriched population of 4,000-5,000 malignant epithelial cells acquired by laser capture microdissection using a PixCell IIe LCM system (Arcturus, Mountain View, Calif.). From each tumor sample within the 20-case test set, RNA was isolated from four 8 μm-thick FFPE tissue sections. Isolated RNA was subjected to one round of T7 polymerase in vitro transcription using the RiboAmp™ kit (frozen samples) or another system for FFPE samples according to manufacturer's instructions (Arcturus Bioscience, Inc., Mountain View, Calif. for RiboAmP™). Labeled cRNA was generated by a second round of T7-based RNA in vitro transcription in the presence of 5-[3-Aminoallyl]uridine 5'-triphosphate (Sigma-Aldrich, St. Louis, Mo.). Universal Human Reference RNA (Stratagene, San Diego, Calif.) was amplified in the same manner. The purified aRNA was later conjugated to Cy5 (experimental samples) or Cy3 (reference sample) dye (Amersham Biosciences).

Microarray Analysis

A custom designed 22,000-gene oligonucleotide (60mer) microarray was fabricated using ink-jet in-situ synthesis technology (Agilent Technologies, Palo Alto, Calif.). Cy5-labeled sample RNA and Cy3-labeled reference RNA were co-hybridized at 65° C., 1× hybridization buffer (Agilent Technologies). Slides were washed at 37° C. with 0.1×SSC/ 0.005% Triton X-102. Image analysis was performed using Agilent's image analysis software. Raw Cy5/Cy3 ratios were normalized using intensity-dependent non-linear regression.

A data matrix consisting of normalized Cy5/Cy3 ratios from all samples were median centered for each gene. The variance of each gene over all samples was calculated and the top 25% high variance genes (5,475) selected for further analysis. Identification and permutation testing for significance of differential gene expression were performed using BRB ArrayTools, developed by Dr. Richard Simon and Amy Peng (see http site at linus.nci.nih.gov/BRB-ArrayTools.html). Hierarchical cluster analysis was performed with GeneMaths software (Applied-Maths, Belgium) using cosine correlation and complete linkage. All other statistical procedures (two-sample t-test, receiver operating characteristic analysis, multivariate logistic regression and survival analysis) were performed in the open source R statistical environment (see http site at www.r-project.org). Statistical test of significance of ROC curves was by the method of DeLong ("Comparing the areas under two or more correlated receiver operating characteristic curves: a nonparametric approach." *Biometrics* 44, 837-45 (1988)). Disease free survival was calculated from the date of diagnosis. Events were scored as the first distant metastasis, and patients remaining disease-free at the last follow-up were censored. Survival curves were calculated by the Kaplan-Meier estimates and compared by log-rank tests.

Real-Time Quantitative PCR Analysis

Real-time PCR was performed on 59 of the 60-case training samples (one case was excluded due to insufficient materials) and the 20-case validation samples. Briefly, 2 μg of amplified RNA was converted into double stranded cDNA. For each case 12 ng of cDNA in triplicates was used for real-time PCR with an ABI 7900HT (Applied Biosystems) as described (Gelmini, S. et al. "Quantitative polymerase chain reaction-based homogeneous assay with fluorogenic probes to measure c-erbB-2 oncogene amplification." *Clin Chem* 43, 752-8 (1997)). The sequences of the PCR primer pairs and fluorogenic MGB probe (5' to 3'), respectively, that were used for each gene are as follows:

```
HoxB13
                                         (SEQ ID NO: 38)
       TTCATCCTGACAGTGGCAATAATC, (SEQ ID NO: 39)
       CTAGATAGAAAATATGAGGCTAACGATCAT, (SEQ ID NO: 40)
       VIC-CGATAACCAGTACTAGCTG;

IL17BR
                                         (SEQ ID NO: 41)
       GCATTAACTAACGATTGGAAACTACATT, (SEQ ID NO: 42)
       GGAAGATGCTTTATTGTTGCATTATC, (SEQ ID NO: 43)
       VIC-ACAACTTCAAAGCTGTTTTA.
```

Relative expression levels of HOXB13 in normal, DCIS and IDC samples were calculated as follows. First, all CT values are adjusted by subtracting the highest CT (40) among all samples, then relative expression=$\frac{1}{2}$^CT.

In Situ Hybridization

Dig-labeled RNA probes were prepared using DIG RNA labeling kit (SP6/T7) from Roche Applied Science, following the protocol provided with the kit. In situ hybridization was performed on frozen tissue sections as described (Long et al.).

TABLE 1

Patients and tumor characteristics of training set.

| Sample ID | Tumor type | Size | Grade | Nodes | ER | PR | Age | DFS | Status |
|---|---|---|---|---|---|---|---|---|---|
| 1389 | D | 1.7 | 2 | 0/1 | Pos | Pos | 80 | 94 | 0 |
| 648 | D | 1.1 | 2 | 0/15 | Pos | ND | 62 | 160 | 0 |
| 289 | D | 3 | 2 | 0/15 | Pos | ND | 75 | 63 | 1 |
| 749 | D | 1.8 | 2 | 2/9 | Pos | Pos | 61 | 137 | 0 |
| 420 | D/L | 2 | 3 | ND | Pos | Pos | 72 | 58 | 1 |
| 633 | D | 2.7 | 3 | 0/11 | Pos | ND | 61 | 20 | 1 |
| 662 | D | 1 | 3 | 6/11 | Pos | Pos | 79 | 27 | 1 |
| 849 | D | 2 | 1 | 0/26 | Pos | Neg | 75 | 23 | 1 |
| 356 | D | 1 | 2 | 2/20 | Pos | ND | 58 | 24 | 1 |
| 1304 | D | 2 | 3 | 0/14 | Pos | Pos | 57 | 20 | 1 |
| 1419 | D | 2.5 | 2 | 1/8 | Pos | Pos | 59 | 86 | 0 |
| 1093 | D | 1 | 3 | 1/14 | Pos | Pos | 66 | 85 | 0 |
| 1047 | D/L | 2.6 | 2 | 0/18 | Pos | Neg | 70 | 128 | 0 |
| 1037 | D/L | 1.5 | 2 | 0/4 | Pos | Pos | 85 | 83 | 0 |
| 319 | D | 4 | 2 | 1/13 | Pos | ND | 67 | 44 | 1 |
| 25 | D | 3.5 | 2 | 0/9 | Neg | Pos | 62 | 75 | 1 |
| 180 | D | 1.6 | 2 | 2/19 | Pos | Pos | 69 | 169 | 0 |
| 687 | D | 3.5 | 3 | 3/16 | Pos | ND | 73 | 142 | 0 |
| 856 | D | 1.6 | 2 | 0/16 | Pos | Pos | 73 | 88 | 0 |
| 1045 | D | 2.5 | 3 | 1/12 | Pos | Neg | 73 | 121 | 0 |
| 1205 | D | 2.7 | 2 | 1/19 | Pos | Pos | 71 | 88 | 0 |
| 1437 | D | 1.7 | 2 | 2/22 | Pos | Pos | 67 | 89 | 0 |
| 1507 | D | 3.7 | 3 | 0/40 | Pos | Pos | 70 | 70 | 0 |
| 469 | D | 1 | 1 | 0/19 | Pos | ND | 66 | 161 | 0 |
| 829 | D | 1.2 | 2 | 0/9 | Pos | ND | 69 | 136 | 0 |
| 868 | D | 3 | 3 | 0/13 | Pos | Pos | 65 | 130 | 0 |
| 1206 | D | 4.1 | 3 | 0/15 | Pos | Neg | 84 | 56 | 1 |
| 843 | D | 3.4 | 2 | 11/20 | Pos | Neg | 76 | 122 | 1 |

TABLE 1-continued

Patients and tumor characteristics of training set.

| Sample ID | Tumor type | Size | Grade | Nodes | ER | PR | Age | DFS | Status |
|---|---|---|---|---|---|---|---|---|---|
| 342 | D | 3 | 2 | 9/21 | Pos | ND | 62 | 102 | 1 |
| 1218 | D | 4.5 | 1 | 3/16 | Pos | Pos | 62 | 10 | 1 |
| 547 | D/L | 1.5 | 2 | ND | Pos | ND | 74 | 129 | 1 |
| 1125 | D | 2.6 | 2 | 0/18 | Pos | Pos | 54 | 123 | 0 |
| 1368 | D | 2.6 | 2 | ND | Pos | Pos | 82 | 63 | 0 |
| 605 | D | 2.2 | 2 | 6/18 | Pos | ND | 70 | 110 | 0 |
| 59 | L | 3 | 2 | 33/38 | Pos | ND | 70 | 21 | 1 |
| 68 | D | 3 | 2 | 0/17 | Pos | ND | 53 | 38 | 1 |
| 317 | D | 1.2 | 3 | 1/10 | Pos | Pos | 71 | 5 | 1 |
| 374 | D | 1 | 3 | 0/15 | Pos | Neg | 57 | 47 | 1 |
| 823 | D | 2 | 2 | 0/6 | Pos | Pos | 51 | 69 | 1 |
| 280 | D | 2.2 | 3 | 0/12 | Pos | ND | 66 | 44 | 1 |
| 651 | D | 4.7 | 3 | 10/13 | Pos | ND | 48 | 137 | 1 |
| 763 | D | 1.8 | 2 | 0/14 | Pos | Pos | 63 | 118 | 0 |
| 1085 | D | 4.7 | 2 | 0/8 | Pos | Pos | 48 | 101 | 1 |
| 1363 | D | 2.1 | 2 | 0/15 | Pos | Pos | 56 | 114 | 0 |
| 295 | D | 3.5 | 2 | 3/21 | Pos | Pos | 52 | 118 | 1 |
| 871 | D | 4 | 3 | 0/16 | Pos | Neg | 61 | 6 | 1 |
| 1343 | D | 2.5 | 3 | ND | Pos | Pos | 79 | 21 | 1 |
| 140 | L | >2.0 | 2 | 18/28 | Pos | ND | 63 | 43 | 1 |
| 260 | D/L | 0.9 | 2 | 1/13 | Pos | ND | 73 | 42 | 1 |
| 297 | D | 0.8 | 2 | 1/16 | Pos | Pos | 66 | 169 | 0 |
| 1260 | D | 3.5 | 2 | 0/14 | Pos | Pos | 58 | 79 | 0 |
| 1405 | D | 1 | 3 | ND | Pos | Pos | 81 | 95 | 0 |
| 518 | L | 5.5 | 2 | 3/20 | Pos | ND | 68 | 156 | 0 |
| 607 | D | 1.2 | 2 | 5/14 | Pos | Pos | 76 | 114 | 0 |
| 638 | D | 2 | 2 | 1/24 | Pos | Pos | 67 | 148 | 0 |
| 655 | D | 2 | 3 | ND | Pos | Pos | 73 | 143 | 0 |
| 772 | D | 2.5 | 2 | 0/18 | Pos | Pos | 68 | 69 | 1 |
| 878 | D/L | 1.6 | 2 | 0/9 | Pos | Neg | 76 | 138 | 0 |
| 1279 | D | 2 | 2 | 0/12 | Pos | Pos | 68 | 102 | 0 |
| 1370 | D | 2 | 2 | ND | Pos | Pos | 73 | 61 | 0 |

Abbreviations: D, ductal; L, lobular; D/L, ductal and lobular features; pos, positive; neg, negative; ND, not determined; ER, estrogen receptor; PR, progesterone receptor; DFS, disease-free survival (number of months); status = 1, recurred; status = 0, disease-free.

Example 2

Identification of Differentially Expressed Genes

Gene expression profiling was performed using a 22,000-gene oligonucleotide microarray as described above. In the initial analysis, isolated RNA from frozen tumor-tissue sections taken from the archived primary biopsies were used. The resulting expression dataset was first filtered based on overall variance of each gene with the top 5,475 high-variance genes (75th percentile) selected for further analysis. Using this reduced dataset, t-test was performed on each gene comparing the tamoxifen responders and non-responders, leading to identification of 19 differentially expressed genes at the P value cutoff of 0.001 (Table 2). The probability of selecting this many or more differentially expressed genes by chance was estimated to be 0.04 by randomly permuting the patient class with respect to treatment outcome and repeating the t-test procedure 2,000 times. This analysis thus demonstrated the existence of statistically significant differences in gene expression between the primary breast cancers of tamoxifen responders and non-responders.

TABLE 2

19-gene signature identified by t-test in the Sections dataset

| | Parametric p-value | Mean in responders | Mean in non-responders | Fold difference of means | GB acc | Description |
|---|---|---|---|---|---|---|
| 1 | 1.96E−05 | 0.759 | 1.317 | 0.576 | AW006861 | SCYA4|small inducible cytokine A4 |
| 2 | 2.43E−05 | 1.31 | 0.704 | 1.861 | AI240933 | ESTs |
| 3 | 8.08E−05 | 0.768 | 1.424 | 0.539 | X59770 | IL1R2|interleukin 1 receptor, type II |
| 4 | 9.57E−05 | 0.883 | 1.425 | 0.62 | AB000520 | APS|adaptor protein with pleckstrin homology and src homology 2 domains |
| 5 | 9.91E−05 | 1.704 | 0.659 | 2.586 | AF208111 | IL17BR|interleukin 17B receptor |
| 6 | 0.0001833 | 0.831 | 1.33 | 0.625 | AI820604 | ESTs |
| 7 | 0.0001935 | 0.853 | 1.459 | 0.585 | AI087057 | DOK2|docking protein 2, 56 kD |
| 8 | 0.0001959 | 1.29 | 0.641 | 2.012 | AJ272267 | CHDH|choline dehydrogenase |
| 9 | 0.0002218 | 1.801 | 0.943 | 1.91 | N30081 | ESTs, Weakly similar to I38022 hypothetical protein [H. sapiens] |
| 10 | 0.0004234 | 1.055 | 2.443 | 0.432 | AI700363 | ESTs |
| 11 | 0.0004357 | 0.451 | 1.57 | 0.287 | AL117406 | ABCC11|ATP-binding cassette, sub-family C (CFTR/MRP), member 11 |
| 12 | 0.0004372 | 1.12 | 3.702 | 0.303 | BC007092 | HOXB13|homeo box B13 |

TABLE 2-continued

19-gene signature identified by t-test in the Sections dataset

| | Parametric p-value | Mean in responders | Mean in non-responders | Fold difference of means | GB acc | Description |
|---|---|---|---|---|---|---|
| 13 | 0.0005436 | 0.754 | 1.613 | 0.467 | M92432 | GUCY2D\|guanylate cyclase 2D, membrane (retina-specific) |
| 14 | 0.0005859 | 1.315 | 0.578 | 2.275 | AL050227 | Homo sapiens mRNA; cDNA DKFZp586M0723 (from clone DKFZp586M0723) |
| 15 | 0.000635 | 1.382 | 0.576 | 2.399 | AW613732 | Homo sapiens cDNA FLJ31137 fis, clone IMR322001049 |
| 16 | 0.0008714 | 0.794 | 1.252 | 0.634 | BC007783 | SCYA3\|small inducible cytokine A3 |
| 17 | 0.0008912 | 2.572 | 1.033 | 2.49 | X81896 | C11orf25\|chromosome 11 open reading frame 25 |
| 18 | 0.0009108 | 0.939 | 1.913 | 0.491 | BC004960 | MGC10955\|hypothetical protein MGC10955 |
| 19 | 0.0009924 | 1.145 | 0.719 | 1.592 | AK027250 | Homo sapiens cDNA: FLJ23597 fis, clone LNG15281 |

To refine our analysis to the tumor cells and circumvent potential variability attributable to stromal cell contamination, the same cohort was reanalyzed following laser-capture microdissection (LCM) of tumor cells within each tissue section. Using variance based gene filtering and t-test screening identical to that utilized for the whole tissue section dataset, 9 differentially expressed gene sequences were identified with P<0.001 (Table 3).

TABLE 3

9-gene signature identified by t-test in the LCM dataset

| | Parametric p-value | Mean in responders | Mean in non-responders | Fold difference of means | GB acc | Description |
|---|---|---|---|---|---|---|
| 1 | 2.67E-05 | 1.101 | 4.891 | 0.225 | BC007092 | HOXB13\|homeo box B13 |
| 2 | 0.0003393 | 1.045 | 2.607 | 0.401 | AI700363 | ESTs |
| 3 | 0.0003736 | 0.64 | 1.414 | 0.453 | NM_014298 | QPRT\|quinolinate phosphoribosyltransferase (nicotinate-nucleotide pyrophosphorylase (carboxylating)) |
| 4 | 0.0003777 | 1.642 | 0.694 | 2.366 | AF208111 | IL17BR\|interleukin 17B receptor |
| 5 | 0.0003895 | 0.631 | 1.651 | 0.382 | AF033199 | ZNF204\|zinc finger protein 204 |
| 6 | 0.0004524 | 1.97 | 0.576 | 3.42 | AI688494 | FLJ13189\|hypothetical protein FLJ13189 |
| 7 | 0.0005329 | 1.178 | 0.694 | 1.697 | AI240933 | ESTs |
| 8 | 0.0007403 | 0.99 | 1.671 | 0.592 | AL157459 | Homo sapiens mRNA; cDNA DKFZp434B0425 (from clone DKFZp434B0425) |
| 9 | 0.0007739 | 0.723 | 1.228 | 0.589 | BC002480 | FLJ13352\|hypothetical protein FLJ13352 |

Only 3 genes were identified as differentially expressed in both the LCM and whole tissue section analyses: the homeobox gene HOXB13 (identified twice as AI700363 and BC007092), the interleukin 17B receptor IL17BR (AF208111), and the voltage-gated calcium channel CACNA1D (AI240933). HOXB13 was differentially overexpressed in tamoxifen nonresponsive cases, whereas IL17BR and CACNA1D were overexpressed in tamoxifen responsive cases. Based on their identification as tumor-derived markers significantly associated with clinical outcome in two independent analyses, the utility of each of these genes was evaluated by itself and in combination with the others.

To define the sensitivity and specificity of HOXB13, IL17BR and CACNA1D expression as markers of clinical outcome, Receiver Operating Characteristic (ROC) analysis (Pepe, M. S. "An interpretation for the ROC curve and inference using GLM procedures." Biometrics 56, 352-9 (2000)) was used. For data derived from whole tissue sections, the Area Under the Curve (AUC) values for IL17BR, HOXB13 and CACNA1D were 0.79, 0.67 and 0.81 for IL17BR, HOXB13 and CACNA1D, respectively (see Table 4 and FIG. 1, upper portion). ROC analysis of the data generated from the microdissected tumor cells yielded AUC values of 0.76, 0.8, and 0.76 for these genes (see Table 4 and FIG. 1, lower portion).

TABLE 4

ROC analysis of using IL17BR, CACNA1D and HOXB13 expression to predict tamoxifen response

| | Tissue Sections | | LCM | |
|---|---|---|---|---|
| | AUC | P value | AUC | P value |
| IL17BR | 0.79 | 1.58E-06 | 0.76 | 2.73E-05 |
| CACNA1D | 0.81 | 3.02E-08 | 0.76 | 1.59E-05 |
| HOXB13 | 0.67 | 0.012 | 0.79 | 9.94E-07 |
| ESR1 | 0.55 | 0.277 | 0.63 | 0.038 |

TABLE 4-continued

ROC analysis of using IL17BR, CACNA1D and HOXB13 expression to predict tamoxifen response

| | Tissue Sections | | LCM | |
|---|---|---|---|---|
| | AUC | P value | AUC | P value |
| PGR | 0.63 | 0.036 | 0.63 | 0.033 |
| ERBB2 | 0.69 | 0.004 | 0.64 | 0.027 |
| EGFR | 0.56 | 0.200 | 0.61 | 0.068 |

AUC, area under the curve; P values are AUC >0.5.

A statistical test of significance indicated that these AUC values are all significantly greater than 0.5, the expected value from the null model that predicts clinical outcome randomly. Therefore, these three genes have potential utility for predicting clinical outcome of adjuvant tamoxifen therapy. As comparison, markers that are currently useful in evaluating the likelihood of response to tamoxifen were analyzed in comparison. The levels of ER (gene symbol ESR1) and progesterone receptor (PR, gene symbol PGR) are known to be positively correlated with tamoxifen response (see Fernandez, M. D., et al. "Quantitative oestrogen and progesterone receptor values in primary breast cancer and predictability of response to endocrine therapy." *Clin Oncol* 9, 245-50 (1983); Ferno, M. et al. "Results of two or five years of adjuvant tamoxifen correlated to steroid receptor and S-phase levels." South Sweden Breast Cancer Group, and South-East Sweden Breast Cancer Group. *Breast Cancer Res Treat* 59, 69-76 (2000); Nardelli, G. B., et al. "Estrogen and progesterone receptors status in the prediction of response of breast cancer to endocrine therapy (preliminary report)." *Eur J Gynaecol Oncol* 7, 151-8 (1986); and Osborne, C. K., et al. "The value of estrogen and progesterone receptors in the treatment of breast cancer." U 46, 2884-8 (1980)).

In addition, growth factor signaling pathways (EGFR, ERBB2) are thought to negatively regulate estrogen-dependent signaling, and hence contribute to loss of responsiveness to tamoxifen (see Dowsett, M. "Overexpression of HER-2 as a resistance mechanism to hormonal therapy for breast cancer." *Endocr Relat Cancer* 8, 191-5 (2001)). ROC analysis of these genes confirmed their correlation with clinical outcome, but with AUC values ranging only from 0.55 to 0.69, reaching statistical significance for PGR and ERBB2 (see Table 4).

The LCM dataset is particularly relevant, since EGFR, ERBB2, ESR1 and PGR are currently measured at the tumor cell level using either immunohistochemistry or fluorescence in situ hybridization. As individual markers of clinical outcome, HOXB13, IL17BR and CAC1D all outperformed ESR1, PGR, EGFR and ERBB2 (see Table 4).

Example 3

Identification of the HOXB13:IL17BR Expression Ratio

HOXB13:IL17BR expression ratio was identified as a robust composite predictor of outcome as follows. Since HOXB13 and IL17BR have opposing patterns of expression, the expression ratio of HOXB13 over IL17BR was examined to determine whether it provides a better composite predictor of tamoxifen response. Indeed, both t-test and ROC analyses demonstrated that the two-gene ratio had a stronger correlation with treatment outcome than either gene alone, both in the whole tissue sections and LCM datasets (see Table 5). AUC values for HOXB13:IL17BR reached 0.81 for the tissue sections dataset and 0.84 for the LCM dataset. Pairing HOXB13 with CACNA1D or analysis of all three markers together did not provide additional predictive power.

TABLE 5

HOXB13:IL17BR ratio is a stronger predictor of treatment outcome

| | | t-test | | ROC | |
|---|---|---|---|---|---|
| | | t-statistic | P value | AUC | P value |
| Tissue Section | IL17BR | 4.15 | 1.15E−04 | 0.79 | 1.58E−06 |
| | HOXB13 | −3.57 | 1.03E−03 | 0.67 | 0.01 |
| | HOXB13:IL17BR | −4.91 | 1.48E−05 | 0.81 | 1.08E−07 |
| LCM | IL17BR | 3.70 | 5.44E−04 | 0.76 | 2.73E−05 |
| | HOXB13 | −4.39 | 8.00E−05 | 0.79 | 9.94E−07 |
| | HOXB13:IL17BR | −5.42 | 2.47E−06 | 0.84 | 4.40E−11 |

AUC, area under the curve;
P values are AUC > 0.5.

The HOXB13/IL7BR ratio was compared to well-established prognostic factors for breast cancer, such as patient age, tumor size, grade and lymph node status (see Fitzgibbons, P. L. et al. "Prognostic factors in breast cancer. College of American Pathologists Consensus Statement 1999." *Arch Pathol Lab Med* 124, 966-78 (2000)). Univariate logistic regression analysis indicated that only tumor size was marginally significant in this cohort (P=0.04); this was not surprising given that the responder group was closely matched to the non-responder group with respect to tumor size, tumor grade and lymph node status during patient selection. Among the known positive (ESR1 and PGR) and negative (ERBB2 and EGFR) predictors of tamoxifen response, ROC analysis of the tissue sections data indicated that only PGR and ERBB2 were significant (see Table 4). Therefore, a comparison of logistic regression models containing the HOXB13:IL17BR ratio either by itself or in combination with tumor size, and expression levels of PGR and ERBB2, were made (see Table 6). The HOXB13:IL17BR ratio alone was a highly significant predictor (P=0.0003) and had an odds ratio of 10.2 (95% CI 2.9-35.6). In the multivariate model, HOXB13:IL17BR ratio is the only significant variable (P=0.002) with an odds ratio of 7.3 (95% CI 2.1-26). Thus, the expression ratio of HOXB13:IL17BR is a strong independent predictor of treatment outcome in the setting of adjuvant tamoxifen therapy.

TABLE 6

Logistic Regression Analysis

Univariate Model

| Predictor | Odds Ratio | 95% CI | P Value |
|---|---|---|---|
| HOXB13:IL17BR | 10.17 | 2.9-35.6 | 0.0003 |

Multivariate Model

| Predictors | Odds Ratio | 95% CI | P Value |
|---|---|---|---|
| Tumor size | 1.5 | 0.7-3.5 | 0.3289 |
| PGR | 0.8 | 0.3-1.8 | 0.5600 |
| ERBB2 | 1.7 | 0.8-3.8 | 0.1620 |
| HOXB13:IL17BR | 7.3 | 2.1-26.3 | 0.0022 |

All predictors are continuous variables. Gene expression values were from microarray measurements. Odds ratio is the inter-quartile odds ratio, based on the difference of a predictor from its lower quartile (0.25) to its upper quartile (0.75); CI, confidence interval.

Example 4

Independent Validation of HOXB13: IL17BR Expression Ratio

Figure 2:
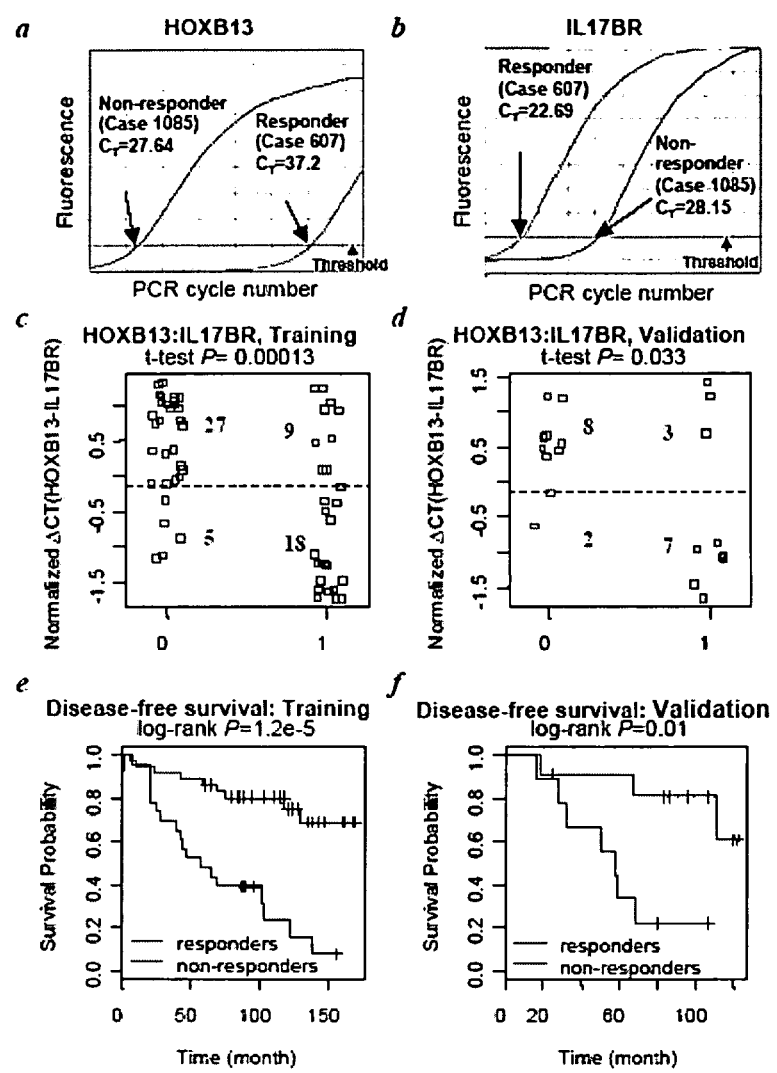
FIG. 2 contains six parts relating to the validation of a ratio of HOXB13 expression to IL17BR expression as an indicator of responsiveness, or lack thereof, to TAM. Parts a and b show the results of gene expression analysis of HOXB13 and IL17BR sequences by Q-PCR in both Responder and Non-responder samples. Plots of the Responder and Non-responder training and validation data sets are shown in Parts c and d, where "0" indicates Responder datapoints in both and "1" indicates Non-responder datapoints in both. Parts e and f show plots of the Responder and Non-responder training and validation data sets as a function of survival, where the upper line in each Part represents the Responders and the lower line represents the Non-responders.

The reduction of a complex microarray signature to a two-gene expression ratio allows the use of simpler detection strategies, such as real-time quantitative PCR (RT-QPCR) analysis. The HOXB13:IL7BR expression ratio by RT-QPCR using frozen tissue sections that were available from 59 of the 60 training cases were analyzed (FIG. 2, part a). RT-QPCR data were highly concordant with the microarray data of frozen tumor specimens (correlation coefficient r=0.83 for HOXB13, 0.93 for IL17BR). In addition, the PCR-derived HOXB13:IL17BR ratios, represented as ΔCTs, where CT is the PCR amplification cycles to reach a predetermined threshold amount (e.g., FIG. 2, parts a and b) and ΔCT is the CT difference between HOXB13 and IL17BR, were highly correlated with the microarray-derived data (r=0.83) and with treatment outcome (t test P=0.0001, FIG. 2, part c). Thus, conventional RT-QPCR analysis for the expression ratio of HOXB13 to IL17BR appears to be equivalent to microarray-based analysis of frozen tumor specimens.

To validate the predictive utility of HOXB13:IL17BR expression ratio in an independent patient cohort, 20 additional ER-positive early-stage primary breast tumors from women treated with adjuvant tamoxifen only at MGH between 1991 and 2000, and for which medical records and paraffin-embedded tissues were available, were identified. Of the 20 archival cases, 10 had recurred with a median time to recurrence of 5 years, and 10 had remained disease-free with a median follow up of 9 years (see Table 7 for details).

RNA was extracted from formalin-fixed paraffin-embedded (FFPE) whole tissue sections, linearly amplified, and used as template for RT-QPCR analysis. Consistent with the results of the training cohort, the HOXB13:IL17BR expression ratio in this independent patient cohort was highly correlated with clinical outcome (t test P=0.035) with higher HOXB13 expression (lower ΔCTs) correlating with poor outcome (FIG. 2, part d). To test the predictive accuracy of the HOXB13:IL17BR ratio, the RT-QPCR data from the frozen tissue sections (n=59) was used to build a logistic regression model. In this training set, the model predicted treatment outcome with an overall accuracy of 76% (P=0.000065, 95% confidence interval 63%-86%). The positive and negative predictive values were 78% and 75%, respectively. Applying this model to the 20 independent patients in the validation cohort, treatment outcome for 15 of the 20 patients was correctly predicted (overall accuracy 75%, P=0.04, 95% confidence interval 51%-91%), with positive and negative predictive values of 78% and 73%, respectively.

Kaplan-Meier analysis of the patient groups as predicted by the model resulted in significantly different disease-free survival curves in both the training set and the independent test set (FIG. 2, parts e and f).

ADDITIONAL REFERENCES

Ma, X. J. et al. Gene expression profiles of human breast cancer progression. Proc Natl Acad Sci USA 100, 5974-9 (2003).

Nicholson, R. I. et al. Epidermal growth factor receptor expression in breast cancer: association with response to endocrine therapy. Breast Cancer Res Treat 29, 117-25 (1994).

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the inven-

TABLE 7

Patient and tumor characteristics of the validation set.

| Sample | Tumor Type | Size | Grade | Nodes | ER | PR | Age | DFS | Status |
|---|---|---|---|---|---|---|---|---|---|
| Test 1 | D | 1.9 | 3 | 0/10 | Pos | Pos | 69 | 15 | 1 |
| Test 2 | D | 1.7 | 3 | 0/19 | Pos | Pos | 61 | 117 | 1 |
| Test 3 | D | 1.7 | 2 | 0/26 | Pos | ND | 65 | 18 | 1 |
| Test 4 | D | 1.2 | 2 | 0/19 | Pos | Pos | 63 | 69 | 1 |
| Test 5 | D | 1.7 | 2 | 2/2 | Pos | Pos | 60 | 52 | 1 |
| Test 6 | D | 1.1 | 1 | 0/10 | Pos | Pos | 54 | 59 | 1 |
| Test 7 | D | >1.6 | 2 | 0/17 | Pos | Neg | 66 | 32 | 1 |
| Test 8 | L | 2.6 | 1–2 | 0/14 | Pos | Pos | 58 | 67 | 1 |
| Test 9 | D | 1.2 | 2 | ND | Pos | Pos | 93 | 58 | 1 |
| Test 10 | D | 4 | 3 | 0/20 | Pos | Pos | 66 | 27 | 1 |
| Test 11 | D | 1.1 | 2 | 0/19 | Pos | Pos | 64 | 97 | 0 |
| Test 12 | D | 2.7 | 2 | 0/10 | Pos | Pos | 66 | 120 | 0 |
| Test 13 | D | 0.9 | 1 | 0/22 | Pos | Pos | 66 | 123 | 0 |
| Test 14 | D | 2.1 | 2 | 0/16 | Pos | Pos | 57 | 83 | 0 |
| Test 15 | D | 0.8 | 1–2 | 0/8 | Pos | Pos | 74 | 80 | 0 |
| Test 16 | D | 1 | 2 | 0/13 | Pos | Pos | 74 | 93 | 0 |
| Test 17 | D | 1.6 | 2 | 0/29 | Pos | Pos | 66 | 121 | 0 |
| Test 18 | L | 1.5 | 1–2 | 0/8 | Pos | Pos | 65 | 25 | 0 |
| Test 19 | D | 1.5 | 3 | 0/16 | Pos | Pos | 60 | 108 | 0 |
| Test 20* | L | 4 | 1–2 | 0/19 | Pos | Pos | 60 | 108 | 0 |

Abbreviations: Same as supplemental Table 1.
*Patient received tamoxifen for 2 years.

tion and including such departures from the present disclosure as come within known or customary practice within the art to which the invention pertains and as may be applied to the essential features hereinbefore set forth.

What is claimed is:

1. A method for treating a human subject having ER+ (estrogen receptor positive) breast cancer, comprising
    assaying a breast cancer cell sample from the human subject by determining a ratio of HoxB13 and IL17BR mRNA expression levels in the breast cancer cell sample;
    comparing the ratio of HoxB13 and IL17BR mRNA expression levels in the breast cancer cell sample to a HoxB13 and IL17BR mRNA expression level threshold ratio,
    wherein a ratio of HoxB13 and IL17BR mRNA expression levels above the threshold ratio indicates an outcome comprising cancer recurrence via metastasis following tamoxifen or letrozole treatment, and
    treating the human subject with an alternative therapy other than tamoxifen or letrozole, if the ratio of HoxB13 and IL17BR mRNA expression levels is above the threshold ratio, wherein the alternative therapy other than tamoxifen or letrozole comprises a selective estrogen receptor modulator (SERM), a selective estrogen receptor downregulator (SERD), an aromatase inhibitor (AI), surgical ovarian ablation, or chemical ovarian ablation.

2. The method of claim 1, wherein said mRNA expression levels are determined by quantitative PCR.

3. The method of claim 1, wherein said assaying comprises RT-PCR (reverse transcription polymerase chain reaction).

4. The method of claim 3, wherein the ratio of HoxB13 and IL17BR mRNA expression levels is expressed as ΔCT, wherein CT is the PCR amplification cycle in which the HoxB13 or IL17BR mRNA reaches a threshold amount, and wherein ΔCT is the CT difference between HoxB13 or IL17BR mRNA.

5. The method of claim 1, wherein said breast cancer cell sample is a formalin fixed paraffin embedded (FFPE), ductal lavage or fine needle aspiration sample.

6. The method of claim 1, wherein said breast cancer cell sample is a section of tissue from a subject or comprises cells microdissected from said section.

7. The method of claim 1, wherein the alternative therapy other than tamoxifen or letrozole comprises a selective estrogen receptor modulator (SERM), a selective estrogen receptor downregulator (SERD), or an aromatase inhibitor (AI).

8. The method of claim 1, wherein the alternative therapy other than tamoxifen or letrozole comprises anastrozole, vorozole, exemestane, androstenedione, or formestane.

9. The method of claim 1, wherein the alternative therapy other than tamoxifen or letrozole comprises surgical or chemical ovarian ablation.

\* \* \* \* \*